US008551492B2

(12) United States Patent
Hafner et al.

(10) Patent No.: US 8,551,492 B2
(45) Date of Patent: Oct. 8, 2013

(54) VACCINE PEPTIDE COMBINATIONS AGAINST CAT ALLERGY

(75) Inventors: Roderick Peter Hafner, Oxford (GB); Mark Larche, Ontario (CA); Anthony Barrington Kay, London (GB)

(73) Assignee: Circassia Limited, Oxford (GB)

( * ) Notice: Subject to any disclaimer, the term of this patent is extended or adjusted under 35 U.S.C. 154(b) by 433 days.

(21) Appl. No.: 12/602,313

(22) PCT Filed: May 30, 2008

(86) PCT No.: PCT/GB2008/001827
§ 371 (c)(1),
(2), (4) Date: May 13, 2010

(87) PCT Pub. No.: WO2008/145998
PCT Pub. Date: Dec. 4, 2008

(65) Prior Publication Data
US 2010/0239599 A1 Sep. 23, 2010

(30) Foreign Application Priority Data
Jun. 1, 2007 (GB) .................................. 0710529.9

(51) Int. Cl.
A61K 38/00 (2006.01)
A61K 38/04 (2006.01)
A61K 39/00 (2006.01)
A61K 39/35 (2006.01)
A61K 39/36 (2006.01)
C07K 2/00 (2006.01)
C07K 4/00 (2006.01)
C07K 5/00 (2006.01)
C07K 7/00 (2006.01)
C07K 14/00 (2006.01)
C07K 16/00 (2006.01)
C07K 17/00 (2006.01)

(52) U.S. Cl.
USPC .................... 424/185.1; 424/275.1; 530/300; 530/326; 530/327

(58) Field of Classification Search
None
See application file for complete search history.

(56) References Cited

U.S. PATENT DOCUMENTS

| | | | |
|---|---|---|---|
| 4,442,212 | A | 4/1984 | Briggs |
| 5,547,669 | A | 8/1996 | Rogers et al. |
| 5,820,862 | A | 10/1998 | Garman et al. |
| 6,019,972 | A | 2/2000 | Gefter et al. |
| 6,204,036 | B1 | 3/2001 | Metzner et al. |
| 6,982,326 | B1 | 1/2006 | Griffith et al. |
| 7,786,257 | B2 | 8/2010 | Murray et al. |
| 2004/0071718 | A1 | 4/2004 | Tsai |
| 2005/0107585 | A1 | 5/2005 | Murray et al. |
| 2006/0024334 | A1* | 2/2006 | Larche et al. ............. 424/275.1 |
| 2006/0057641 | A1 | 3/2006 | Morgenstern et al. |
| 2008/0293624 | A1 | 11/2008 | Hageman et al. |

FOREIGN PATENT DOCUMENTS

| | | |
|---|---|---|
| CN | 1283997 A | 2/2001 |
| EP | 0044532 | 1/1982 |
| EP | 1958645 | 8/2008 |
| WO | WO 93/08279 | 4/1993 |
| WO | WO 93/20842 | 10/1993 |
| WO | WO 94/21675 | 9/1994 |
| WO | WO 94/24281 | 10/1994 |
| WO | WO 94/27634 | 12/1994 |
| WO | WO 95/06728 | 3/1995 |
| WO | WO 95/20599 | 8/1995 |
| WO | WO 95/28424 | 10/1995 |
| WO | WO 96/13517 | 5/1996 |
| WO | WO 97/00027 | 1/1997 |
| WO | WO 99/32135 | 7/1999 |
| WO | WO 99/34826 | 7/1999 |
| WO | WO 00/44781 | 8/2000 |
| WO | WO 02/16410 A2 | 2/2002 |
| WO | WO 02/062834 A3 | 8/2002 |
| WO | WO 02/080848 A2 | 10/2002 |
| WO | WO 03/042344 | 5/2003 |
| WO | WO 03/047618 | 6/2003 |
| WO | WO 03/082924 A1 | 10/2003 |
| WO | WO 2004/078098 A2 | 9/2004 |
| WO | WO 2005/000891 A2 | 1/2005 |
| WO | WO 2005/047323 | 5/2005 |
| WO | WO 2006/017773 | 2/2006 |
| WO | WO-2006075253 A2 | 7/2006 |
| WO | WO 2006/082313 A3 | 8/2006 |
| WO | WO 2006/083906 | 8/2006 |
| WO | WO 2007/129093 A2 | 11/2007 |
| WO | WO 2008/115428 | 9/2008 |
| WO | WO 2008/145998 A1 | 12/2008 |

OTHER PUBLICATIONS

Alexander et al., "Fel d 1-Derived T Cell Peptide Therapy Induces Recruitment of $CD4^+CD25^+$; $CD4^+$ Interferon-gamma$^+$ T Helper Type 1 Cells to Sites of Allergen-Induced Late-Phase Skin Reactions in Cat-Allergic Subjects," Clin. Exp. Allergy 35:52-58, 2005.
Alexander et al., "The Effect of Fel d 1-Derived T-Cell Peptides on Upper and Lower Airway Outcome Measurements in Cat-Allergic Subjects," Allergy 60:1269-1274, 2005.
Ali et al., "The Potential of Peptide Immunotherapy in Allergy and Asthma," Curr. Allergy Asthma Rep. 2:151-158, 2002.
Haselden et al., "Late Asthmatic Reactions Provoked by Intradermal Injection of T-Cell Peptide Epitopes are not Associated with Bronchial Mucosal Infiltration of Eosinophils or $T_H2$-Type Cells or with Elevated Concentrations of Histamine or Eicosanoids in Bronchoalveolar Fluid," J. Allergy Clin. Immunol. 180:394-401, 2001.
Haselden et al., "Proliferation and Release of IL-5 and IFN-gamma by Peripheral Blood Mononuclear Cells from Cat-Allergic Asthmatics and Rhinitics, Non-Cat-Allergic Asthmatics, and Normal Controls to Peptides Derived from Fel d 1 Chain 1," J. Allergy Clin. Immunol. 108:349-356, 2001.

(Continued)

Primary Examiner — Nora Rooney
(74) Attorney, Agent, or Firm — Clark & Elbing LLP

(57) ABSTRACT

The present invention relates to compositions comprising peptides for preventing or treating allergy to cats, and in particular to optimal combinations of peptides.

7 Claims, 10 Drawing Sheets

(56) References Cited

OTHER PUBLICATIONS

Kay et al., "Allergen Immunotherapy with Cat Allergen Peptides," Springer Semin. Immunopathol. 25:391-399, 2004.
Oldfield et al., "Effect of T-Cell Peptides Derived from Fel d 1 on Allergic Reactions and Cytokine Production in Patients Sensitive to Cats: A Randomised Controlled Trial," Lancet 360:47-53, 2002.
Verhoef et al., "T Cell Epitope Immunotherapy Induces a CD4+ T Cell Population with Regulatory Activity," PLoS Med. 2(e78):0253-0261, 2005.
Immonen et al., "T Cell Epitope-Containing Peptides of the Major Dog Allergen Can f 1 as Candidates for Allergen Immunotherapy," *J. Immunol.* 175: 3614-3620 (2005).
Larché et al., "Peptide-based therapeutic vaccines for allergic and autoimmune diseases," *Nature Medicine Supplement* 11(4): S69-S76 (2005).
Nicodemus et al., "Integrated Clinical Experience with Tolerogenic Peptides," *Int. Arch. Allergy Immunol.* 113: 326-328 (1997).
Schenk et al., "T-cell epitopes of Phl p 1, major pollen allergen of timothy grass (*Phleum pratense*): Evidence for crossreacting and non-crossreacting T-cell epitopes within grass group I allergens," *J. Allergy Clin. Immunol.* 96(6):986-996 (1995).
Texier et al., "HLA-DR Restricted Peptide Candidates for Bee Venom Immunotherapy," *J. Immunol.* 164: 3177-3184 (2000).
Virtanen, "Prospects for peptide-based immunotherapy for dog allergy," *Curr. Opin. Clin. Immunol.* 6: 461-465 (2006).
Observations on Response to Opposition for European Patent Application No. 2079481, dated May 8, 2013 (7 pages).
Banga et al., "Therapeutic Peptides and Proteins Formulation, Processing, and Delivery System, Second Edition," Chapter 3, pp. 67-89 (2005).
Cromwell et al., "Transition of Recombinant Allergens from Bench to Clinical Application," Methods 32:300-312, 2004.
Dick et al., "Proteolytic Processing of Ovalbumin and P-galactosidase by the Proteasome to Yield Antigenic Peptides," J. Immunol. 152(8): 3884-3894 (1994).
Ebner et al., "Nonallergic Individuals Recognize the Same T Cell Epitopes of Bet v 1, the Major Birch Pollen Allergen, as Atopic Patients," J. Immunol. 154:1932-1940, 1995.
Gotte et al., "Oligomerization of ribonuclease A under reducing conditions," Biochimica et Biophysica Acta, vol. 1784:638-650, 2008.
Harris et al., "Permissive Recognition of a Mycobacterial T-Cell Epitope: Localization of Overlapping Epitope Core Sequences Recognized in Association with Multiple Major Histocompatibility Complex Class II I-A Molecules," Immunology 84:555-561, 1995.
Jeannin et al., "Immunogenicity and Antigenicity of Synthetic Peptides Derived from the Mite Allergen *Der p* I," Mol. Immunol. 30:1511-1518, 1993.
Krco et al., "Immune Response of HLA-DQ Transgenic Mice to House Dust Mite Allergen p2: Identification of HLA-DQ Restricted Minimal Epitopes and Critical Residues," Clin. Immunol. 97:154-161, 2000.
Kristensen et al., "Induction of T Cell Responses to the Invariant Chain Derived Peptide CLIP in Mice Immunized with the Group 1 Allergen of House Dust Mite," Int. Immunol. 8:1091-1098, 1996.
Larché et al., "Peptide-Based Therapeutic Vaccines for Allergic and Autoimmune Diseases," Nat. Med. 11:569-576, 2005.
Mustafa, "Identification of Mycobacterial Peptide Epitopes Recognized by CD4+ T Cells in Association with Multiple Major Histocompatibility Complex Class II Molecules," Nutrition 11:657-660, 1995.
Nagato et al., "Functional Analysis of Birch Pollen Allergen Bet v 1-Specific Regulatory T Cells," J. Immunol. 178:1189-1198, 2007.
Ohkuri et al., "Identification of a Novel NY-ESO-1 Promiscuous Helper Epitope Presented by Multiple MHC Class II Molecules Found Frequently in the Japanese Population," Cancer Sci. 98:1092-1098, 2007.
Rao et al., "Mapping of Thyroglobulin Epitopes: Presentation of a 9mer Pathogenic Peptide by Different Mouse MHC Class II Isotypes," Immunogenetics 40:352-359, 1994.
Schafer et al., "Prediction of Well-Conserved HIV-1 Ligands Using a Matrix-Based Algorithm, EpiMatrix," Vaccine 16:1880-1884, 1998.
Tamborini et al., "Biochemical and Immunological Characterization of Recombinant Allergen Lol p 1," Eur. J. Biochem. 249:886-894, 1997.
Texier et al., "Emerging Principles for the Design of Promiscuous HLA-DR-Restricted Peptides: An Example from the Major Bee Venom Allergen," Eur. J. Immunol. 32:3699-3707, 2002.
Verhoef et al., "Threshold Signaling of Human Th0 Cells in Activation and Anergy: Modulation of Effector Function by Altered TCR Ligand," J. Immunol. 164:6034-6040, 2000.
van de Wal et al., "Peptide Binding Characteristics of the Coeliac Disease-Associated DQ($\alpha$1*0501, $\beta$1*0201) Molecule," Immunogenetics 44:246-253, 1996.
Walker et al., "Mapping Major and Minor T-Cell Epitopes in Vitro and Their Immunogenic or Tolerogenic Effect in Vivo in Non-Human Primates," Immunology 80:209-216, 1993.
Zhu et al., "T Cell Epitope Mapping of Ragweed Pollen Allergen *Ambrosia artemisiifolia* (Amb a 5) and *Ambrosia trifida* (Amb t 5) and the Role of Free Sulfhydryl Groups in T Cell Recognition," J. Immunol. 155:5064-5073, 1995.
UK Search Report from Great Britain Patent Application GB0723337.2, dated Mar. 25, 2008.
International Search Report from International Application No. PCT/GB2008/002779, dated Apr. 2, 2009 (date of completion of search) and Apr. 14, 2009 (date of mailing of report).
Written Opinion from International Application No. PCT/GB2008/002779, dated Apr. 2, 2009 (date of completion of opinion) and Apr. 14, 2009 (date of mailing of opinion).
Great Britain Search Report for Application No. GB0821806.7, dated Mar. 23, 2009.
International Search Report and Written Opinion for Application No. PCT/GB2009/002767, dated Apr. 29, 2011.

* cited by examiner

Figure 1

```
                        1         10        20        30        40        50        60     69
                        EICPAVKRDVDLFLTGTPDEYVEQVAQYKALPVVLENARILKNCVDAKMTEEDKENALSLLDKIYTSPL
Fel d1 chain 1

MLA01    1-17           EICPAVKRDVDLFLTGTPDEY
MLA02    12-28                     LFLTGTPDEYVEQVAQY                                                DR3, DR15
MLA03    23-38                                EQVAQYKALPVVLENA                                      DR7, DR15
MLA04    29-45                                      KALPVVLENARILKNCV      DR1, DR4, DR7, DR11, DR15, DRB5, DRB4
MLA05    39-55                                                RILKNCVDARMTEEDKE   DR1, DR4, DR7, DR11, DR13, DR15, DRB5, DRB4
MLA06    48-63                                                         KMTEEDKENALSLLDK           DR1, DR4, DR15, DRB5, DRB4
MLA07    54-69                                                                KENALSLLDKIYTSPL    DR7, DR11, DR15

Fel d1 chain 2
                        VRMAETCPIFYDVFFAVANGNELLLKLSLTKVNATEPERTAMKKIQDCYVENGLISRVLDGLVMTTISSSKDCMGEAVQNTVEDLKNTLGR MLA08    1-16           VRMAETCPIFYDVFFA                                                            DR1, DRB4
MLA09    7-23                  CPIFYDVFFAVANGNEL                                                    DR7, DRB5 (weak)
MLA10    20-35                             GNELLLKLSLTKVNAT      DR1, DR4, DR7, DR11, DR13, DR15, DRB5, DRB4
MLA11    29-44                                      LTKVNATEPERTAMKK
MLA12    40-55                                                TAMKKIQDCYVENGLI  DR1, DR7, DR15, DRB4
MLA13    48-63                                                        CYVENGLISRVLDGLV
MLA14    56-71                                                                SRVLDGLVMTTISSSK  DR1, DR4, DR11, DRB4
MLA15    67-82                                                                        ISSSKDCMGEAVQNTV   DR1, DR4, DR15
MLA16    77-92                                                                                AVQNTVEDLKNTLGR    DR3, DR4
```

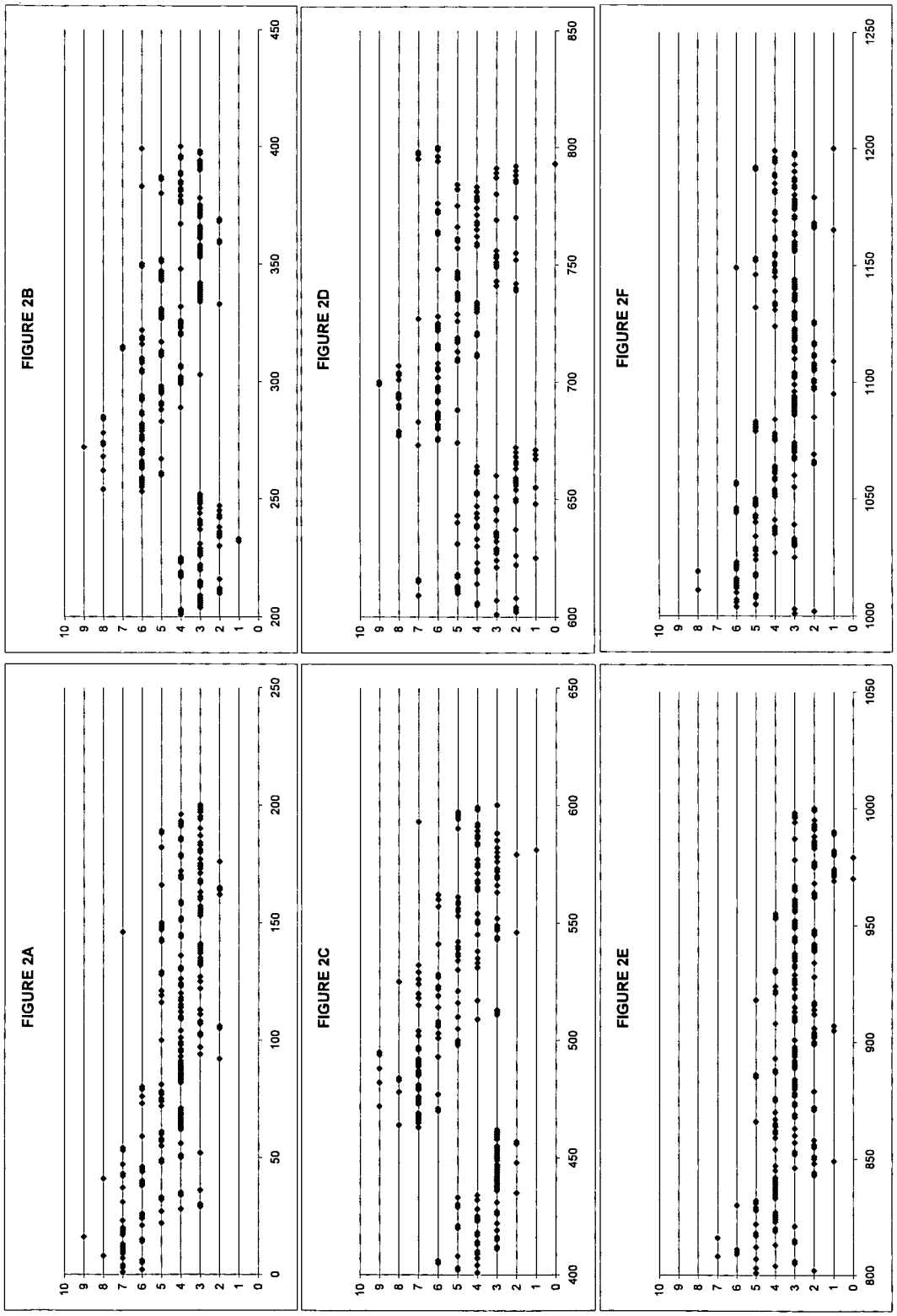

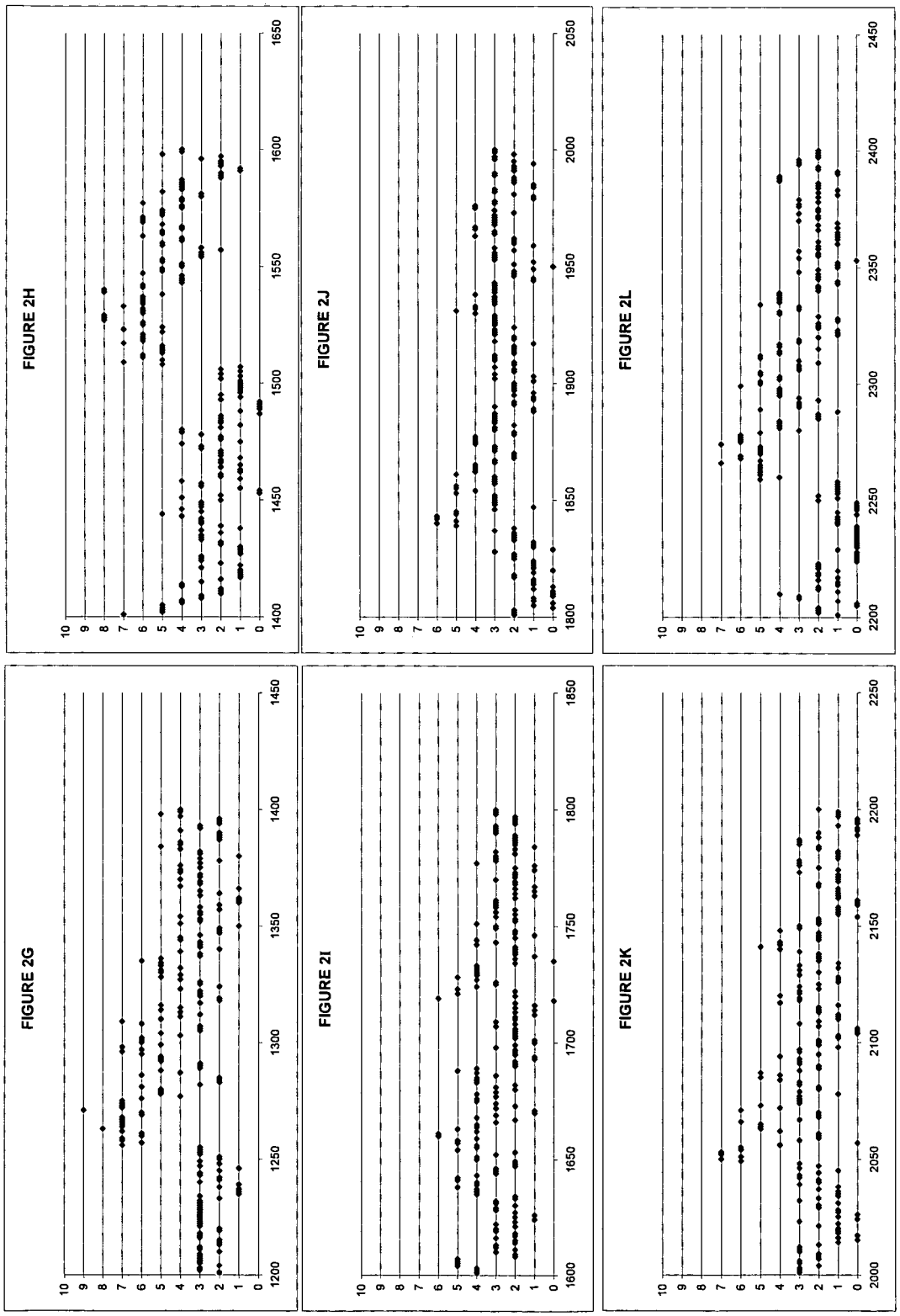

SEQUENCE LISTING

<160> NUMBER OF SEQ ID NOS: 125

<210> SEQ ID NO 1
<211> LENGTH: 13
<212> TYPE: PRT
<213> ORGANISM: Felis catus

<400> SEQUENCE: 1

Cys Pro Ala Val Lys Arg Asp Val Asp Leu Phe Leu Thr

```
<210> SEQ ID NO 2
<211> LENGTH: 16
<212> TYPE: PRT
<213> ORGANISM: Felis catus

<400> SEQUENCE: 2

Glu Gln Val Ala Gln Tyr Lys Ala Leu Pro Val Val Leu Glu Asn Ala
1               5                   10                  15

<210> SEQ ID NO 3
<211> LENGTH: 17
<212> TYPE: PRT
<213> ORGANISM: Felis catus

<400> SEQUENCE: 3

Lys Ala Leu Pro Val Val Leu Glu Asn Ala Arg Ile Leu Lys Asn Cys
1               5                   10                  15

Val

<210> SEQ ID NO 4
<211> LENGTH: 17
<212> TYPE: PRT
<213> ORGANISM: Felis catus

<400> SEQUENCE: 4

Arg Ile Leu Lys Asn Cys Val Asp Ala Lys Met Thr Glu Glu Asp Lys
1               5                   10                  15

Glu

<210> SEQ ID NO 5
<211> LENGTH: 16
<212> TYPE: PRT
<213> ORGANISM: Felis catus

<400> SEQUENCE: 5

Lys Glu Asn Ala Leu Ser Leu Leu Asp Lys Ile Tyr Thr Ser Pro Leu
1               5                   10                  15

<210> SEQ ID NO 6
<211> LENGTH: 16
<212> TYPE: PRT
<213> ORGANISM: Felis catus

<400> SEQUENCE: 6

Thr Ala Met Lys Lys Ile Gln Asp Cys Tyr Val Glu Asn Gly Leu Ile
1               5                   10                  15

<210> SEQ ID NO 7
<211> LENGTH: 16
<212> TYPE: PRT
<213> ORGANISM: Felis catus

<400> SEQUENCE: 7

Ser Arg Val Leu Asp Gly Leu Val Met Thr Thr Ile Ser Ser Ser Lys
1               5                   10                  15

<210> SEQ ID NO 8
<211> LENGTH: 17
<212> TYPE: PRT
<213> ORGANISM: Felis catus

<400> SEQUENCE: 8
```

```
Leu Phe Leu Thr Gly Thr Pro Asp Glu Tyr Val Glu Gln Val Ala Gln
1               5                   10                  15

Tyr

<210> SEQ ID NO 9
<211> LENGTH: 16
<212> TYPE: PRT
<213> ORGANISM: Felis catus

<400> SEQUENCE: 9

Lys Met Thr Glu Glu Asp Lys Glu Asn Ala Leu Ser Leu Leu Asp Lys
1               5                   10                  15

<210> SEQ ID NO 10
<211> LENGTH: 16
<212> TYPE: PRT
<213> ORGANISM: Felis catus

<400> SEQUENCE: 10

Leu Thr Lys Val Asn Ala Thr Glu Pro Glu Arg Thr Ala Met Lys Lys
1               5                   10                  15

<210> SEQ ID NO 11
<211> LENGTH: 16
<212> TYPE: PRT
<213> ORGANISM: Felis catus

<400> SEQUENCE: 11

Ile Ser Ser Ser Lys Asp Cys Met Gly Glu Ala Val Gln Asn Thr Val
1               5                   10                  15

<210> SEQ ID NO 12
<211> LENGTH: 16
<212> TYPE: PRT
<213> ORGANISM: Felis catus

<400> SEQUENCE: 12

Ala Val Gln Asn Thr Val Glu Asp Leu Lys Leu Asn Thr Leu Gly Arg
1               5                   10                  15

<210> SEQ ID NO 13
<211> LENGTH: 16
<212> TYPE: PRT
<213> ORGANISM: Felis catus

<400> SEQUENCE: 13

Val Lys Met Ala Glu Thr Cys Pro Ile Phe Tyr Asp Val Phe Phe Ala
1               5                   10                  15

<210> SEQ ID NO 14
<211> LENGTH: 17
<212> TYPE: PRT
<213> ORGANISM: Felis catus

<400> SEQUENCE: 14

Cys Pro Ile Phe Tyr Asp Val Phe Phe Ala Val Ala Asn Gly Asn Glu
1               5                   10                  15

Leu

<210> SEQ ID NO 15
<211> LENGTH: 16
<212> TYPE: PRT
<213> ORGANISM: Felis catus

<400> SEQUENCE: 15
```

```
Gly Asn Glu Leu Leu Lys Leu Ser Leu Thr Lys Val Asn Ala Thr
1               5                   10                  15

<210> SEQ ID NO 16
<211> LENGTH: 16
<212> TYPE: PRT
<213> ORGANISM: Felis catus

<400> SEQUENCE: 16

Cys Tyr Val Glu Asn Gly Leu Ile Ser Arg Val Leu Asp Gly Leu Val
1               5                   10                  15

<210> SEQ ID NO 17
<211> LENGTH: 13
<212> TYPE: PRT
<213> ORGANISM: Artificial
<220> FEATURE:
<223> OTHER INFORMATION: Reference peptide for HLA-DR1, HLA-DR4 and
      HLA- DR11

<400> SEQUENCE: 17

Pro Lys Tyr Val Lys Gln Asn Thr Leu Lys Leu Ala Thr
1               5                   10

<210> SEQ ID NO 18
<211> LENGTH: 15
<212> TYPE: PRT
<213> ORGANISM: Artificial
<220> FEATURE:
<223> OTHER INFORMATION: Reference peptide for HLA-DR3

<400> SEQUENCE: 18

Ala Lys Thr Ile Ala Tyr Asp Glu Glu Ala Arg Arg Gly Leu Glu
1               5                   10                  15

<210> SEQ ID NO 19
<211> LENGTH: 13
<212> TYPE: PRT
<213> ORGANISM: Artificial
<220> FEATURE:
<223> OTHER INFORMATION: Reference peptide for HLA-DR7

<400> SEQUENCE: 19

Ala Ala Tyr Ala Ala Ala Lys Ala Ala Ala Leu Ala Ala
1               5                   10

<210> SEQ ID NO 20
<211> LENGTH: 16
<212> TYPE: PRT
<213> ORGANISM: Artificial
<220> FEATURE:
<223> OTHER INFORMATION: Reference peptide for HLA-DR13

<400> SEQUENCE: 20

Thr Glu Arg Val Arg Leu Val Thr Arg His Ile Tyr Asn Arg Glu Glu
1               5                   10                  15

<210> SEQ ID NO 21
<211> LENGTH: 16
<212> TYPE: PRT
<213> ORGANISM: Artificial
<220> FEATURE:
<223> OTHER INFORMATION: Reference peptide for HLA-DR15

<400> SEQUENCE: 21

Glu Ala Glu Gln Leu Arg Arg Ala Tyr Leu Asp Gly Thr Gly Val Glu
1               5                   10                  15
```

<210> SEQ ID NO 22
<211> LENGTH: 14
<212> TYPE: PRT
<213> ORGANISM: Artificial
<220> FEATURE:
<223> OTHER INFORMATION: Reference peptide for HLA-B4

<400> SEQUENCE: 22

Ala Gly Asp Leu Leu Ala Ile Glu Thr Asp Lys Ala Thr Ile
1               5                   10

<210> SEQ ID NO 23
<211> LENGTH: 320
<212> TYPE: PRT
<213> ORGANISM: Dermatophagoides pteronyssinus

<400> SEQUENCE: 23

Met Lys Ile Val Leu Ala Ile Ala Ser Leu Leu Ala Leu Ser Ala Val
1               5                   10                  15

Tyr Ala Arg Pro Ser Ser Ile Lys Thr Phe Glu Glu Tyr Lys Lys Ala
            20                  25                  30

Phe Asn Lys Ser Tyr Ala Thr Phe Glu Asp Glu Glu Ala Ala Arg Lys
        35                  40                  45

Asn Phe Leu Glu Ser Val Lys Tyr Val Gln Ser Asn Gly Gly Ala Ile
    50                  55                  60

Asn His Leu Ser Asp Leu Ser Leu Asp Glu Phe Lys Asn Arg Phe Leu
65                  70                  75                  80

Met Ser Ala Glu Ala Phe Glu His Leu Lys Thr Gln Phe Asp Leu Asn
                85                  90                  95

Ala Glu Thr Asn Ala Cys Ser Ile Asn Gly Asn Ala Pro Ala Glu Ile
            100                 105                 110

Asp Leu Arg Gln Met Arg Thr Val Thr Pro Ile Arg Met Gln Gly Gly
        115                 120                 125

Cys Gly Ser Cys Trp Ala Phe Ser Gly Val Ala Ala Thr Glu Ser Ala
130                 135                 140

Tyr Leu Ala Tyr Arg Asn Gln Ser Leu Asp Leu Ala Glu Gln Glu Leu
145                 150                 155                 160

Val Asp Cys Ala Ser Gln His Gly Cys His Gly Asp Thr Ile Pro Arg
                165                 170                 175

Gly Ile Glu Tyr Ile Gln His Asn Gly Val Val Gln Glu Ser Tyr Tyr
            180                 185                 190

Arg Tyr Val Ala Arg Glu Gln Ser Cys Arg Arg Pro Asn Ala Gln Arg
        195                 200                 205

Phe Gly Ile Ser Asn Tyr Cys Gln Ile Tyr Pro Pro Asn Val Asn Lys
    210                 215                 220

Ile Arg Glu Ala Leu Ala Gln Thr His Ser Ala Ile Ala Val Ile Ile
225                 230                 235                 240

Gly Ile Lys Asp Leu Asp Ala Phe Arg His Tyr Asp Gly Arg Thr Ile
                245                 250                 255

Ile Gln Arg Asp Asn Gly Tyr Gln Pro Asn Tyr His Ala Val Asn Ile
            260                 265                 270

Val Gly Tyr Ser Asn Ala Gln Gly Val Asp Tyr Trp Ile Val Arg Asn
        275                 280                 285

Ser Trp Asp Thr Asn Trp Gly Asp Asn Gly Tyr Gly Tyr Phe Ala Ala
    290                 295                 300

Asn Ile Asp Leu Met Met Ile Glu Glu Tyr Pro Tyr Val Val Ile Leu

<210> SEQ ID NO 24
<211> LENGTH: 146
<212> TYPE: PRT
<213> ORGANISM: Dermatophagoides pteronyssinus

<400> SEQUENCE: 24

Met Met Tyr Lys Ile Leu Cys Leu Ser Leu Leu Val Ala Ala Val Ala
1               5                   10                  15

Arg Asp Gln Val Asp Val Lys Asp Cys Ala Asn His Glu Ile Lys Lys
            20                  25                  30

Val Leu Val Pro Gly Cys His Gly Ser Glu Pro Cys Ile Ile His Arg
        35                  40                  45

Gly Lys Pro Phe Gln Leu Glu Ala Val Phe Glu Ala Asn Gln Asn Thr
    50                  55                  60

Lys Thr Ala Lys Ile Glu Ile Lys Ala Ser Ile Asp Gly Leu Glu Val
65                  70                  75                  80

Asp Val Pro Gly Ile Asp Pro Asn Ala Cys His Tyr Met Lys Cys Pro
                85                  90                  95

Leu Val Lys Gly Gln Gln Tyr Asp Ile Lys Tyr Thr Trp Asn Val Pro
            100                 105                 110

Lys Ile Ala Pro Lys Ser Glu Asn Val Val Thr Val Lys Val Met
        115                 120                 125

Gly Asp Asp Gly Val Leu Ala Cys Ala Ile Ala Thr His Ala Lys Ile
    130                 135                 140

Arg Asp
145

<210> SEQ ID NO 25
<211> LENGTH: 261
<212> TYPE: PRT
<213> ORGANISM: Dermatophagoides pteronyssinus

<400> SEQUENCE: 25

Met Ile Ile Tyr Asn Ile Leu Ile Val Leu Leu Leu Ala Ile Asn Thr
1               5                   10                  15

Leu Ala Asn Pro Ile Leu Pro Ala Ser Pro Asn Ala Thr Ile Val Gly
            20                  25                  30

Gly Glu Lys Ala Leu Ala Gly Glu Cys Pro Tyr Gln Ile Ser Leu Gln
        35                  40                  45

Ser Ser Ser His Phe Cys Gly Gly Thr Ile Leu Asp Glu Tyr Trp Ile
    50                  55                  60

Leu Thr Ala Ala His Cys Val Ala Gly Gln Thr Ala Ser Lys Leu Ser
65                  70                  75                  80

Ile Arg Tyr Asn Ser Leu Lys His Ser Leu Gly Gly Glu Lys Ile Ser
                85                  90                  95

Val Ala Lys Ile Phe Ala His Glu Lys Tyr Asp Ser Tyr Gln Ile Asp
            100                 105                 110

Asn Asp Ile Ala Leu Ile Lys Leu Lys Ser Pro Met Lys Leu Asn Gln
        115                 120                 125

Lys Asn Ala Lys Ala Val Gly Leu Pro Ala Lys Gly Ser Asp Val Lys
    130                 135                 140

Val Gly Asp Gln Val Arg Val Ser Gly Trp Gly Tyr Leu Glu Glu Gly
145                 150                 155                 160

Ser Tyr Ser Leu Pro Ser Glu Leu Arg Arg Val Asp Ile Ala Val Val
                165                 170                 175

```
Ser Arg Lys Glu Cys Asn Glu Leu Tyr Ser Lys Ala Asn Ala Glu Val
            180                 185                 190

Thr Asp Asn Met Ile Cys Gly Gly Asp Val Ala Asn Gly Gly Lys Asp
        195                 200                 205

Ser Cys Gln Gly Asp Ser Gly Pro Val Val Asp Val Lys Asn Asn
    210                 215                 220

Gln Val Val Gly Ile Val Ser Trp Gly Tyr Gly Cys Ala Arg Lys Gly
225                 230                 235                 240

Tyr Pro Gly Val Tyr Thr Arg Val Gly Asn Phe Ile Asp Trp Ile Glu
                245                 250                 255

Ser Lys Arg Ser Gln
            260

<210> SEQ ID NO 26
<211> LENGTH: 19
<212> TYPE: PRT
<213> ORGANISM: Dermatophagoides pteronyssinus
<220> FEATURE:
<221> NAME/KEY: misc_feature
<222> LOCATION: (3)..(3)
<223> OTHER INFORMATION: unknown or other
<220> FEATURE:
<221> NAME/KEY: misc_feature
<222> LOCATION: (10)..(10)
<223> OTHER INFORMATION: unknown or other
<220> FEATURE:
<221> NAME/KEY: misc_feature
<222> LOCATION: (16)..(16)
<223> OTHER INFORMATION: unknown or other

<400> SEQUENCE: 26

Lys Tyr Xaa Asn Pro His Phe Ile Gly Xaa Arg Ser Val Ile Thr Xaa
1               5                   10                  15

Leu Met Glu

<210> SEQ ID NO 27
<211> LENGTH: 132
<212> TYPE: PRT
<213> ORGANISM: Dermatophagoides pteronyssinus

<400> SEQUENCE: 27

Met Lys Phe Ile Ile Ala Phe Phe Val Ala Thr Leu Ala Val Met Thr
1               5                   10                  15

Val Ser Gly Glu Asp Lys Lys His Asp Tyr Gln Asn Glu Phe Asp Phe
            20                  25                  30

Leu Leu Met Glu Arg Ile His Glu Gln Ile Lys Lys Gly Glu Leu Ala
        35                  40                  45

Leu Phe Tyr Leu Gln Glu Gln Ile Asn His Phe Glu Glu Lys Pro Thr
    50                  55                  60

Lys Glu Met Lys Asp Lys Ile Val Ala Glu Met Asp Thr Ile Ile Ala
65                  70                  75                  80

Met Ile Asp Gly Val Arg Gly Val Leu Asp Arg Leu Met Gln Arg Lys
                85                  90                  95

Asp Leu Asp Ile Phe Glu Gln Tyr Asn Leu Glu Met Ala Lys Lys Ser
            100                 105                 110

Gly Asp Ile Leu Glu Arg Asp Leu Lys Lys Glu Ala Arg Val Lys
        115                 120                 125

Lys Ile Glu Val
    130
```

```
<210> SEQ ID NO 28
<211> LENGTH: 20
<212> TYPE: PRT
<213> ORGANISM: Dermatophagoides pteronyssinus
<220> FEATURE:
<221> NAME/KEY: misc_feature
<222> LOCATION: (4)..(4)
<223> OTHER INFORMATION: unknown or other

<400> SEQUENCE: 28

Ala Ile Gly Xaa Gln Pro Ala Ala Glu Ala Glu Ala Pro Phe Gln Ile
1               5                   10                  15

Ser Leu Met Lys
            20

<210> SEQ ID NO 29
<211> LENGTH: 215
<212> TYPE: PRT
<213> ORGANISM: Dermatophagoides pteronyssinus

<400> SEQUENCE: 29

Met Met Lys Leu Leu Ile Ala Ala Ala Phe Val Ala Val Ser
1               5                   10                  15

Ala Asp Pro Ile His Tyr Asp Lys Ile Thr Glu Glu Ile Asn Lys Ala
            20                  25                  30

Val Asp Glu Ala Val Ala Ala Ile Glu Lys Ser Glu Thr Phe Asp Pro
        35                  40                  45

Met Lys Val Pro Asp His Ser Asp Lys Phe Glu Arg His Ile Gly Ile
    50                  55                  60

Ile Asp Leu Lys Gly Glu Leu Asp Met Arg Asn Ile Gln Val Arg Gly
65                  70                  75                  80

Leu Lys Gln Met Lys Arg Val Gly Asp Ala Asn Val Lys Ser Glu Asp
                85                  90                  95

Gly Val Val Lys Ala His Leu Leu Val Gly Val His Asp Asp Val Val
            100                 105                 110

Ser Met Glu Tyr Asp Leu Ala Tyr Lys Leu Gly Asp Leu His Pro Asn
        115                 120                 125

Thr His Val Ile Ser Asp Ile Gln Asp Phe Val Val Glu Leu Ser Leu
    130                 135                 140

Glu Val Ser Glu Glu Gly Asn Met Thr Leu Thr Ser Phe Glu Val Arg
145                 150                 155                 160

Gln Phe Ala Asn Val Val Asn His Ile Gly Gly Leu Ser Ile Leu Asp
                165                 170                 175

Pro Ile Phe Ala Val Leu Ser Asp Val Leu Thr Ala Ile Phe Gln Asp
            180                 185                 190

Thr Val Arg Ala Glu Met Thr Lys Val Leu Ala Pro Ala Phe Lys Lys
        195                 200                 205

Glu Leu Glu Arg Asn Asn Gln
    210                 215

<210> SEQ ID NO 30
<211> LENGTH: 18
<212> TYPE: PRT
<213> ORGANISM: Dermatophagoides pteronyssinus

<400> SEQUENCE: 30

Ile Val Gly Gly Ser Asn Ala Ser Pro Gly Asp Ala Val Tyr Gln Ile
1               5                   10                  15

Ala Leu
```

```
<210> SEQ ID NO 31
<211> LENGTH: 319
<212> TYPE: PRT
<213> ORGANISM: Dermatophagoides farinae

<400> SEQUENCE: 31
```

Met Lys Phe Val Leu Ala Ile Ala Ser Leu Leu Val Leu Thr Val Tyr
1               5                   10                  15

Ala Arg Pro Ala Ser Ile Lys Thr Phe Glu Phe Lys Lys Ala Phe Asn
                20                  25                  30

Lys Asn Tyr Ala Thr Val Glu Glu Glu Val Ala Arg Lys Asn Phe
            35                  40                  45

Leu Glu Ser Leu Lys Tyr Val Glu Ala Asn Lys Gly Ala Ile Asn His
        50                  55                  60

Leu Ser Asp Leu Ser Leu Asp Glu Phe Lys Asn Arg Tyr Leu Met Ser
65                  70                  75                  80

Ala Glu Ala Phe Glu Gln Leu Lys Thr Gln Phe Asp Leu Asn Ala Glu
                85                  90                  95

Thr Ser Ala Cys Arg Ile Asn Ser Val Asn Val Pro Ser Glu Leu Asp
            100                 105                 110

Leu Arg Ser Leu Arg Thr Val Thr Pro Ile Arg Met Gln Gly Gly Cys
        115                 120                 125

Gly Ser Cys Trp Ala Phe Ser Gly Val Ala Ala Thr Glu Ser Ala Tyr
130                 135                 140

Leu Ala Tyr Arg Asn Thr Ser Leu Asp Leu Ser Glu Gln Glu Leu Val
145                 150                 155                 160

Asp Cys Ala Ser Gln His Gly Cys His Gly Asp Thr Ile Pro Arg Gly
                165                 170                 175

Ile Glu Tyr Ile Gln Gln Asn Gly Val Val Glu Glu Arg Ser Tyr Pro
            180                 185                 190

Tyr Val Ala Arg Glu Gln Arg Cys Arg Arg Pro Asn Ser Gln His Tyr
        195                 200                 205

Gly Ile Ser Asn Tyr Cys Gln Ile Tyr Pro Pro Asp Val Lys Gln Ile
210                 215                 220

Arg Glu Ala Leu Thr Gln Thr His Thr Ala Ile Ala Val Ile Ile Gly
225                 230                 235                 240

Ile Lys Asp Leu Arg Ala Phe Gln His Tyr Asp Gly Arg Thr Ile Ile
                245                 250                 255

Gln His Asp Asn Gly Tyr Gln Pro Asn Tyr His Ala Val Asn Ile Val
            260                 265                 270

Gly Tyr Gly Ser Thr Gln Gly Asp Asp Tyr Trp Ile Val Arg Asn Ser
        275                 280                 285

Trp Asp Thr Thr Trp Gly Asp Ser Gly Tyr Gly Tyr Phe Gln Ala Gly
        290                 295                 300

Asn Asn Leu Met Met Ile Glu Gly Tyr Pro Tyr Val Val Ile Met
305                 310                 315

```
<210> SEQ ID NO 32
<211> LENGTH: 146
<212> TYPE: PRT
<213> ORGANISM: Dermatophagoides farinae

<400> SEQUENCE: 32
```

Met Ile Ser Lys Ile Leu Cys Leu Ser Leu Leu Val Ala Ala Val Val
1               5                   10                  15

Ala Asp Gln Val Asp Val Lys Asp Cys Ala Asn Asn Glu Ile Lys Lys

```
                      20                  25                  30
Val Met Val Asp Gly Cys His Gly Ser Asp Pro Cys Ile Ile His Arg
         35                  40                  45

Gly Lys Pro Phe Thr Leu Glu Ala Leu Phe Asp Ala Asn Gln Asn Thr
 50                  55                  60

Lys Thr Ala Lys Ile Glu Ile Lys Ala Ser Leu Asp Gly Leu Glu Ile
 65                  70                  75                  80

Asp Val Pro Gly Ile Asp Thr Asn Ala Cys His Phe Met Lys Cys Pro
                 85                  90                  95

Leu Val Lys Gly Gln Gln Tyr Asp Ile Lys Tyr Thr Trp Asn Val Pro
                100                 105                 110

Lys Ile Ala Pro Lys Ser Glu Asn Val Val Thr Val Lys Leu Ile
             115                 120                 125

Gly Asp Asn Gly Val Leu Ala Cys Ala Ile Ala Thr His Gly Lys Ile
130                 135                 140

Arg Asp
145

<210> SEQ ID NO 33
<211> LENGTH: 259
<212> TYPE: PRT
<213> ORGANISM: Dermatophagoides farinae

<400> SEQUENCE: 33

Met Met Ile Leu Thr Ile Val Val Leu Leu Ala Ala Asn Ile Leu Ala
 1               5                  10                  15

Thr Pro Ile Leu Pro Ser Ser Pro Asn Ala Thr Ile Val Gly Gly Val
                 20                  25                  30

Lys Ala Gln Ala Gly Asp Cys Pro Tyr Gln Ile Ser Leu Gln Ser Ser
             35                  40                  45

Ser His Phe Cys Gly Gly Ser Ile Leu Asp Glu Tyr Trp Ile Leu Thr
 50                  55                  60

Ala Ala His Cys Val Asn Gly Gln Ser Ala Lys Lys Leu Ser Ile Arg
65                  70                  75                  80

Tyr Asn Thr Leu Lys His Ala Ser Gly Gly Glu Lys Ile Gln Val Ala
                 85                  90                  95

Glu Ile Tyr Gln His Glu Asn Tyr Asp Ser Met Thr Ile Asp Asn Asp
                100                 105                 110

Val Ala Leu Ile Lys Leu Lys Thr Pro Met Thr Leu Asp Gln Thr Asn
             115                 120                 125

Ala Lys Pro Val Pro Leu Pro Ala Gln Gly Ser Asp Val Lys Val Gly
130                 135                 140

Asp Lys Ile Arg Val Ser Gly Trp Gly Tyr Leu Gln Glu Gly Ser Tyr
145                 150                 155                 160

Ser Leu Pro Ser Glu Leu Gln Arg Val Asp Ile Asp Val Val Ser Arg
                165                 170                 175

Glu Gln Cys Asp Gln Leu Tyr Ser Lys Ala Gly Ala Asp Val Ser Glu
                180                 185                 190

Asn Met Ile Cys Gly Gly Asp Val Ala Asn Gly Gly Val Asp Ser Cys
             195                 200                 205

Gln Gly Asp Ser Gly Gly Pro Val Val Asp Val Ala Thr Lys Gln Ile
         210                 215                 220

Val Gly Ile Val Ser Trp Gly Tyr Gly Cys Ala Arg Lys Gly Tyr Pro
225                 230                 235                 240

Gly Val Tyr Thr Arg Val Gly Asn Phe Val Asp Trp Ile Glu Ser Lys
```

Arg Ser Gln

<210> SEQ ID NO 34
<211> LENGTH: 20
<212> TYPE: PRT
<213> ORGANISM: Dermatophagoides farinae

<400> SEQUENCE: 34

Ala Val Gly Gly Gln Asp Ala Asp Leu Ala Glu Ala Pro Phe Gln Ile
1               5                   10                  15

Ser Leu Leu Lys
            20

<210> SEQ ID NO 35
<211> LENGTH: 213
<212> TYPE: PRT
<213> ORGANISM: Dermatophagoides farinae

<400> SEQUENCE: 35

Met Met Lys Phe Leu Leu Ile Ala Ala Val Ala Phe Val Ala Val Ser
1               5                   10                  15

Ala Asp Pro Ile His Tyr Asp Lys Ile Thr Glu Glu Ile Asn Lys Ala
                20                  25                  30

Ile Asp Asp Ala Ile Ala Ala Ile Glu Gln Ser Glu Thr Ile Asp Pro
            35                  40                  45

Met Lys Val Pro Asp His Ala Asp Lys Phe Glu Arg His Val Gly Ile
        50                  55                  60

Val Asp Phe Lys Gly Glu Leu Ala Met Arg Asn Ile Glu Ala Arg Gly
65                  70                  75                  80

Leu Lys Gln Met Lys Arg Gln Gly Asp Ala Asn Val Lys Gly Glu Glu
                85                  90                  95

Gly Ile Val Lys Ala His Leu Leu Ile Gly Val His Asp Asp Ile Val
            100                 105                 110

Ser Met Glu Tyr Asp Leu Ala Tyr Lys Leu Gly Asp Leu His Pro Thr
        115                 120                 125

Thr His Val Ile Ser Asp Ile Gln Asp Phe Val Val Ala Leu Ser Leu
    130                 135                 140

Glu Ile Ser Asp Glu Gly Asn Ile Thr Met Thr Ser Phe Glu Val Arg
145                 150                 155                 160

Gln Phe Ala Asn Val Val Asn His Ile Gly Gly Leu Ser Ile Leu Asp
                165                 170                 175

Pro Ile Phe Gly Val Leu Ser Asp Val Leu Thr Ala Ile Phe Gln Asp
            180                 185                 190

Thr Val Arg Lys Glu Met Thr Lys Val Leu Ala Pro Ala Phe Lys Arg
        195                 200                 205

Glu Leu Glu Lys Asn
    210

<210> SEQ ID NO 36
<211> LENGTH: 138
<212> TYPE: PRT
<213> ORGANISM: Hevea brasiliensis

<400> SEQUENCE: 36

Met Ala Glu Asp Glu Asp Asn Gln Gln Gly Gln Gly Glu Gly Leu Lys
1               5                   10                  15

Tyr Leu Gly Phe Val Gln Asp Ala Ala Thr Tyr Ala Val Thr Thr Phe

```
                    20                  25                  30
Ser Asn Val Tyr Leu Phe Ala Lys Asp Lys Ser Gly Pro Leu Gln Pro
            35                  40                  45

Gly Val Asp Ile Ile Glu Gly Pro Val Lys Asn Val Ala Val Pro Leu
            50                  55                  60

Tyr Asn Arg Phe Ser Tyr Ile Pro Asn Gly Ala Leu Lys Phe Val Asp
65                  70                  75                  80

Ser Thr Val Val Ala Ser Val Thr Ile Ile Asp Arg Ser Leu Pro Pro
                85                  90                  95

Ile Val Lys Asp Ala Ser Ile Gln Val Val Ser Ala Ile Arg Ala Ala
            100                 105                 110

Pro Glu Ala Ala Arg Ser Leu Ala Ser Ser Leu Pro Gly Gln Thr Lys
            115                 120                 125

Ile Leu Ala Lys Val Phe Tyr Gly Glu Asn
            130                 135
```

```
<210> SEQ ID NO 37
<211> LENGTH: 204
<212> TYPE: PRT
<213> ORGANISM: Hevea brasiliensis

<400> SEQUENCE: 37

Met Ala Glu Glu Val Glu Glu Arg Leu Lys Tyr Leu Asp Phe Val
1               5                   10                  15

Arg Ala Ala Gly Val Tyr Ala Val Asp Ser Phe Ser Thr Leu Tyr Leu
            20                  25                  30

Tyr Ala Lys Asp Ile Ser Gly Pro Leu Lys Pro Gly Val Asp Thr Ile
            35                  40                  45

Glu Asn Val Val Lys Thr Val Thr Pro Val Tyr Tyr Ile Pro Leu
            50                  55                  60

Glu Ala Val Lys Phe Val Asp Lys Thr Val Asp Val Ser Val Thr Ser
65                  70                  75                  80

Leu Asp Gly Val Val Pro Pro Val Ile Lys Gln Val Ser Ala Gln Thr
                85                  90                  95

Tyr Ser Val Ala Gln Asp Ala Pro Arg Ile Val Leu Asp Val Ala Ser
            100                 105                 110

Ser Val Phe Asn Thr Gly Val Gln Glu Gly Ala Lys Ala Leu Tyr Ala
            115                 120                 125

Asn Leu Glu Pro Lys Ala Glu Gln Tyr Ala Val Ile Thr Trp Arg Ala
            130                 135                 140

Leu Asn Lys Leu Pro Leu Val Pro Gln Val Ala Asn Val Val Pro
145                 150                 155                 160

Thr Ala Val Tyr Phe Ser Glu Lys Tyr Asn Asp Val Val Arg Gly Thr
                165                 170                 175

Thr Glu Gln Gly Tyr Arg Val Ser Ser Tyr Leu Pro Leu Leu Pro Thr
            180                 185                 190

Glu Lys Ile Thr Lys Val Phe Gly Asp Glu Ala Ser
            195                 200
```

```
<210> SEQ ID NO 38
<211> LENGTH: 263
<212> TYPE: PRT
<213> ORGANISM: Lolium perenne

<400> SEQUENCE: 38

Met Ala Ser Ser Ser Ser Val Leu Leu Val Val Ala Leu Phe Ala Val
1               5                   10                  15
```

Phe Leu Gly Ser Ala His Gly Ile Ala Lys Val Pro Gly Pro Asn
                20                  25                  30

Ile Thr Ala Glu Tyr Gly Asp Lys Trp Leu Asp Ala Lys Ser Thr Trp
            35                  40                  45

Tyr Gly Lys Pro Thr Gly Ala Gly Pro Lys Asp Asn Gly Gly Ala Cys
 50                  55                  60

Gly Tyr Lys Asn Val Asp Lys Ala Pro Phe Asn Gly Met Thr Gly Cys
 65                  70                  75                  80

Gly Asn Thr Pro Ile Phe Lys Asp Gly Arg Gly Cys Gly Ser Cys Phe
                85                  90                  95

Glu Ile Lys Cys Thr Lys Pro Glu Ser Cys Ser Gly Glu Ala Val Thr
                100                 105                 110

Val Thr Ile Thr Asp Asp Asn Glu Glu Pro Ile Ala Pro Tyr His Phe
                115                 120                 125

Asp Leu Ser Gly His Ala Phe Gly Ser Met Ala Lys Lys Gly Glu Glu
        130                 135                 140

Gln Asn Val Arg Ser Ala Gly Glu Leu Glu Leu Gln Phe Arg Arg Val
145                 150                 155                 160

Lys Cys Lys Tyr Pro Asp Asp Thr Lys Pro Thr Phe His Val Glu Lys
                165                 170                 175

Ala Ser Asn Pro Asn Tyr Leu Ala Ile Leu Val Lys Tyr Val Asp Gly
                180                 185                 190

Asp Gly Asp Val Val Ala Val Asp Ile Lys Glu Lys Gly Lys Asp Lys
            195                 200                 205

Trp Ile Glu Leu Lys Glu Ser Trp Gly Ala Val Trp Arg Ile Asp Thr
210                 215                 220

Pro Asp Lys Leu Thr Gly Pro Phe Thr Val Arg Tyr Thr Thr Glu Gly
225                 230                 235                 240

Gly Thr Lys Ser Glu Phe Glu Asp Val Ile Pro Glu Gly Trp Lys Ala
                245                 250                 255

Asp Thr Ser Tyr Ser Ala Lys
                260

<210> SEQ ID NO 39
<211> LENGTH: 97
<212> TYPE: PRT
<213> ORGANISM: Lolium perenne

<400> SEQUENCE: 39

Ala Ala Pro Val Glu Phe Thr Val Glu Lys Gly Ser Asp Glu Lys Asn
1               5                   10                  15

Leu Ala Leu Ser Ile Lys Tyr Asn Lys Glu Gly Asp Ser Met Ala Glu
                20                  25                  30

Val Glu Leu Lys Glu His Gly Ser Asn Glu Trp Leu Ala Leu Lys Lys
            35                  40                  45

Asn Gly Asp Gly Val Trp Glu Ile Lys Ser Asp Lys Pro Leu Lys Gly
 50                  55                  60

Pro Phe Asn Phe Arg Phe Val Ser Glu Lys Gly Met Arg Asn Val Phe
 65                  70                  75                  80

Asp Asp Val Val Pro Ala Asp Phe Lys Val Gly Thr Thr Tyr Lys Pro
                85                  90                  95

Glu

<210> SEQ ID NO 40
<211> LENGTH: 97

```
<212> TYPE: PRT
<213> ORGANISM: Lolium perenne

<400> SEQUENCE: 40

Thr Lys Val Asp Leu Thr Val Glu Lys Gly Ser Asp Ala Lys Thr Leu
1               5                   10                  15

Val Leu Asn Ile Lys Tyr Thr Arg Pro Gly Asp Thr Leu Ala Glu Val
                20                  25                  30

Glu Leu Arg Gln His Gly Ser Glu Trp Glu Pro Met Thr Lys Lys
            35                  40                  45

Gly Asn Leu Trp Glu Val Lys Ser Ala Lys Pro Leu Thr Gly Pro Met
50                  55                  60

Asn Phe Arg Phe Leu Ser Lys Gly Gly Met Lys Asn Val Phe Asp Glu
65                  70                  75                  80

Val Ile Pro Thr Ala Phe Thr Val Gly Lys Thr Tyr Thr Pro Glu Tyr
                85                  90                  95

Asn

<210> SEQ ID NO 41
<211> LENGTH: 308
<212> TYPE: PRT
<213> ORGANISM: Lolium perenne

<400> SEQUENCE: 41

Met Ala Val Gln Lys Tyr Thr Val Ala Leu Phe Leu Arg Arg Gly Pro
1               5                   10                  15

Arg Gly Gly Pro Gly Arg Ser Tyr Ala Ala Asp Ala Gly Tyr Thr Pro
                20                  25                  30

Ala Ala Ala Ala Thr Pro Ala Thr Pro Ala Ala Thr Pro Ala Gly Gly
            35                  40                  45

Trp Arg Glu Gly Asp Asp Arg Arg Ala Glu Ala Gly Gly Arg Gln
50                  55                  60

Arg Leu Ala Ser Arg Gln Pro Trp Pro Pro Leu Pro Thr Pro Leu Arg
65                  70                  75                  80

Arg Thr Ser Ser Arg Ser Ser Arg Pro Pro Ser Pro Ser Pro Pro Arg
                85                  90                  95

Ala Ser Ser Pro Thr Ser Ala Ala Lys Ala Pro Gly Leu Ile Pro Lys
            100                 105                 110

Leu Asp Thr Ala Tyr Asp Val Ala Tyr Lys Ala Ala Glu Ala His Pro
            115                 120                 125

Arg Gly Gln Val Arg Arg Leu Arg His Cys Pro His Arg Ser Leu Arg
130                 135                 140

Val Ile Ala Gly Ala Leu Glu Val His Ala Val Lys Pro Ala Thr Glu
145                 150                 155                 160

Glu Val Leu Ala Ala Lys Ile Pro Thr Gly Glu Leu Gln Ile Val Asp
                165                 170                 175

Lys Ile Asp Ala Ala Phe Lys Ile Ala Ala Thr Ala Ala Asn Ala Ala
            180                 185                 190

Pro Thr Asn Asp Lys Phe Thr Val Phe Glu Ser Ala Phe Asn Lys Ala
            195                 200                 205

Leu Asn Glu Cys Thr Gly Gly Ala Met Arg Pro Thr Ser Ser Ser Pro
210                 215                 220

Pro Ser Arg Pro Arg Ser Ser Arg Pro Thr Pro Pro Ser Pro Ala
225                 230                 235                 240

Ala Pro Glu Val Lys Tyr Ala Val Phe Glu Ala Ala Leu Thr Lys Ala
                245                 250                 255
```

```
Ile Thr Ala Met Thr Gln Ala Gln Lys Ala Gly Lys Pro Ala Ala
            260                 265                 270

Ala Ala Thr Ala Ala Ala Thr Val Ala Thr Ala Ala Thr Ala Ala
        275                 280                 285

Ala Val Leu Pro Pro Leu Leu Val Val Gln Ser Leu Ile Ser Leu
    290                 295                 300

Leu Ile Tyr Tyr
305

<210> SEQ ID NO 42
<211> LENGTH: 339
<212> TYPE: PRT
<213> ORGANISM: Lolium perenne

<400> SEQUENCE: 42

Met Ala Val Gln Lys His Thr Val Ala Leu Phe Leu Ala Val Ala Leu
1               5                   10                  15

Val Ala Gly Pro Ala Ala Ser Tyr Ala Ala Asp Ala Gly Tyr Ala Pro
                20                  25                  30

Ala Thr Pro Ala Thr Pro Ala Ala Pro Ala Thr Ala Ala Thr Pro Ala
            35                  40                  45

Thr Pro Ala Thr Pro Ala Thr Pro Ala Ala Val Pro Ser Gly Lys Ala
50                  55                  60

Thr Thr Glu Glu Gln Lys Leu Ile Glu Lys Ile Asn Ala Gly Phe Lys
65                  70                  75                  80

Ala Ala Val Ala Ala Ala Val Val Pro Pro Ala Asp Lys Tyr Lys
                85                  90                  95

Thr Phe Val Glu Thr Phe Gly Thr Ala Thr Asn Lys Ala Phe Val Glu
            100                 105                 110

Gly Leu Ala Ser Gly Tyr Ala Asp Gln Ser Lys Asn Gln Leu Thr Ser
        115                 120                 125

Lys Leu Asp Ala Ala Leu Lys Leu Ala Tyr Glu Ala Ala Gln Gly Ala
130                 135                 140

Thr Pro Glu Ala Lys Tyr Asp Ala Tyr Val Ala Thr Leu Thr Glu Ala
145                 150                 155                 160

Leu Arg Val Ile Ala Gly Thr Leu Glu Val His Ala Val Lys Pro Ala
                165                 170                 175

Ala Glu Glu Val Lys Val Gly Ala Ile Pro Ala Ala Glu Val Gln Leu
            180                 185                 190

Ile Asp Lys Val Asp Ala Ala Tyr Arg Thr Ala Ala Thr Ala Ala Asn
        195                 200                 205

Ala Ala Pro Ala Asn Asp Lys Phe Thr Val Phe Glu Asn Thr Phe Asn
210                 215                 220

Asn Ala Ile Lys Val Ser Leu Gly Ala Ala Tyr Asp Ser Tyr Lys Phe
225                 230                 235                 240

Ile Pro Thr Leu Val Ala Ala Val Lys Gln Ala Tyr Ala Ala Lys Gln
                245                 250                 255

Ala Thr Ala Pro Glu Val Lys Tyr Thr Val Ser Glu Thr Ala Leu Lys
            260                 265                 270

Lys Ala Val Thr Ala Met Ser Glu Ala Glu Lys Glu Ala Thr Pro Ala
        275                 280                 285

Ala Ala Ala Thr Ala Thr Pro Thr Pro Ala Ala Thr Ala Thr Ala
290                 295                 300

Thr Pro Ala Ala Ala Tyr Ala Thr Ala Thr Pro Ala Ala Ala Thr Ala
305                 310                 315                 320
```

Thr Ala Thr Pro Ala Ala Ala Thr Ala Thr Pro Ala Ala Ala Gly Gly
              325                 330                 335

Tyr Lys Val

<210> SEQ ID NO 43
<211> LENGTH: 339
<212> TYPE: PRT
<213> ORGANISM: Lolium perenne

<400> SEQUENCE: 43

Met Ala Val Gln Lys His Thr Val Ala Leu Phe Leu Ala Val Ala Leu
1               5                   10                  15

Val Ala Gly Pro Ala Ala Ser Tyr Ala Ala Asp Ala Gly Tyr Ala Pro
                20                  25                  30

Ala Thr Pro Ala Thr Pro Ala Ala Pro Ala Thr Ala Thr Pro Ala
            35                  40                  45

Thr Pro Ala Thr Pro Ala Thr Pro Ala Ala Val Pro Ser Gly Lys Ala
    50                  55                  60

Thr Thr Glu Glu Gln Lys Leu Ile Glu Lys Ile Asn Ala Gly Phe Lys
65                  70                  75                  80

Ala Ala Val Ala Ala Ala Val Val Pro Pro Ala Asp Lys Tyr Lys
                85                  90                  95

Thr Phe Val Glu Thr Phe Gly Thr Ala Thr Asn Lys Ala Phe Val Glu
                100                 105                 110

Gly Leu Ala Ser Gly Tyr Ala Asp Gln Ser Lys Asn Gln Leu Thr Ser
            115                 120                 125

Lys Leu Asp Ala Ala Leu Lys Leu Ala Tyr Glu Ala Ala Gln Gly Ala
    130                 135                 140

Thr Pro Glu Ala Lys Tyr Asp Ala Tyr Val Ala Thr Leu Thr Glu Ala
145                 150                 155                 160

Leu Arg Val Ile Ala Gly Thr Leu Glu Val His Ala Val Lys Pro Ala
                165                 170                 175

Ala Glu Glu Val Lys Val Gly Ala Ile Pro Ala Ala Glu Val Gln Leu
            180                 185                 190

Ile Asp Lys Val Asp Ala Ala Tyr Arg Thr Ala Ala Thr Ala Ala Asn
    195                 200                 205

Ala Ala Pro Ala Asn Asp Lys Phe Thr Val Phe Glu Asn Thr Phe Asn
210                 215                 220

Asn Ala Ile Lys Val Ser Leu Gly Ala Ala Tyr Asp Ser Tyr Lys Phe
225                 230                 235                 240

Ile Pro Thr Leu Val Ala Ala Val Lys Gln Ala Tyr Ala Ala Lys Gln
                245                 250                 255

Ala Thr Ala Pro Glu Val Lys Tyr Thr Val Ser Glu Thr Ala Leu Lys
            260                 265                 270

Lys Ala Val Thr Ala Met Ser Glu Ala Lys Glu Ala Thr Pro Ala
    275                 280                 285

Ala Ala Ala Thr Ala Thr Pro Thr Pro Ala Ala Thr Ala Thr Ala
290                 295                 300

Thr Pro Ala Ala Ala Tyr Ala Thr Ala Thr Pro Ala Ala Thr Ala
305                 310                 315                 320

Thr Ala Thr Pro Ala Ala Ala Thr Ala Thr Pro Ala Ala Ala Gly Gly
                325                 330                 335

Tyr Lys Val

```
<210> SEQ ID NO 44
<211> LENGTH: 134
<212> TYPE: PRT
<213> ORGANISM: Lolium perenne
<220> FEATURE:
<221> NAME/KEY: misc_feature
<222> LOCATION: (103)..(103)
<223> OTHER INFORMATION: unknown or other

<400> SEQUENCE: 44

Asp Lys Gly Pro Gly Phe Val Val Thr Gly Arg Val Tyr Cys Asp Pro
1               5                   10                  15

Cys Arg Ala Gly Phe Glu Thr Asn Val Ser His Asn Val Glu Gly Ala
            20                  25                  30

Thr Val Ala Val Asp Cys Arg Pro Phe Asp Gly Gly Glu Ser Lys Leu
        35                  40                  45

Lys Ala Glu Ala Thr Thr Asp Lys Asp Gly Trp Tyr Lys Ile Glu Ile
    50                  55                  60

Asp Gln Asp His Gln Glu Ile Cys Glu Val Val Leu Ala Lys Ser
65                  70                  75                  80

Pro Asp Lys Ser Cys Ser Glu Ile Glu Glu Phe Arg Asp Arg Ala Arg
                85                  90                  95

Val Pro Leu Thr Ser Asn Xaa Gly Ile Lys Gln Gln Gly Ile Arg Tyr
            100                 105                 110

Ala Asn Pro Ile Ala Phe Phe Arg Lys Glu Pro Leu Lys Glu Cys Gly
        115                 120                 125

Gly Ile Leu Gln Ala Tyr
    130

<210> SEQ ID NO 45
<211> LENGTH: 145
<212> TYPE: PRT
<213> ORGANISM: Olea europaea

<400> SEQUENCE: 45

Glu Asp Ile Pro Gln Pro Pro Val Ser Gln Phe His Ile Gln Gly Gln
1               5                   10                  15

Val Tyr Cys Asp Thr Cys Arg Ala Gly Phe Ile Thr Glu Leu Ser Glu
            20                  25                  30

Phe Ile Pro Gly Ala Ser Leu Arg Leu Gln Cys Lys Asp Lys Glu Asn
        35                  40                  45

Gly Asp Val Thr Phe Thr Glu Val Gly Tyr Thr Arg Ala Glu Gly Leu
    50                  55                  60

Tyr Ser Met Leu Val Glu Arg Asp His Lys Asn Glu Phe Cys Glu Ile
65                  70                  75                  80

Thr Leu Ile Ser Ser Gly Arg Lys Asp Cys Asn Glu Ile Pro Thr Glu
                85                  90                  95

Gly Trp Ala Lys Pro Ser Leu Phe Lys Leu Asn Thr Val Asn Gly
            100                 105                 110

Thr Thr Arg Thr Val Asn Pro Leu Gly Phe Phe Lys Lys Glu Ala Leu
        115                 120                 125

Pro Lys Cys Ala Gln Val Tyr Asn Lys Leu Gly Met Tyr Pro Pro Asn
    130                 135                 140

Met
145

<210> SEQ ID NO 46
<211> LENGTH: 133
<212> TYPE: PRT
```

-continued

<213> ORGANISM: Parietaria judaica

<400> SEQUENCE: 46

Met Arg Thr Val Ser Met Ala Ala Leu Val Val Ile Ala Ala Leu
1               5                   10                  15

Ala Trp Thr Ser Ser Ala Glu Pro Ala Pro Ala Pro Gly Glu
                20                  25                  30

Glu Ala Cys Gly Lys Val Val Gln Asp Ile Met Pro Cys Leu His Phe
            35                  40                  45

Val Lys Gly Glu Lys Glu Pro Ser Lys Glu Cys Cys Ser Gly Thr
50                  55                      60

Lys Lys Leu Ser Glu Glu Val Lys Thr Thr Glu Gln Lys Arg Glu Ala
65                  70                  75                  80

Cys Lys Cys Ile Val Arg Ala Thr Lys Gly Ile Ser Gly Ile Lys Asn
                85                  90                  95

Glu Leu Val Ala Glu Val Pro Lys Lys Cys Asp Ile Lys Thr Thr Leu
            100                 105                 110

Pro Pro Ile Thr Ala Asp Phe Asp Cys Ser Lys Ile Gln Ser Thr Ile
        115                 120                 125

Phe Arg Gly Tyr Tyr
    130

<210> SEQ ID NO 47
<211> LENGTH: 133
<212> TYPE: PRT
<213> ORGANISM: Parietaria judaica

<400> SEQUENCE: 47

Met Val Arg Ala Leu Met Pro Cys Leu Pro Phe Val Gln Gly Lys Glu
1               5                   10                  15

Lys Glu Pro Ser Lys Gly Cys Cys Ser Gly Ala Lys Arg Leu Asp Gly
                20                  25                  30

Glu Thr Lys Thr Gly Pro Gln Arg Val His Ala Cys Glu Cys Ile Gln
            35                  40                  45

Thr Ala Met Lys Thr Tyr Ser Asp Ile Asp Gly Lys Leu Val Ser Glu
50                  55                  60

Val Pro Lys His Cys Gly Ile Val Asp Ser Lys Leu Pro Pro Ile Asp
65                  70                  75                  80

Val Asn Met Asp Cys Lys Thr Val Gly Val Val Pro Arg Gln Pro Gln
                85                  90                  95

Leu Pro Val Ser Leu Arg His Gly Pro Val Thr Gly Pro Ser Asp Pro
            100                 105                 110

Ala His Lys Ala Arg Leu Glu Arg Pro Gln Ile Arg Val Pro Pro Pro
        115                 120                 125

Ala Pro Glu Lys Ala
    130

<210> SEQ ID NO 48
<211> LENGTH: 133
<212> TYPE: PRT
<213> ORGANISM: Parietaria judaica

<400> SEQUENCE: 48

Met Arg Thr Val Ser Met Ala Ala Leu Val Val Ile Ala Ala Leu
1               5                   10                  15

Ala Trp Thr Ser Ser Ala Glu Leu Ala Ser Ala Pro Ala Pro Gly Glu
                20                  25                  30

-continued

Gly Pro Cys Gly Lys Val Val His Ile Met Pro Cys Leu Lys Phe
            35                  40                  45

Val Lys Gly Glu Glu Lys Pro Ser Lys Ser Cys Ser Gly Thr
 50                  55                  60

Lys Lys Leu Ser Glu Glu Val Lys Thr Thr Glu Gln Lys Arg Glu Ala
 65                  70                  75                  80

Cys Lys Cys Ile Val Ala Ala Thr Lys Gly Ile Ser Gly Ile Lys Asn
                     85                  90                  95

Glu Leu Val Ala Glu Val Pro Lys Lys Cys Gly Ile Thr Thr Thr Leu
                    100                 105                 110

Pro Pro Ile Thr Ala Asp Phe Asp Cys Ser Lys Ile Glu Ser Thr Ile
                    115                 120                 125

Phe Arg Gly Tyr Tyr
                    130

<210> SEQ ID NO 49
<211> LENGTH: 176
<212> TYPE: PRT
<213> ORGANISM: Parietaria judaica

<400> SEQUENCE: 49

Met Arg Thr Val Ser Ala Pro Ser Ala Val Ala Leu Val Val Ile Val
 1               5                  10                  15

Ala Ala Gly Leu Ala Trp Thr Ser Leu Ala Ser Val Ala Pro Pro Ala
                    20                  25                  30

Pro Ala Pro Gly Ser Glu Glu Thr Cys Gly Thr Val Val Arg Ala Leu
                    35                  40                  45

Met Pro Cys Leu Pro Phe Val Gln Gly Lys Glu Lys Glu Pro Ser Lys
 50                  55                  60

Gly Cys Cys Ser Gly Ala Lys Arg Leu Asp Gly Glu Thr Lys Thr Gly
 65                  70                  75                  80

Leu Gln Arg Val His Ala Cys Glu Cys Ile Gln Thr Ala Met Lys Thr
                     85                  90                  95

Tyr Ser Asp Ile Asp Gly Lys Leu Val Ser Glu Val Pro Lys His Cys
                    100                 105                 110

Gly Ile Val Asp Ser Lys Leu Pro Pro Ile Asp Val Asn Met Asp Cys
                    115                 120                 125

Lys Thr Leu Gly Val Val Pro Arg Gln Pro Gln Leu Pro Val Ser Leu
 130                 135                 140

Arg His Gly Pro Val Thr Gly Pro Ser Asp Pro Ala His Lys Ala Arg
 145                 150                 155                 160

Leu Glu Arg Pro Gln Ile Arg Val Pro Pro Ala Pro Glu Lys Ala
                    165                 170                 175

<210> SEQ ID NO 50
<211> LENGTH: 138
<212> TYPE: PRT
<213> ORGANISM: Parietaria judaica

<400> SEQUENCE: 50

Met Arg Thr Val Ser Ala Arg Ser Ser Val Ala Leu Val Val Ile Val
 1               5                  10                  15

Ala Ala Val Leu Val Trp Thr Ser Ser Ala Ser Val Ala Pro Ala Pro
                    20                  25                  30

Ala Pro Gly Ser Glu Glu Thr Cys Gly Thr Val Val Gly Ala Leu Met
                    35                  40                  45

Pro Cys Leu Pro Phe Val Gln Gly Lys Glu Lys Glu Pro Ser Lys Gly

```
                50                  55                  60
Cys Cys Ser Gly Ala Lys Arg Leu Asp Gly Glu Thr Lys Thr Gly Pro
 65                  70                  75                  80

Gln Arg Val His Ala Cys Glu Cys Ile Gln Thr Ala Met Lys Thr Tyr
                 85                  90                  95

Ser Asp Ile Asp Gly Lys Leu Val Ser Glu Val Pro Lys His Cys Gly
                100                 105                 110

Ile Val Asp Ser Lys Leu Pro Pro Ile Asp Val Asn Met Asp Cys Lys
                115                 120                 125

Thr Leu Gly Val Leu His Tyr Lys Gly Asn
                130                 135

<210> SEQ ID NO 51
<211> LENGTH: 143
<212> TYPE: PRT
<213> ORGANISM: Parietaria judaica

<400> SEQUENCE: 51

Met Val Arg Ala Leu Met Pro Cys Leu Pro Phe Val Gln Gly Lys Glu
  1               5                  10                  15

Lys Glu Pro Ser Lys Gly Cys Cys Ser Gly Ala Lys Arg Leu Asp Gly
                 20                  25                  30

Glu Thr Lys Thr Gly Pro Gln Arg Val His Ala Cys Glu Cys Ile Gln
                 35                  40                  45

Thr Ala Met Lys Thr Tyr Ser Asp Ile Asp Gly Lys Leu Val Ser Glu
                 50                  55                  60

Val Pro Lys His Cys Gly Ile Val Asp Ser Lys Leu Pro Pro Ile Asp
 65                  70                  75                  80

Val Asn Met Asp Cys Lys Thr Val Gly Val Pro Arg Gln Pro Gln
                 85                  90                  95

Leu Pro Val Ser Leu Arg His Gly Pro Val Thr Gly Pro Ser Arg Ser
                100                 105                 110

Arg Pro Pro Thr Lys His Gly Trp Arg Asp Pro Arg Leu Glu Phe Arg
                115                 120                 125

Pro Pro His Arg Lys Lys Pro Asn Pro Ala Phe Ser Thr Leu Gly
                130                 135                 140

<210> SEQ ID NO 52
<211> LENGTH: 263
<212> TYPE: PRT
<213> ORGANISM: Phleum pratense

<400> SEQUENCE: 52

Met Ala Ser Ser Ser Ser Val Leu Leu Val Val Val Leu Phe Ala Val
  1               5                  10                  15

Phe Leu Gly Ser Ala Tyr Gly Ile Pro Lys Val Pro Pro Gly Pro Asn
                 20                  25                  30

Ile Thr Ala Thr Tyr Gly Asp Lys Trp Leu Asp Ala Lys Ser Thr Trp
                 35                  40                  45

Tyr Gly Lys Pro Thr Gly Ala Gly Pro Lys Asp Asn Gly Gly Ala Cys
                 50                  55                  60

Gly Tyr Lys Asp Val Asp Lys Pro Pro Phe Ser Gly Met Thr Gly Cys
 65                  70                  75                  80

Gly Asn Thr Pro Ile Phe Lys Ser Gly Arg Gly Cys Gly Ser Cys Phe
                 85                  90                  95

Glu Ile Lys Cys Thr Lys Pro Glu Ala Cys Ser Gly Glu Pro Val Val
                100                 105                 110
```

```
Val His Ile Thr Asp Asp Asn Glu Glu Pro Ile Ala Pro Tyr His Phe
        115                 120                 125

Asp Leu Ser Gly His Ala Phe Gly Ala Met Ala Lys Lys Gly Asp Glu
        130                 135                 140

Gln Lys Leu Arg Ser Ala Gly Glu Leu Glu Leu Gln Phe Arg Arg Val
145                 150                 155                 160

Lys Cys Lys Tyr Pro Glu Gly Thr Lys Val Thr Phe His Val Glu Lys
                165                 170                 175

Gly Ser Asn Pro Asn Tyr Leu Ala Leu Leu Val Lys Tyr Val Asn Gly
                180                 185                 190

Asp Gly Asp Val Val Ala Val Asp Ile Lys Glu Lys Gly Lys Asp Lys
                195                 200                 205

Trp Ile Glu Leu Lys Glu Ser Trp Gly Ala Ile Trp Arg Ile Asp Thr
210                 215                 220

Pro Asp Lys Leu Thr Gly Pro Phe Thr Val Arg Tyr Thr Thr Glu Gly
225                 230                 235                 240

Gly Thr Lys Thr Glu Ala Glu Asp Val Ile Pro Glu Gly Trp Lys Ala
                245                 250                 255

Asp Thr Ser Tyr Glu Ser Lys
                260

<210> SEQ ID NO 53
<211> LENGTH: 262
<212> TYPE: PRT
<213> ORGANISM: Phleum pratense

<400> SEQUENCE: 53

Met Ala Ser Ser Ser Val Leu Leu Val Val Ala Leu Phe Ala Val
1               5                   10                  15

Phe Leu Gly Ser Ala His Gly Ile Pro Lys Val Pro Pro Gly Pro Asn
                20                  25                  30

Ile Thr Ala Thr Tyr Gly Asp Lys Trp Leu Asp Ala Lys Ser Thr Trp
            35                  40                  45

Tyr Gly Lys Pro Thr Ala Ala Gly Pro Lys Asp Asn Gly Gly Ala Cys
    50                  55                  60

Gly Tyr Lys Asp Val Asp Lys Pro Pro Phe Ser Gly Met Thr Gly Cys
65                  70                  75                  80

Gly Asn Thr Pro Ile Phe Lys Ser Gly Arg Gly Cys Gly Ser Cys Phe
                85                  90                  95

Glu Ile Lys Cys Thr Lys Pro Glu Ala Cys Ser Gly Glu Pro Val Val
            100                 105                 110

Val His Ile Thr Asp Asp Asn Glu Glu Pro Ile Ala Ala Tyr His Phe
        115                 120                 125

Asp Leu Ser Gly Ile Ala Phe Gly Ser Met Ala Lys Lys Gly Asp Glu
        130                 135                 140

Gln Lys Leu Arg Ser Ala Gly Glu Val Glu Ile Gln Phe Arg Arg Val
145                 150                 155                 160

Lys Cys Lys Tyr Pro Glu Gly Thr Lys Val Thr Phe His Val Glu Lys
                165                 170                 175

Gly Ser Asn Pro Asn Tyr Leu Ala Leu Leu Val Lys Phe Ser Gly Asp
                180                 185                 190

Gly Asp Val Val Ala Val Asp Ile Lys Glu Lys Gly Lys Asp Lys Trp
        195                 200                 205

Ile Ala Leu Lys Glu Ser Trp Gly Ala Ile Trp Arg Ile Asp Thr Pro
210                 215                 220
```

Glu Val Leu Lys Gly Pro Phe Thr Val Arg Tyr Thr Thr Glu Gly Gly
225                 230                 235                 240

Thr Lys Ala Arg Ala Lys Asp Val Ile Pro Glu Gly Trp Lys Ala Asp
            245                 250                 255

Thr Ala Tyr Glu Ser Lys
            260

<210> SEQ ID NO 54
<211> LENGTH: 122
<212> TYPE: PRT
<213> ORGANISM: Phleum pratense

<400> SEQUENCE: 54

Met Ser Met Ala Ser Ser Ser Ser Ser Leu Leu Ala Met Ala Val
1               5                   10                  15

Leu Ala Ala Leu Phe Ala Gly Ala Trp Cys Val Pro Lys Val Thr Phe
                20                  25                  30

Thr Val Glu Lys Gly Ser Asn Glu Lys His Leu Ala Val Leu Val Lys
            35                  40                  45

Tyr Glu Gly Asp Thr Met Ala Glu Val Glu Leu Arg Glu His Gly Ser
        50                  55                  60

Asp Glu Trp Val Ala Met Thr Lys Gly Glu Gly Val Trp Thr Phe
65                  70                  75                  80

Asp Ser Glu Glu Pro Leu Gln Gly Pro Phe Asn Phe Arg Phe Leu Thr
                85                  90                  95

Glu Lys Gly Met Lys Asn Val Phe Asp Asp Val Val Pro Glu Lys Tyr
            100                 105                 110

Thr Ile Gly Ala Thr Tyr Ala Pro Glu Glu
        115                 120

<210> SEQ ID NO 55
<211> LENGTH: 276
<212> TYPE: PRT
<213> ORGANISM: Phleum pratense

<400> SEQUENCE: 55

Ala Asp Leu Gly Tyr Gly Gly Pro Ala Thr Pro Ala Ala Pro Ala Glu
1               5                   10                  15

Ala Ala Pro Ala Gly Lys Ala Thr Thr Glu Glu Gln Lys Leu Ile Glu
                20                  25                  30

Lys Ile Asn Asp Gly Phe Lys Ala Ala Leu Ala Ala Ala Ala Gly Val
            35                  40                  45

Pro Pro Ala Asp Lys Tyr Lys Thr Phe Val Ala Thr Phe Gly Ala Ala
        50                  55                  60

Ser Asn Lys Ala Phe Ala Glu Gly Leu Ser Ala Glu Pro Lys Gly Ala
65                  70                  75                  80

Ala Glu Ser Ser Ser Lys Ala Ala Leu Thr Ser Lys Leu Asp Ala Ala
                85                  90                  95

Tyr Lys Leu Ala Tyr Lys Thr Ala Glu Gly Ala Thr Pro Glu Ala Lys
            100                 105                 110

Tyr Asp Ala Tyr Val Ala Thr Leu Ser Glu Ala Leu Arg Ile Ile Ala
        115                 120                 125

Gly Thr Leu Glu Val His Ala Val Lys Pro Ala Ala Glu Glu Val Lys
    130                 135                 140

Val Ile Pro Ala Gly Glu Leu Gln Val Ile Glu Lys Val Asp Ser Ala
145                 150                 155                 160

```
Phe Lys Val Ala Ala Thr Ala Ala Asn Ala Ala Pro Ala Asn Asp Lys
                165                 170                 175

Phe Thr Val Phe Glu Ala Ala Phe Asn Asn Ala Ile Lys Ala Ser Thr
            180                 185                 190

Gly Gly Ala Tyr Glu Ser Tyr Lys Phe Ile Pro Ala Leu Glu Ala Ala
        195                 200                 205

Val Lys Gln Ala Tyr Ala Ala Thr Val Ala Thr Ala Pro Glu Val Lys
    210                 215                 220

Tyr Thr Val Phe Glu Thr Ala Leu Lys Lys Ala Phe Thr Ala Met Ser
225                 230                 235                 240

Glu Ala Gln Lys Ala Ala Lys Pro Ala Thr Glu Ala Thr Ala Thr Ala
                245                 250                 255

Thr Ala Ala Val Gly Ala Ala Thr Gly Ala Ala Thr Ala Ala Thr Gly
            260                 265                 270

Gly Tyr Lys Val
        275

<210> SEQ ID NO 56
<211> LENGTH: 276
<212> TYPE: PRT
<213> ORGANISM: Phleum pratense

<400> SEQUENCE: 56

Ala Asp Leu Gly Tyr Gly Gly Pro Ala Thr Pro Ala Ala Pro Ala Glu
1               5                   10                  15

Ala Ala Pro Ala Gly Lys Ala Thr Thr Glu Glu Gln Lys Leu Ile Glu
                20                  25                  30

Lys Ile Asn Asp Gly Phe Lys Ala Ala Leu Ala Ala Ala Ala Gly Val
            35                  40                  45

Pro Pro Ala Asp Lys Tyr Lys Thr Phe Val Ala Thr Phe Gly Ala Ala
    50                  55                  60

Ser Asn Lys Ala Phe Ala Glu Gly Leu Ser Ala Glu Pro Lys Gly Ala
65                  70                  75                  80

Ala Glu Ser Ser Ser Lys Ala Ala Leu Thr Ser Lys Leu Asp Ala Ala
                85                  90                  95

Tyr Lys Leu Ala Tyr Lys Thr Ala Glu Gly Ala Thr Pro Glu Ala Lys
            100                 105                 110

Tyr Asp Ala Tyr Val Ala Thr Leu Ser Glu Ala Leu Arg Ile Ile Ala
        115                 120                 125

Gly Thr Leu Glu Val His Ala Val Lys Pro Ala Ala Glu Glu Val Lys
    130                 135                 140

Val Ile Pro Ala Gly Glu Leu Gln Val Ile Glu Lys Val Asp Ser Ala
145                 150                 155                 160

Phe Lys Val Ala Ala Thr Ala Ala Asn Ala Ala Pro Ala Asn Asp Lys
                165                 170                 175

Phe Thr Val Phe Glu Ala Ala Phe Asn Asn Ala Ile Lys Ala Ser Thr
            180                 185                 190

Gly Gly Ala Tyr Glu Ser Tyr Lys Phe Ile Pro Ala Leu Glu Ala Ala
        195                 200                 205

Val Lys Gln Ala Tyr Ala Ala Thr Val Ala Thr Ala Pro Glu Val Lys
    210                 215                 220

Tyr Thr Val Phe Glu Thr Ala Leu Lys Lys Ala Ile Thr Ala Met Ser
225                 230                 235                 240

Glu Ala Gln Lys Ala Ala Lys Pro Ala Thr Glu Ala Thr Ala Thr Ala
                245                 250                 255
```

```
Thr Ala Ala Val Gly Ala Ala Thr Gly Ala Ala Thr Ala Ala Thr Gly
            260                 265                 270

Gly Tyr Lys Val
        275

<210> SEQ ID NO 57
<211> LENGTH: 284
<212> TYPE: PRT
<213> ORGANISM: Phleum pratense

<400> SEQUENCE: 57

Ala Ala Ala Ala Val Pro Arg Arg Gly Pro Arg Gly Gly Pro Gly Arg
1               5                   10                  15

Ser Tyr Thr Ala Asp Ala Gly Tyr Ala Pro Ala Thr Pro Ala Ala Ala
            20                  25                  30

Gly Ala Ala Ala Gly Lys Ala Thr Glu Glu Gln Lys Leu Ile Glu
        35                  40                  45

Asp Ile Asn Val Gly Phe Lys Ala Ala Val Ala Ala Ala Ala Ser Val
    50                  55                  60

Pro Ala Ala Asp Lys Phe Lys Thr Phe Glu Ala Ala Phe Thr Ser Ser
65                  70                  75                  80

Ser Lys Ala Ala Ala Ala Lys Ala Pro Gly Leu Val Pro Lys Leu Asp
                85                  90                  95

Ala Ala Tyr Ser Val Ala Tyr Lys Ala Ala Val Gly Ala Thr Pro Glu
            100                 105                 110

Ala Lys Phe Asp Ser Phe Val Ala Ser Leu Thr Glu Ala Leu Arg Val
        115                 120                 125

Ile Ala Gly Ala Leu Glu Val His Ala Val Lys Pro Val Thr Glu Glu
130                 135                 140

Pro Gly Met Ala Lys Ile Pro Ala Gly Glu Leu Gln Ile Ile Asp Lys
145                 150                 155                 160

Ile Asp Ala Ala Phe Lys Val Ala Ala Thr Ala Ala Thr Ala Pro
                165                 170                 175

Ala Asp Asp Lys Phe Thr Val Phe Glu Ala Ala Phe Asn Lys Ala Ile
            180                 185                 190

Lys Glu Ser Thr Gly Gly Ala Tyr Asp Thr Tyr Lys Cys Ile Pro Ser
        195                 200                 205

Leu Glu Ala Ala Val Lys Gln Ala Tyr Ala Ala Thr Val Ala Ala Ala
    210                 215                 220

Pro Gln Val Lys Tyr Ala Val Phe Glu Ala Ala Leu Thr Lys Ala Ile
225                 230                 235                 240

Thr Ala Met Ser Glu Val Gln Lys Val Ser Gln Pro Ala Thr Gly Ala
                245                 250                 255

Ala Thr Val Ala Ala Gly Ala Ala Thr Thr Ala Ala Gly Ala Ala Ser
            260                 265                 270

Gly Ala Ala Thr Val Ala Ala Gly Gly Tyr Lys Val
        275                 280

<210> SEQ ID NO 58
<211> LENGTH: 286
<212> TYPE: PRT
<213> ORGANISM: Phleum pratense

<400> SEQUENCE: 58

Ala Asp Leu Gly Tyr Gly Pro Ala Thr Pro Ala Ala Pro Ala Ala Gly
1               5                   10                  15

Tyr Thr Pro Ala Thr Pro Ala Ala Pro Ala Gly Ala Asp Ala Ala Gly
```

```
                 20                  25                  30
Lys Ala Thr Thr Glu Glu Gln Lys Leu Ile Glu Lys Ile Asn Ala Gly
             35                  40                  45

Phe Lys Ala Ala Leu Ala Gly Ala Gly Val Gln Pro Ala Asp Lys Tyr
         50                  55                  60

Arg Thr Phe Val Ala Thr Phe Gly Pro Ala Ser Asn Lys Ala Phe Ala
65                  70                  75                  80

Glu Gly Leu Ser Gly Glu Pro Lys Gly Ala Ala Glu Ser Ser Ser Lys
                 85                  90                  95

Ala Ala Leu Thr Ser Lys Leu Asp Ala Ala Tyr Lys Leu Ala Tyr Lys
            100                 105                 110

Thr Ala Glu Gly Ala Thr Pro Glu Ala Lys Tyr Asp Ala Tyr Val Ala
            115                 120                 125

Thr Leu Ser Glu Ala Leu Arg Ile Ile Ala Gly Thr Leu Glu Val His
            130                 135                 140

Ala Val Lys Pro Ala Ala Glu Glu Val Lys Val Ile Pro Ala Gly Glu
145                 150                 155                 160

Leu Gln Val Ile Glu Lys Val Asp Ala Ala Phe Lys Val Ala Ala Thr
                165                 170                 175

Ala Ala Asn Ala Ala Pro Ala Asn Asp Lys Phe Thr Val Phe Glu Ala
            180                 185                 190

Ala Phe Asn Asp Glu Ile Lys Ala Ser Thr Gly Gly Ala Tyr Glu Ser
            195                 200                 205

Tyr Lys Phe Ile Pro Ala Leu Glu Ala Ala Val Lys Gln Ala Tyr Ala
            210                 215                 220

Ala Thr Val Ala Thr Ala Pro Glu Val Lys Tyr Thr Val Phe Glu Thr
225                 230                 235                 240

Ala Leu Lys Lys Ala Ile Thr Ala Met Ser Glu Ala Gln Lys Ala Ala
                245                 250                 255

Lys Pro Ala Ala Ala Ala Thr Ala Thr Ala Thr Ala Ala Val Gly Ala
            260                 265                 270

Ala Thr Gly Ala Ala Thr Ala Ala Thr Gly Gly Tyr Lys Val
            275                 280                 285

<210> SEQ ID NO 59
<211> LENGTH: 287
<212> TYPE: PRT
<213> ORGANISM: Phleum pratense

<400> SEQUENCE: 59

Met Ala Val Gln Lys Tyr Thr Val Ala Leu Phe Leu Ala Val Ala Leu
1                5                  10                  15

Val Ala Gly Pro Ala Ala Ser Tyr Ala Ala Asp Ala Gly Tyr Ala Pro
                 20                  25                  30

Ala Thr Pro Ala Ala Ala Gly Ala Glu Ala Gly Lys Ala Thr Thr Glu
             35                  40                  45

Glu Gln Lys Leu Ile Glu Asp Ile Asn Val Gly Phe Lys Ala Ala Val
         50                  55                  60

Ala Ala Ala Ala Ser Val Pro Ala Ala Asp Lys Phe Lys Thr Phe Glu
65                  70                  75                  80

Ala Ala Phe Thr Ser Ser Ser Lys Ala Ala Thr Ala Lys Ala Pro Gly
                 85                  90                  95

Leu Val Pro Lys Leu Asp Ala Ala Tyr Ser Val Ser Tyr Lys Ala Ala
            100                 105                 110

Val Gly Ala Thr Pro Glu Ala Lys Phe Asp Ser Phe Val Ala Ser Leu
```

```
                 115                 120                 125
Thr Glu Ala Leu Arg Val Ile Ala Gly Ala Leu Glu Val His Ala Val
    130                 135                 140
Lys Pro Val Thr Glu Pro Gly Met Ala Lys Ile Pro Ala Gly Glu
145                 150                 155                 160
Leu Gln Ile Ile Asp Lys Ile Asp Ala Ala Phe Lys Val Ala Ala Thr
                165                 170                 175
Ala Ala Ala Thr Ala Pro Ala Asp Thr Val Phe Glu Ala Ala Phe Asn
            180                 185                 190
Lys Ala Ile Lys Glu Ser Thr Gly Gly Ala Tyr Asp Thr Tyr Lys Cys
        195                 200                 205
Ile Pro Ser Leu Glu Ala Ala Val Lys Gln Ala Tyr Ala Ala Thr Val
    210                 215                 220
Ala Ala Ala Pro Gln Val Lys Tyr Ala Val Phe Glu Ala Ala Leu Thr
225                 230                 235                 240
Lys Ala Ile Thr Ala Met Ser Glu Val Gln Lys Val Ser Gln Pro Ala
                245                 250                 255
Thr Gly Ala Ala Thr Val Ala Ala Gly Ala Ala Thr Thr Ala Ala Gly
            260                 265                 270
Ala Ala Ser Gly Ala Ala Thr Val Ala Ala Gly Gly Tyr Lys Val
        275                 280                 285

<210> SEQ ID NO 60
<211> LENGTH: 290
<212> TYPE: PRT
<213> ORGANISM: Phleum pratense

<400> SEQUENCE: 60

Met Ala Val Gln Lys Tyr Thr Val Ala Leu Phe Leu Ala Val Ala Leu
1               5                   10                  15
Val Ala Gly Pro Ala Ala Ser Tyr Ala Ala Asp Ala Gly Tyr Ala Pro
            20                  25                  30
Ala Thr Pro Ala Ala Gly Ala Glu Ala Gly Lys Ala Thr Thr Glu
        35                  40                  45
Glu Gln Lys Leu Ile Glu Asp Ile Asn Val Gly Phe Lys Ala Ala Val
    50                  55                  60
Ala Ala Ala Ala Ser Val Pro Ala Ala Asp Lys Phe Lys Thr Phe Glu
65                  70                  75                  80
Ala Ala Phe Thr Ser Ser Lys Ala Ala Thr Ala Lys Ala Pro Gly
                85                  90                  95
Leu Val Pro Lys Leu Asp Ala Ala Tyr Ser Val Ala Tyr Lys Ala Ala
            100                 105                 110
Val Gly Ala Thr Pro Glu Ala Lys Phe Asp Ser Phe Val Ala Ser Leu
        115                 120                 125
Thr Glu Ala Leu Arg Val Ile Ala Gly Ala Leu Glu Val His Ala Val
    130                 135                 140
Lys Pro Val Thr Glu Asp Pro Ala Trp Pro Lys Ile Pro Ala Gly Glu
145                 150                 155                 160
Leu Gln Ile Ile Asp Lys Ile Asp Ala Ala Phe Lys Val Ala Ala Thr
                165                 170                 175
Ala Ala Ala Thr Ala Pro Ala Asp Asp Lys Phe Thr Val Phe Glu Ala
            180                 185                 190
Ala Phe Asn Lys Ala Ile Lys Glu Ser Thr Gly Gly Ala Tyr Asp Thr
        195                 200                 205
Tyr Lys Cys Ile Pro Ser Leu Glu Ala Ala Val Lys Gln Ala Tyr Ala
```

```
            210                 215                 220
Ala Thr Val Ala Ala Pro Gln Val Lys Tyr Ala Val Phe Glu Ala
225                 230                 235                 240

Ala Leu Thr Lys Ala Ile Thr Ala Met Ser Glu Val Gln Lys Val Ser
                245                 250                 255

Gln Pro Ala Thr Gly Ala Ala Thr Val Ala Ala Gly Ala Ala Thr Thr
            260                 265                 270

Ala Thr Gly Ala Ala Ser Gly Ala Ala Thr Val Ala Ala Gly Gly Tyr
                275                 280                 285

Lys Val
    290

<210> SEQ ID NO 61
<211> LENGTH: 265
<212> TYPE: PRT
<213> ORGANISM: Phleum pratense

<400> SEQUENCE: 61

Ala Asp Ala Gly Tyr Ala Pro Ala Thr Pro Ala Ala Ala Gly Ala Glu
1               5                   10                  15

Ala Gly Lys Ala Thr Thr Glu Glu Gln Lys Leu Ile Glu Asp Ile Asn
                20                  25                  30

Val Gly Phe Lys Ala Ala Val Ala Ala Ala Ser Val Pro Ala Ala
            35                  40                  45

Asp Lys Phe Lys Thr Phe Glu Ala Ala Phe Thr Ser Ser Ser Lys Ala
50                  55                  60

Ala Thr Ala Lys Ala Pro Gly Leu Val Pro Lys Leu Asp Ala Ala Tyr
65                  70                  75                  80

Ser Val Ala Tyr Lys Ala Ala Val Gly Ala Thr Pro Glu Ala Lys Phe
                85                  90                  95

Asp Ser Phe Val Ala Ser Leu Thr Glu Ala Leu Arg Val Ile Ala Gly
            100                 105                 110

Ala Leu Glu Val His Ala Val Lys Pro Val Thr Glu Glu Pro Gly Met
        115                 120                 125

Ala Lys Ile Pro Ala Gly Glu Leu Gln Ile Ile Asp Lys Ile Asp Ala
    130                 135                 140

Ala Phe Lys Val Ala Ala Thr Ala Ala Thr Ala Pro Ala Asp Asp
145                 150                 155                 160

Lys Phe Thr Val Phe Glu Ala Ala Phe Asn Lys Ala Ile Lys Glu Ser
                165                 170                 175

Thr Gly Gly Ala Tyr Asp Thr Tyr Lys Cys Ile Pro Ser Leu Glu Ala
            180                 185                 190

Ala Val Lys Gln Ala Tyr Ala Ala Thr Val Ala Ala Ala Pro Gln Val
        195                 200                 205

Lys Tyr Ala Val Phe Glu Ala Ala Leu Thr Lys Ala Ile Thr Ala Met
    210                 215                 220

Ser Glu Val Gln Lys Val Ser Gln Pro Ala Thr Gly Ala Ala Thr Val
225                 230                 235                 240

Ala Ala Gly Ala Ala Thr Thr Ala Ala Gly Ala Ala Ser Gly Ala Ala
                245                 250                 255

Thr Val Ala Ala Gly Gly Tyr Lys Val
            260                 265

<210> SEQ ID NO 62
<211> LENGTH: 295
<212> TYPE: PRT
```

<213> ORGANISM: Phleum pratense

<400> SEQUENCE: 62

| | | | | | | | | | | | | | | |
|---|---|---|---|---|---|---|---|---|---|---|---|---|---|---|
| Ser | Val | Lys | Arg | Ser | Asn | Gly | Ser | Ala | Glu | Val | His | Arg | Gly | Ala | Val |
| 1 | | | | 5 | | | | | 10 | | | | | 15 |
| Pro | Arg | Arg | Gly | Pro | Arg | Gly | Gly | Pro | Gly | Arg | Ser | Tyr | Ala | Ala | Asp |
| | | | 20 | | | | | 25 | | | | | 30 | | |
| Ala | Gly | Tyr | Ala | Pro | Ala | Thr | Pro | Ala | Ala | Gly | Ala | Glu | Ala | Gly |
| | | 35 | | | | | 40 | | | | | 45 | | |
| Lys | Ala | Thr | Thr | Glu | Glu | Gln | Lys | Leu | Ile | Glu | Asp | Ile | Asn | Val | Gly |
| 50 | | | | | 55 | | | | | 60 | | | | | |
| Phe | Lys | Ala | Ala | Val | Ala | Ala | Ala | Ser | Val | Pro | Ala | Ala | Asp | Lys |
| 65 | | | | 70 | | | | | 75 | | | | | 80 |
| Phe | Lys | Thr | Phe | Glu | Ala | Ala | Phe | Thr | Ser | Ser | Lys | Ala | Ala | Thr |
| | | | | 85 | | | | | 90 | | | | | 95 |
| Ala | Lys | Ala | Pro | Gly | Leu | Val | Pro | Lys | Leu | Asp | Ala | Ala | Tyr | Ser | Val |
| | | | 100 | | | | | 105 | | | | | 110 | | |
| Ala | Tyr | Lys | Ala | Ala | Val | Gly | Ala | Thr | Pro | Glu | Ala | Lys | Phe | Asp | Ser |
| | | 115 | | | | | 120 | | | | | 125 | | | |
| Phe | Val | Ala | Ser | Leu | Thr | Glu | Ala | Leu | Arg | Val | Ile | Ala | Gly | Ala | Leu |
| 130 | | | | | 135 | | | | | 140 | | | | | |
| Glu | Val | His | Ala | Val | Lys | Pro | Val | Thr | Glu | Glu | Pro | Gly | Met | Ala | Lys |
| 145 | | | | | 150 | | | | | 155 | | | | | 160 |
| Ile | Pro | Ala | Gly | Glu | Leu | Gln | Ile | Ile | Asp | Lys | Ile | Asp | Ala | Ala | Phe |
| | | | | 165 | | | | | 170 | | | | | 175 | |
| Lys | Val | Ala | Ala | Thr | Ala | Ala | Ala | Thr | Ala | Pro | Ala | Asp | Asp | Lys | Phe |
| | | | 180 | | | | | 185 | | | | | 190 | | |
| Thr | Val | Phe | Glu | Ala | Ala | Phe | Asn | Lys | Ala | Ile | Lys | Glu | Ser | Thr | Gly |
| | | 195 | | | | | 200 | | | | | 205 | | | |
| Gly | Ala | Tyr | Asp | Thr | Tyr | Lys | Cys | Ile | Pro | Ser | Leu | Glu | Ala | Ala | Val |
| 210 | | | | | 215 | | | | | 220 | | | | | |
| Lys | Gln | Ala | Tyr | Ala | Ala | Thr | Val | Ala | Ala | Pro | Gln | Val | Lys | Tyr |
| 225 | | | | | 230 | | | | | 235 | | | | | 240 |
| Ala | Val | Phe | Glu | Ala | Ala | Leu | Thr | Lys | Ala | Ile | Thr | Ala | Met | Ser | Glu |
| | | | | 245 | | | | | 250 | | | | | 255 | |
| Val | Gln | Lys | Val | Ser | Gln | Pro | Ala | Thr | Gly | Ala | Ala | Thr | Val | Ala | Ala |
| | | | 260 | | | | | 265 | | | | | 270 | | |
| Gly | Ala | Ala | Thr | Thr | Ala | Ala | Gly | Ala | Ala | Ser | Gly | Ala | Ala | Thr | Val |
| | | 275 | | | | | 280 | | | | | 285 | | | |
| Ala | Ala | Gly | Gly | Tyr | Lys | Val |
| | | 290 | | | | 295 |

<210> SEQ ID NO 63
<211> LENGTH: 312
<212> TYPE: PRT
<213> ORGANISM: Phleum pratense

<400> SEQUENCE: 63

| | | | | | | | | | | | | | | |
|---|---|---|---|---|---|---|---|---|---|---|---|---|---|---|
| Met | Ala | Val | His | Gln | Tyr | Thr | Val | Ala | Leu | Phe | Leu | Ala | Val | Ala | Leu |
| 1 | | | | 5 | | | | | 10 | | | | | 15 | |
| Val | Ala | Gly | Pro | Ala | Gly | Ser | Tyr | Ala | Ala | Asp | Leu | Gly | Tyr | Gly | Pro |
| | | | 20 | | | | | 25 | | | | | 30 | | |
| Ala | Thr | Pro | Ala | Ala | Pro | Ala | Ala | Gly | Tyr | Thr | Pro | Ala | Thr | Pro | Ala |
| | | 35 | | | | | 40 | | | | | 45 | | | |
| Ala | Pro | Ala | Gly | Ala | Glu | Pro | Ala | Gly | Lys | Ala | Thr | Thr | Glu | Glu | Gln |
| | 50 | | | | | 55 | | | | | 60 | | | | |

```
Lys Leu Ile Glu Lys Ile Asn Ala Gly Phe Lys Ala Ala Leu Ala Ala
 65                  70                  75                  80

Ala Ala Gly Val Pro Pro Ala Asp Lys Tyr Arg Thr Phe Val Ala Thr
                 85                  90                  95

Phe Gly Ala Ala Ser Asn Lys Ala Phe Ala Glu Gly Leu Ser Gly Glu
            100                 105                 110

Pro Lys Gly Ala Ala Glu Ser Ser Lys Ala Ala Leu Thr Ser Lys
        115                 120                 125

Leu Asp Ala Ala Tyr Lys Leu Ala Tyr Lys Thr Ala Glu Gly Ala Thr
    130                 135                 140

Pro Glu Ala Lys Tyr Asp Ala Tyr Val Ala Thr Val Ser Glu Ala Leu
145                 150                 155                 160

Arg Ile Ile Ala Gly Thr Leu Glu Val His Ala Val Lys Pro Ala Ala
                165                 170                 175

Glu Glu Val Lys Val Ile Pro Ala Gly Glu Leu Gln Val Ile Glu Lys
            180                 185                 190

Val Asp Ala Ala Phe Lys Val Ala Ala Thr Ala Asn Ala Ala Pro
        195                 200                 205

Ala Asn Asp Lys Phe Thr Val Phe Glu Ala Ala Phe Asn Asp Ala Ile
    210                 215                 220

Lys Ala Ser Thr Gly Gly Ala Tyr Glu Ser Tyr Lys Phe Ile Pro Ala
225                 230                 235                 240

Leu Glu Ala Ala Val Lys Gln Ala Tyr Ala Ala Thr Val Ala Thr Ala
                245                 250                 255

Pro Glu Val Lys Tyr Thr Val Phe Glu Thr Ala Leu Lys Lys Ala Ile
            260                 265                 270

Thr Ala Met Ser Glu Ala Gln Lys Ala Ala Lys Pro Ala Ala Ala Ala
        275                 280                 285

Thr Ala Thr Ala Thr Ala Ala Val Gly Ala Ala Thr Gly Ala Ala Thr
    290                 295                 300

Ala Ala Thr Gly Gly Tyr Lys Val
305                 310
```

<210> SEQ ID NO 64
<211> LENGTH: 276
<212> TYPE: PRT
<213> ORGANISM: Phleum pratense

<400> SEQUENCE: 64

```
Ala Asp Leu Gly Tyr Gly Gly Pro Ala Thr Pro Ala Ala Pro Ala Glu
  1               5                  10                  15

Ala Ala Pro Ala Gly Lys Ala Thr Thr Glu Glu Gln Lys Leu Ile Glu
                 20                  25                  30

Lys Ile Asn Asp Gly Phe Lys Ala Ala Leu Ala Ala Ala Ala Gly Val
             35                  40                  45

Pro Pro Ala Asp Lys Tyr Lys Thr Phe Val Ala Thr Phe Gly Ala Ala
 50                  55                  60

Ser Asn Lys Ala Phe Ala Glu Gly Leu Ser Ala Glu Pro Lys Gly Ala
 65                  70                  75                  80

Ala Glu Ser Ser Ser Lys Ala Ala Leu Thr Ser Lys Leu Asp Ala Ala
                 85                  90                  95

Tyr Lys Leu Ala Tyr Lys Thr Ala Glu Gly Ala Thr Pro Glu Ala Lys
            100                 105                 110

Tyr Asp Ala Tyr Val Ala Thr Leu Ser Glu Ala Leu Arg Ile Ile Ala
            115                 120                 125
```

```
Gly Thr Leu Glu Val His Ala Val Lys Pro Ala Ala Glu Glu Val Lys
            130                 135                 140

Val Ile Pro Ala Gly Glu Leu Gln Val Ile Glu Lys Val Asp Ser Ala
145                 150                 155                 160

Phe Lys Val Ala Ala Thr Ala Ala Asn Ala Ala Pro Ala Asn Asp Lys
                165                 170                 175

Phe Thr Val Phe Glu Ala Ala Phe Asn Asn Ala Ile Lys Ala Ser Thr
            180                 185                 190

Gly Gly Ala Tyr Glu Ser Tyr Lys Phe Ile Pro Ala Leu Glu Ala Ala
                195                 200                 205

Val Lys Gln Ala Tyr Ala Ala Thr Val Ala Thr Ala Pro Glu Val Lys
210                 215                 220

Tyr Thr Val Phe Glu Thr Ala Leu Lys Lys Ala Phe Thr Ala Met Ser
225                 230                 235                 240

Glu Ala Gln Lys Ala Ala Lys Pro Ala Thr Glu Ala Thr Ala Thr Ala
                245                 250                 255

Thr Ala Ala Val Gly Ala Ala Thr Gly Ala Ala Thr Ala Ala Thr Gly
            260                 265                 270

Gly Tyr Lys Val
            275

<210> SEQ ID NO 65
<211> LENGTH: 284
<212> TYPE: PRT
<213> ORGANISM: Phleum pratense

<400> SEQUENCE: 65

Ala Ala Ala Ala Val Pro Arg Arg Gly Pro Arg Gly Gly Pro Gly Arg
1               5                   10                  15

Ser Tyr Thr Ala Asp Ala Gly Tyr Ala Pro Ala Thr Pro Ala Ala Ala
            20                  25                  30

Gly Ala Ala Ala Gly Lys Ala Thr Glu Glu Gln Lys Leu Ile Glu
        35                  40                  45

Asp Ile Asn Val Gly Phe Lys Ala Ala Val Ala Ala Ala Ala Ser Val
50                  55                  60

Pro Ala Ala Asp Lys Phe Lys Thr Phe Glu Ala Ala Phe Thr Ser Ser
65                  70                  75                  80

Ser Lys Ala Ala Ala Ala Lys Ala Pro Gly Leu Val Pro Lys Leu Asp
                85                  90                  95

Ala Ala Tyr Ser Val Ala Tyr Lys Ala Ala Val Gly Ala Thr Pro Glu
            100                 105                 110

Ala Lys Phe Asp Ser Phe Val Ala Ser Leu Thr Glu Ala Leu Arg Val
            115                 120                 125

Ile Ala Gly Ala Leu Glu Val His Ala Val Lys Pro Val Thr Glu Glu
130                 135                 140

Pro Gly Met Ala Lys Ile Pro Ala Gly Glu Leu Gln Ile Ile Asp Lys
145                 150                 155                 160

Ile Asp Ala Ala Phe Lys Val Ala Thr Ala Ala Thr Ala Pro
            165                 170                 175

Ala Asp Asp Lys Phe Thr Val Phe Glu Ala Ala Phe Asn Lys Ala Ile
            180                 185                 190

Lys Glu Ser Thr Gly Gly Ala Tyr Asp Thr Tyr Lys Cys Ile Pro Ser
            195                 200                 205

Leu Glu Ala Ala Val Lys Gln Ala Tyr Ala Ala Thr Val Ala Ala Ala
210                 215                 220
```

```
Pro Gln Val Lys Tyr Ala Val Phe Glu Ala Ala Leu Thr Lys Ala Ile
225                 230                 235                 240

Thr Ala Met Ser Glu Val Gln Lys Val Ser Gln Pro Ala Thr Gly Ala
            245                 250                 255

Ala Thr Val Ala Ala Gly Ala Ala Thr Ala Ala Gly Ala Ala Ser
        260                 265                 270

Gly Ala Ala Thr Val Ala Ala Gly Gly Tyr Lys Val
        275                 280

<210> SEQ ID NO 66
<211> LENGTH: 286
<212> TYPE: PRT
<213> ORGANISM: Phleum pratense

<400> SEQUENCE: 66

Ala Asp Leu Gly Tyr Gly Pro Ala Thr Pro Ala Ala Pro Ala Ala Gly
1               5                   10                  15

Tyr Thr Pro Ala Thr Pro Ala Ala Pro Ala Gly Ala Asp Ala Ala Gly
            20                  25                  30

Lys Ala Thr Thr Glu Glu Gln Lys Leu Ile Glu Lys Ile Asn Ala Gly
        35                  40                  45

Phe Lys Ala Ala Leu Ala Gly Ala Gly Val Gln Pro Ala Asp Lys Tyr
50                  55                  60

Arg Thr Phe Val Ala Thr Phe Gly Pro Ala Ser Asn Lys Ala Phe Ala
65                  70                  75                  80

Glu Gly Leu Ser Gly Glu Pro Lys Gly Ala Ala Glu Ser Ser Ser Lys
                85                  90                  95

Ala Ala Leu Thr Ser Lys Leu Asp Ala Ala Tyr Lys Leu Ala Tyr Lys
            100                 105                 110

Thr Ala Glu Gly Ala Thr Pro Glu Ala Lys Tyr Asp Ala Tyr Val Ala
        115                 120                 125

Thr Leu Ser Glu Ala Leu Arg Ile Ile Ala Gly Thr Leu Glu Val His
    130                 135                 140

Ala Val Lys Pro Ala Ala Glu Glu Val Lys Val Ile Pro Ala Gly Glu
145                 150                 155                 160

Leu Gln Val Ile Glu Lys Val Asp Ala Ala Phe Lys Val Ala Ala Thr
                165                 170                 175

Ala Ala Asn Ala Ala Pro Ala Asn Asp Lys Phe Thr Val Phe Glu Ala
            180                 185                 190

Ala Phe Asn Asp Glu Ile Lys Ala Ser Thr Gly Gly Ala Tyr Glu Ser
        195                 200                 205

Tyr Lys Phe Ile Pro Ala Leu Glu Ala Ala Val Lys Gln Ala Tyr Ala
    210                 215                 220

Ala Thr Val Ala Thr Ala Pro Glu Val Lys Tyr Thr Val Phe Glu Thr
225                 230                 235                 240

Ala Leu Lys Lys Ala Ile Thr Ala Met Ser Glu Ala Gln Lys Ala Ala
                245                 250                 255

Lys Pro Ala Ala Ala Ala Thr Ala Thr Ala Thr Ala Val Gly Ala
            260                 265                 270

Ala Thr Gly Ala Ala Thr Ala Ala Thr Gly Gly Tyr Lys Val
        275                 280                 285

<210> SEQ ID NO 67
<211> LENGTH: 281
<212> TYPE: PRT
<213> ORGANISM: Phleum pratense
```

<400> SEQUENCE: 67

| | | | | | | | | | | | | | | |
|---|---|---|---|---|---|---|---|---|---|---|---|---|---|---|
|Ala|Val|Pro|Arg|Arg|Gly|Pro|Arg|Gly|Gly|Pro|Gly|Arg|Ser|Tyr|Ala
1| | | |5| | | | |10| | | | |15| |

Ala Asp Ala Gly Tyr Ala Pro Ala Thr Pro Ala Ala Gly Ala Glu
        20              25              30

Ala Gly Lys Ala Thr Thr Glu Glu Gln Lys Leu Ile Glu Asp Ile Asn
        35              40              45

Val Gly Phe Lys Ala Ala Val Ala Ala Ala Ser Val Pro Ala Gly
    50              55              60

Asp Lys Phe Lys Thr Phe Glu Ala Ala Phe Thr Ser Ser Ser Lys Ala
65            70              75              80

Ala Thr Ala Lys Ala Pro Gly Leu Val Pro Lys Leu Asp Ala Ala Tyr
            85              90              95

Ser Val Ala Tyr Lys Ala Ala Val Gly Ala Thr Pro Glu Ala Lys Phe
        100             105             110

Asp Ser Phe Val Ala Ser Leu Thr Glu Ala Leu Arg Val Ile Ala Gly
        115             120             125

Ala Leu Glu Val His Ala Val Lys Pro Val Thr Glu Glu Pro Gly Met
130              135             140

Ala Lys Ile Pro Ala Gly Glu Leu Gln Ile Ile Asp Lys Ile Asp Ala
145            150              155             160

Ala Phe Lys Val Ala Ala Thr Ala Ala Thr Ala Pro Ala Asp Asp
        165             170             175

Lys Phe Thr Val Phe Glu Ala Ala Phe Asn Lys Ala Ile Lys Glu Ser
        180             185             190

Thr Gly Gly Ala Tyr Asp Thr Tyr Lys Cys Ile Pro Ser Leu Glu Ala
        195             200             205

Ala Val Lys Gln Ala Tyr Ala Ala Thr Val Ala Ala Pro Gln Val
        210             215             220

Lys Tyr Ala Val Phe Glu Ala Ala Leu Thr Lys Ala Ile Thr Ala Met
225            230              235             240

Ser Glu Val Gln Lys Val Ser Gln Pro Ala Thr Gly Ala Ala Thr Val
        245             250             255

Ala Ala Gly Ala Ala Thr Thr Ala Thr Gly Ala Ala Ser Gly Ala Ala
        260             265             270

Thr Val Ala Ala Gly Gly Tyr Lys Val
    275              280

<210> SEQ ID NO 68
<211> LENGTH: 280
<212> TYPE: PRT
<213> ORGANISM: Phleum pratense

<400> SEQUENCE: 68

Met Ala Val Pro Arg Arg Gly Pro Arg Gly Gly Pro Gly Arg Ser Tyr
1              5              10              15

Thr Ala Asp Ala Gly Tyr Ala Pro Ala Thr Pro Ala Ala Gly Ala
        20             25             30

Ala Ala Gly Lys Ala Thr Thr Glu Glu Gln Lys Leu Ile Glu Asp Ile
        35             40             45

Asn Val Gly Phe Lys Ala Ala Val Ala Ala Arg Gln Arg Pro Ala Ala
    50              55              60

Asp Lys Phe Lys Thr Phe Glu Ala Ala Ser Pro Arg His Pro Arg Pro
65            70              75              80

```
Leu Arg Gln Gly Ala Gly Leu Val Pro Lys Leu Asp Ala Ala Tyr Ser
                 85                  90                  95

Val Ala Tyr Lys Ala Ala Val Gly Ala Thr Pro Glu Ala Lys Phe Asp
            100                 105                 110

Ser Phe Val Ala Ser Leu Thr Glu Ala Leu Arg Val Ile Ala Gly Ala
        115                 120                 125

Leu Glu Val His Ala Val Lys Pro Val Thr Glu Glu Pro Gly Met Ala
    130                 135                 140

Lys Ile Pro Ala Gly Glu Leu Gln Ile Ile Asp Lys Ile Asp Ala Ala
145                 150                 155                 160

Phe Lys Val Ala Ala Thr Ala Ala Thr Ala Pro Ala Asp Asp Lys
                165                 170                 175

Phe Thr Val Phe Glu Ala Ala Phe Asn Lys Ala Ile Lys Glu Ser Thr
            180                 185                 190

Gly Gly Ala Tyr Asp Thr Tyr Lys Cys Ile Pro Ser Leu Glu Ala Ala
        195                 200                 205

Val Lys Gln Ala Tyr Ala Ala Thr Val Ala Ala Ala Glu Val Lys
    210                 215                 220

Tyr Ala Val Phe Glu Ala Ala Leu Thr Lys Ala Ile Thr Ala Met Ser
225                 230                 235                 240

Glu Val Gln Lys Val Ser Gln Pro Ala Thr Gly Ala Ala Thr Val Ala
                245                 250                 255

Ala Gly Ala Ala Thr Thr Ala Ala Gly Ala Ala Ser Gly Ala Ala Thr
            260                 265                 270

Val Ala Ala Gly Gly Tyr Lys Val
        275                 280

<210> SEQ ID NO 69
<211> LENGTH: 312
<212> TYPE: PRT
<213> ORGANISM: Phleum pratense

<400> SEQUENCE: 69

Met Ala Val His Gln Tyr Thr Val Ala Leu Phe Leu Ala Val Ala Leu
1               5                   10                  15

Val Ala Gly Pro Ala Ala Ser Tyr Ala Ala Asp Leu Gly Tyr Gly Pro
            20                  25                  30

Ala Thr Pro Ala Ala Pro Ala Gly Tyr Thr Pro Ala Thr Pro Ala
        35                  40                  45

Ala Pro Ala Glu Ala Ala Pro Ala Gly Lys Ala Thr Thr Glu Glu Gln
    50                  55                  60

Lys Leu Ile Glu Lys Ile Asn Ala Gly Phe Lys Ala Ala Leu Ala Ala
65                  70                  75                  80

Ala Ala Gly Val Gln Pro Ala Asp Lys Tyr Arg Thr Phe Val Ala Thr
                85                  90                  95

Phe Gly Ala Ala Ser Asn Lys Ala Phe Ala Glu Gly Leu Ser Gly Glu
            100                 105                 110

Pro Lys Gly Ala Ala Glu Ser Ser Lys Ala Ala Leu Thr Ser Lys
        115                 120                 125

Leu Asp Ala Ala Tyr Lys Leu Ala Tyr Lys Thr Ala Glu Gly Ala Thr
    130                 135                 140

Pro Glu Ala Lys Tyr Asp Ala Tyr Val Ala Thr Leu Ser Glu Ala Leu
145                 150                 155                 160

Arg Ile Ile Ala Gly Thr Leu Glu Val His Ala Val Lys Pro Ala Ala
                165                 170                 175
```

```
Glu Glu Val Lys Val Ile Pro Ala Gly Glu Leu Gln Val Ile Glu Lys
            180                 185                 190

Val Asp Ala Ala Phe Lys Val Ala Thr Ala Ala Asn Ala Ala Pro
        195                 200                 205

Ala Asn Asp Lys Phe Thr Val Phe Glu Ala Ala Phe Asn Asp Ala Ile
210                 215                 220

Lys Ala Ser Thr Gly Gly Ala Tyr Glu Ser Tyr Lys Phe Ile Pro Ala
225                 230                 235                 240

Leu Glu Ala Ala Val Lys Gln Ala Tyr Ala Ala Thr Val Ala Thr Ala
                245                 250                 255

Pro Glu Val Lys Tyr Thr Val Phe Glu Thr Ala Leu Lys Lys Ala Ile
            260                 265                 270

Thr Ala Met Ser Glu Ala Gln Lys Ala Ala Lys Pro Ala Ala Ala Ala
        275                 280                 285

Thr Ala Thr Ala Thr Ala Ala Val Gly Ala Ala Thr Gly Ala Ala Thr
        290                 295                 300

Ala Ala Thr Gly Gly Tyr Lys Val
305                 310

<210> SEQ ID NO 70
<211> LENGTH: 257
<212> TYPE: PRT
<213> ORGANISM: Phleum pratense

<400> SEQUENCE: 70

Glu Ala Pro Ala Gly Lys Ala Thr Thr Glu Glu Gln Lys Leu Ile Glu
1               5                   10                  15

Lys Ile Asn Ala Gly Phe Lys Ala Ala Leu Ala Arg Arg Leu Gln Pro
            20                  25                  30

Ala Asp Lys Tyr Arg Thr Phe Val Ala Thr Phe Gly Pro Ala Ser Asn
        35                  40                  45

Lys Ala Phe Ala Glu Gly Leu Ser Gly Glu Pro Lys Gly Ala Ala Glu
    50                  55                  60

Ser Ser Ser Lys Ala Ala Leu Thr Ser Lys Leu Asp Ala Ala Tyr Lys
65                  70                  75                  80

Leu Ala Tyr Lys Thr Ala Glu Gly Ala Thr Pro Glu Ala Lys Tyr Asp
                85                  90                  95

Ala Tyr Val Ala Thr Leu Ser Glu Ala Leu Arg Ile Ile Ala Gly Thr
            100                 105                 110

Leu Glu Val His Ala Val Lys Pro Ala Ala Glu Glu Val Lys Val Ile
        115                 120                 125

Pro Ala Ala Glu Leu Gln Val Ile Glu Lys Val Asp Ala Ala Phe Lys
    130                 135                 140

Val Ala Ala Thr Ala Ala Asn Ala Ala Pro Ala Asn Asp Lys Phe Thr
145                 150                 155                 160

Val Phe Glu Ala Ala Phe Asn Asp Glu Ile Lys Ala Ser Thr Gly Gly
                165                 170                 175

Ala Tyr Glu Ser Tyr Lys Phe Ile Pro Ala Leu Glu Ala Ala Val Lys
            180                 185                 190

Gln Ala Tyr Ala Ala Thr Val Ala Thr Ala Pro Glu Val Lys Tyr Thr
        195                 200                 205

Val Phe Glu Thr Ala Leu Lys Lys Ala Ile Thr Ala Met Ser Glu Ala
    210                 215                 220

Gln Lys Ala Ala Lys Pro Pro Leu Pro Pro Pro Gln Pro Pro
225                 230                 235                 240
```

```
Pro Leu Ala Ala Thr Gly Ala Ala Thr Ala Ala Thr Gly Gly Tyr Lys
                245                 250                 255
Val

<210> SEQ ID NO 71
<211> LENGTH: 312
<212> TYPE: PRT
<213> ORGANISM: Phleum pratense

<400> SEQUENCE: 71

Met Ala Val His Gln Tyr Thr Val Ala Leu Phe Leu Ala Val Ala Leu
1               5                   10                  15

Val Ala Gly Pro Ala Ala Ser Tyr Ala Ala Asp Leu Gly Tyr Gly Pro
                20                  25                  30

Ala Thr Pro Ala Ala Pro Ala Ala Gly Tyr Thr Pro Ala Thr Pro Ala
            35                  40                  45

Ala Pro Ala Glu Ala Ala Pro Ala Gly Lys Ala Thr Thr Glu Glu Gln
        50                  55                  60

Lys Leu Ile Glu Lys Ile Asn Ala Gly Phe Lys Ala Ala Leu Ala Ala
65                  70                  75                  80

Ala Ala Gly Val Gln Pro Ala Asp Lys Tyr Arg Thr Phe Val Ala Thr
                85                  90                  95

Phe Gly Ala Ala Ser Asn Lys Ala Phe Ala Glu Gly Leu Ser Gly Glu
            100                 105                 110

Pro Lys Gly Ala Ala Glu Ser Ser Lys Ala Ala Leu Thr Ser Lys
        115                 120                 125

Leu Asp Ala Ala Tyr Lys Leu Ala Tyr Lys Thr Ala Glu Gly Ala Thr
130                 135                 140

Pro Glu Ala Lys Tyr Asp Ala Tyr Val Ala Thr Leu Ser Glu Ala Leu
145                 150                 155                 160

Arg Ile Ile Ala Gly Thr Leu Glu Val His Ala Val Lys Pro Ala Ala
                165                 170                 175

Glu Glu Val Lys Val Ile Pro Ala Gly Glu Leu Gln Val Ile Glu Lys
            180                 185                 190

Val Asp Ala Ala Phe Lys Val Ala Ala Thr Ala Ala Asn Ala Ala Pro
        195                 200                 205

Ala Asn Asp Lys Phe Thr Val Phe Glu Ala Ala Phe Asn Asp Ala Ile
    210                 215                 220

Lys Ala Ser Thr Gly Gly Ala Tyr Glu Ser Tyr Lys Phe Ile Pro Ala
225                 230                 235                 240

Leu Glu Ala Ala Val Lys Gln Ala Tyr Ala Ala Thr Val Ala Thr Ala
                245                 250                 255

Pro Glu Val Lys Tyr Thr Val Phe Glu Thr Ala Leu Lys Lys Ala Ile
            260                 265                 270

Thr Ala Met Ser Glu Ala Gln Lys Ala Ala Lys Pro Ala Ala Ala
        275                 280                 285

Thr Ala Thr Ala Thr Ala Ala Val Gly Ala Ala Thr Gly Ala Ala Thr
    290                 295                 300

Ala Ala Thr Gly Gly Tyr Lys Val
305                 310

<210> SEQ ID NO 72
<211> LENGTH: 280
<212> TYPE: PRT
<213> ORGANISM: Phleum pratense

<400> SEQUENCE: 72
```

```
Met Ala Val Pro Arg Arg Gly Pro Arg Gly Pro Gly Arg Ser Tyr
1               5                   10                  15

Thr Ala Asp Ala Gly Tyr Ala Pro Ala Thr Pro Ala Ala Gly Ala
                20                  25                  30

Ala Ala Gly Lys Ala Thr Thr Glu Glu Gln Lys Leu Ile Glu Asp Ile
        35                  40                  45

Asn Val Gly Phe Lys Ala Ala Val Ala Ala Arg Gln Arg Pro Ala Ala
    50                  55                  60

Asp Lys Phe Lys Thr Phe Glu Ala Ala Ser Pro Arg His Pro Arg Pro
65              70                  75                  80

Leu Arg Gln Gly Ala Gly Leu Val Pro Lys Leu Asp Ala Ala Tyr Ser
                85                  90                  95

Val Ala Tyr Lys Ala Ala Val Gly Ala Thr Pro Glu Ala Lys Phe Asp
            100                 105                 110

Ser Phe Val Ala Ser Leu Thr Glu Ala Leu Arg Val Ile Ala Gly Ala
        115                 120                 125

Leu Glu Val His Ala Val Lys Pro Val Thr Glu Glu Pro Gly Met Ala
130             135                 140

Lys Ile Pro Ala Gly Glu Leu Gln Ile Ile Asp Lys Ile Asp Ala Ala
145                 150                 155                 160

Phe Lys Val Ala Ala Thr Ala Ala Thr Ala Pro Ala Asp Asp Lys
                165                 170                 175

Phe Thr Val Phe Glu Ala Ala Phe Asn Lys Ala Ile Lys Glu Ser Thr
            180                 185                 190

Gly Gly Ala Tyr Asp Thr Tyr Lys Cys Ile Pro Ser Leu Glu Ala Ala
        195                 200                 205

Val Lys Gln Ala Tyr Ala Ala Thr Val Ala Ala Ala Glu Val Lys
    210                 215                 220

Tyr Ala Val Phe Glu Ala Ala Leu Thr Lys Ala Ile Thr Ala Met Ser
225                 230                 235                 240

Glu Val Gln Lys Val Ser Gln Pro Ala Thr Gly Ala Ala Thr Val Ala
                245                 250                 255

Ala Gly Ala Ala Thr Thr Ala Ala Gly Ala Ala Ser Gly Ala Ala Thr
            260                 265                 270

Val Ala Ala Gly Gly Tyr Lys Val
        275                 280

<210> SEQ ID NO 73
<211> LENGTH: 285
<212> TYPE: PRT
<213> ORGANISM: Phleum pratense

<400> SEQUENCE: 73

Ala Asp Leu Gly Tyr Gly Pro Ala Thr Pro Ala Ala Pro Ala Ala Gly
1               5                   10                  15

Tyr Thr Pro Ala Thr Pro Ala Ala Pro Ala Gly Ala Asp Ala Ala Gly
                20                  25                  30

Lys Ala Thr Thr Glu Glu Gln Lys Leu Ile Glu Lys Ile Asn Ala Gly
            35                  40                  45

Phe Lys Ala Ala Leu Ala Gly Ala Gly Val Gln Pro Ala Asp Lys Tyr
        50                  55                  60

Arg Thr Phe Val Ala Thr Phe Gly Pro Ala Ser Asn Lys Ala Phe Ala
65              70                  75                  80

Glu Gly Leu Ser Gly Glu Pro Lys Gly Ala Ala Glu Ser Ser Ser Lys
                85                  90                  95
```

```
Ala Ala Leu Thr Ser Lys Leu Asp Ala Ala Tyr Lys Leu Ala Tyr Lys
            100                 105                 110

Thr Ala Glu Gly Ala Thr Pro Glu Ala Lys Tyr Asp Ala Tyr Val Ala
            115                 120                 125

Thr Leu Ser Glu Ala Leu Arg Ile Ile Ala Gly Thr Leu Glu Val His
            130                 135                 140

Ala Val Lys Pro Ala Ala Glu Glu Val Lys Val Ile Pro Ala Gly Glu
145                 150                 155                 160

Leu Gln Val Ile Glu Lys Val Asp Ala Ala Phe Lys Val Ala Ala Thr
                165                 170                 175

Ala Ala Asn Ala Ala Pro Ala Asn Asp Lys Phe Thr Val Phe Glu Ala
            180                 185                 190

Ala Phe Asn Asp Glu Ile Lys Ala Ser Thr Gly Gly Ala Tyr Glu Ser
            195                 200                 205

Tyr Lys Phe Ile Pro Ala Leu Glu Ala Ala Val Lys Gln Ala Tyr Ala
            210                 215                 220

Ala Thr Val Ala Thr Ala Pro Glu Val Lys Tyr Thr Val Phe Glu Thr
225                 230                 235                 240

Ala Leu Lys Lys Ala Ile Thr Ala Met Ser Glu Ala Gln Lys Ala Ala
                245                 250                 255

Lys Pro Pro Leu Pro Pro Pro Gln Pro Pro Leu Ala Ala
            260                 265                 270

Thr Gly Ala Ala Thr Ala Ala Thr Gly Gly Tyr Lys Val
            275                 280                 285

<210> SEQ ID NO 74
<211> LENGTH: 312
<212> TYPE: PRT
<213> ORGANISM: Phleum pratense

<400> SEQUENCE: 74

Met Ala Val His Gln Tyr Thr Val Ala Leu Phe Leu Ala Val Ala Leu
1               5                   10                  15

Val Ala Gly Pro Ala Ala Ser Tyr Ala Ala Asp Leu Gly Tyr Gly Pro
            20                  25                  30

Ala Thr Pro Ala Ala Pro Ala Ala Gly Tyr Thr Pro Ala Thr Pro Ala
            35                  40                  45

Ala Pro Ala Glu Ala Ala Pro Ala Gly Lys Ala Thr Thr Glu Glu Gln
        50                  55                  60

Lys Leu Ile Glu Lys Ile Asn Ala Gly Phe Lys Ala Ala Leu Ala Ala
65                  70                  75                  80

Ala Ala Gly Val Gln Pro Ala Asp Lys Tyr Arg Thr Phe Val Ala Thr
                85                  90                  95

Phe Gly Ala Ala Ser Asn Lys Ala Phe Ala Glu Gly Leu Ser Gly Glu
            100                 105                 110

Pro Lys Gly Ala Ala Glu Ser Ser Lys Ala Ala Leu Thr Ser Lys
            115                 120                 125

Leu Asp Ala Ala Tyr Lys Leu Ala Tyr Lys Thr Ala Glu Gly Ala Thr
            130                 135                 140

Pro Glu Ala Lys Tyr Asp Ala Tyr Val Ala Thr Leu Ser Glu Ala Leu
145                 150                 155                 160

Arg Ile Ile Ala Gly Thr Leu Glu Val His Ala Val Lys Pro Ala Ala
                165                 170                 175

Glu Glu Val Lys Val Ile Pro Ala Gly Glu Leu Gln Val Ile Glu Lys
            180                 185                 190
```

```
Val Asp Ala Ala Phe Lys Val Ala Thr Ala Ala Asn Ala Ala Pro
        195                 200                 205

Ala Asn Asp Lys Phe Thr Val Phe Glu Ala Ala Phe Asn Asp Ala Ile
        210                 215                 220

Lys Ala Ser Thr Gly Gly Ala Tyr Glu Ser Tyr Lys Phe Ile Pro Ala
225                 230                 235                 240

Leu Glu Ala Ala Val Lys Gln Ala Tyr Ala Thr Val Ala Thr Ala
                245                 250                 255

Pro Glu Val Lys Tyr Thr Val Phe Glu Thr Ala Leu Lys Lys Ala Ile
                260                 265                 270

Thr Ala Met Ser Glu Ala Gln Lys Ala Ala Lys Pro Ala Ala Ala
        275                 280                 285

Thr Ala Thr Ala Thr Ala Val Gly Ala Ala Thr Gly Ala Ala Thr
        290                 295                 300

Ala Ala Thr Gly Gly Tyr Lys Val
305                 310
```

<210> SEQ ID NO 75
<211> LENGTH: 138
<212> TYPE: PRT
<213> ORGANISM: Phleum pratense

<400> SEQUENCE: 75

```
Met Ala Ala His Lys Phe Met Val Ala Met Phe Leu Ala Val Ala Val
1               5                   10                  15

Val Leu Gly Leu Ala Thr Ser Pro Thr Ala Glu Gly Gly Lys Ala Thr
                20                  25                  30

Thr Glu Glu Gln Lys Leu Ile Glu Asp Val Asn Ala Ser Phe Arg Ala
        35                  40                  45

Ala Met Ala Thr Thr Ala Asn Val Pro Pro Ala Asp Lys Tyr Lys Thr
    50                  55                  60

Phe Glu Ala Ala Phe Thr Val Ser Ser Lys Arg Asn Leu Ala Asp Ala
65                  70                  75                  80

Val Ser Lys Ala Pro Gln Leu Val Pro Lys Leu Asp Glu Val Tyr Asn
                85                  90                  95

Ala Ala Tyr Asn Ala Ala Asp His Ala Ala Pro Glu Asp Lys Tyr Glu
            100                 105                 110

Ala Phe Val Leu His Phe Ser Glu Ala Leu Arg Ile Ile Ala Gly Thr
        115                 120                 125

Pro Glu Val His Ala Val Lys Pro Gly Ala
        130                 135
```

<210> SEQ ID NO 76
<211> LENGTH: 57
<212> TYPE: PRT
<213> ORGANISM: Phleum pratense

<400> SEQUENCE: 76

```
Ser Lys Ala Pro Gln Leu Val Pro Lys Leu Asp Glu Val Tyr Asn Ala
1               5                   10                  15

Ala Tyr Asn Ala Ala Asp His Ala Ala Pro Glu Asp Lys Tyr Glu Ala
                20                  25                  30

Phe Val Leu His Phe Ser Glu Ala Leu His Ile Ile Ala Gly Thr Pro
        35                  40                  45

Glu Val His Ala Val Lys Pro Gly Ala
    50                  55
```

-continued

<210> SEQ ID NO 77
<211> LENGTH: 80
<212> TYPE: PRT
<213> ORGANISM: Phleum pratense

<400> SEQUENCE: 77

Ala Asp Lys Tyr Lys Thr Phe Glu Ala Ala Phe Thr Val Ser Ser Lys
1               5                   10                  15

Arg Asn Leu Ala Asp Ala Val Ser Lys Ala Pro Gln Leu Val Pro Lys
            20                  25                  30

Leu Asp Glu Val Tyr Asn Ala Ala Tyr Asn Ala Ala Asp His Ala Ala
        35                  40                  45

Pro Glu Asp Lys Tyr Glu Ala Phe Val Leu His Phe Ser Glu Ala Leu
50                  55                  60

His Ile Ile Ala Gly Thr Pro Glu Val His Ala Val Lys Pro Gly Ala
65                  70                  75                  80

<210> SEQ ID NO 78
<211> LENGTH: 106
<212> TYPE: PRT
<213> ORGANISM: Phleum pratense

<400> SEQUENCE: 78

Thr Glu Glu Gln Lys Leu Ile Glu Asp Val Asn Ala Ser Phe Arg Ala
1               5                   10                  15

Ala Met Ala Thr Thr Ala Asn Val Pro Pro Ala Asp Lys Tyr Lys Thr
            20                  25                  30

Leu Glu Ala Ala Phe Thr Val Ser Ser Lys Arg Asn Leu Ala Asp Ala
        35                  40                  45

Val Ser Lys Ala Pro Gln Leu Val Pro Lys Leu Asp Glu Val Tyr Asn
    50                  55                  60

Ala Ala Tyr Asn Ala Ala Asp His Ala Ala Pro Glu Asp Lys Tyr Glu
65                  70                  75                  80

Ala Phe Val Leu His Phe Ser Glu Ala Leu Arg Ile Ile Ala Gly Thr
                85                  90                  95

Pro Glu Val His Ala Val Lys Pro Gly Ala
            100                 105

<210> SEQ ID NO 79
<211> LENGTH: 138
<212> TYPE: PRT
<213> ORGANISM: Phleum pratense

<400> SEQUENCE: 79

Met Ala Ala His Lys Phe Met Val Ala Met Phe Leu Ala Val Ala Val
1               5                   10                  15

Val Leu Gly Leu Ala Thr Ser Pro Thr Ala Glu Gly Gly Lys Ala Thr
            20                  25                  30

Thr Glu Glu Gln Lys Leu Ile Glu Asp Ile Asn Ala Ser Phe Arg Ala
        35                  40                  45

Ala Met Ala Thr Thr Ala Asn Val Pro Pro Ala Asp Lys Tyr Lys Thr
    50                  55                  60

Phe Glu Ala Ala Phe Thr Val Ser Ser Lys Arg Asn Leu Ala Asp Ala
65                  70                  75                  80

Val Ser Lys Ala Pro Gln Leu Val Pro Lys Leu Asp Glu Val Tyr Asn
                85                  90                  95

Ala Ala Tyr Asn Ala Ala Asp His Ala Ala Pro Glu Asp Lys Tyr Glu
            100                 105                 110

```
Ala Phe Val Leu His Phe Ser Glu Ala Leu His Ile Ile Ala Gly Thr
            115                 120                 125

Pro Glu Val His Ala Val Lys Pro Gly Ala
        130                 135

<210> SEQ ID NO 80
<211> LENGTH: 132
<212> TYPE: PRT
<213> ORGANISM: Phleum pratense

<400> SEQUENCE: 80

Met Val Ala Met Phe Leu Ala Val Ala Val Leu Gly Leu Ala Thr
1               5                   10                  15

Ser Pro Thr Ala Glu Gly Gly Lys Ala Thr Thr Glu Glu Gln Lys Leu
            20                  25                  30

Ile Glu Asp Val Asn Ala Ser Phe Arg Ala Ala Met Ala Thr Thr Ala
            35                  40                  45

Asn Val Pro Pro Ala Asp Lys Tyr Lys Thr Phe Glu Ala Ala Phe Thr
50                  55                  60

Val Ser Ser Lys Arg Asn Leu Ala Asp Ala Val Ser Lys Ala Pro Gln
65                  70                  75                  80

Leu Val Pro Lys Leu Asp Glu Val Tyr Asn Ala Ala Tyr Asn Ala Ala
                85                  90                  95

Asp His Ala Ala Pro Glu Asp Lys Tyr Glu Ala Phe Val Leu His Phe
            100                 105                 110

Ser Glu Ala Leu Arg Ile Ile Ala Gly Thr Pro Glu Val His Ala Val
            115                 120                 125

Lys Pro Gly Ala
    130

<210> SEQ ID NO 81
<211> LENGTH: 78
<212> TYPE: PRT
<213> ORGANISM: Phleum pratense

<400> SEQUENCE: 81

Met Ala Asp Asp Met Glu Arg Ile Phe Lys Arg Phe Asp Thr Asn Gly
1               5                   10                  15

Asp Gly Lys Ile Ser Leu Ser Glu Leu Thr Asp Ala Leu Arg Thr Leu
            20                  25                  30

Gly Ser Thr Ser Ala Asp Glu Val Gln Arg Met Met Ala Glu Ile Asp
            35                  40                  45

Thr Asp Gly Asp Gly Phe Ile Asp Phe Asn Glu Phe Ile Ser Phe Cys
    50                  55                  60

Asn Ala Asn Pro Gly Leu Met Lys Asp Val Ala Lys Val Phe
65                  70                  75

<210> SEQ ID NO 82
<211> LENGTH: 131
<212> TYPE: PRT
<213> ORGANISM: Phleum pratense

<400> SEQUENCE: 82

Met Ser Trp Gln Thr Tyr Val Asp Glu His Leu Met Cys Glu Ile Glu
1               5                   10                  15

Gly His His Leu Ala Ser Ala Ala Ile Leu Gly His Asp Gly Thr Val
            20                  25                  30

Trp Ala Gln Ser Ala Asp Phe Pro Gln Phe Lys Pro Glu Glu Ile Thr
```

```
                    35                  40                  45
Gly Ile Met Lys Asp Phe Asp Glu Pro Gly His Leu Ala Pro Thr Gly
 50                  55                  60

Met Phe Val Ala Gly Ala Lys Tyr Met Val Ile Gln Gly Glu Pro Gly
 65                  70                  75                  80

Arg Val Ile Arg Gly Lys Lys Gly Ala Gly Ile Thr Ile Lys Lys
                     85                  90                  95

Thr Gly Gln Ala Leu Val Val Gly Ile Tyr Asp Glu Pro Met Thr Pro
                    100                 105                 110

Gly Gln Cys Asn Met Val Val Glu Arg Leu Gly Asp Tyr Leu Val Glu
                    115                 120                 125

Gln Gly Met
            130

<210> SEQ ID NO 83
<211> LENGTH: 227
<212> TYPE: PRT
<213> ORGANISM: Vespula vulgaris

<400> SEQUENCE: 83

Met Glu Ile Ser Gly Leu Val Tyr Leu Ile Ile Val Thr Ile Ile
 1               5                  10                  15

Asp Leu Pro Tyr Gly Lys Ala Asn Asn Tyr Cys Lys Ile Lys Cys Leu
                 20                  25                  30

Lys Gly Gly Val His Thr Ala Cys Lys Tyr Gly Ser Leu Lys Pro Asn
             35                  40                  45

Cys Gly Asn Lys Val Val Val Ser Tyr Gly Leu Thr Lys Gln Glu Lys
 50                  55                  60

Gln Asp Ile Leu Lys Glu His Asn Asp Phe Arg Gln Lys Ile Ala Arg
 65                  70                  75                  80

Gly Leu Glu Thr Arg Gly Asn Pro Gly Pro Gln Pro Pro Ala Lys Asn
                 85                  90                  95

Met Lys Asn Leu Val Trp Asn Asp Glu Leu Ala Tyr Val Ala Gln Val
            100                 105                 110

Trp Ala Asn Gln Cys Gln Tyr Gly His Asp Thr Cys Arg Asp Val Ala
            115                 120                 125

Lys Tyr Gln Val Gly Gln Asn Val Ala Leu Thr Gly Ser Thr Ala Ala
130                 135                 140

Lys Tyr Asp Asp Pro Val Lys Leu Val Lys Met Trp Glu Asp Glu Val
145                 150                 155                 160

Lys Asp Tyr Asn Pro Lys Lys Phe Ser Gly Asn Asp Phe Leu Lys
                165                 170                 175

Thr Gly His Tyr Thr Gln Met Val Trp Ala Asn Thr Lys Glu Val Gly
            180                 185                 190

Cys Gly Ser Ile Lys Tyr Ile Gln Glu Lys Trp His Lys His Tyr Leu
            195                 200                 205

Val Cys Asn Tyr Gly Pro Ser Gly Asn Phe Met Asn Glu Glu Leu Tyr
210                 215                 220

Gln Thr Lys
225

<210> SEQ ID NO 84
<211> LENGTH: 300
<212> TYPE: PRT
<213> ORGANISM: Vespula maculifrons

<400> SEQUENCE: 84
```

```
Gly Pro Lys Cys Pro Phe Asn Ser Asp Thr Val Ser Ile Ile Ile Glu
 1               5                  10                  15

Thr Arg Glu Asn Arg Asn Arg Asp Leu Tyr Thr Leu Gln Thr Leu Gln
             20                  25                  30

Asn His Pro Glu Phe Lys Lys Thr Ile Thr Arg Pro Val Val Phe
             35                  40                  45

Ile Thr His Gly Phe Thr Ser Ser Ala Ser Glu Lys Asn Phe Ile Asn
 50                  55                  60

Leu Ala Lys Ala Leu Val Asp Lys Asp Asn Tyr Met Val Ile Ser Ile
 65                  70                  75                  80

Asp Trp Gln Thr Ala Ala Cys Thr Asn Glu Tyr Pro Gly Leu Lys Tyr
                 85                  90                  95

Ala Tyr Tyr Pro Thr Ala Ala Ser Asn Thr Arg Leu Val Gly Gln Tyr
                100                 105                 110

Ile Ala Thr Ile Thr Gln Lys Leu Val Lys Asp Tyr Lys Ile Ser Met
            115                 120                 125

Ala Asn Ile Arg Leu Ile Gly His Ser Leu Gly Ala His Val Ser Gly
130                 135                 140

Phe Ala Gly Lys Arg Val Gln Glu Leu Lys Leu Gly Lys Tyr Ser Glu
145                 150                 155                 160

Ile Ile Gly Leu Asp Pro Ala Arg Pro Ser Phe Asp Ser Asn His Cys
                165                 170                 175

Ser Glu Arg Leu Cys Glu Thr Asp Ala Glu Tyr Val Gln Ile Ile His
            180                 185                 190

Thr Ser Asn Tyr Leu Gly Thr Glu Lys Ile Leu Gly Thr Val Asp Phe
        195                 200                 205

Tyr Met Asn Asn Gly Lys Asn Pro Gly Cys Gly Arg Phe Phe Ser
210                 215                 220

Glu Val Cys Ser His Thr Arg Ala Val Ile Tyr Met Ala Glu Cys Ile
225                 230                 235                 240

Lys His Glu Cys Cys Leu Ile Gly Ile Pro Arg Ser Lys Ser Ser Gln
                245                 250                 255

Pro Ile Ser Arg Cys Thr Lys Gln Glu Cys Val Cys Val Gly Leu Asn
                260                 265                 270

Ala Lys Lys Tyr Pro Ser Arg Gly Ser Phe Tyr Val Pro Val Glu Ser
            275                 280                 285

Thr Ala Pro Phe Cys Asn Asn Lys Gly Lys Ile Ile
290                 295                 300

<210> SEQ ID NO 85
<211> LENGTH: 336
<212> TYPE: PRT
<213> ORGANISM: Vespula vulgaris

<400> SEQUENCE: 85

Met Glu Glu Asn Met Asn Leu Lys Tyr Leu Leu Leu Phe Val Tyr Phe
 1               5                  10                  15

Val Gln Val Leu Asn Cys Cys Tyr Gly His Gly Asp Pro Leu Ser Tyr
             20                  25                  30

Glu Leu Asp Arg Gly Pro Lys Cys Pro Phe Asn Ser Asp Thr Val Ser
             35                  40                  45

Ile Ile Ile Glu Thr Arg Glu Asn Arg Asn Arg Asp Leu Tyr Thr Leu
 50                  55                  60

Gln Thr Leu Gln Asn His Pro Glu Phe Lys Lys Thr Ile Thr Arg
 65                  70                  75                  80
```

```
Pro Val Val Phe Ile Thr His Gly Phe Thr Ser Ser Ala Ser Glu Thr
                85                  90                  95

Asn Phe Ile Asn Leu Ala Lys Ala Leu Val Asp Lys Asp Asn Tyr Met
            100                 105                 110

Val Ile Ser Ile Asp Trp Gln Thr Ala Ala Cys Thr Asn Glu Ala Ala
        115                 120                 125

Gly Leu Lys Tyr Leu Tyr Tyr Pro Thr Ala Ala Arg Asn Thr Arg Leu
    130                 135                 140

Val Gly Gln Tyr Ile Ala Thr Ile Thr Gln Lys Leu Val Lys His Tyr
145                 150                 155                 160

Lys Ile Ser Met Ala Asn Ile Arg Leu Ile Gly His Ser Leu Gly Ala
                165                 170                 175

His Ala Ser Gly Phe Ala Gly Lys Lys Val Gln Glu Leu Lys Leu Gly
            180                 185                 190

Lys Tyr Ser Glu Ile Ile Gly Leu Asp Pro Ala Arg Pro Ser Phe Asp
        195                 200                 205

Ser Asn His Cys Ser Glu Arg Leu Cys Glu Thr Asp Ala Glu Tyr Val
    210                 215                 220

Gln Ile Ile His Thr Ser Asn Tyr Leu Gly Thr Glu Lys Thr Leu Gly
225                 230                 235                 240

Thr Val Asp Phe Tyr Met Asn Asn Gly Lys Asn Gln Pro Gly Cys Gly
                245                 250                 255

Arg Phe Phe Ser Glu Val Cys Ser His Ser Arg Ala Val Ile Tyr Met
            260                 265                 270

Ala Glu Cys Ile Lys His Glu Cys Cys Leu Ile Gly Ile Pro Lys Ser
        275                 280                 285

Lys Ser Ser Gln Pro Ile Ser Ser Cys Thr Lys Gln Glu Cys Val Cys
    290                 295                 300

Val Gly Leu Asn Ala Lys Lys Tyr Pro Ser Arg Gly Ser Phe Tyr Val
305                 310                 315                 320

Pro Val Glu Ser Thr Ala Pro Phe Cys Asn Asn Lys Gly Lys Ile Ile
                325                 330                 335

<210> SEQ ID NO 86
<211> LENGTH: 331
<212> TYPE: PRT
<213> ORGANISM: Vespula vulgaris

<400> SEQUENCE: 86

Ser Glu Arg Pro Lys Arg Val Phe Asn Ile Tyr Trp Asn Val Pro Thr
1               5                   10                  15

Phe Met Cys His Gln Tyr Asp Leu Tyr Phe Asp Glu Val Thr Asn Phe
            20                  25                  30

Asn Ile Lys Arg Asn Ser Lys Asp Asp Phe Gln Gly Asp Lys Ile Ala
        35                  40                  45

Ile Phe Tyr Asp Pro Gly Glu Phe Pro Ala Leu Leu Ser Leu Lys Asp
    50                  55                  60

Gly Lys Tyr Lys Lys Arg Asn Gly Gly Val Pro Gln Glu Gly Asn Ile
65                  70                  75                  80

Thr Ile His Leu Gln Lys Phe Ile Glu Asn Leu Asp Lys Ile Tyr Pro
                85                  90                  95

Asn Arg Asn Phe Ser Gly Ile Gly Val Ile Asp Phe Glu Arg Trp Arg
            100                 105                 110

Pro Ile Phe Arg Gln Asn Trp Gly Asn Met Lys Ile His Lys Asn Phe
        115                 120                 125
```

Ser Ile Asp Leu Val Arg Asn Glu His Pro Thr Trp Asn Lys Lys Met
130                 135                 140

Ile Glu Leu Glu Ala Ser Lys Arg Phe Glu Lys Tyr Ala Arg Phe Phe
145                 150                 155                 160

Met Glu Glu Thr Leu Lys Leu Ala Lys Lys Thr Arg Lys Gln Ala Asp
                165                 170                 175

Trp Gly Tyr Tyr Gly Tyr Pro Tyr Cys Phe Asn Met Ser Pro Asn Asn
                180                 185                 190

Leu Val Pro Glu Cys Asp Val Thr Ala Met His Glu Asn Asp Lys Met
            195                 200                 205

Ser Trp Leu Phe Asn Asn Gln Asn Val Leu Leu Pro Ser Val Tyr Val
        210                 215                 220

Arg Gln Glu Leu Thr Pro Asp Gln Arg Ile Gly Leu Val Gln Gly Arg
225                 230                 235                 240

Val Lys Glu Ala Val Arg Ile Ser Asn Asn Leu Lys His Ser Pro Lys
                245                 250                 255

Val Leu Ser Tyr Trp Trp Tyr Val Tyr Gln Asp Glu Thr Asn Thr Phe
                260                 265                 270

Leu Thr Glu Thr Asp Val Lys Lys Thr Phe Gln Glu Ile Val Ile Asn
            275                 280                 285

Gly Gly Asp Gly Ile Ile Ile Trp Gly Ser Ser Ser Asp Val Asn Ser
        290                 295                 300

Leu Ser Lys Cys Lys Arg Leu Gln Asp Tyr Leu Leu Thr Val Leu Gly
305                 310                 315                 320

Pro Ile Ala Ile Asn Val Thr Glu Ala Val Asn
                325                 330

<210> SEQ ID NO 87
<211> LENGTH: 206
<212> TYPE: PRT
<213> ORGANISM: Vespula vidua

<400> SEQUENCE: 87

Lys Val Asn Tyr Cys Lys Ile Lys Cys Leu Lys Gly Gly Val His Thr
1               5                   10                  15

Ala Cys Lys Tyr Gly Thr Ser Thr Lys Pro Asn Cys Gly Lys Met Val
                20                  25                  30

Val Lys Ala Tyr Gly Leu Thr Glu Ala Glu Lys Gln Glu Ile Leu Lys
            35                  40                  45

Val His Asn Asp Phe Arg Gln Lys Val Ala Lys Gly Leu Glu Thr Arg
        50                  55                  60

Gly Asn Pro Gly Pro Gln Pro Pro Ala Lys Asn Met Asn Asn Leu Val
65                  70                  75                  80

Trp Asn Asp Glu Leu Ala Asn Ile Ala Gln Val Trp Ala Ser Gln Cys
                85                  90                  95

Asn Tyr Gly His Asp Thr Cys Lys Asp Thr Glu Lys Tyr Pro Val Gly
                100                 105                 110

Gln Asn Ile Ala Lys Arg Ser Thr Thr Ala Ala Leu Phe Asp Ser Pro
            115                 120                 125

Gly Lys Leu Val Lys Met Trp Glu Asn Glu Val Lys Asp Phe Asn Pro
130                 135                 140

Asn Ile Glu Trp Ser Lys Asn Asn Leu Lys Lys Thr Gly His Tyr Thr
145                 150                 155                 160

Gln Met Val Trp Ala Lys Thr Lys Glu Ile Gly Cys Gly Ser Val Lys
                165                 170                 175

```
Tyr Val Lys Asp Glu Trp Tyr Thr His Tyr Leu Val Cys Asn Tyr Gly
            180                 185                 190

Pro Ser Gly Asn Phe Arg Asn Glu Lys Leu Tyr Glu Lys Lys
            195                 200             205

<210> SEQ ID NO 88
<211> LENGTH: 160
<212> TYPE: PRT
<213> ORGANISM: Betula pendula

<400> SEQUENCE: 88

Met Gly Val Phe Asn Tyr Glu Thr Glu Thr Thr Ser Val Ile Pro Ala
1               5                   10                  15

Ala Arg Leu Phe Lys Ala Phe Ile Leu Asp Gly Asp Asn Leu Phe Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Ser Phe Pro Glu Gly Phe Pro
    50                  55                  60

Phe Lys Tyr Val Lys Asp Arg Val Asp Glu Val Asp His Thr Asn Phe
65                  70                  75                  80

Lys Tyr Asn Tyr Ser Val Ile Glu Gly Gly Pro Ile Gly Asp Thr Leu
                85                  90                  95

Glu Lys Ile Ser Asn Glu Ile Lys Ile Val Ala Thr Pro Asp Gly Gly
            100                 105                 110

Ser Ile Leu Lys Ile Ser Asn Lys Tyr His Thr Lys Gly Asp His Glu
        115                 120                 125

Val Lys Ala Glu Gln Val Lys Ala Ser Lys Glu Met Gly Glu Thr Leu
    130                 135                 140

Leu Arg Ala Val Glu Ser Tyr Leu Leu Ala His Ser Asp Ala Tyr Asn
145                 150                 155                 160

<210> SEQ ID NO 89
<211> LENGTH: 133
<212> TYPE: PRT
<213> ORGANISM: Betula pendula

<400> SEQUENCE: 89

Met Ser Trp Gln Thr Tyr Val Asp Glu His Leu Met Cys Asp Ile Asp
1               5                   10                  15

Gly Gln Ala Ser Asn Ser Leu Ala Ser Ala Ile Val Gly His Asp Gly
            20                  25                  30

Ser Val Trp Ala Gln Ser Ser Ser Phe Pro Gln Phe Lys Pro Gln Glu
        35                  40                  45

Ile Thr Gly Ile Met Lys Asp Phe Glu Glu Pro Gly His Leu Ala Pro
    50                  55                  60

Thr Gly Leu His Leu Gly Gly Ile Lys Tyr Met Val Ile Gln Gly Glu
65                  70                  75                  80

Ala Gly Ala Val Ile Arg Gly Lys Lys Gly Ser Gly Gly Ile Thr Ile
                85                  90                  95

Lys Lys Thr Gly Gln Ala Leu Val Phe Gly Ile Tyr Glu Glu Pro Val
            100                 105                 110

Thr Pro Gly Gln Cys Asn Met Val Val Glu Arg Leu Gly Asp Tyr Leu
        115                 120                 125

Ile Asp Gln Gly Leu
    130
```

-continued

<210> SEQ ID NO 90
<211> LENGTH: 205
<212> TYPE: PRT
<213> ORGANISM: Betula pendula

<400> SEQUENCE: 90

Met Pro Cys Ser Thr Glu Ala Met Glu Lys Ala Gly His Gly His Ala
1               5                   10                  15

Ser Thr Pro Arg Lys Arg Ser Leu Ser Asn Ser Ser Phe Arg Leu Arg
            20                  25                  30

Ser Glu Ser Leu Asn Thr Leu Arg Leu Arg Arg Ile Phe Asp Leu Phe
        35                  40                  45

Asp Lys Asn Ser Asp Gly Ile Ile Thr Val Asp Glu Leu Ser Arg Ala
    50                  55                  60

Leu Asn Leu Leu Gly Leu Glu Thr Asp Leu Ser Glu Leu Glu Ser Thr
65                  70                  75                  80

Val Lys Ser Phe Thr Arg Glu Gly Asn Ile Gly Leu Gln Phe Glu Asp
                85                  90                  95

Phe Ile Ser Leu His Gln Ser Leu Asn Asp Ser Tyr Phe Ala Tyr Gly
            100                 105                 110

Gly Glu Asp Glu Asp Asn Glu Glu Asp Met Arg Lys Ser Ile Leu
        115                 120                 125

Ser Gln Glu Glu Ala Asp Ser Phe Gly Gly Phe Lys Val Phe Asp Glu
    130                 135                 140

Asp Gly Asp Gly Tyr Ile Ser Ala Arg Glu Leu Gln Met Val Leu Gly
145                 150                 155                 160

Lys Leu Gly Phe Ser Glu Gly Ser Glu Ile Asp Arg Val Glu Lys Met
                165                 170                 175

Ile Val Ser Val Asp Ser Asn Arg Asp Gly Arg Val Asp Phe Phe Glu
            180                 185                 190

Phe Lys Asp Met Met Arg Ser Val Leu Val Arg Ser Ser
        195                 200                 205

<210> SEQ ID NO 91
<211> LENGTH: 85
<212> TYPE: PRT
<213> ORGANISM: Betula pendula

<400> SEQUENCE: 91

Met Ala Asp Asp His Pro Gln Asp Lys Ala Glu Arg Glu Arg Ile Phe
1               5                   10                  15

Lys Arg Phe Asp Ala Asn Gly Asp Gly Lys Ile Ser Ala Ala Glu Leu
            20                  25                  30

Gly Glu Ala Leu Lys Thr Leu Gly Ser Ile Thr Pro Asp Glu Val Lys
        35                  40                  45

His Met Met Ala Glu Ile Asp Thr Asp Gly Asp Gly Phe Ile Ser Phe
    50                  55                  60

Gln Glu Phe Thr Asp Phe Gly Arg Ala Asn Arg Gly Leu Leu Lys Asp
65                  70                  75                  80

Val Ala Lys Ile Phe
                85

<210> SEQ ID NO 92
<211> LENGTH: 24
<212> TYPE: PRT
<213> ORGANISM: Quercus alba
<220> FEATURE:
<221> NAME/KEY: misc_feature

```
<222> LOCATION: (5)..(5)
<223> OTHER INFORMATION: unknown or other
<220> FEATURE:
<221> NAME/KEY: misc_feature
<222> LOCATION: (17)..(17)
<223> OTHER INFORMATION: unknown or other

<400> SEQUENCE: 92

Gly Val Phe Thr Xaa Glu Ser Gln Glu Thr Ser Val Ile Ala Pro Ala
1               5                   10                  15

Xaa Leu Phe Lys Ala Leu Phe Leu
            20

<210> SEQ ID NO 93
<211> LENGTH: 40
<212> TYPE: PRT
<213> ORGANISM: Carpinus betulus
<220> FEATURE:
<221> NAME/KEY: misc_feature
<222> LOCATION: (39)..(39)
<223> OTHER INFORMATION: unknown or other

<400> SEQUENCE: 93

Gly Val Phe Asn Tyr Glu Ala Glu Thr Pro Ser Val Ile Pro Ala Ala
1               5                   10                  15

Arg Leu Phe Lys Ser Tyr Val Leu Asp Gly Asp Lys Leu Ile Pro Lys
            20                  25                  30

Val Ala Pro Gln Ala Ile Xaa Lys
            35                  40

<210> SEQ ID NO 94
<211> LENGTH: 44
<212> TYPE: PRT
<213> ORGANISM: Alnus glutinosa

<400> SEQUENCE: 94

Gly Val Phe Asn Tyr Glu Ala Glu Thr Pro Ser Val Ile Pro Ala Ala
1               5                   10                  15

Arg Leu Phe Lys Ala Phe Ile Leu Asp Gly Asp Lys Leu Leu Pro Lys
            20                  25                  30

Val Ala Pro Glu Ala Val Ser Ser Val Glu Asn Ile
            35                  40

<210> SEQ ID NO 95
<211> LENGTH: 110
<212> TYPE: PRT
<213> ORGANISM: Betula pendula

<400> SEQUENCE: 95

Val Gln Cys Met Gln Val Trp Pro Pro Leu Gly Leu Lys Lys Phe Glu
1               5                   10                  15

Thr Leu Ser Tyr Leu Pro Pro Leu Ser Ser Glu Gln Leu Ala Lys Glu
            20                  25                  30

Val Asp Tyr Leu Leu Arg Lys Asn Leu Ile Pro Cys Leu Glu Phe Glu
            35                  40                  45

Leu Glu His Gly Phe Val Tyr Arg Glu His Asn Arg Ser Pro Gly Tyr
        50                  55                  60

Tyr Asp Gly Arg Tyr Trp Thr Met Trp Lys Leu Pro Met Phe Gly Cys
65                  70                  75                  80

Asn Asp Ser Ser Gln Val Leu Lys Glu Leu Glu Glu Cys Lys Lys Ala
                85                  90                  95

Tyr Pro Ser Ala Phe Ile Arg Ile Ile Gly Phe Asp Asp Lys
```

<210> SEQ ID NO 96
<211> LENGTH: 626
<212> TYPE: PRT
<213> ORGANISM: Arachis hypogaea

<400> SEQUENCE: 96

Met Arg Gly Arg Val Ser Pro Leu Met Leu Leu Gly Ile Leu Val
1               5                   10                  15

Leu Ala Ser Val Ser Ala Thr His Ala Lys Ser Ser Pro Tyr Gln Lys
            20                  25                  30

Lys Thr Glu Asn Pro Cys Ala Gln Arg Cys Leu Gln Ser Cys Gln Gln
            35                  40                  45

Glu Pro Asp Asp Leu Lys Gln Lys Ala Cys Glu Ser Arg Cys Thr Lys
50                  55                  60

Leu Glu Tyr Asp Pro Arg Cys Val Tyr Asp Pro Arg Gly His Thr Gly
65                  70                  75                  80

Thr Thr Asn Gln Arg Ser Pro Pro Gly Glu Arg Thr Arg Gly Arg Gln
                85                  90                  95

Pro Gly Asp Tyr Asp Asp Asp Arg Arg Gln Pro Arg Arg Glu Glu Gly
            100                 105                 110

Gly Arg Trp Gly Pro Ala Gly Pro Arg Glu Arg Glu Arg Glu Glu Asp
            115                 120                 125

Trp Arg Gln Pro Arg Glu Asp Trp Arg Arg Pro Ser His Gln Gln Pro
130                 135                 140

Arg Lys Ile Arg Pro Glu Gly Arg Glu Gly Glu Gln Glu Trp Gly Thr
145                 150                 155                 160

Pro Gly Ser His Val Arg Glu Glu Thr Ser Arg Asn Asn Pro Phe Tyr
                165                 170                 175

Phe Pro Ser Arg Arg Phe Ser Thr Arg Tyr Gly Asn Gln Asn Gly Arg
            180                 185                 190

Ile Arg Val Leu Gln Arg Phe Asp Gln Arg Ser Arg Gln Phe Gln Asn
            195                 200                 205

Leu Gln Asn His Arg Ile Val Gln Ile Glu Ala Lys Pro Asn Thr Leu
    210                 215                 220

Val Leu Pro Lys His Ala Asp Ala Asp Asn Ile Leu Val Ile Gln Gln
225                 230                 235                 240

Gly Gln Ala Thr Val Thr Val Ala Asn Gly Asn Asn Arg Lys Ser Phe
                245                 250                 255

Asn Leu Asp Glu Gly His Ala Leu Arg Ile Pro Ser Gly Phe Ile Ser
            260                 265                 270

Tyr Ile Leu Asn Arg His Asp Asn Gln Asn Leu Arg Val Ala Lys Ile
            275                 280                 285

Ser Met Pro Val Asn Thr Pro Gly Gln Phe Glu Asp Phe Phe Pro Ala
290                 295                 300

Ser Ser Arg Asp Gln Ser Ser Tyr Leu Gln Gly Phe Ser Arg Asn Thr
305                 310                 315                 320

Leu Glu Ala Ala Phe Asn Ala Glu Phe Asn Glu Ile Arg Arg Val Leu
                325                 330                 335

Leu Glu Glu Asn Ala Gly Gly Glu Gln Glu Glu Arg Gly Gln Arg Arg
            340                 345                 350

Trp Ser Thr Arg Ser Ser Glu Asn Asn Glu Gly Val Ile Val Lys Val
            355                 360                 365

Ser Lys Glu His Val Glu Glu Leu Thr Lys His Ala Lys Ser Val Ser

```
                    370                 375                 380
Lys Lys Gly Ser Glu Glu Gly Asp Ile Thr Asn Pro Ile Asn Leu
385                 390                 395                 400

Arg Glu Gly Glu Pro Asp Leu Ser Asn Phe Gly Lys Leu Phe Glu
                405                 410                 415

Val Lys Pro Asp Lys Lys Asn Pro Gln Leu Gln Asp Leu Asp Met Met
                420                 425                 430

Leu Thr Cys Val Glu Ile Lys Gly Ala Leu Met Leu Pro His Phe
                435                 440                 445

Asn Ser Lys Ala Met Val Ile Val Val Asn Lys Gly Thr Gly Asn
450                 455                 460

Leu Glu Leu Val Ala Val Arg Lys Glu Gln Gln Arg Gly Arg Arg
465                 470                 475                 480

Glu Glu Glu Glu Asp Glu Glu Glu Glu Gly Ser Asn Arg Glu
                485                 490                 495

Val Arg Arg Tyr Thr Ala Arg Leu Lys Glu Gly Asp Val Phe Ile Met
                500                 505                 510

Pro Ala Ala His Pro Val Ala Ile Asn Ala Ser Ser Glu Leu His Leu
                515                 520                 525

Leu Gly Phe Gly Ile Asn Ala Glu Asn His Arg Ile Phe Leu Ala
530                 535                 540

Gly Asp Lys Asp Asn Val Ile Asp Gln Ile Glu Lys Gln Ala Lys Asp
545                 550                 555                 560

Leu Ala Phe Pro Gly Ser Gly Glu Gln Val Glu Lys Leu Ile Lys Asn
                565                 570                 575

Gln Lys Glu Ser His Phe Val Ser Ala Arg Pro Gln Ser Gln Ser Gln
                580                 585                 590

Ser Pro Ser Ser Pro Glu Lys Glu Ser Pro Glu Lys Glu Asp Gln Glu
            595                 600                 605

Glu Glu Asn Gln Gly Gly Lys Gly Pro Leu Leu Ser Ile Leu Lys Ala
610                 615                 620

Phe Asn
625

<210> SEQ ID NO 97
<211> LENGTH: 392
<212> TYPE: PRT
<213> ORGANISM: Ambrosia artemisiifolia

<400> SEQUENCE: 97

Met Gly Ile Lys His Cys Cys Tyr Ile Leu Tyr Phe Thr Leu Ala Leu
1                   5                   10                  15

Val Thr Leu Leu Gln Pro Val Arg Ser Ala Glu Asp Leu Gln Gln Ile
                20                  25                  30

Leu Pro Ser Ala Asn Glu Thr Arg Ser Leu Thr Thr Cys Gly Thr Tyr
            35                  40                  45

Asn Ile Ile Asp Gly Cys Trp Arg Gly Lys Ala Asp Trp Ala Glu Asn
50                  55                  60

Arg Lys Ala Leu Ala Asp Cys Ala Gln Gly Phe Ala Lys Gly Thr Ile
65                  70                  75                  80

Gly Gly Lys Asp Gly Asp Ile Tyr Thr Val Thr Ser Glu Leu Asp Asp
                85                  90                  95

Asp Val Ala Asn Pro Lys Glu Gly Thr Leu Arg Phe Gly Ala Ala Gln
            100                 105                 110

Asn Arg Pro Leu Trp Ile Ile Phe Ala Arg Asp Met Val Ile Arg Leu
```

```
                115                 120                 125
Asp Arg Glu Leu Ala Ile Asn Asn Asp Lys Thr Ile Asp Gly Arg Gly
130                 135                 140

Ala Lys Val Glu Ile Ile Asn Ala Gly Phe Ala Ile Tyr Asn Val Lys
145                 150                 155                 160

Asn Ile Ile Ile His Asn Ile Met His Asp Ile Val Asn Pro
                165                 170                 175

Gly Gly Leu Ile Lys Ser His Asp Gly Pro Val Pro Arg Lys Gly
                180                 185                 190

Ser Asp Gly Asp Ala Ile Gly Ile Ser Gly Ser Gln Ile Trp Ile
                195                 200                 205

Asp His Cys Ser Leu Ser Lys Ala Val Asp Gly Leu Ile Asp Ala Lys
210                 215                 220

His Gly Ser Thr His Phe Thr Val Ser Asn Cys Leu Phe Thr Gln His
225                 230                 235                 240

Gln Tyr Leu Leu Leu Phe Trp Asp Phe Asp Glu Arg Gly Met Leu Cys
                245                 250                 255

Thr Val Ala Phe Asn Lys Phe Thr Asp Asn Val Asp Gln Arg Met Pro
                260                 265                 270

Asn Leu Arg His Gly Phe Val Gln Val Val Asn Asn Tyr Glu Arg
                275                 280                 285

Trp Gly Ser Tyr Ala Leu Gly Gly Ser Ala Gly Pro Thr Ile Leu Ser
290                 295                 300

Gln Gly Asn Arg Phe Leu Ala Ser Asp Ile Lys Lys Glu Val Val Gly
305                 310                 315                 320

Arg Tyr Gly Glu Ser Ala Met Ser Glu Ser Ile Asn Trp Asn Trp Arg
                325                 330                 335

Ser Tyr Met Asp Val Phe Glu Asn Gly Ala Ile Phe Val Pro Ser Gly
                340                 345                 350

Val Asp Pro Val Leu Thr Pro Glu Gln Asn Ala Gly Met Ile Pro Ala
                355                 360                 365

Glu Pro Gly Glu Ala Val Leu Arg Leu Thr Ser Ser Ala Gly Val Leu
370                 375                 380

Ser Cys Gln Pro Gly Ala Pro Cys
385                 390
```

<210> SEQ ID NO 98
<211> LENGTH: 397
<212> TYPE: PRT
<213> ORGANISM: Ambrosia artemisiifolia

<400> SEQUENCE: 98

```
Met Gly Ile Lys His Cys Cys Tyr Ile Leu Tyr Phe Thr Leu Ala Leu
1               5                   10                  15

Val Thr Leu Val Gln Ala Gly Arg Leu Gly Glu Glu Val Asp Ile Leu
                20                  25                  30

Pro Ser Pro Asn Asp Thr Arg Arg Ser Leu Gln Gly Cys Glu Ala His
                35                  40                  45

Asn Ile Ile Asp Lys Cys Trp Arg Cys Lys Pro Asp Trp Ala Glu Asn
50                  55                  60

Arg Gln Ala Leu Gly Asn Cys Ala Gln Gly Phe Gly Lys Ala Thr His
65                  70                  75                  80

Gly Gly Lys Trp Gly Asp Ile Tyr Met Val Thr Ser Asp Gln Asp Asp
                85                  90                  95

Asp Val Val Asn Pro Lys Glu Gly Thr Leu Arg Phe Gly Ala Thr Gln
```

```
                100                 105                 110
Asp Arg Pro Leu Trp Ile Ile Phe Gln Arg Asp Met Ile Ile Tyr Leu
            115                 120                 125

Gln Gln Glu Met Val Val Thr Ser Asp Lys Thr Ile Asp Gly Arg Gly
            130                 135                 140

Ala Lys Val Glu Leu Val Tyr Gly Gly Ile Thr Leu Met Asn Val Lys
145                 150                 155                 160

Asn Val Ile Ile His Asn Ile Asp Ile His Asp Val Arg Val Leu Pro
                165                 170                 175

Gly Gly Arg Ile Lys Ser Asn Gly Gly Pro Ala Ile Pro Arg His Gln
            180                 185                 190

Ser Asp Gly Asp Ala Ile His Val Thr Gly Ser Ser Asp Ile Trp Ile
            195                 200                 205

Asp His Cys Thr Leu Ser Lys Ser Phe Asp Gly Leu Val Asp Val Asn
            210                 215                 220

Trp Gly Ser Thr Gly Val Thr Ile Ser Asn Cys Lys Phe Thr His His
225                 230                 235                 240

Glu Lys Ala Val Leu Leu Gly Ala Ser Asp Thr His Phe Gln Asp Leu
                245                 250                 255

Lys Met His Val Thr Leu Ala Tyr Asn Ile Phe Thr Asn Thr Val His
                260                 265                 270

Glu Arg Met Pro Arg Cys Arg Phe Gly Phe Gln Ile Val Asn Asn
            275                 280                 285

Phe Tyr Asp Arg Trp Asp Lys Tyr Ala Ile Gly Gly Ser Ser Asn Pro
            290                 295                 300

Thr Ile Leu Ser Gln Gly Asn Lys Phe Val Ala Pro Asp Phe Ile Tyr
305                 310                 315                 320

Lys Lys Asn Val Cys Leu Arg Thr Gly Ala Gln Glu Pro Glu Trp Met
                325                 330                 335

Thr Trp Asn Trp Arg Thr Gln Asn Asp Val Leu Glu Asn Gly Ala Ile
                340                 345                 350

Phe Val Ala Ser Gly Ser Asp Pro Val Leu Thr Ala Glu Gln Asn Ala
                355                 360                 365

Gly Met Met Gln Ala Glu Pro Gly Asp Met Val Pro Gln Leu Thr Met
            370                 375                 380

Asn Ala Gly Val Leu Thr Cys Ser Pro Gly Ala Pro Cys
385                 390                 395

<210> SEQ ID NO 99
<211> LENGTH: 397
<212> TYPE: PRT
<213> ORGANISM: Ambrosia artemisiifolia

<400> SEQUENCE: 99

Met Gly Ile Lys Gln Cys Cys Tyr Ile Leu Tyr Phe Thr Leu Ala Leu
1               5                   10                  15

Val Ala Leu Leu Gln Pro Val Arg Ser Ala Glu Gly Val Gly Glu Ile
            20                  25                  30

Leu Pro Ser Val Asn Glu Thr Arg Ser Leu Gln Ala Cys Glu Ala Leu
            35                  40                  45

Asn Ile Ile Asp Lys Cys Trp Arg Gly Lys Ala Asp Trp Glu Asn Asn
            50                  55                  60

Arg Gln Ala Leu Ala Asp Cys Ala Gln Gly Phe Ala Lys Gly Thr Tyr
65              70                  75                  80

Gly Gly Lys Trp Gly Asp Val Tyr Thr Val Thr Ser Asn Leu Asp Asp
```

```
                85                  90                  95
Asp Val Ala Asn Pro Lys Glu Gly Thr Leu Arg Phe Ala Ala Ala Gln
                100                 105                 110

Asn Arg Pro Leu Trp Ile Ile Phe Lys Asn Asp Met Val Ile Asn Leu
            115                 120                 125

Asn Gln Glu Leu Val Val Asn Ser Asp Lys Thr Ile Asp Gly Arg Gly
        130                 135                 140

Val Lys Val Glu Ile Ile Asn Gly Gly Leu Thr Leu Met Asn Val Lys
145                 150                 155                 160

Asn Ile Ile Ile His Asn Ile Asn Ile His Asp Val Lys Val Leu Pro
                165                 170                 175

Gly Gly Met Ile Lys Ser Asn Asp Gly Pro Pro Ile Leu Arg Gln Ala
            180                 185                 190

Ser Asp Gly Asp Thr Ile Asn Val Ala Gly Ser Ser Gln Ile Trp Ile
        195                 200                 205

Asp His Cys Ser Leu Ser Lys Ser Phe Asp Gly Leu Val Asp Val Thr
    210                 215                 220

Leu Gly Ser Thr His Val Thr Ile Ser Asn Cys Lys Phe Thr Gln Gln
225                 230                 235                 240

Ser Lys Ala Ile Leu Leu Gly Ala Asp Asp Thr His Val Gln Asp Lys
                245                 250                 255

Gly Met Leu Ala Thr Val Ala Phe Asn Met Phe Thr Asp Asn Val Asp
            260                 265                 270

Gln Arg Met Pro Arg Cys Arg Phe Gly Phe Gln Val Val Asn Asn
        275                 280                 285

Asn Tyr Asp Arg Trp Gly Thr Tyr Ala Ile Gly Gly Ser Ser Ala Pro
    290                 295                 300

Thr Ile Leu Cys Gln Gly Asn Arg Phe Leu Ala Pro Asp Asp Gln Ile
305                 310                 315                 320

Lys Lys Asn Val Leu Ala Arg Thr Gly Thr Gly Ala Ala Glu Ser Met
                325                 330                 335

Ala Trp Asn Trp Arg Ser Asp Lys Asp Leu Leu Glu Asn Gly Ala Ile
            340                 345                 350

Phe Val Thr Ser Gly Ser Asp Pro Val Leu Thr Pro Val Gln Ser Ala
        355                 360                 365

Gly Met Ile Pro Ala Glu Pro Gly Glu Ala Ala Ile Lys Leu Thr Ser
    370                 375                 380

Ser Ala Gly Val Phe Ser Cys His Pro Gly Ala Pro Cys
385                 390                 395

<210> SEQ ID NO 100
<211> LENGTH: 398
<212> TYPE: PRT
<213> ORGANISM: Ambrosia artemisiifolia

<400> SEQUENCE: 100

Met Gly Ile Lys His Cys Cys Tyr Ile Leu Tyr Phe Thr Leu Ala Leu
1               5                   10                  15

Val Thr Leu Leu Gln Pro Val Arg Ser Ala Glu Asp Val Glu Glu Phe
            20                  25                  30

Leu Pro Ser Ala Asn Glu Thr Arg Arg Ser Leu Lys Ala Cys Glu Ala
        35                  40                  45

His Asn Ile Ile Asp Lys Cys Trp Arg Cys Lys Ala Asp Trp Ala Asn
    50                  55                  60

Asn Arg Gln Ala Leu Ala Asp Cys Ala Gln Gly Phe Ala Lys Gly Thr
```

```
                65                  70                  75                  80
Tyr Gly Gly Lys His Gly Asp Val Tyr Thr Val Thr Ser Asp Lys Asp
                    85                  90                  95

Asp Asp Val Ala Asn Pro Lys Glu Gly Thr Leu Arg Phe Ala Ala Ala
                100                 105                 110

Gln Asn Arg Pro Leu Trp Ile Ile Phe Lys Arg Asn Met Val Ile His
            115                 120                 125

Leu Asn Gln Glu Leu Val Val Asn Ser Asp Lys Thr Ile Asp Gly Arg
        130                 135                 140

Gly Val Lys Val Asn Ile Val Asn Ala Gly Leu Thr Leu Met Asn Val
145                 150                 155                 160

Lys Asn Ile Ile Ile His Asn Ile Asn Ile His Asp Ile Lys Val Cys
                165                 170                 175

Pro Gly Gly Met Ile Lys Ser Asn Asp Gly Pro Pro Ile Leu Arg Gln
                180                 185                 190

Gln Ser Asp Gly Asp Ala Ile Asn Val Ala Gly Ser Ser Gln Ile Trp
            195                 200                 205

Ile Asp His Cys Ser Leu Ser Lys Ala Ser Asp Gly Leu Leu Asp Ile
        210                 215                 220

Thr Leu Gly Ser Ser His Val Thr Val Ser Asn Cys Lys Phe Thr Gln
225                 230                 235                 240

His Gln Phe Val Leu Leu Gly Ala Asp Asp Thr His Tyr Gln Asp
                245                 250                 255

Lys Gly Met Leu Ala Thr Val Ala Phe Asn Met Phe Thr Asp His Val
                260                 265                 270

Asp Gln Arg Met Pro Arg Cys Arg Phe Gly Phe Gln Val Val Asn
            275                 280                 285

Asn Asn Tyr Asp Arg Trp Gly Thr Tyr Ala Ile Gly Gly Ser Ser Ala
        290                 295                 300

Pro Thr Ile Leu Ser Gln Gly Asn Arg Phe Phe Ala Pro Asp Asp Ile
305                 310                 315                 320

Ile Lys Lys Asn Val Leu Ala Arg Thr Gly Thr Gly Asn Ala Glu Ser
                325                 330                 335

Met Ser Trp Asn Trp Arg Thr Asp Arg Asp Leu Leu Glu Asn Gly Ala
                340                 345                 350

Ile Phe Leu Pro Ser Gly Ser Asp Pro Val Leu Thr Pro Glu Gln Lys
            355                 360                 365

Ala Gly Met Ile Pro Ala Glu Pro Gly Glu Ala Val Leu Arg Leu Thr
        370                 375                 380

Ser Ser Ala Gly Val Leu Ser Cys His Gln Gly Ala Pro Cys
385                 390                 395

<210> SEQ ID NO 101
<211> LENGTH: 396
<212> TYPE: PRT
<213> ORGANISM: Ambrosia artemisiifolia

<400> SEQUENCE: 101

Met Gly Ile Lys His Cys Cys Tyr Ile Leu Tyr Phe Thr Leu Ala Leu
1               5                   10                  15

Val Thr Leu Leu Gln Pro Val Arg Ser Ala Glu Asp Leu Gln Glu Ile
                20                  25                  30

Leu Pro Val Asn Glu Thr Arg Arg Leu Thr Thr Ser Gly Ala Tyr Asn
            35                  40                  45

Ile Ile Asp Gly Cys Trp Arg Gly Lys Ala Asp Trp Ala Glu Asn Arg
```

```
              50                  55                  60
Lys Ala Leu Ala Asp Cys Ala Gln Gly Phe Gly Lys Gly Thr Val Gly
 65                  70                  75                  80

Gly Lys Asp Gly Asp Ile Tyr Thr Val Thr Ser Glu Leu Asp Asp Asp
                 85                  90                  95

Val Ala Asn Pro Lys Glu Gly Thr Leu Arg Phe Gly Ala Ala Gln Asn
            100                 105                 110

Arg Pro Leu Trp Ile Ile Phe Glu Arg Asp Met Val Ile Arg Leu Asp
        115                 120                 125

Lys Glu Met Val Val Asn Ser Asp Lys Thr Ile Asp Gly Arg Gly Ala
130                 135                 140

Lys Val Glu Ile Ile Asn Ala Gly Phe Thr Leu Asn Gly Val Lys Asn
145                 150                 155                 160

Val Ile Ile His Asn Ile Asn Met His Asp Val Lys Val Asn Pro Gly
                165                 170                 175

Gly Leu Ile Lys Ser Asn Asp Gly Pro Ala Ala Pro Arg Ala Gly Ser
            180                 185                 190

Asp Gly Asp Ala Ile Ser Ile Ser Gly Ser Ser Gln Ile Trp Ile Asp
        195                 200                 205

His Cys Ser Leu Ser Lys Ser Val Asp Gly Leu Val Asp Ala Lys Leu
210                 215                 220

Gly Thr Thr Arg Leu Thr Val Ser Asn Ser Leu Phe Thr Gln His Gln
225                 230                 235                 240

Phe Val Leu Leu Phe Gly Ala Gly Asp Glu Asn Ile Glu Asp Arg Gly
                245                 250                 255

Met Leu Ala Thr Val Ala Phe Asn Thr Phe Thr Asp Asn Val Asp Gln
            260                 265                 270

Arg Met Pro Arg Cys Arg His Gly Phe Phe Gln Val Asn Asn Asn
        275                 280                 285

Tyr Asp Lys Trp Gly Ser Tyr Ala Ile Gly Gly Ser Ala Ser Pro Thr
290                 295                 300

Ile Leu Ser Gln Gly Asn Arg Phe Cys Ala Pro Asp Glu Arg Ser Lys
305                 310                 315                 320

Lys Asn Val Leu Gly Arg His Gly Glu Ala Ala Glu Ser Met Lys
                325                 330                 335

Trp Asn Trp Arg Thr Asn Lys Asp Val Leu Glu Asn Gly Ala Ile Phe
            340                 345                 350

Val Ala Ser Gly Val Asp Pro Val Leu Thr Pro Glu Gln Ser Ala Gly
        355                 360                 365

Met Ile Pro Ala Glu Pro Gly Glu Ser Ala Leu Ser Leu Thr Ser Ser
370                 375                 380

Ala Gly Val Leu Ser Cys Gln Pro Gly Ala Pro Cys
385                 390                 395

<210> SEQ ID NO 102
<211> LENGTH: 373
<212> TYPE: PRT
<213> ORGANISM: Cryptomeria japonica

<400> SEQUENCE: 102

Met Asp Ser Pro Cys Leu Val Ala Leu Leu Val Phe Ser Phe Val Ile
  1               5                  10                  15

Gly Ser Cys Phe Ser Asp Asn Pro Ile Asp Ser Cys Trp Arg Gly Asp
             20                  25                  30

Ser Asn Trp Ala Gln Asn Arg Met Lys Leu Ala Asp Cys Ala Val Gly
```

```
                35                  40                  45
Phe Gly Ser Ser Thr Met Gly Gly Lys Gly Gly Asp Leu Tyr Thr Val
 50                  55                  60

Thr Asn Ser Asp Asp Asp Pro Val Asn Pro Pro Gly Thr Leu Arg Tyr
 65                  70                  75                  80

Gly Ala Thr Arg Asp Arg Pro Leu Trp Ile Ile Phe Ser Gly Asn Met
                 85                  90                  95

Asn Ile Lys Leu Lys Met Pro Met Tyr Ile Ala Gly Tyr Lys Thr Phe
            100                 105                 110

Asp Gly Arg Gly Ala Gln Val Tyr Ile Gly Asn Gly Gly Pro Cys Val
            115                 120                 125

Phe Ile Lys Arg Val Ser Asn Val Ile His Gly Leu Tyr Leu Tyr
130                 135                 140

Gly Cys Ser Thr Ser Val Leu Gly Asn Val Leu Ile Asn Glu Ser Phe
145                 150                 155                 160

Gly Val Glu Pro Val His Pro Gln Asp Gly Asp Ala Leu Thr Leu Arg
                165                 170                 175

Thr Ala Thr Asn Ile Trp Ile Asp His Asn Ser Phe Ser Asn Ser Ser
            180                 185                 190

Asp Gly Leu Val Asp Val Thr Leu Thr Ser Thr Gly Val Thr Ile Ser
            195                 200                 205

Asn Asn Leu Phe Phe Asn His Lys Val Met Ser Leu Gly His Asp
210                 215                 220

Asp Ala Tyr Ser Asp Asp Lys Ser Met Lys Val Thr Val Ala Phe Asn
225                 230                 235                 240

Gln Phe Gly Pro Asn Cys Gly Gln Arg Met Pro Arg Ala Arg Tyr Gly
                245                 250                 255

Leu Val His Val Ala Asn Asn Tyr Asp Pro Trp Thr Ile Tyr Ala
            260                 265                 270

Ile Gly Gly Ser Ser Asn Pro Thr Ile Leu Ser Glu Gly Asn Ser Phe
            275                 280                 285

Thr Ala Pro Asn Glu Ser Tyr Lys Lys Gln Val Thr Ile Arg Ile Gly
290                 295                 300

Cys Lys Thr Ser Ser Ser Cys Ser Asn Trp Val Trp Gln Ser Thr Gln
305                 310                 315                 320

Asp Val Phe Tyr Asn Gly Ala Tyr Phe Val Ser Ser Gly Lys Tyr Glu
                325                 330                 335

Gly Gly Asn Ile Tyr Thr Lys Leu Glu Ala Phe Asn Val Glu Asn Gly
            340                 345                 350

Asn Ala Thr Pro His Leu Thr Gln Asn Ala Gly Val Leu Thr Cys Ser
            355                 360                 365

Leu Ser Lys Arg Cys
    370

<210> SEQ ID NO 103
<211> LENGTH: 374
<212> TYPE: PRT
<213> ORGANISM: Cryptomeria japonica

<400> SEQUENCE: 103

Met Asp Ser Pro Cys Leu Val Ala Leu Leu Val Leu Ser Phe Val Ile
 1               5                  10                  15

Gly Ser Cys Phe Ser Asp Asn Pro Ile Asp Ser Cys Trp Arg Gly Asp
             20                  25                  30

Ser Asn Trp Ala Gln Asn Arg Met Lys Leu Ala Asp Cys Ala Val Gly
```

```
              35                  40                  45
Phe Gly Ser Ser Thr Met Gly Gly Lys Gly Gly Asp Leu Tyr Thr Val
 50                  55                  60

Thr Asn Ser Asp Asp Asp Pro Val Asn Pro Ala Pro Gly Thr Leu Arg
 65                  70                  75                  80

Tyr Gly Ala Thr Arg Asp Arg Pro Leu Trp Ile Ile Phe Ser Gly Asn
                 85                  90                  95

Met Asn Ile Lys Leu Lys Met Pro Met Tyr Ile Ala Gly Tyr Lys Thr
            100                 105                 110

Phe Asp Gly Arg Gly Ala Gln Val Tyr Ile Gly Asn Gly Pro Cys
        115                 120                 125

Val Phe Ile Lys Arg Val Ser Asn Val Ile Ile His Gly Leu His Leu
        130                 135                 140

Tyr Gly Cys Ser Thr Ser Val Leu Gly Asn Val Leu Ile Asn Glu Ser
145                 150                 155                 160

Phe Gly Val Glu Pro Val His Pro Gln Asp Gly Asp Ala Leu Thr Leu
                165                 170                 175

Arg Thr Ala Thr Asn Ile Trp Ile Asp His Asn Ser Phe Ser Asn Ser
            180                 185                 190

Ser Asp Gly Leu Val Asp Val Thr Leu Ser Ser Thr Gly Val Thr Ile
        195                 200                 205

Ser Asn Asn Leu Phe Phe Asn His His Lys Val Met Leu Leu Gly His
        210                 215                 220

Asp Asp Ala Tyr Ser Asp Asp Lys Ser Met Lys Val Thr Val Ala Phe
225                 230                 235                 240

Asn Gln Phe Gly Pro Asn Cys Gly Gln Arg Met Pro Arg Ala Arg Tyr
                245                 250                 255

Gly Leu Val His Val Ala Asn Asn Tyr Asp Pro Trp Thr Ile Tyr
            260                 265                 270

Ala Ile Gly Gly Ser Ser Asn Pro Thr Ile Leu Ser Glu Gly Asn Ser
        275                 280                 285

Phe Thr Ala Pro Asn Glu Ser Tyr Lys Lys Gln Val Thr Ile Arg Ile
290                 295                 300

Gly Cys Lys Thr Ser Ser Ser Cys Ser Asn Trp Val Trp Gln Ser Thr
305                 310                 315                 320

Gln Asp Val Phe Tyr Asn Gly Ala Tyr Phe Val Ser Ser Gly Lys Tyr
                325                 330                 335

Glu Gly Gly Asn Ile Tyr Thr Lys Lys Glu Ala Phe Asn Val Glu Asn
            340                 345                 350

Gly Asn Ala Thr Pro Gln Leu Thr Lys Asn Ala Gly Val Leu Thr Cys
        355                 360                 365

Ser Leu Ser Lys Arg Cys
        370

<210> SEQ ID NO 104
<211> LENGTH: 514
<212> TYPE: PRT
<213> ORGANISM: Cryptomeria japonica

<400> SEQUENCE: 104

Met Ala Met Lys Leu Ile Ala Pro Met Ala Phe Leu Ala Met Gln Leu
  1               5                  10                  15

Ile Ile Met Ala Ala Ala Glu Asp Gln Ser Ala Gln Ile Met Leu Asp
             20                  25                  30

Ser Val Val Glu Lys Tyr Leu Arg Ser Asn Arg Ser Leu Arg Lys Val
```

```
                    35                  40                  45
Glu His Ser Arg His Asp Ala Ile Asn Ile Phe Asn Val Glu Lys Tyr
 50                  55                  60
Gly Ala Val Gly Asp Gly Lys His Asp Cys Thr Glu Ala Phe Ser Thr
 65                  70                  75                  80
Ala Trp Gln Ala Ala Cys Lys Asn Pro Ser Ala Met Leu Leu Val Pro
                     85                  90                  95
Gly Ser Lys Lys Phe Val Val Asn Leu Phe Asn Gly Pro Cys
                100                 105                 110
Gln Pro His Phe Thr Phe Lys Val Asp Gly Ile Ile Ala Ala Tyr Gln
                115                 120                 125
Asn Pro Ala Ser Trp Lys Asn Arg Ile Trp Leu Gln Phe Ala Lys
                130                 135                 140
Leu Thr Gly Phe Thr Leu Met Gly Lys Gly Val Ile Asp Gly Gln Gly
145                 150                 155                 160
Lys Gln Trp Trp Ala Gly Gln Cys Lys Trp Val Asn Gly Arg Glu Ile
                    165                 170                 175
Cys Asn Asp Arg Asp Arg Pro Thr Ala Ile Lys Phe Asp Phe Ser Thr
                180                 185                 190
Gly Leu Ile Ile Gln Gly Leu Lys Leu Met Asn Ser Pro Glu Phe His
                195                 200                 205
Leu Val Phe Gly Asn Cys Glu Gly Val Lys Ile Ile Gly Ile Ser Ile
                210                 215                 220
Thr Ala Pro Arg Asp Ser Pro Asn Thr Asp Gly Ile Asp Ile Phe Ala
225                 230                 235                 240
Ser Lys Asn Phe His Leu Gln Lys Asn Thr Ile Gly Thr Gly Asp Asp
                    245                 250                 255
Cys Val Ala Ile Gly Thr Gly Ser Ser Asn Ile Val Ile Glu Asp Leu
                260                 265                 270
Ile Cys Gly Pro Gly His Gly Ile Ser Ile Gly Ser Leu Gly Arg Glu
                275                 280                 285
Asn Ser Arg Ala Glu Val Ser Tyr Val His Val Asn Gly Ala Lys Phe
290                 295                 300
Ile Asp Thr Gln Asn Gly Leu Arg Ile Lys Thr Trp Gln Gly Gly Ser
305                 310                 315                 320
Gly Met Ala Ser His Ile Ile Tyr Glu Asn Val Glu Met Ile Asn Ser
                    325                 330                 335
Glu Asn Pro Ile Leu Ile Asn Gln Phe Tyr Cys Thr Ser Ala Ser Ala
                340                 345                 350
Cys Gln Asn Gln Arg Ser Ala Val Gln Ile Gln Asp Val Thr Tyr Lys
                355                 360                 365
Asn Ile Arg Gly Thr Ser Ala Thr Ala Ala Ile Gln Leu Lys Cys
                370                 375                 380
Ser Asp Ser Met Pro Cys Lys Asp Ile Lys Leu Ser Asp Ile Ser Leu
385                 390                 395                 400
Lys Leu Thr Ser Gly Lys Ile Ala Ser Cys Leu Asn Asp Asn Ala Asn
                    405                 410                 415
Gly Tyr Phe Ser Gly His Val Ile Pro Ala Cys Lys Asn Leu Ser Pro
                420                 425                 430
Ser Ala Lys Arg Lys Glu Ser Lys Ser His Lys His Pro Lys Thr Val
                435                 440                 445
Met Val Glu Asn Met Arg Ala Tyr Asp Lys Gly Asn Arg Thr Arg Ile
450                 455                 460
```

```
Leu Leu Gly Ser Arg Pro Pro Asn Cys Thr Asn Lys Cys His Gly Cys
465                 470                 475                 480

Ser Pro Cys Lys Ala Lys Leu Val Ile Val His Arg Ile Met Pro Gln
                485                 490                 495

Glu Tyr Tyr Pro Gln Arg Trp Ile Cys Ser Cys His Gly Lys Ile Tyr
            500                 505                 510

His Pro

<210> SEQ ID NO 105
<211> LENGTH: 514
<212> TYPE: PRT
<213> ORGANISM: Cryptomeria japonica

<400> SEQUENCE: 105

Met Ala Met Lys Phe Ile Ala Pro Met Ala Phe Val Ala Met Gln Leu
1               5                   10                  15

Ile Ile Met Ala Ala Ala Glu Asp Gln Ser Ala Gln Ile Met Leu Asp
                20                  25                  30

Ser Asp Ile Glu Gln Tyr Leu Arg Ser Asn Arg Ser Leu Arg Lys Val
            35                  40                  45

Glu His Ser Arg His Asp Ala Ile Asn Ile Phe Asn Val Glu Lys Tyr
        50                  55                  60

Gly Ala Val Gly Asp Gly Lys His Asp Cys Thr Glu Ala Phe Ser Thr
65                  70                  75                  80

Ala Trp Gln Ala Ala Cys Lys Lys Pro Ser Ala Met Leu Leu Val Pro
                85                  90                  95

Gly Asn Lys Lys Phe Val Val Asn Asn Leu Phe Phe Asn Gly Pro Cys
                100                 105                 110

Gln Pro His Phe Thr Phe Lys Val Asp Gly Ile Ile Ala Ala Tyr Gln
            115                 120                 125

Asn Pro Ala Ser Trp Lys Asn Asn Arg Ile Trp Leu Gln Phe Ala Lys
130                 135                 140

Leu Thr Gly Phe Thr Leu Met Gly Lys Gly Val Ile Asp Gly Gln Gly
145                 150                 155                 160

Lys Gln Trp Trp Ala Gly Gln Cys Lys Trp Val Asn Gly Arg Glu Ile
                165                 170                 175

Cys Asn Asp Arg Asp Arg Pro Thr Ala Ile Lys Phe Asp Phe Ser Thr
            180                 185                 190

Gly Leu Ile Ile Gln Gly Leu Lys Leu Met Asn Ser Pro Glu Phe His
        195                 200                 205

Leu Val Phe Gly Asn Cys Glu Gly Val Lys Ile Ile Gly Ile Ser Ile
    210                 215                 220

Thr Ala Pro Arg Asp Ser Pro Asn Thr Asp Gly Ile Asp Ile Phe Ala
225                 230                 235                 240

Ser Lys Asn Phe His Leu Gln Lys Asn Thr Ile Gly Thr Gly Asp Asp
                245                 250                 255

Cys Val Ala Ile Gly Thr Gly Ser Ser Asn Ile Val Ile Glu Asp Leu
            260                 265                 270

Ile Cys Gly Pro Gly His Gly Ile Ser Ile Gly Ser Leu Gly Arg Glu
        275                 280                 285

Asn Ser Arg Ala Glu Val Ser Tyr Val His Val Asn Gly Ala Lys Phe
    290                 295                 300

Ile Asp Thr Gln Asn Gly Leu Arg Ile Lys Thr Trp Gln Gly Gly Ser
305                 310                 315                 320

Gly Met Ala Ser His Ile Ile Tyr Glu Asn Val Glu Met Ile Asn Ser
```

```
                    325                 330                 335
Glu Asn Pro Ile Leu Ile Asn Gln Phe Tyr Cys Thr Ser Ala Ser Ala
                340                 345                 350

Cys Gln Asn Gln Arg Ser Ala Val Gln Ile Gln Asp Val Thr Tyr Lys
            355                 360                 365

Asn Ile Arg Gly Thr Ser Ala Thr Ala Ala Ile Gln Leu Lys Cys
        370                 375                 380

Ser Asp Ser Met Pro Cys Lys Asp Ile Lys Leu Ser Asp Ile Ser Leu
385                 390                 395                 400

Lys Leu Thr Ser Gly Lys Ile Ala Ser Cys Leu Asn Asp Asn Ala Asn
                405                 410                 415

Gly Tyr Phe Ser Gly His Val Ile Pro Ala Cys Lys Asn Leu Ser Pro
            420                 425                 430

Ser Ala Lys Arg Lys Glu Ser Lys Ser His Lys His Pro Lys Thr Val
        435                 440                 445

Met Val Lys Asn Met Gly Ala Tyr Asp Lys Gly Asn Arg Thr Arg Ile
    450                 455                 460

Leu Leu Gly Ser Arg Pro Pro Asn Cys Thr Asn Lys Cys His Gly Cys
465                 470                 475                 480

Ser Pro Cys Lys Ala Lys Leu Val Ile Val His Arg Ile Met Pro Gln
                485                 490                 495

Glu Tyr Tyr Pro Gln Arg Trp Met Cys Ser Arg His Gly Lys Ile Tyr
            500                 505                 510

His Pro

<210> SEQ ID NO 106
<211> LENGTH: 373
<212> TYPE: PRT
<213> ORGANISM: Cryptomeria japonica

<400> SEQUENCE: 106

Met Asp Ser Pro Cys Leu Val Ala Leu Leu Val Leu Ser Phe Val Ile
1               5                   10                  15

Gly Ser Cys Phe Ser Asp Asn Pro Ile Asp Ser Cys Trp Arg Gly Asp
            20                  25                  30

Ser Asn Trp Ala Gln Asn Arg Met Lys Leu Ala Asp Cys Ala Val Gly
        35                  40                  45

Phe Gly Ser Ser Thr Met Gly Lys Gly Gly Asp Leu Tyr Thr Val
    50                  55                  60

Thr Asn Ser Asp Asp Pro Val Asn Pro Gly Thr Leu Arg Tyr
65                  70                  75                  80

Gly Ala Thr Arg Asp Arg Pro Leu Trp Ile Ile Phe Ser Gly Asn Met
                85                  90                  95

Asn Ile Lys Leu Lys Met Pro Met Tyr Ile Ala Gly Tyr Lys Thr Phe
            100                 105                 110

Asp Gly Arg Gly Ala Gln Val Tyr Ile Gly Asn Gly Gly Pro Cys Val
        115                 120                 125

Phe Ile Lys Arg Val Ser Asn Val Ile Ile His Gly Leu His Leu Tyr
    130                 135                 140

Gly Cys Ser Thr Ser Val Leu Gly Asn Val Leu Ile Asn Glu Ser Phe
145                 150                 155                 160

Gly Val Glu Pro Val His Pro Gln Asp Gly Asp Ala Leu Thr Leu Arg
                165                 170                 175

Thr Ala Thr Asn Ile Trp Ile Asp His Asn Ser Phe Ser Asn Ser Ser
            180                 185                 190
```

```
Asp Gly Leu Val Asp Val Thr Leu Ser Ser Thr Gly Val Thr Ile Ser
            195                 200                 205

Asn Asn Leu Phe Phe Asn His His Lys Val Met Leu Leu Gly His Asp
        210                 215                 220

Asp Ala Tyr Ser Asp Asp Lys Ser Met Lys Val Thr Val Ala Phe Asn
225                 230                 235                 240

Gln Phe Gly Pro Asn Cys Gly Gln Arg Met Pro Arg Ala Arg Tyr Gly
            245                 250                 255

Leu Val His Val Ala Asn Asn Tyr Asp Pro Trp Thr Ile Tyr Ala
            260                 265                 270

Ile Gly Gly Ser Ser Asn Pro Thr Ile Leu Ser Glu Gly Asn Ser Phe
            275                 280                 285

Thr Ala Pro Asn Glu Ser Tyr Lys Lys Gln Val Thr Ile Arg Ile Gly
            290                 295                 300

Cys Lys Thr Ser Ser Cys Ser Asn Trp Val Trp Gln Ser Thr Gln
305                 310                 315                 320

Asp Val Phe Tyr Asn Gly Ala Tyr Phe Val Ser Ser Gly Lys Tyr Glu
            325                 330                 335

Gly Gly Asn Ile Tyr Thr Lys Lys Glu Ala Phe Asn Val Glu Asn Gly
            340                 345                 350

Asn Ala Thr Pro Gln Leu Thr Lys Asn Ala Gly Val Leu Thr Cys Ser
            355                 360                 365

Leu Ser Lys Arg Cys
            370

<210> SEQ ID NO 107
<211> LENGTH: 374
<212> TYPE: PRT
<213> ORGANISM: Cryptomeria japonica

<400> SEQUENCE: 107

Met Asp Ser Pro Cys Leu Val Ala Leu Leu Val Phe Ser Phe Val Ile
1               5                   10                  15

Gly Ser Cys Phe Ser Asp Asn Pro Ile Asp Ser Cys Trp Arg Gly Asp
            20                  25                  30

Ser Asn Trp Ala Gln Asn Arg Met Lys Leu Ala Asp Cys Ala Val Gly
        35                  40                  45

Phe Gly Ser Ser Thr Met Gly Lys Gly Gly Asp Leu Tyr Thr Val
    50                  55                  60

Thr Asn Ser Asp Asp Pro Val Asn Pro Ala Pro Gly Thr Leu Arg
65                  70                  75                  80

Tyr Gly Ala Thr Arg Asp Arg Pro Leu Trp Ile Ile Phe Ser Gly Asn
            85                  90                  95

Met Asn Ile Lys Leu Lys Met Pro Met Tyr Ile Ala Gly Tyr Lys Thr
            100                 105                 110

Phe Asp Gly Arg Gly Ala Gln Val Tyr Ile Gly Asn Gly Gly Pro Cys
        115                 120                 125

Val Phe Ile Lys Arg Val Ser Asn Val Ile Ile His Gly Leu Tyr Leu
    130                 135                 140

Tyr Gly Cys Ser Thr Ser Val Leu Gly Asn Val Leu Ile Asn Glu Ser
145                 150                 155                 160

Phe Gly Val Glu Pro Val His Pro Gln Asp Gly Asp Ala Leu Thr Leu
            165                 170                 175

Arg Thr Ala Thr Asn Ile Trp Ile Asp His Asn Ser Phe Ser Asn Ser
            180                 185                 190
```

```
Ser Asp Gly Leu Val Asp Val Thr Leu Thr Ser Thr Gly Val Thr Ile
        195                 200                 205

Ser Asn Asn Leu Phe Phe Asn His His Lys Val Met Ser Leu Gly His
        210                 215                 220

Asp Asp Ala Tyr Ser Asp Lys Ser Met Lys Val Thr Val Ala Phe
225                 230                 235                 240

Asn Gln Phe Gly Pro Asn Cys Gly Gln Arg Met Pro Arg Ala Arg Tyr
        245                 250                 255

Gly Leu Val His Val Ala Asn Asn Tyr Asp Pro Trp Thr Ile Tyr
        260                 265                 270

Ala Ile Gly Gly Ser Ser Asn Pro Thr Ile Leu Ser Glu Gly Asn Ser
        275                 280                 285

Phe Thr Ala Pro Asn Glu Ser Tyr Lys Lys Gln Val Thr Ile Arg Ile
        290                 295                 300

Gly Cys Lys Thr Ser Ser Ser Cys Ser Asn Trp Val Trp Gln Ser Thr
305                 310                 315                 320

Gln Asp Val Phe Tyr Asn Gly Ala Tyr Phe Ser Ser Gly Lys Tyr
        325                 330                 335

Glu Gly Gly Asn Ile Tyr Thr Lys Lys Glu Ala Phe Asn Val Glu Asn
        340                 345                 350

Gly Asn Ala Thr Pro His Leu Thr Gln Asn Ala Gly Val Leu Thr Cys
        355                 360                 365

Ser Leu Ser Lys Arg Cys
        370

<210> SEQ ID NO 108
<211> LENGTH: 174
<212> TYPE: PRT
<213> ORGANISM: Canis familiaris

<400> SEQUENCE: 108

Met Lys Thr Leu Leu Thr Ile Gly Phe Ser Leu Ile Ala Ile Leu
1               5                   10                  15

Gln Ala Gln Asp Thr Pro Ala Leu Gly Lys Asp Thr Val Ala Val Ser
                20                  25                  30

Gly Lys Trp Tyr Leu Lys Ala Met Thr Ala Asp Gln Glu Val Pro Glu
        35                  40                  45

Lys Pro Asp Ser Val Thr Pro Met Ile Leu Lys Ala Gln Lys Gly Gly
    50                  55                  60

Asn Leu Glu Ala Lys Ile Thr Met Leu Thr Asn Gly Gln Cys Gln Asn
65                  70                  75                  80

Ile Thr Val Val Leu His Lys Thr Ser Glu Pro Gly Lys Tyr Thr Ala
                85                  90                  95

Tyr Glu Gly Gln Arg Val Val Phe Ile Gln Pro Ser Pro Val Arg Asp
                100                 105                 110

His Tyr Ile Leu Tyr Cys Glu Gly Glu Leu His Gly Arg Gln Ile Arg
        115                 120                 125

Met Ala Lys Leu Leu Gly Arg Asp Pro Glu Gln Ser Gln Glu Ala Leu
    130                 135                 140

Glu Asp Phe Arg Glu Phe Ser Arg Ala Lys Gly Leu Asn Gln Glu Ile
145                 150                 155                 160

Leu Glu Leu Ala Gln Ser Glu Thr Cys Ser Pro Gly Gly Gln
                165                 170

<210> SEQ ID NO 109
```

```
<211> LENGTH: 24
<212> TYPE: PRT
<213> ORGANISM: Canis familiaris

<400> SEQUENCE: 109

Glu Ala Tyr Lys Ser Glu Ile Ala His Arg Tyr Asn Asp Leu Gly Glu
1               5                   10                  15

Glu His Phe Arg Gly Leu Val Leu
            20

<210> SEQ ID NO 110
<211> LENGTH: 265
<212> TYPE: PRT
<213> ORGANISM: Canis familiaris

<400> SEQUENCE: 110

Leu Ser Ser Ala Lys Glu Arg Phe Lys Cys Ala Ser Leu Gln Lys Phe
1               5                   10                  15

Gly Asp Arg Ala Phe Lys Ala Trp Ser Val Ala Arg Leu Ser Gln Arg
            20                  25                  30

Phe Pro Lys Ala Asp Phe Ala Glu Ile Ser Lys Val Val Thr Asp Leu
        35                  40                  45

Thr Lys Val His Lys Glu Cys Cys His Gly Asp Leu Leu Glu Cys Ala
50                  55                  60

Asp Asp Arg Ala Asp Leu Ala Lys Tyr Met Cys Glu Asn Gln Asp Ser
65                  70                  75                  80

Ile Ser Thr Lys Leu Lys Glu Cys Cys Asp Lys Pro Val Leu Glu Lys
                85                  90                  95

Ser Gln Cys Leu Ala Glu Val Glu Arg Asp Glu Leu Pro Gly Asp Leu
            100                 105                 110

Pro Ser Leu Ala Ala Asp Phe Val Glu Asp Lys Glu Val Cys Lys Asn
        115                 120                 125

Tyr Gln Glu Ala Lys Asp Val Phe Leu Gly Thr Phe Leu Tyr Glu Tyr
    130                 135                 140

Ser Arg Arg His Pro Glu Tyr Ser Val Ser Leu Leu Leu Arg Leu Ala
145                 150                 155                 160

Lys Glu Tyr Glu Ala Thr Leu Glu Lys Cys Cys Ala Thr Asp Asp Pro
                165                 170                 175

Pro Thr Cys Tyr Ala Lys Val Leu Asp Glu Phe Lys Pro Leu Val Asp
            180                 185                 190

Glu Pro Gln Asn Leu Val Lys Thr Asn Cys Glu Leu Phe Glu Lys Leu
        195                 200                 205

Gly Glu Tyr Gly Phe Gln Asn Ala Leu Leu Val Arg Tyr Thr Lys Lys
    210                 215                 220

Ala Pro Gln Val Ser Thr Pro Thr Leu Val Val Glu Val Ser Arg Lys
225                 230                 235                 240

Leu Gly Lys Val Gly Thr Lys Cys Cys Lys Lys Pro Glu Ser Glu Arg
                245                 250                 255

Met Ser Cys Ala Asp Asp Phe Leu Ser
            260                 265

<210> SEQ ID NO 111
<211> LENGTH: 180
<212> TYPE: PRT
<213> ORGANISM: Canis familiaris

<400> SEQUENCE: 111

Met Gln Leu Leu Leu Leu Thr Val Gly Leu Ala Leu Ile Cys Gly Leu
```

```
  1               5                   10                  15
Gln Ala Gln Glu Gly Asn His Glu Pro Gln Gly Gly Leu Glu Glu
                20                  25                  30

Leu Ser Gly Arg Trp His Ser Val Ala Leu Ala Ser Asn Lys Ser Asp
            35                  40                  45

Leu Ile Lys Pro Trp Gly His Phe Arg Val Phe Ile His Ser Met Ser
 50                  55                  60

Ala Lys Asp Gly Asn Leu His Gly Asp Ile Leu Ile Pro Gln Asp Gly
 65                  70                  75                  80

Gln Cys Glu Lys Val Ser Leu Thr Ala Phe Lys Thr Ala Thr Ser Asn
                85                  90                  95

Lys Phe Asp Leu Glu Tyr Trp Gly His Asn Asp Leu Tyr Leu Ala Glu
                100                 105                 110

Val Asp Pro Lys Ser Tyr Leu Ile Leu Tyr Met Ile Asn Gln Tyr Asn
                115                 120                 125

Asp Asp Thr Ser Leu Val Ala His Leu Met Val Arg Asp Leu Ser Arg
                130                 135                 140

Gln Gln Asp Phe Leu Pro Ala Phe Glu Ser Val Cys Glu Asp Ile Gly
145                 150                 155                 160

Leu His Lys Asp Gln Ile Val Val Leu Ser Asp Asp Arg Cys Gln
                165                 170                 175

Gly Ser Arg Asp
                180

<210> SEQ ID NO 112
<211> LENGTH: 187
<212> TYPE: PRT
<213> ORGANISM: Equus caballus

<400> SEQUENCE: 112

Met Lys Leu Leu Leu Leu Cys Leu Gly Leu Ile Leu Val Cys Ala Gln
 1               5                   10                  15

Gln Glu Glu Asn Ser Asp Val Ala Ile Arg Asn Phe Asp Ile Ser Lys
                20                  25                  30

Ile Ser Gly Glu Trp Tyr Ser Ile Phe Leu Ala Ser Asp Val Lys Glu
            35                  40                  45

Lys Ile Glu Glu Asn Gly Ser Met Arg Val Phe Val Asp Val Ile Arg
 50                  55                  60

Ala Leu Asp Asn Ser Ser Leu Tyr Ala Glu Tyr Gln Thr Lys Val Asn
 65                  70                  75                  80

Gly Glu Cys Thr Glu Phe Pro Met Val Phe Asp Lys Thr Glu Glu Asp
                85                  90                  95

Gly Val Tyr Ser Leu Asn Tyr Asp Gly Tyr Asn Val Phe Arg Ile Ser
                100                 105                 110

Glu Phe Glu Asn Asp Glu His Ile Ile Leu Tyr Leu Val Asn Phe Asp
                115                 120                 125

Lys Asp Arg Pro Phe Gln Leu Phe Glu Phe Tyr Ala Arg Glu Pro Asp
                130                 135                 140

Val Ser Pro Glu Ile Lys Glu Glu Phe Val Lys Ile Val Gln Lys Arg
145                 150                 155                 160

Gly Ile Val Lys Glu Asn Ile Ile Asp Leu Thr Lys Ile Asp Arg Cys
                165                 170                 175

Phe Gln Leu Arg Gly Asn Gly Val Ala Gln Ala
                180                 185
```

```
<210> SEQ ID NO 113
<211> LENGTH: 29
<212> TYPE: PRT
<213> ORGANISM: Equus caballus
<220> FEATURE:
<221> NAME/KEY: misc_feature
<222> LOCATION: (3)..(3)
<223> OTHER INFORMATION: unknown or other
<220> FEATURE:
<221> NAME/KEY: misc_feature
<222> LOCATION: (28)..(28)
<223> OTHER INFORMATION: unknown or other

<400> SEQUENCE: 113

Ser Gln Xaa Pro Gln Ser Glu Thr Asp Tyr Ser Gln Leu Ser Gly Glu
1               5                   10                  15

Trp Asn Thr Ile Tyr Gly Ala Ala Ser Asn Ile Xaa Lys
            20                  25

<210> SEQ ID NO 114
<211> LENGTH: 211
<212> TYPE: PRT
<213> ORGANISM: Euroglyphus maynei

<400> SEQUENCE: 114

Thr Tyr Ala Cys Ser Ile Asn Ser Val Ser Leu Pro Ser Glu Leu Asp
1               5                   10                  15

Leu Arg Ser Leu Arg Thr Val Thr Pro Ile Arg Met Gln Gly Gly Cys
            20                  25                  30

Gly Ser Cys Trp Ala Phe Ser Gly Val Ala Ser Thr Glu Ser Ala Tyr
        35                  40                  45

Leu Ala Tyr Arg Asn Met Ser Leu Asp Leu Ala Glu Gln Glu Leu Val
    50                  55                  60

Asp Cys Ala Ser Gln Asn Gly Cys His Gly Asp Thr Ile Pro Arg Gly
65                  70                  75                  80

Ile Glu Tyr Ile Gln Gln Asn Gly Val Val Gln Glu His Tyr Tyr Pro
                85                  90                  95

Tyr Val Ala Arg Glu Gln Ser Cys His Arg Pro Asn Ala Gln Arg Tyr
            100                 105                 110

Gly Leu Lys Asn Tyr Cys Gln Ile Ser Pro Pro Asp Ser Asn Lys Ile
        115                 120                 125

Arg Gln Ala Leu Thr Gln Thr His Thr Ala Val Ala Val Ile Ile Gly
    130                 135                 140

Ile Lys Asp Leu Asn Ala Phe Arg His Tyr Asp Gly Arg Thr Ile Met
145                 150                 155                 160

Gln His Asp Asn Gly Tyr Gln Pro Asn Tyr His Ala Val Asn Ile Val
                165                 170                 175

Gly Tyr Gly Asn Thr Gln Gly Val Asp Tyr Trp Ile Val Arg Asn Ser
            180                 185                 190

Trp Asp Thr Thr Trp Gly Asp Asn Gly Tyr Gly Tyr Phe Ala Ala Asn
        195                 200                 205

Ile Asn Leu
    210

<210> SEQ ID NO 115
<211> LENGTH: 211
<212> TYPE: PRT
<213> ORGANISM: Euroglyphus maynei

<400> SEQUENCE: 115

Thr Tyr Ala Cys Ser Ile Asn Ser Val Ser Leu Pro Ser Glu Leu Asp
```

```
                1               5                   10                  15
Leu Arg Ser Leu Arg Thr Val Thr Pro Ile Arg Met Gln Gly Gly Cys
                20                  25                  30

Gly Ser Cys Trp Ala Phe Ser Gly Val Ala Ser Thr Glu Ser Ala Tyr
                35                  40                  45

Leu Ala Tyr Arg Asn Met Ser Leu Asp Leu Ala Glu Gln Glu Leu Val
                50                  55                  60

Asp Cys Ala Ser Gln Asn Gly Cys His Gly Asp Thr Ile Pro Arg Gly
65                  70                  75                  80

Ile Glu Tyr Ile Gln Gln Asn Gly Val Val Gln Glu His Tyr Tyr Pro
                85                  90                  95

Tyr Val Ala Arg Glu Gln Ser Cys His Arg Pro Asn Ala Gln Arg Tyr
                100                 105                 110

Gly Leu Lys Asn Tyr Cys Gln Ile Ser Pro Pro Asp Ser Asn Lys Ile
                115                 120                 125

Arg Gln Ala Leu Thr Gln Thr His Thr Ala Val Ala Val Ile Ile Gly
                130                 135                 140

Ile Lys Asp Leu Asn Ala Phe Arg His Tyr Asp Gly Arg Thr Ile Met
145                 150                 155                 160

Gln His Asp Asn Gly Tyr Gln Pro Asn Tyr His Ala Val Asn Ile Val
                165                 170                 175

Gly Tyr Gly Asn Thr Gln Gly Val Asp Tyr Trp Ile Val Arg Asn Ser
                180                 185                 190

Trp Asp Thr Thr Trp Gly Asp Asn Gly Tyr Gly Tyr Phe Ala Ala Asn
                195                 200                 205

Ile Asn Leu
        210

<210> SEQ ID NO 116
<211> LENGTH: 211
<212> TYPE: PRT
<213> ORGANISM: Euroglyphus maynei

<400> SEQUENCE: 116

Glu Thr Asn Ala Cys Ser Ile Asn Gly Asn Ala Pro Ala Glu Ile Asp
1               5                   10                  15

Leu Arg Gln Met Arg Thr Val Thr Pro Ile Arg Met Gln Gly Gly Cys
                20                  25                  30

Gly Ser Cys Trp Ala Phe Ser Gly Val Ala Ala Thr Glu Ser Ala Tyr
                35                  40                  45

Leu Ala Tyr Arg Asn Gln Ser Leu Asp Leu Ala Glu Gln Glu Leu Val
                50                  55                  60

Asp Cys Ala Ser Gln His Gly Cys His Gly Asp Thr Ile Pro Arg Gly
65                  70                  75                  80

Ile Glu Tyr Ile Gln His Asn Gly Val Val Gln Glu Ser Tyr Tyr Arg
                85                  90                  95

Tyr Val Ala Arg Glu Gln Ser Cys Arg Arg Pro Asn Ala Gln Arg Phe
                100                 105                 110

Gly Ile Ser Asn Tyr Cys Gln Ile Tyr Pro Pro Asn Ala Asn Lys Ile
                115                 120                 125

Arg Glu Ala Leu Ala Gln Thr His Ser Ala Ile Ala Val Ile Ile Gly
                130                 135                 140

Ile Lys Asp Leu Asp Ala Phe Arg His Tyr Asp Gly Arg Thr Ile Ile
145                 150                 155                 160

Gln Arg Asp Asn Gly Tyr Gln Pro Asn Tyr His Ala Val Asn Ile Val
```

```
                       165                 170                 175

Gly Tyr Ser Asn Ala Gln Gly Val Asp Tyr Trp Ile Val Arg Asn Ser
            180                 185                 190

Trp Asp Thr Asn Trp Gly Asp Asn Gly Tyr Gly Tyr Phe Ala Ala Asn
        195                 200                 205

Ile Asp Leu
    210

<210> SEQ ID NO 117
<211> LENGTH: 212
<212> TYPE: PRT
<213> ORGANISM: Euroglyphus maynei

<400> SEQUENCE: 117

Glu Thr Ser Ala Cys Arg Ile Asn Ser Val Asn Val Pro Ser Glu Leu
1               5                  10                  15

Asp Leu Arg Ser Leu Arg Thr Val Thr Pro Ile Arg Met Gln Gly Gly
            20                  25                  30

Cys Gly Ser Cys Trp Ala Phe Ser Gly Val Ala Ala Thr Glu Ser Ala
        35                  40                  45

Tyr Leu Ala Tyr Arg Asn Thr Ser Leu Asp Leu Ser Glu Gln Glu Leu
    50                  55                  60

Val Asp Cys Ala Ser Gln His Gly Cys His Gly Asp Thr Ile Pro Arg
65                  70                  75                  80

Gly Ile Glu Tyr Ile Gln Gln Asn Gly Val Val Glu Glu Arg Ser Tyr
                85                  90                  95

Pro Tyr Val Ala Arg Glu Gln Gln Cys Arg Arg Pro Asn Ser Gln His
            100                 105                 110

Tyr Gly Ile Ser Asn Tyr Cys Gln Ile Tyr Pro Pro Asp Val Lys Gln
        115                 120                 125

Ile Arg Glu Ala Leu Thr Gln Thr His Thr Ala Ile Ala Val Ile Ile
    130                 135                 140

Gly Ile Lys Asp Leu Arg Ala Phe Gln His Tyr Asp Gly Arg Thr Ile
145                 150                 155                 160

Ile Gln His Asp Asn Gly Tyr Gln Pro Asn Tyr His Ala Val Asn Ile
                165                 170                 175

Val Gly Tyr Gly Ser Thr Gln Gly Val Asp Tyr Trp Ile Val Arg Asn
            180                 185                 190

Ser Trp Asp Thr Thr Trp Gly Asp Ser Gly Tyr Gly Tyr Phe Gln Ala
        195                 200                 205

Gly Asn Asn Leu
    210

<210> SEQ ID NO 118
<211> LENGTH: 307
<212> TYPE: PRT
<213> ORGANISM: Poa pratensis

<400> SEQUENCE: 118

Met Ala Val Gln Lys Tyr Thr Val Ala Leu Phe Leu Val Ala Leu Val
1               5                  10                  15

Val Gly Pro Ala Ala Ser Tyr Ala Ala Asp Leu Ser Tyr Gly Ala Pro
            20                  25                  30

Ala Thr Pro Ala Ala Pro Ala Ala Gly Tyr Thr Pro Ala Ala Pro Ala
        35                  40                  45

Gly Ala Ala Pro Lys Ala Thr Thr Asp Glu Gln Lys Met Ile Glu Lys
    50                  55                  60
```

```
Ile Asn Val Gly Phe Lys Ala Ala Val Ala Ala Gly Gly Val Pro
65                  70                  75                  80

Ala Ala Asn Lys Tyr Lys Thr Phe Val Ala Thr Phe Gly Ala Ala Ser
                85                  90                  95

Asn Lys Ala Phe Ala Glu Ala Leu Ser Thr Glu Pro Lys Gly Ala Ala
            100                 105                 110

Val Asp Ser Ser Lys Ala Ala Leu Thr Ser Lys Leu Asp Ala Ala Tyr
            115                 120                 125

Lys Leu Ala Tyr Lys Ser Ala Glu Gly Ala Thr Pro Glu Ala Lys Tyr
            130                 135                 140

Asp Asp Tyr Val Ala Thr Leu Ser Glu Ala Leu Arg Ile Ile Ala Gly
145                 150                 155                 160

Thr Leu Glu Val His Gly Val Lys Pro Ala Ala Glu Glu Val Lys Ala
                165                 170                 175

Thr Pro Ala Gly Glu Leu Gln Val Ile Asp Lys Val Asp Ala Ala Phe
            180                 185                 190

Lys Val Ala Ala Thr Ala Ala Asn Ala Ala Pro Ala Asn Asp Lys Phe
            195                 200                 205

Thr Val Phe Glu Ala Ala Phe Asn Asp Ala Ile Lys Ala Ser Thr Gly
            210                 215                 220

Gly Ala Tyr Gln Ser Tyr Lys Phe Ile Pro Ala Leu Glu Ala Ala Val
225                 230                 235                 240

Lys Gln Ser Tyr Ala Ala Thr Val Ala Thr Ala Pro Ala Val Lys Tyr
            245                 250                 255

Thr Val Phe Glu Thr Ala Leu Lys Lys Ala Ile Thr Ala Met Ser Gln
            260                 265                 270

Ala Gln Lys Ala Ala Lys Pro Ala Ala Ala Thr Gly Thr Ala Thr
            275                 280                 285

Ala Ala Val Gly Ala Ala Thr Gly Ala Ala Thr Ala Ala Ala Gly Gly
            290                 295                 300

Tyr Lys Val
305

<210> SEQ ID NO 119
<211> LENGTH: 333
<212> TYPE: PRT
<213> ORGANISM: Poa pratensis

<400> SEQUENCE: 119

Met Ala Val His Gln Tyr Thr Val Ala Leu Phe Leu Ala Val Ala Leu
1               5                   10                  15

Val Ala Gly Pro Ala Ala Ser Tyr Ala Ala Asp Val Gly Tyr Gly Ala
                20                  25                  30

Pro Ala Thr Leu Ala Thr Pro Ala Thr Pro Ala Ala Pro Ala Ala Gly
            35                  40                  45

Tyr Thr Pro Ala Ala Pro Ala Gly Ala Ala Pro Lys Ala Thr Thr Asp
        50                  55                  60

Glu Gln Lys Leu Ile Glu Lys Ile Asn Ala Gly Phe Lys Ala Ala Val
65                  70                  75                  80

Ala Ala Ala Ala Gly Val Pro Ala Val Asp Lys Tyr Lys Thr Phe Val
                85                  90                  95

Ala Thr Phe Gly Thr Ala Ser Asn Lys Ala Phe Ala Glu Ala Leu Ser
            100                 105                 110

Thr Glu Pro Lys Gly Ala Ala Ala Ser Ser Asn Ala Val Leu Thr
            115                 120                 125
```

```
Ser Lys Leu Asp Ala Ala Tyr Lys Leu Ala Tyr Lys Ser Ala Glu Gly
    130                 135                 140

Ala Thr Pro Glu Ala Lys Tyr Asp Ala Tyr Val Ala Thr Leu Ser Glu
145                 150                 155                 160

Ala Leu Arg Ile Ile Ala Gly Thr Leu Glu Val His Ala Val Lys Pro
                165                 170                 175

Ala Gly Glu Glu Val Lys Ala Ile Pro Ala Gly Glu Leu Gln Val Ile
            180                 185                 190

Asp Lys Val Asp Ala Ala Phe Lys Val Ala Thr Ala Ala Asn Ala
        195                 200                 205

Ala Pro Ala Asn Asp Lys Phe Thr Val Phe Glu Ala Ala Phe Asn Asp
    210                 215                 220

Ala Ile Lys Ala Ser Thr Gly Gly Ala Tyr Gln Ser Tyr Lys Phe Ile
225                 230                 235                 240

Pro Ala Leu Glu Ala Ala Val Lys Gln Ser Tyr Ala Ala Thr Val Ala
                245                 250                 255

Thr Ala Pro Ala Val Lys Tyr Thr Val Phe Glu Thr Ala Leu Lys Lys
            260                 265                 270

Ala Ile Thr Ala Met Ser Gln Ala Gln Lys Ala Ala Lys Pro Ala Ala
        275                 280                 285

Ala Val Thr Ala Thr Ala Thr Gly Ala Val Gly Ala Ala Thr Gly Ala
    290                 295                 300

Val Gly Ala Ala Thr Gly Ala Ala Thr Ala Ala Gly Gly Tyr Lys
305                 310                 315                 320

Thr Gly Ala Ala Thr Pro Thr Ala Gly Gly Tyr Lys Val
                325                 330

<210> SEQ ID NO 120
<211> LENGTH: 373
<212> TYPE: PRT
<213> ORGANISM: Poa pratensis

<400> SEQUENCE: 120

Met Asp Lys Ala Asn Gly Ala Tyr Lys Thr Ala Leu Lys Ala Ala Ser
1               5                   10                  15

Ala Val Ala Pro Ala Glu Lys Phe Pro Val Phe Gln Ala Thr Phe Asp
                20                  25                  30

Lys Asn Leu Lys Glu Gly Leu Ser Gly Pro Asp Ala Val Gly Phe Ala
            35                  40                  45

Lys Lys Leu Asp Ala Phe Ile Gln Thr Ser Tyr Leu Ser Thr Lys Ala
        50                  55                  60

Ala Glu Pro Lys Glu Lys Phe Asp Leu Phe Val Leu Ser Leu Thr Glu
65                  70                  75                  80

Val Leu Arg Phe Met Ala Gly Ala Val Lys Ala Pro Ala Ser Lys
                85                  90                  95

Phe Pro Ala Lys Pro Ala Pro Lys Val Ala Ala Tyr Thr Pro Ala Ala
                100                 105                 110

Pro Ala Gly Ala Ala Pro Lys Ala Thr Thr Asp Glu Gln Lys Leu Ile
            115                 120                 125

Glu Lys Ile Asn Val Gly Phe Lys Ala Ala Val Ala Ala Ala Gly
        130                 135                 140

Val Pro Ala Ala Ser Lys Tyr Lys Thr Phe Val Ala Thr Phe Gly Ala
145                 150                 155                 160

Ala Ser Asn Lys Ala Phe Ala Glu Ala Leu Ser Thr Glu Pro Lys Gly
                165                 170                 175
```

```
Ala Ala Val Ala Ser Ser Lys Ala Val Leu Thr Ser Lys Leu Asp Ala
            180                 185                 190

Ala Tyr Lys Leu Ala Tyr Lys Ser Ala Glu Gly Ala Thr Pro Glu Ala
        195                 200                 205

Lys Tyr Asp Ala Tyr Val Ala Thr Leu Ser Glu Ala Leu Arg Ile Ile
210                 215                 220

Ala Gly Thr Leu Glu Val His Gly Val Lys Pro Ala Ala Glu Val
225                 230                 235                 240

Lys Ala Ile Pro Ala Gly Glu Leu Gln Val Ile Asp Lys Val Asp Ala
            245                 250                 255

Ala Phe Lys Val Ala Ala Thr Ala Ala Asn Ala Ala Pro Ala Asn Asp
        260                 265                 270

Lys Phe Thr Val Phe Glu Ala Ala Phe Asn Asp Ala Ile Lys Ala Ser
275                 280                 285

Thr Gly Gly Ala Tyr Gln Ser Tyr Lys Phe Ile Pro Ala Leu Glu Ala
            290                 295                 300

Ala Val Lys Gln Ser Tyr Ala Ala Thr Val Ala Thr Ala Pro Ala Val
305                 310                 315                 320

Lys Tyr Thr Val Phe Glu Thr Ala Leu Lys Lys Ala Ile Thr Ala Met
            325                 330                 335

Ser Gln Ala Gln Lys Ala Ala Lys Pro Ala Ala Val Thr Gly Thr
        340                 345                 350

Ala Thr Ser Ala Val Gly Ala Ala Thr Gly Ala Ala Thr Ala Ala Ala
            355                 360                 365

Gly Gly Tyr Lys Val
        370

<210> SEQ ID NO 121
<211> LENGTH: 685
<212> TYPE: PRT
<213> ORGANISM: Periplaneta americana

<400> SEQUENCE: 121

Met Lys Thr Ala Leu Val Phe Ala Ala Val Val Ala Phe Val Ala Ala
1               5                   10                  15

Arg Phe Pro Asp His Lys Asp Tyr Lys Gln Leu Ala Asp Lys Gln Phe
            20                  25                  30

Leu Ala Lys Gln Arg Asp Val Leu Arg Leu Phe His Arg Val His Gln
        35                  40                  45

His Asn Ile Leu Asn Asp Gln Val Glu Val Gly Ile Pro Met Thr Ser
    50                  55                  60

Lys Gln Thr Ser Ala Thr Thr Val Pro Pro Ser Gly Glu Ala Val His
65                  70                  75                  80

Gly Val Leu Gln Glu Gly His Ala Arg Pro Arg Gly Glu Pro Phe Ser
                85                  90                  95

Val Asn Tyr Glu Lys His Arg Glu Gln Ala Ile Met Leu Tyr Asp Leu
            100                 105                 110

Leu Tyr Phe Ala Asn Asp Tyr Asp Thr Phe Tyr Lys Thr Ala Cys Trp
        115                 120                 125

Ala Arg Asp Arg Val Asn Glu Gly Met Phe Met Tyr Ser Phe Ser Ile
    130                 135                 140

Ala Val Phe His Arg Asp Asp Met Gln Gly Val Met Leu Pro Pro
145                 150                 155                 160

Tyr Glu Val Tyr Pro Tyr Leu Phe Val Asp His Asp Val Ile His Met
                165                 170                 175
```

```
Ala Gln Lys Tyr Trp Met Lys Asn Ala Gly Ser Gly Glu His His Ser
            180                 185                 190

His Val Ile Pro Val Asn Phe Thr Leu Arg Thr Gln Asp His Leu Leu
        195                 200                 205

Ala Tyr Phe Thr Ser Asp Val Asn Leu Asn Ala Phe Asn Thr Tyr Tyr
    210                 215                 220

Arg Tyr Tyr Tyr Pro Ser Trp Tyr Asn Thr Thr Leu Tyr Gly His Asn
225                 230                 235                 240

Ile Asp Arg Arg Gly Glu Gln Phe Tyr Thr Tyr Lys Gln Ile Tyr
                245                 250                 255

Ala Arg Tyr Phe Leu Glu Arg Leu Ser Asn Asp Leu Pro Asp Val Tyr
                260                 265                 270

Pro Phe Tyr Tyr Ser Lys Pro Val Lys Ser Ala Tyr Asn Pro Asn Leu
            275                 280                 285

Arg Tyr His Asn Gly Glu Glu Met Pro Val Arg Pro Ser Asn Met Tyr
        290                 295                 300

Val Thr Asn Phe Asp Leu Tyr Tyr Ile Ala Asp Ile Lys Asn Tyr Glu
305                 310                 315                 320

Lys Arg Val Glu Asp Ala Ile Asp Phe Gly Tyr Ala Phe Asp Glu His
                325                 330                 335

Met Lys Pro His Ser Leu Tyr His Asp Val His Gly Met Glu Tyr Leu
            340                 345                 350

Ala Asp Met Ile Glu Gly Asn Met Asp Ser Pro Asn Phe Tyr Phe Tyr
        355                 360                 365

Gly Ser Ile Tyr His Met Tyr His Ser Met Ile Gly His Ile Val Asp
    370                 375                 380

Pro Tyr His Lys Met Gly Leu Ala Pro Ser Leu Glu His Pro Glu Thr
385                 390                 395                 400

Val Leu Arg Asp Pro Val Phe Tyr Gln Leu Trp Lys Arg Val Asp His
                405                 410                 415

Leu Phe Gln Lys Tyr Lys Asn Arg Leu Pro Arg Tyr Thr His Asp Glu
            420                 425                 430

Leu Ala Phe Glu Gly Val Lys Val Glu Asn Val Asp Val Gly Lys Leu
        435                 440                 445

Tyr Thr Tyr Phe Glu Gln Tyr Asp Met Ser Leu Asp Met Ala Val Tyr
    450                 455                 460

Val Asn Asn Val Asp Gln Ile Ser Asn Val Asp Val Gln Leu Ala Val
465                 470                 475                 480

Arg Leu Asn His Lys Pro Phe Thr Tyr Asn Ile Glu Val Ser Ser Asp
                485                 490                 495

Lys Ala Gln Asp Val Tyr Val Ala Val Phe Leu Gly Pro Lys Tyr Asp
            500                 505                 510

Tyr Leu Gly Arg Glu Tyr Asp Leu Asn Asp Arg His Tyr Phe Val
        515                 520                 525

Glu Met Asp Arg Phe Pro Tyr His Val Gly Ala Gly Lys Thr Val Ile
    530                 535                 540

Glu Arg Asn Ser His Asp Ser Asn Ile Ile Ala Pro Glu Arg Asp Ser
545                 550                 555                 560

Tyr Arg Thr Phe Tyr Lys Lys Val Gln Glu Ala Tyr Glu Gly Lys Ser
                565                 570                 575

Gln Tyr Tyr Val Asp Lys Gly His Asn Tyr Cys Gly Tyr Pro Glu Asn
            580                 585                 590

Leu Leu Ile Pro Lys Gly Lys Lys Gly Gly Gln Ala Tyr Thr Phe Tyr
```

```
                595                 600                 605
Val Ile Val Thr Pro Tyr Val Lys Gln Asp Glu His Asp Phe Glu Pro
            610                 615                 620

Tyr Asn Tyr Lys Ala Phe Ser Tyr Cys Gly Val Gly Ser Glu Arg Lys
625                 630                 635                 640

Tyr Pro Asp Asn Lys Pro Leu Gly Tyr Pro Phe Asp Arg Lys Ile Tyr
                645                 650                 655

Ser Asn Asp Phe Tyr Thr Pro Asn Met Tyr Phe Lys Asp Val Ile Ile
            660                 665                 670

Phe His Lys Lys Tyr Asp Glu Val Gly Val Gln Gly His
            675                 680                 685

<210> SEQ ID NO 122
<211> LENGTH: 446
<212> TYPE: PRT
<213> ORGANISM: Periplaneta americana

<400> SEQUENCE: 122

Ile Asn Glu Ile His Ser Ile Ile Gly Leu Pro Pro Phe Val Pro Pro
1               5                   10                  15

Ser Arg Arg His Ala Arg Arg Gly Val Gly Ile Asn Gly Leu Ile Asp
            20                  25                  30

Asp Val Ile Ala Ile Leu Pro Val Asp Glu Leu Lys Ala Leu Phe Gln
        35                  40                  45

Glu Lys Leu Glu Thr Ser Pro Asp Phe Lys Ala Leu Tyr Asp Ala Ile
    50                  55                  60

Arg Ser Pro Glu Phe Gln Ser Ile Ile Ser Thr Leu Asn Ala Met Gln
65                  70                  75                  80

Arg Ser Glu His His Gln Asn Leu Arg Asp Lys Gly Val Asp Val Asp
                85                  90                  95

His Phe Ile Gln Leu Ile Arg Ala Leu Phe Gly Leu Ser Arg Ala Ala
            100                 105                 110

Arg Asn Leu Gln Asp Asp Leu Asn Asp Phe Leu His Ser Leu Glu Pro
        115                 120                 125

Ile Ser Pro Arg His Arg His Gly Leu Pro Arg Gln Arg Arg Arg Ser
    130                 135                 140

Ala Arg Val Ser Ala Tyr Leu His Ala Asp Asp Phe His Lys Ile Ile
145                 150                 155                 160

Thr Thr Ile Glu Ala Leu Pro Glu Phe Ala Asn Phe Tyr Asn Phe Leu
                165                 170                 175

Lys Glu His Gly Leu Asp Val Val Asp Tyr Ile Asn Glu Ile His Ser
            180                 185                 190

Ile Ile Gly Leu Pro Pro Phe Val Pro Pro Ser Arg Arg His Ala Arg
        195                 200                 205

Arg Gly Val Gly Ile Asn Gly Leu Ile Asp Asp Val Ile Ala Ile Leu
    210                 215                 220

Pro Val Asp Glu Leu Lys Ala Leu Phe Gln Glu Lys Leu Glu Thr Ser
225                 230                 235                 240

Pro Asp Phe Lys Ala Leu Tyr Asp Ala Ile Arg Ser Pro Glu Phe Gln
                245                 250                 255

Ser Ile Ile Ser Thr Leu Asn Ala Met Pro Glu Tyr Gln Glu Leu Leu
            260                 265                 270

Gln Asn Leu Arg Asp Lys Gly Val Asp Val Asp His Phe Ile Arg Val
        275                 280                 285

Asp Gln Gly Thr Leu Arg Thr Leu Ser Ser Gly Gln Arg Asn Leu Gln
```

```
                    290                 295                 300
Asp Asp Leu Asn Asp Phe Leu Ala Leu Ile Pro Thr Asp Gln Ile Leu
305                 310                 315                 320

Ala Ile Ala Met Asp Tyr Leu Ala Asn Asp Ala Glu Val Gln Glu Leu
                325                 330                 335

Val Ala Tyr Leu Gln Ser Asp Asp Phe His Lys Ile Ile Thr Thr Ile
                340                 345                 350

Glu Ala Leu Pro Glu Phe Ala Asn Phe Tyr Asn Phe Leu Lys Glu His
                355                 360                 365

Gly Leu Asp Val Val Asp Tyr Ile Asn Glu Ile His Ser Ile Ile Gly
            370                 375                 380

Leu Pro Pro Phe Val Pro Pro Ser Gln Arg His Ala Arg Arg Gly Val
385                 390                 395                 400

Gly Ile Asn Gly Leu Ile Asp Asp Val Ile Ala Ile Leu Pro Val Asp
                405                 410                 415

Glu Leu Lys Ala Leu Phe Gln Glu Lys Leu Glu Thr Ser Pro Asp Phe
                420                 425                 430

Lys Ala Leu Tyr Asp Ala Ile Asp Leu Arg Ser Ser Arg Ala
                435                 440                 445

<210> SEQ ID NO 123
<211> LENGTH: 350
<212> TYPE: PRT
<213> ORGANISM: Blattella germanica

<400> SEQUENCE: 123

Met Ile Gly Leu Lys Leu Val Thr Val Leu Phe Ala Val Ala Thr Ile
1               5                   10                  15

Thr His Ala Ala Glu Leu Gln Arg Val Pro Leu Tyr Lys Leu Val His
                20                  25                  30

Val Phe Ile Asn Thr Gln Tyr Ala Gly Ile Thr Lys Ile Gly Asn Gln
            35                  40                  45

Asn Phe Leu Thr Val Phe Asp Ser Thr Ser Cys Asn Val Val Val Ala
        50                  55                  60

Ser Gln Glu Cys Val Gly Gly Ala Cys Val Cys Pro Asn Leu Gln Lys
65                  70                  75                  80

Tyr Glu Lys Leu Lys Pro Lys Tyr Ile Ser Asp Gly Asn Val Gln Val
                85                  90                  95

Lys Phe Phe Asp Thr Gly Ser Ala Val Gly Arg Gly Ile Glu Asp Ser
                100                 105                 110

Leu Thr Ile Ser Asn Leu Thr Thr Ser Gln Gln Asp Ile Val Leu Ala
            115                 120                 125

Asp Glu Leu Ser Gln Glu Val Cys Ile Leu Ser Ala Asp Val Val Val
        130                 135                 140

Gly Ile Ala Ala Pro Gly Cys Pro Asn Ala Leu Lys Gly Lys Thr Val
145                 150                 155                 160

Leu Glu Asn Phe Val Glu Glu Asn Leu Ile Ala Pro Val Phe Ser Ile
                165                 170                 175

His His Ala Arg Phe Gln Asp Gly Glu His Phe Gly Glu Ile Ile Phe
                180                 185                 190

Gly Gly Ser Asp Trp Lys Tyr Val Asp Gly Glu Phe Thr Tyr Val Pro
            195                 200                 205

Leu Val Gly Asp Asp Ser Trp Lys Phe Arg Leu Asp Gly Val Lys Ile
        210                 215                 220

Gly Asp Thr Thr Val Ala Pro Ala Gly Thr Gln Ala Ile Ile Asp Thr
```

```
            225                 230                 235                 240
Ser Lys Ala Ile Ile Val Gly Pro Lys Ala Tyr Val Asn Pro Ile Asn
                245                 250                 255

Glu Ala Ile Gly Cys Val Val Glu Lys Thr Thr Thr Arg Arg Ile Cys
            260                 265                 270

Lys Leu Asp Cys Ser Lys Ile Pro Ser Leu Pro Asp Val Thr Phe Val
            275                 280                 285

Ile Asn Gly Arg Asn Phe Asn Ile Ser Ser Gln Tyr Tyr Ile Gln Gln
            290                 295                 300

Asn Gly Asn Leu Cys Tyr Ser Gly Phe Gln Pro Cys Gly His Ser Asp
305                 310                 315                 320

His Phe Phe Ile Gly Asp Phe Val Asp His Tyr Tyr Ser Glu Phe
                325                 330                 335

Asn Trp Glu Asn Lys Thr Met Gly Phe Gly Arg Ser Val Glu
                340                 345                 350

<210> SEQ ID NO 124
<211> LENGTH: 182
<212> TYPE: PRT
<213> ORGANISM: Blattella germanica

<400> SEQUENCE: 124

Ala Val Leu Ala Leu Cys Ala Thr Asp Thr Leu Ala Asn Glu Asp Cys
1               5                   10                  15

Phe Arg His Glu Ser Leu Val Pro Asn Leu Asp Tyr Glu Arg Phe Arg
                20                  25                  30

Gly Ser Trp Ile Ile Ala Ala Gly Thr Ser Glu Ala Leu Thr Gln Tyr
            35                  40                  45

Lys Cys Trp Ile Asp Arg Phe Ser Tyr Asp Asp Ala Leu Val Ser Lys
        50                  55                  60

Tyr Thr Asp Ser Gln Gly Lys Asn Arg Thr Thr Ile Arg Gly Arg Thr
65                  70                  75                  80

Lys Phe Glu Gly Asn Lys Phe Thr Ile Asp Tyr Asn Asp Lys Gly Lys
                85                  90                  95

Ala Phe Ser Ala Pro Tyr Ser Val Leu Ala Thr Asp Tyr Glu Asn Tyr
            100                 105                 110

Ala Ile Val Glu Gly Cys Pro Ala Ala Ala Asn Gly His Val Ile Tyr
        115                 120                 125

Val Gln Ile Arg Phe Ser Val Arg Arg Phe His Pro Lys Leu Gly Asp
    130                 135                 140

Lys Glu Met Ile Gln His Tyr Thr Leu Asp Gln Val Asn Gln His Lys
145                 150                 155                 160

Lys Ala Ile Glu Glu Asp Leu Lys His Phe Asn Leu Lys Tyr Glu Asp
                165                 170                 175

Leu His Ser Thr Cys His
            180

<210> SEQ ID NO 125
<211> LENGTH: 200
<212> TYPE: PRT
<213> ORGANISM: Blattella germanica

<400> SEQUENCE: 125

Tyr Lys Leu Thr Tyr Cys Pro Val Lys Ala Leu Gly Glu Pro Ile Arg
1               5                   10                  15

Phe Leu Leu Ser Tyr Gly Glu Lys Asp Phe Glu Asp Tyr Arg Phe Gln
                20                  25                  30
```

```
Glu Gly Asp Trp Pro Asn Leu Lys Pro Ser Met Pro Phe Gly Lys Thr
        35                  40                  45
Pro Val Leu Glu Ile Asp Gly Lys Gln Thr His Gln Ser Val Ala Ile
        50                  55                  60
Ser Arg Tyr Leu Gly Lys Gln Phe Gly Leu Ser Gly Lys Asp Asp Trp
65                  70                  75                  80
Glu Asn Leu Glu Ile Asp Met Ile Val Asp Thr Ile Ser Asp Phe Arg
                85                  90                  95
Ala Ala Ile Ala Asn Tyr His Tyr Asp Ala Asp Glu Asn Ser Lys Gln
                100                 105                 110
Lys Lys Trp Asp Pro Leu Lys Lys Glu Thr Ile Pro Tyr Tyr Thr Lys
            115                 120                 125
Lys Phe Asp Glu Val Val Lys Ala Asn Gly Gly Tyr Leu Ala Ala Gly
        130                 135                 140
Lys Leu Thr Trp Ala Asp Phe Tyr Phe Val Ala Ile Leu Asp Tyr Leu
145                 150                 155                 160
Asn His Met Ala Lys Glu Asp Leu Val Ala Asn Gln Pro Asn Leu Lys
                165                 170                 175
Ala Leu Arg Glu Lys Val Leu Gly Leu Pro Ala Ile Lys Ala Trp Val
            180                 185                 190
Ala Lys Arg Pro Pro Thr Asp Leu
            195                 200
```

VACCINE PEPTIDE COMBINATIONS AGAINST CAT ALLERGY

CROSS-REFERENCE TO RELATED APPLICATIONS

This application is the U.S. national stage filing under 35 U.S.C. §371 of international application PCT/GB2008/001827, filed May 30, 2008, which claims priority from Great Britain Patent Application No. 0710529.9, filed Jun. 1, 2007.

FIELD OF THE INVENTION

The present invention relates to compositions comprising peptides for preventing or treating allergy to cats, and in particular to optimal combinations of peptides

BACKGROUND OF THE INVENTION

T-cell antigen recognition requires antigen presenting cells (APCs) to present antigen fragments (peptides) on their cell surface in association with molecules of the major histocompatibility complex (MHC). T cells use their antigen specific T-cell receptors (TCRs) to recognise the antigen fragments presented by the APC. Such recognition acts as a trigger to the immune system to generate a range of responses to eradicate the antigen which has been recognised.

Recognition of external antigens by the immune system of an organism, such as man, can in some cases result in diseases, known as atopic conditions. Examples of the latter are the allergic diseases including asthma, atopic dermatitis and allergic rhinitis. In this group of diseases, B lymphocytes generate antibodies of the IgE class (in humans) which bind externally derived antigens, which are referred to in this context as allergens since these molecules elicit an allergic response. Production of allergen-specific IgE is dependent upon T lymphocytes which are also activated by (are specific for) the allergen. Allergen-specific IgE antibodies bind to the surface of cells such as basophils and mast cells by virtue of the expression by these cells of surface receptors for IgE.

Crosslinking of surface bound IgE molecules by allergen results in degranulation of these effector cells causing release of inflammatory mediators such as histamine, 5-hydroxytryptamine and lipid mediators such as the sulphidoleukotrienes. In addition to IgE-dependent events, certain allergic diseases such as asthma are characterised by IgE-independent events.

Allergic IgE-mediated diseases are currently treated with agents which provide symptomatic relief or prevention. Examples of such agents are anti-histamines, β2 agonists, and glucocorticosteroids. In addition, some IgE-mediated diseases are treated by desensitisation procedures that involve the periodic injection of allergen components or extracts. Desensitisation treatments may induce an IgG response that competes with IgE for allergen, or they may induce specific suppressor T cells that block the synthesis of IgE directed against allergen. This form of treatment is not always effective and poses the risk of provoking serious side effects, particularly general anaphylactic shock. This can be fatal unless recognised immediately and treated with adrenaline. A therapeutic treatment that would decrease or eliminate the unwanted allergic-immune response to a particular allergen, without altering the immune reactivity to other foreign antigens or triggering an allergic response itself would be of great benefit to allergic individuals.

Approximately 10% of the worlds human population are allergic to cats (*Felis domesticus*) and up to 67% of asthmatic patients are sensitive to cat allergens. The major allergen produced by cats is the glycoprotein Fel d1, which elicits a response in 90-95% of patients suffering from cat allergy. A therapeutic or preventative treatment would therefore be of great benefit to humans that suffer or are at risk of suffering from cat allergy.

SUMMARY OF THE INVENTION

The present inventors have discovered that certain combinations of peptide fragments of the Fel d1 protein are particularly useful in desensitising individuals to Fel d1 allergen. The polypeptide combinations of the invention have been selected for their ability to bind to many MHC Class II molecules, and cause T cell proliferation with minimal histamine release. The compositions, products, vectors and formulations of the invention may therefore be provided to individuals for preventing or treating allergy to cats by tolerisation.

The polypeptides of the invention were initially selected as potential T cell epitopes through use of peptide—MHC binding assays. See for example FIG. 1 which demonstrates the ability of a range of peptides derived from Fel d1 chains 1 and 2 to bind to multiple DR types in MHC class II binding assays These candidate polypeptides were then further screened for potential use in tolerisation.

A difficulty associated with approaches to desensitisation based on peptide immunisation lies in how to select an appropriate size and region of the allergen as the basis for the peptide to be used for immunisation. The size of the peptide of choice is crucial. If the peptide is too small, the vaccine would not be effective in inducing an immunological response. If the peptides are too large, or if the whole antigen is introduced into an individual, there is the risk of inducing adverse reactions, such as anaphylaxis, which may be fatal.

The polypeptides of the invention have been selected to retain T cell specificity whilst being small enough in size to not possess significant tertiary structure that would enable them to retain the conformation of an IgE-binding epitope of the whole molecule. The polypeptides of the invention therefore do not induce significant crosslinking of adjacent specific IgE molecules on cells such as mast cells and basophils and consequently do not cause significant histamine release.

The peptides of the invention are advantageous in that upon administration to a sample of T cells they result in T cell proliferation whilst causing minimal histamine release. This is demonstrated in Example 2. The polypeptides of the invention are capable of inducing a late phase response in a cat allergic individual. The composition, products and formulations of the invention comprising these polypeptides or polynucleotides that are capable of expressing these polypeptides are therefore useful and effective in reducing hypersensitivity to Fel d1 allergen in individuals that are sensitised to this allergen.

A further advantage of the invention is the ability of the combinations of peptides to broadly target Major Histocompatibility Complex (MHC) molecules. T cell receptors (TCRs) are highly variable in their specificity. Variability is generated, as with antibody molecules, through gene recombination events within the cell. TCRs recognise antigen in the form of short peptides bound to molecules encoded by the genes of the Major Histocompatibility Complex (MHC). These gene products are the same molecules that give rise to "tissue types" used in transplantation and are also referred to as Human Leukocyte Antigen molecules (HLAs) which terms may be used interchangeably. Individual MHC molecules possess peptide binding grooves which, due to their shape and charge are only capable of binding a limited group of peptides. The peptides bound by one MHC molecule may not necessarily be bound by other MEW molecules.

When a protein molecule such as an antigen or allergen is taken up by antigen presenting cells such as B lymphocytes, dendritic cells, monocytes and macrophages, the molecule is enzymatically degraded within the cell. The process of degradation gives rise to peptide fragments of the molecule which, if they are of the appropriate size, charge and shape, may then bind within the peptide binding groove of certain MHC molecules and be subsequently displayed upon the surface of antigen presenting cells. If the peptide/MHC complexes are present upon the antigen presenting cell surface in sufficient numbers they may then activate T cells which bear the appropriate peptide/MHC-specific T cell receptors.

Due to the polymorphic nature of the MHC, individuals in an outbred population such as man will express different combinations of MHC molecules on their cell surfaces. Since different MHC molecules can bind different peptides from the same molecule based on the size, charge and shape of the peptide, different individuals will display a different repertoire of peptides bound to their MHC molecules. Identification of universal MHC-binding peptide epitopes in an outbred population such as man is more difficult than in inbred animals (such as certain strains of laboratory mice). On the basis of differential MHC expression between individuals and the inherent differences in peptide binding and presentation which this brings, it is unlikely that a single peptide can be identified which will be of use for desensitisation therapy in man.

The peptide combination of the invention, however, provides a broad coverage of efficacy over the human population by targeting the majority of the population's MHC. It would not, for example, be necessary to type the patient or individual to determine which MHC Class II molecules he or she possesses in order to determine what peptide or combination of peptides would be effective. A vaccine formulated with the peptides of the invention would therefore have broad utility.

The inventors' work has produced peptide combinations with the following characteristics:
the combination binds to many different MHC Class II molecules (see FIG. 2 which shows the large number of combinations that do not bind to many different MHC molecules)
the combinations produce the same or less histamine release than the whole allergen and/or have a cytokine release profile equivalent to the whole allergen
the peptides of the combinations are soluble.

Accordingly, the present invention provides a composition for use in preventing or treating allergy to cats by tolerisation comprising:
a) four or more polypeptides selected from any of SEQ ID NO: 1, 2, 3, 4, 5, 6, 7, 8, 9, 10, 11 or 12, and optionally
b) one, two or three polypeptides having the following characteristics:
  (i) comprising sequence having at least 65% sequence identity to at least 9 or more contiguous amino acids in any of SEQ ID NO: 1, 2, 3, 4, 5, 6, 7, 8, 9, 10, 11 or 12 not selected in a); and
  (ii) 9 to 30 amino acids in length.
Preferably, the composition of the invention comprises either:
  (i) at least two peptides which exhibit strong binding and at least one peptide which exhibits moderate binding to each member of a panel of HLA molecules; or
  (ii) at least one peptide which exhibits strong binding and at least two peptides which exhibit moderate binding to each member of said panel of HLA molecules;

wherein the panel of HLA molecules comprises at least seven different HLA molecules encoded by different alleles which have a cumulative frequency in an outbred human population of at least 80%; and/or
  (iii) wherein the composition is capable of inducing histamine release in a sample from a cat allergic individual at a level which is no higher than 5% above the histamine release induced in a sample from the same individual by whole Fel d 1 allergen; and/or
  (iv) wherein the composition induces a cytokine release profile in a PBMC sample from a cat allergic individual which is equivalent to the cytokine release profile in a sample from the same individual induced by whole Fel d 1 allergen.

Typically the outbred human population is Caucasian, and/or the panel of HLA molecules comprises at least HLA-DR1, DR3, DR4, DR7, DR11, DR13 and DR15; and optionally also comprises HLA-DRB4 and DRB5.

DESCRIPTION OF THE DRAWINGS

FIG. 1—Peptides derived from Fel d1 chains 1 (MLA01—related to SEQ ID NO: 1, MLA02—SEQ ID NO: 8, MLA03—SEQ ID NO: 2, MLA04—SEQ ID NO: 3, MLA05—SEQ ID NO: 4, MLA06—SEQ ID NO: 9 and MLA07—SEQ ID NO: 5) and 2 (MLA08—SEQ ID NO: 13, MLA09—SEQ ID NO: 14, MLA10—SEQ ID NO: 15, MLA11—SEQ ID NO: 10, MLA12—SEQ ID NO: 6, MLA13—SEQ ID NO: 16, MLA14—SEQ ID NO: 7, MLA15—SEQ ID NO: 11 and MLA16—SEQ ID NO: 12) were tested for ability to bind to multiple DR types in MHC class II binding assays. Peptides that showed promiscuous binding characteristics were selected and combined to generate mixtures of peptides that bind to a broad population of MHC class II types.

FIG. 3 summarises proliferative responses to peptides and antigens. The percentage of individuals mounting a detectable proliferative response is shown in the black bars. Grey (weak), white (moderate) and hashed (strong) bars provide a breakdown of the quality of these responses. Quality is arbitrarily defined by Stimulation Index (SI: ratio of counts in the presence of antigen/peptide divided by counts in medium alone). Thus for peptide 1 (MLA01), 12% of subjects made a proliferative response and of these 92% were weak, none were moderate and 8% were high. Proliferative responses to individual peptides/antigens were variable (black bar). 92% of subjects had positive proliferative responses to the positive control antigen PPD. The majority of these were strong responses (hashed bar). 75% of subjects responded to cat dander extract, with 59% of the responses (i.e. 59% of the 75%) being weak. The response to the mixture of 7 preferred peptides (SEQ ID NOS: 1 TO 7) was almost identical to cat dander extract (CAT).

FIG. 4 summarises the percentage of individuals who mounted a detectable response to each of the peptides/antigens by production of the three cytokines measured. The positive control antigen PPD elicited a cytokine production in almost all individuals (IFN-γ: 91%, IL-13: 97% and IL-10: 96%). Whole cat allergen and the mixture of 7 peptides elicited a cytokine response in approximately 80% or more of subjects. Individual peptides elicited responses of differing frequency. In general cytokine production appeared to be a more sensitive method of detecting responses with larger percentages of individuals giving positive cytokine responses than proliferative responses. In most cases, IL-10 secretion was detected in the largest number of subjects and IFN-γ detected least frequently.

DESCRIPTION OF THE SEQUENCES MENTIONED HEREIN

Figure 2M:
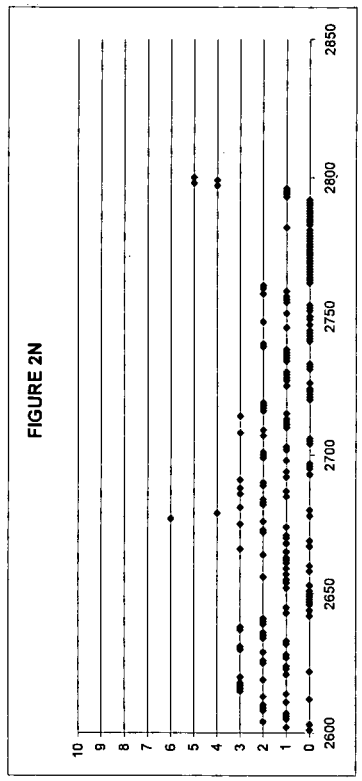
FIG. 2—Graphical representation of peptide mixtures showing those which bind to a broad population of MHC class II types.
Figure 2O:
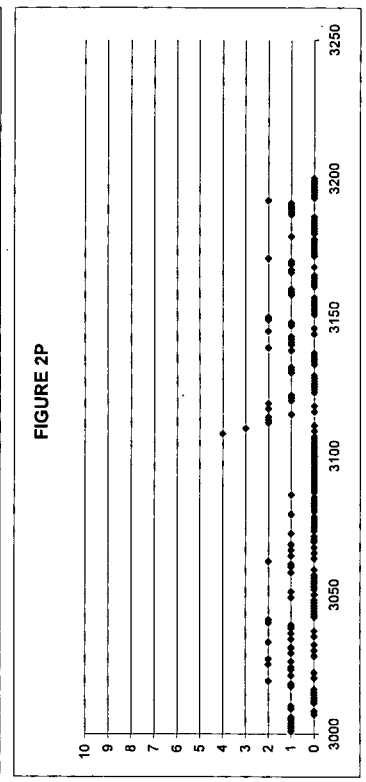
Figure 2N:
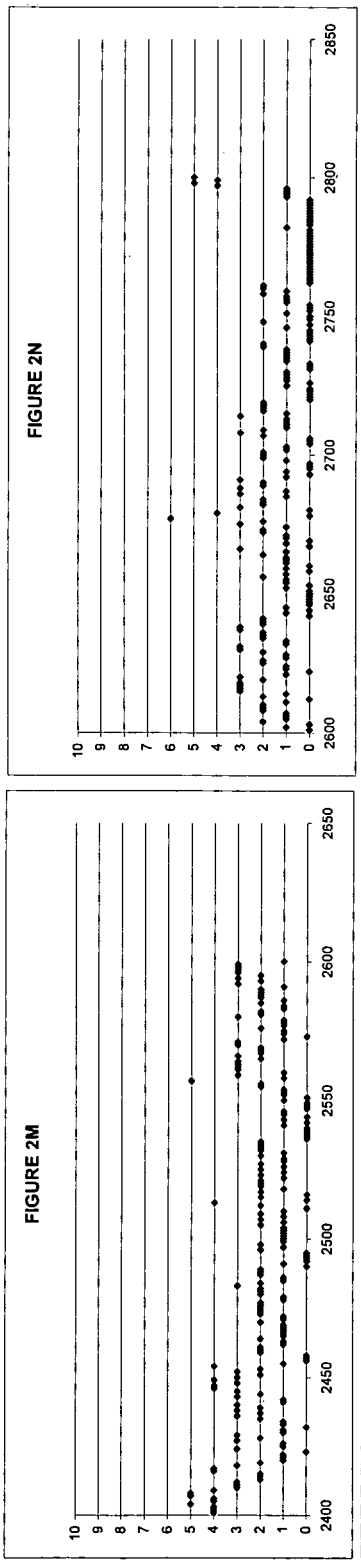
Figure 2P:
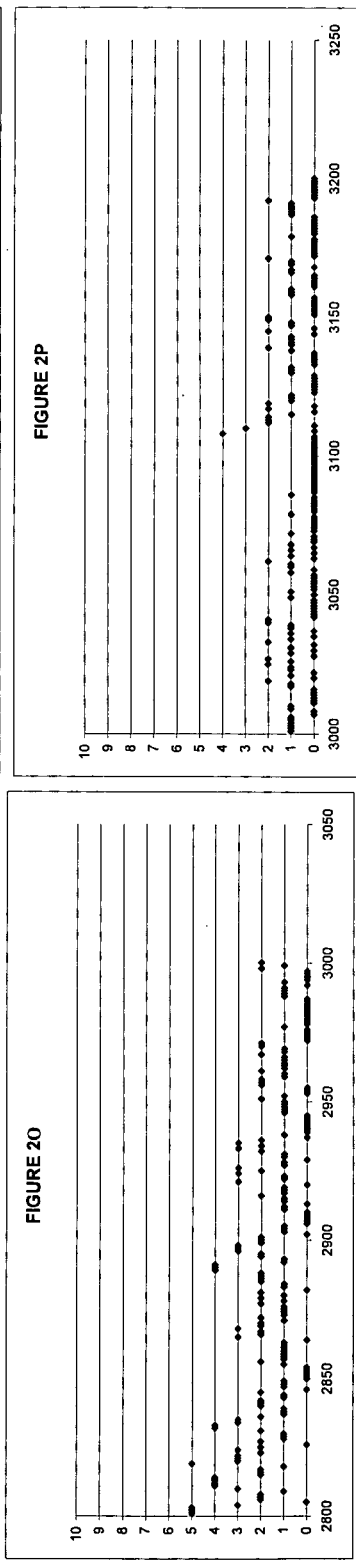
Figure 2Q:
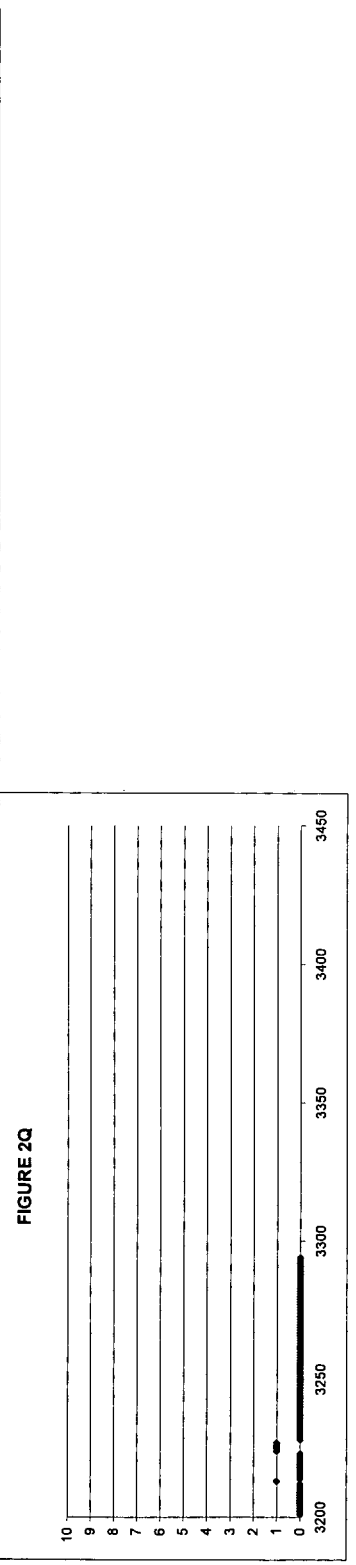

SEQ ID NO: 1 to 16 provide the polypeptide sequences of the invention. SEQ ID NOS: 1 to 16 correspond to peptides MLA01, MLA03, MLA04, MLA05, MLA07, MLA12, MLA14, MLA02, MLA06, MLA11, MLA15, MLA16, MLA08, MLA09, MLA10 and MLA13 respectively in the Examples and FIG. 1.

DETAILED DESCRIPTION OF THE INVENTION

The invention provides a composition for use in preventing or treating allergy to cats by tolerisation comprising:
a) four or more polypeptides selected from any of SEQ ID NO: 1, 2, 3, 4, 5, 6, 7, 8, 9, 10, 11 or 12, and optionally
b) one, two or three polypeptides having the following characteristics:
(i) comprising sequence having at least 65% sequence identity to at least 9 contiguous amino acids in any of SEQ ID NO: 1, 2, 3, 4, 5, 6, 7, 8, 9, 10, 11 or 12 not selected in a); and
(ii) 9 to 30 amino acids in length.
The invention also provides products and formulations comprising the polypeptides of the invention and compositions, products and vectors comprising polynucleotides capable of expressing the polypeptides of the invention for use in preventing or treating cat allergy by tolerisation.

Peptide Fragments of Fel d1 Protein

The major allergen produced by the domestic cat *Felis catus* (*Felis domesticus*) is the glycoprotein Fel d1. This 39 kDa protein is formed from two 17 kDa subunits, each consisting of two disulphide-linked peptides (Fel d1 Chain 1 and Chain 2). The amino acid sequence of Fel d1 is disclosed in WO 91/06571. The major source of the Fel d1 protein is the sebaceous glands, although expression is also detected in salivary glands and the anal glands. The function of the Fel d1 protein is currently unknown, although it is possibly a pheromone binding protein.

The peptides of the invention are derived from Fel d1. The terms "peptide" and "polypeptide" are used interchangeably herein. Fel d1 is also referred to herein as "the allergen".

The composition of the invention comprises four or more polypeptides selected from any of SEQ ID NO: 1, 2, 3, 4, 5, 6, 7, 8, 9, 10, 11 or 12. Optionally, the composition may comprise one, two or three further polypeptides. These further polypeptides relate to (i.e. are typically homologues and/or fragments of) the other sequences, i.e. SEQ ID NO: 1, 2, 3, 4, 5, 6, 7, 8, 9, 10, 11 or 12, that are not amongst the four or more polypeptides already selected. The one, two or three further polypeptides may be identical to any of SEQ ID NO: 1, 2, 3, 4, 5, 6, 7, 8, 9, 10, 11 or 12. The composition may therefore comprise four, five, six or seven different polypeptides as provided in any of SEQ ID NO: 1, 2, 3, 4, 5, 6, 7, 8, 9, 10, 11 or 12. However, the optional one, two or three further polypeptides do not need to be 100% identical to any of SEQ ID NO: 1, 2, 3, 4, 5, 6, 7, 8, 9, 10, 11 or 12. They are preferably at least 65% identical to at least 9 or more contiguous amino acids in any of SEQ ID NO: 1, 2, 3, 4, 5, 6, 7, 8, 9, 10, 11 or 12, not already selected for the four or more polypeptides.

In other words, the invention provides a composition for use in the prevention or treatment of cat allergy by tolerisation comprising a) four or more polypeptides selected from any one of the following amino acid sequences:

| | |
|---|---|
| CPAVKRDVDLFLT; | (SEQ ID NO: 1) |
| EQVAQYKALPVVLENA; | (SEQ ID NO: 2) |
| KALPVVLENARILKNCV; | (SEQ ID NO: 3) |
| RILKNCVDAKMTEEDKE; | (SEQ ID NO: 4) |
| KENALSLLDKIYTSPL; | (SEQ ID NO: 5) |
| TAMKKIQDCYVENGLI; | (SEQ ID NO: 6) |
| SRVLDGLVMTTISSSK; | (SEQ ID NO: 7) |
| LFLTGTPDEYVEQVAQY; | (SEQ ID NO: 8) |
| KMTEEDKENALSLLDK; | (SEQ ID NO: 9) |
| LTKVNATEPERTAMKK; | (SEQ ID NO: 10) |
| ISSSKDCMGEAVQNTV; | (SEQ ID NO: 11) |
| AVQNTVEDLKLNTLGR | (SEQ ID NO: 12) |

And optionally, the composition may comprise b) one, two or three further polypeptides having the following characteristics:
(i) comprising sequence having at least 65% sequence identity to at least 9 or more contiguous amino acids in any of SEQ ID NO: 1 to 12 above not selected in a); and
(ii) 9 to 30 amino acids in length.

The invention also provides a product containing a) four or more polypeptides selected from any one of the following amino acid sequences:

```
CPAVKRDVDLFLT;        (SEQ ID NO: 1)
EQVAQYKALPVVLENA;     (SEQ ID NO: 2)
KALPVVLENARILKNCV;    (SEQ ID NO: 3)
RILKNCVDAKMTEEDKE;    (SEQ ID NO: 4)
KENALSLLDKIYTSPL;     (SEQ ID NO: 5)
TAMKKIQDCYVENGLI;     (SEQ ID NO: 6)
SRVLDGLVMTTISSSK;     (SEQ ID NO: 7)
LFLTGTPDEYVEQVAQY;    (SEQ ID NO: 8)
KMTEEDKENALSLLDK;     (SEQ ID NO: 9)
LTKVNATEPERTAMKK;     (SEQ ID NO: 10)
ISSSKDCMGEAVQNTV;     (SEQ ID NO: 11)
AVQNTVEDLKLNTLGR      (SEQ ID NO: 12)
``` and optionally, the product may comprise b) one or more further polypeptides having the following characteristics:
  (i) comprising sequence having at least 65% sequence identity to at least 9 or more contiguous amino acids in any of SEQ ID NO: 1 to 12 above not selected in a); and
  (ii) 9 to 30 amino acids in length,
wherein each different polypeptide is for simultaneous, separate or sequential use in the prevention or treatment of cat allergy by tolerisation.

In more detail therefore, the invention provides a product containing:
  (a) A polypeptide selected from any one of SEQ ID NO: 1, 2, 3, 4, 5, 6, 7, 8, 9, 10, 11 or 12;
  (b) A polypeptide selected from any one of SEQ ID NO: 1, 2, 3, 4, 5, 6, 7, 8, 9, 10, 11 or 12, that is not selected in (a) above;
  (c) A polypeptide selected from any one of SEQ ID NO: 1, 2, 3, 4, 5, 6, 7, 8, 9, 10, 11 or 12, that is not selected in (a) or (b) above;
  (d) A polypeptide selected from any one of SEQ ID NO: 1, 2, 3, 4, 5, 6, 7, 8, 9, 10, 11 or 12, that is not selected in (a), (b) or (c) above; and optionally
  (e) A polypeptide having the following characteristics:
    (i) comprising sequence having at least 65% sequence identity to at least 9 or more contiguous amino acids in any of SEQ ID NO: 1 to 12 not selected in a), b), c) or d) above; and
    (ii) 9 to 30 amino acids in length; and optionally
  (f) A polypeptide fragment of Fel d1 protein having the following characteristics:
    (i) comprising sequence having at least 65% sequence identity to at least 9 or more contiguous amino acids in any of SEQ ID NO: 1 to 12 not selected in a), b), c), d) or e) above; and
    (ii) 9 to 30 amino acids in length; and optionally
  (g) A polypeptide fragment of Fel d1 protein having the following characteristics:
    (i) comprising sequence having at least 65% sequence identity to at least 9 or more contiguous amino acids in any of SEQ ID NO: 1 to 12 not selected in a), b), c), d), e) or f) above; and
    (ii) 9 to 30 amino acids in length;

for simultaneous, separate or sequential use in the prevention or treatment of cat allergy by tolerisation.

The composition or products of the invention may therefore comprise variants of any of SEQ ID NO: 1, 2, 3, 4, 5, 6, 7, 8, 9, 10, 11 or 12. Peptide fragments according to the invention may be derived by truncation, e.g. by removal of one or more amino acids from the N and/or C-terminal ends of a polypeptide. Fragments may also be generated by one or more internal deletions, provided that the core 9 amino acids that makes up the T cell epitope is not substantially disrupted.

For example, a variant of SEQ ID NO: 1 may comprise a fragment of SEQ ID NO: 1, i.e. a shorter sequence. This may include a deletion of one, two, three or four amino acids from the N-terminal end of SEQ ID NO: 1 or from the C-terminal end of SEQ ID NO: 1. Such deletions may be made from both ends of SEQ ID NO: 1. A variant of SEQ ID NO: 1 may include additional amino acids (for example from the cat Fel d1 protein sequence) extending beyond the end(s) of SEQ ID NO: 1. A variant may include a combination of the deletions and additions discussed above. For example, amino acids may be deleted from one end of SEQ ID NO: 1, but additional amino acids from the full length Fel d1 protein sequence may be added at the other end of SEQ ID NO: 1. The same discussion of variants above also applies to SEQ NO: 2, 3, 4, 5, 6, 7, 8, 9, 10, 11 and 12.

A variant peptide may include one or more amino acid substitutions from the amino acid sequence of any of SEQ ID NO: 1, 2, 3, 4, 5, 6, 7, 8, 9, 10, 11 or 12, or a fragment thereof. A variant peptide may comprise sequence having at least 65% sequence identity to at least 9 or more contiguous amino acids in any of SEQ ID NO: 1, 2, 3, 4, 5, 6, 7, 8, 9, 10, 11 or 12. More preferably a suitable variant may comprise at least 70%, at least 75%, at least 80%, at least 85%, at least 90%, at least 95%, or at least 98% amino acid identity to at least 9 contiguous amino acids of any of SEQ ID NO: 1, 2, 3, 4, 5, 6, 7, 8, 9, 10, 11 or 12. This level of amino acid identity may be seen at any section of the peptide, although it is preferably the core region. The level of amino acid identity is over at least 9 contiguous amino acids but it may be at least 10, 11, 12, 13, 14, 15 or at least 16 or 17 amino acids, depending on the size of the peptides of comparison. Accordingly, any of the above-specified levels of identity may be across the entire length of sequence.

In connection with amino acid sequences, "sequence identity" refers to sequences which have the stated value when assessed using ClustalW (Thompson et al., 1994, supra) with the following parameters:
Pairwise alignment parameters—Method: accurate, Matrix: PAM, Gap open penalty: 10.00, Gap extension penalty: 0.10;
Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: GPSNDQEKR. Sequence identity at a particular residue is intended to include identical residues which have simply been derivatized.

A variant peptide may comprise 1, 2, 3, 4, 5 or more, or up to 10 amino acid substitutions from any of SEQ ID NO: 1, 2, 3, 4, 5, 6, 7, 8, 9, 10, 11 or 12. Substitution variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the main amino acids which can be used to select suitable substituents are as follows:

| Ala | aliphatic, hydrophobic, neutral | Met | hydrophobic, neutral |
|---|---|---|---|
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged (+) | Trp | aromatic, hydrophobic, neutral |
| Leu | aliphatic, hydrophobic, neutral | Tyr | aromatic, polar, hydrophobic |

Further variants include those in which instead of the naturally occurring amino acid the amino acid which appears in the sequence is a structural analog thereof. Amino acids used in the sequences may also be modified, e.g. labelled, providing the function of the peptide is not significantly adversely affected. Where the peptide has a sequence that varies from the sequence of any of SEQ ID NO: 1, 2, 3, 4, 5, 6, 7, 8, 9, 10, 11 or 12 or a fragment thereof, the substitutions may occur across the full length of the sequence, within the sequence of any of SEQ ID NO: 1, 2, 3, 4, 5, 6, 7, 8, 9, 10, 11 or 12, or outside the sequence of any of SEQ ID NO: 1, 2, 3, 4, 5, 6, 7, 8, 9, 10, 11 or 12. For example, the variations described herein, such as additions, deletions, substitutions and modifications, may occur within the sequence of any of SEQ ID NO: 1, 2, 3, 4, 5, 6, 7, 8, 9, 10, 11 or 12. A variant peptide may comprise or consist essentially of the amino acid sequence of any of SEQ ID NO: 1, 2, 3, 4, 5, 6, 7, 8, 9, 10, 11 or 12 in which one, two, three, four or more amino acid substitutions have been made. A variant peptide may comprise a fragment of Fel d1 that is larger than any of SEQ ID NO: 1, 2, 3, 4, 5, 6, 7, 8, 9, 10, 11 or 12. In this embodiment, the variations described herein, such as substitutions and modifications, may occur within and/or outside the sequence of any of SEQ ID NO: 1, 2, 3, 4, 5, 6, 7, 8, 9, 10, 11 or 12.

The variant peptides of the invention are 9 to 30 amino acids in length inclusive. Preferably, they may be from 9 to 20 or more preferably 13 to 17 amino acids in length. The peptides may be the same length as the peptide sequences in any one of SEQ ID NO: 1, 2, 3, 4, 5, 6, 7, 8, 9, 10, 11 or 12.

The peptides may be chemically derived from the polypeptide allergen, for example by proteolytic cleavage or can be derived in an intellectual sense from the polypeptide allergen, for example by making use of the amino acid sequence of the polypeptide allergen and synthesising peptides based on the sequence. Peptides may be synthesised using methods well known in the art.

The term "peptide" includes not only molecules in which amino acid residues are joined by peptide (—CO—NH—) linkages but also molecules in which the peptide bond is reversed. Such retro-inverso peptidomimetics may be made using methods known in the art, for example such as those described in Meziere et al (1997) J. Immunol. 159, 3230-3237. This approach involves making pseudopeptides containing changes involving the backbone, and not the orientation of side chains. Meziere et al (1997) show that, at least for MHC class II and T helper cell responses, these pseudopeptides are useful. Retro-inverse peptides, which contain NH—CO bonds instead of CO—NH peptide bonds, are much more resistant to proteolysis.

Similarly, the peptide bond may be dispensed with altogether provided that an appropriate linker moiety which retains the spacing between the carbon atoms of the amino acid residues is used; it is particularly preferred if the linker moiety has substantially the same charge distribution and substantially the same planarity as a peptide bond. It will also be appreciated that the peptide may conveniently be blocked at its N- or C-terminus so as to help reduce susceptibility to exoproteolytic digestion. For example, the N-terminal amino group of the peptides may be protected by reacting with a carboxylic acid and the C-terminal carboxyl group of the peptide may be protected by reacting with an amine. Other examples of modifications include glycosylation and phosphorylation. Another potential modification is that hydrogens on the side chain amines of R or K may be replaced with methylene groups (—$NH_2$→—NH(Me) or —N(Me)$_2$).

Analogues of peptides according to the invention may also include peptide variants that increase or decrease the peptide's half-life in vivo. Examples of analogues capable of increasing the half-life of peptides used according to the invention include peptoid analogues of the peptides, D-amino acid derivatives of the peptides, and peptide-peptoid hybrids. A further embodiment of the variant polypeptides used according to the invention comprises D-amino acid forms of the polypeptide. The preparation of polypeptides using D-amino acids rather than L-amino acids greatly decreases any unwanted breakdown of such an agent by normal metabolic processes, decreasing the amounts of agent which needs to be administered, along with the frequency of its administration.

The peptides provided by the present invention may be derived from splice variants of Fel d1 encoded by mRNA generated by alternative splicing of the primary transcripts encoding the Fel d1 chains. The peptides may also be derived from amino acid mutants, glycosylation variants and other covalent derivatives of Fel d1 which retain at least an MHC-binding property of the allergen. Exemplary derivatives include molecules wherein the peptides of the invention are covalently modified by substitution, chemical, enzymatic, or other appropriate means with a moiety other than a naturally occurring amino acid. Further included are naturally occurring variants of Fel d1 found in different cats. Such a variant may be encoded by an allelic variant or represent an alternative splicing variant.

Variants as described above may be prepared during synthesis of the peptide or by post-production modification, or when the peptide is in recombinant form using the known techniques of site-directed mutagenesis, random mutagenesis, or enzymatic cleavage and/or ligation of nucleic acids.

In accordance with the invention, the further one, two or three peptides that the composition may comprise are preferably functional variants of any of SEQ ID NO: 1, 2, 3, 4, 5, 6, 7, 8, 9, 10, 11 or 12. That is, the peptides are preferably capable of inducing an immune response. In particular, they are capable of inducing a late phase response in a cat allergic individual. This may be tested by the ability of the peptide to induce T cell proliferation in a sample of T cells. Methods of testing the induction of T cell proliferation are well known in the art and one such method is exemplified in Example 2. Preferably the one or more further peptides are capable of causing T cell proliferation in at least 20% of samples of T cells, wherein each sample is obtained from different cat allergic individuals in the population. The compositions of the invention are preferably capable of inducing T cell proliferation in 30% or more samples of T cells obtained from of a panel of cat allergic individuals. More preferably, the compositions are capable of inducing T cell proliferation in 35% or more, 40% or more, 45%, 50%, 55%, 60%, 65%, 70%, 75%, 80%, 85%, or 90% or more of samples obtained from sensitized individuals in a panel. The number of individuals in a panel of cat allergic individuals may be any number greater than one, for example at least 2, 3, 5, 10, 15, 20, 30, 50, 80, or at least 100 individuals. It is preferred if the peptides cause T cell proliferation, but do not lead to the release of histamine from enriched basophils or mast cell preparations from a sensitised individual. There may be some histamine release, but preferably the composition does not cause significantly more histamine release than a composition comprising the 7 different polypeptides shown in SEQ ID NO: 1 to 7.

Suitable variants capable of binding to TCRs may be derived empirically or selected according to known criteria. Within a single peptide there are certain residues which contribute to binding within the MHC antigen binding groove and other residues which interact with hypervariable regions of the T cell receptor (Allen et al (1987) Nature 327: 713-5).

Within the residues contributing to T cell receptor interaction, a hierarchy has been demonstrated which pertains to dependency of T cell activation upon substitution of a given peptide residue. Using peptides which have had one or more T cell receptor contact residues substituted with a different amino acid, several groups have demonstrated profound effects upon the process of T cell activation. Evavold & Allen (1991) Nature 252: 1308-10) demonstrated the dissociation of T cell proliferation and cytokine production. In this in vitro model, a T cell clone specific for residues 64-76 of haemoglobin (in the context of I-E$^k$), was challenged with a peptide analogue in which a conservative substitution of aspartic acid for glutamic acid had been made. This substitution did not significantly interfere with the capacity of the analogue to bind to I-E$^k$.

Following in vitro challenge of a T cell clone with this analogue, no proliferation was detected although IL-4 secretion was maintained, as was the capacity of the clone to help B cell responses. In a subsequent study the same group demonstrated the separation of T cell-mediated cytolysis from cytokine production. In this instance, the former remained unaltered while the latter was impaired. The efficacy of altered peptide ligands in vivo was initially demonstrated in a murine model of EAE (experimental allergic encephalomyelitis) by McDevitt and colleagues (Smilek et al (1991) Proc Natl Acad Sci USA 88: 9633-9637). In this model EAE is induced by immunisation with the encephalitogenic peptide Act-11 of MBP (myelin basic protein). Substitution at position four (lysine) with an alanine residue generated a peptide which bound well to its restricting element (A$\alpha^u$A$\beta^u$), but which was non-immunogenic in the susceptible PL/JxSJLF1 strain and which, furthermore prevented the onset of EAE when administered either before or after immunisation with the encephalitogenic peptide. Thus, residues can be identified in peptides which affect the ability of the peptides to induce various functions of T-cells.

Advantageously, peptides may be designed to favour T-cell proliferation and induction of desensitisation. Metzler and Wraith have demonstrated improved tolerogenic capacity of peptides in which substitutions increasing peptide-MHC affinity have been made (Metzler & Wraith (1993) Int Immunol~: 1159-65). That an altered peptide ligand can cause long-term and profound anergy in cloned T cells was demonstrated by Sloan-Lancaster et al (1993) Nature 363: 156-9.

The compositions of the invention are capable of inducing a late phase response in an individual that is sensitised to Fel d1 allergen. The term "late phase response" includes the meaning as set forth in Allergy and Allergic Diseases (1997) A. B. Kay (Ed.), Blackwell Science, pp 1113-1130. The late phase response may be any late phase response (LPR). Preferably, the peptides are capable of inducing a late asthmatic response (LAR) or a late rhinitic response, or a late phase skin response or a late phase ocular response. Whether or not a particular peptide can give rise to a LPR can be determined using methods well known in the art; a particularly preferred method is that described in Cromwell O, Durham S R, Shaw R J, Mackay J and Kay A B. Provocation tests and measurements of mediators from mast cells and basophils in asthma and allergic rhinitis. In: Handbook of Experimental Immunology (4) Chapter 127, Editor: Weir D M, Blackwell Scientific Publications, 1986.

Thus, preferably, the individual peptides of the invention are able to induce a LPR in an individual who has been sensitised to Fel d1 allergen. Whether or not an individual has been sensitised to the allergen may be determined by well known procedures such as skin prick testing with solutions of allergen extracts, induction of cutaneous LPRs, clinical history, allergen challenge and radioallergosorbent test (RAST) for measurement of allergen specific IgE. Whether or not a particular individual is expected to benefit from treatment may be determined by the physician based, for example, on such tests.

Desensitising or tolerising an individual to Fel d1 allergen means inhibition or dampening of allergic tissue reactions induced by Fel d1 in appropriately sensitised individuals. It has been shown that T cells can be selectively activated, and then rendered unresponsive. Moreover the anergising or elimination of these T-cells leads to desensitisation of the patient for a particular allergen. The desensitisation manifests itself as a reduction in response to an allergen or allergen-derived peptide, or preferably an elimination of such a response, on second and further administrations of the allergen or allergen-derived peptide. The second administration may be made after a suitable period of time has elapsed to allow desensitisation to occur; this is preferably any period between one day and several weeks. An interval of around two weeks is preferred.

Although the compositions of the invention are able to induce a LPR in a cat allergic individual, it should be appreciated that when a composition is used to treat a patient it is preferable that a sufficiently low concentration of the composition is used such that no observable LPR will occur but the response will be sufficient to partially desensitise the T cells such that the next (preferably higher) dose may be given, and so on. In this way the dose is built up to give full desensitisation but often without ever inducing a LPR in the patient. Although, the composition or peptide is able to do so at a higher concentration than is administered.

The compositions of the invention preferably are capable of inducing a late phase response in 50% or more of a panel of cat allergic individuals from the population. More preferably, the compositions are capable of inducing a LPR in 55% or more, 60% or more, 65% or more, 70% or more, 75% or more, 80% or more, 85% or more, or 90% or more of sensitized individuals in a panel. Whether or not the compositions are able to induce a LPR in a certain percentage of a panel of subjects can be determined by methods which are well known in the art.

Properties of Peptide Combinations
MHC Binding

Preferred combinations of peptides typically bind to a large number of different HLA molecules. This is advantageous in that a larger proportion of individuals in a population will be tolerised by the combination. Thus preferred combinations comprise either:

(iii) at least two peptides which exhibit strong binding and at least one peptide which exhibits moderate binding to each member of a panel of HLA molecules; or
(iv) at least one peptide which exhibits strong binding and at least two peptides which exhibit moderate binding to each member of said panel of HLA molecules;

wherein the panel of HLA molecules comprises at least seven different HLA molecules encoded by different alleles which have a cumulative frequency in an outbred human population of at least 80%, or at least 85%, 90%, 95% or 99%.

Strength of MHC binding may be evaluated by any suitable method. Preferred methods include competitive inhibition assays wherein binding is measured relative to a reference peptide. The reference peptide is typically a peptide which is known to be a strong binder for a given MHC molecule. In such an assay, a peptide is a weak binder for a given HLA molecule if it has an IC50 more than 100 fold lower than the reference peptide for the given HLA molecule. A peptide is a moderate binder is it has an IC50 more than 20 fold lower but less than a 100 fold lower than the reference peptide for the given HLA molecule. A peptide is a strong binder if it has an IC50 less than 20 fold lower than the reference peptide for the given HLA molecule.

The outbred human population may be any population, typically a Caucasian population. The panel of HLA molecules typically comprises at least HLA-DR1, DR3, DR4, DR7, DR11, DR13 and DR15; and optionally also comprises HLA-DRB4 and DRB5. Suitable reference peptides for these HLA molecules are:

```
DR1 (DRB1*0101 allele):
HA 306-318 (PKYVKQNTLKLAT);      (SEQ ID NO: 17)

DR3 (DRB1*0301 allele):
MT216 (AKTIAYDEEARRGLE);         (SEQ ID NO: 18)

DR4 (DRB1*0401 allele):
HA 306-318 (PKYVKQNTLKLAT);      (SEQ ID NO: 17)

DR7 (DRB1*0701 allele):
YKL (AAYAAAKAAALAA);             (SEQ ID NO: 19)

DR11 (DRB1*1101 allele):
HA 306-318 (PKYVKQNTLKLAT);      (SEQ ID NO: 17)

DR13 (DRB1*1301 allele):
B1 21-36 (TERVRLVTRHIYNREE);     (SEQ ID NO: 20)

DR15 (DRB1*1501 allele):
A3 152-166 (EAEQLRRAYLDGTGVE);   (SEQ ID NO: 21)

DRB4 (DRB4*0101 allele):
E2/E7 (AGDLLAIETDKATI); and      (SEQ ID NO: 22)

DRB5 (DRB5*0101 allele):
HA 306-318 (PKYVKQNTLKLAT).      (SEQ ID NO: 17)
```

Histamine Release

Preferred combinations of peptides typically induce histamine release in a sample from a cat allergic individual containing basophils or mast cells, which is no higher than 5%, 6%, 7%, 8%, 9% or 10% greater than the histamine release induced in a sample from the same individual or population of individuals by the whole Fel d 1 allergen.

Most preferably, the combination induces histamine release which is no higher than 5%, 6%, 7%, 8%, 9% or 10% greater than the histamine release induced in a sample from the same individual or population of individuals by a composition comprising the 7 different polypeptides shown in SEQ ID NO: 1 to 7.

A sample from a cat allergic individual is typically a sample of peripheral blood mononuclear cells (PBMCs) which may be prepared as is standard in the art. An example of a suitable method involves isolation of PBMCs from a heparinised blood sample obtained from a subject. PBMC's are typically isolated from such a sample by density gradient separation.

Histamine release may be assessed by any suitable method, for example by ELISA. A number of suitable assay kits are commercially available to test levels of histamine release from cells in response to any given histamine release agent. Typically, a sample of approximately $5 \times 10^5$ to $5 \times 10^6$ PBMCs will be incubated with a given histamine release agent at a given concentration. Histamine concentration in the incubation medium or a sample of the incubation medium will be measured at the end of the incubation. Incubation is typically for 30 minutes at 37° C.

Where the histamine release agent is a peptide or combination of peptides it will typically be administered at a number of different dilutions within a concentration range comparable to that which would be expected to be present in vivo. For example, a 10 mg dose of a single peptide entering a blood volume of 5 litres would result in a blood concentration of 2 ng/ml ($2 \times 10^{-6}$ mg/ml). Thus, a suitable concentration range for a peptide or combination of peptides is typically 10 mg/ml to 1 ng/ml. Single, duplicate or triplicate measurement may be made at each tested dilution within said range. Approximately $5 \times 10^5$ PBMCs are typically required for each measurement. Suitable positive controls will also be tested at appropriate concentrations which may be readily determined by the skilled person. Suitable positive controls include whole Fel d 1 allergen or a suitable alternative such as commercially available whole cat dander extract. Spontaneous histamine release by a sample of cells which is not treated with a histamine release agent may also be measured as a negative control/indicator of background histamine release. Where two or more dilutions of a peptide/allergen preparation elicit 10% or more histamine release above background, or where a single value of 10% or more above background is achieved at the highest concentration tested, this will typically be considered a "positive histamine release".

The histamine concentration in the incubation medium of any sample will typically be measured by ELISA. Suitable ELISA assays typically involve adding a histamine acylation agent to a sample of the incubation medium together with a suitable buffer. Acylated histamine is more stable than histamine and samples treated in this way may be stored for longer prior to analysis. Analysis typically involves the addition of alkaline-phosphatase conjugated anti-acyl-histamine reagents, followed by the addition of a suitable chromogenic alkaline-phosphatase substrate. Histamine concentration is determined by measurement of absorbance and comparison to a standard curve calibrated against known histamine concentrations.

Cytokine Release

Preferred combinations of peptides typically induce a cytokine release profile in a sample from a cat allergic individual containing T cells, which is equivalent to the cytokine release profile induced in a sample from the same individual or population of individuals by the whole Fel d 1 allergen.

Most preferably, the combination induces a cytokine release profile in a sample from a cat allergic individual or population of individuals containing T cells, which is equivalent to the cytokine release profile induced in a sample from the same individual or population by a composition comprising the 7 different polypeptides shown in SEQ ID NO: 1 to 7.

A sample from a cat allergic individual or population is typically a sample of peripheral blood mononuclear cells (PBMCs) which may be prepared as is standard in the art. Cytokine release profile may be assessed by any suitable method. Suitable methods include measuring the level of one, two, three or more different cytokines released in a sample in independent assays. Suitable assays include ELISA and Luminex assays.

A cytokine release profile induced in one sample is considered to be equivalent to the cytokine release profile of a different sample when the level of certain specific cytokines produced is similar in both samples. More specifically, the cytokine release profiles of two different samples are considered to be equivalent when the levels of IL-10 and IL-13 produced in one sample differ by no more 5%, 6%, 7%, 8%, 9% or 10% from the levels of IL-10 and IL-13 produced in the second sample.

Thus, a preferred peptide combination induces production of IL-10 and IL-13 at levels which differ by no more than 10% from the levels of IL-10 and IL-13 induced in a sample from the same individual or population of individuals by the whole Fel d 1 allergen.

A typical cytokine release assay is as follows:
250 µl of a 200 µg/ml solution of the appropriate antigen or peptide concentration is distributed into the appropriate wells of, for example, 48 well plates. Plates are then incubated in a humidified 5% $CO_2$ incubator at 37° C. for a maximum of 4 hours. 250 µl of a $5 \times 10^6$ cell/ml PBMC suspension is then added to each well and the plates returned to the incubator for 5 days. Samples of culture supernatant are then harvested as multiple aliquots for use in ELISA assays. The samples may be frozen and stored prior to analysis. One aliquot is tested for the presence of one cytokine. Typically the presence of a cytokine is established using an ELISA assay according to practices standard in the art. The cytokine concentrations in a sample are typically determined by interpolation from standard curves generated in the same assay.

Nucleic Acids and Vectors

The individual peptides that make up the compositions and products of the invention may be administered directly, or may be administered indirectly by expression from an encoding sequence. For example, a polynucleotide may be provided that encodes a peptide of the invention, such as any of the peptides described above. A peptide of the invention may thus be produced from or delivered in the form of a polynucleotide which encodes, and is capable of expressing, it. Any reference herein to the use, delivery or administration of a peptide of the invention is intended to include the indirect use, delivery or administration of such a peptide via expression from a polynucleotide that encodes it.

Accordingly, the invention provides a composition for use in preventing or treating allergy to cats by tolerisation comprising four or more different polynucleotide sequences which when expressed cause the production of a composition for use in preventing or treating allergy to cats by tolerisation comprising:
a) four or more polypeptides selected from any of SEQ ID NO: 1, 2, 3, 4, 5, 6, 7, 8, 9, 10, 11 or 12; and optionally
b) one, two or three polypeptides having the following characteristics:
  (i) comprising sequence having at least 65% sequence identity to at least 9 or more contiguous amino acids in any of SEQ ID NO: 1, 2, 3, 4, 5, 6, 7, 8, 9, 10, 11 or 12, not selected in a); and
  (ii) 9 to 30 amino acids in length.

The invention also provides a product for use in preventing or treating allergy to cats by tolerisation containing:
a) four or more polynucleotides capable of expressing a different polypeptide selected from SEQ ID NO: 1, 2, 3, 4, 5, 6, 7, 8, 9, 10, 11 or 12, and optionally
b) one, two or three polynucleotides capable of expressing different polypeptides having the following characteristics:
  (i) comprising sequence having at least 65% sequence identity to at least 9 or more contiguous amino acids in any of SEQ ID NO: 1, 2, 3, 4, 5, 6, 7, 8, 9, 10, 11 or 12 not selected in a); and
  (ii) 9 to 30 amino acids in length,
wherein each different polypeptide is for simultaneous, separate of sequential use in the prevention or treatment of allergy to cats in a human.

The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or purified form. A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

Polynucleotides of the invention can be synthesised according to methods well known in the art, as described by way of example in Sambrook et al (1989, Molecular Cloning—a laboratory manual; Cold Spring Harbor Press).

The polynucleotide molecules of the present invention may be provided in the form of an expression cassette which includes control sequences operably linked to the inserted sequence, thus allowing for expression of the peptide of the invention in vivo in a targeted subject. These expression cassettes, in turn, are typically provided within vectors (e.g., plasmids or recombinant viral vectors) which are suitable for use as reagents for nucleic acid immunization. Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a peptide of the invention.

The present invention thus includes expression vectors that comprise such polynucleotide sequences. Thus, the present invention provides a vector for use in preventing or treating allergy to cats by tolerisation comprising four or more polynucleotide sequences which encode different polypeptides of the invention and optionally one or more further polynucleotide sequences which encode different polypeptides as defined herein. The vector may comprise 4, 5, 6, 7, 8, 9, 10, 11 or 12 polynucleotide sequences which encode different polypeptides of the invention.

Furthermore, it will be appreciated that the compositions and products of the invention may comprise a mixture of polypeptides and polynucleotides. Accordingly, the invention provides a composition or product as defined herein, wherein in place of any one of the polypeptide is a polynucleotide capable of expressing said polypeptide.

Expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al.

Thus, a polypeptide of the invention may be provided by delivering such a vector to a cell and allowing transcription from the vector to occur. Preferably, a polynucleotide of the invention or for use in the invention in a vector is operably linked to a control sequence which is capable of providing for the expression of the coding sequence by the host cell, i.e. the vector is an expression vector.

"Operably linked" refers to an arrangement of elements wherein the components so described are configured so as to perform their usual function. Thus, a given regulatory sequence, such as a promoter, operably linked to a nucleic acid sequence is capable of effecting the expression of that sequence when the proper enzymes are present. The promoter need not be contiguous with the sequence, so long as it functions to direct the expression thereof. Thus, for example, intervening untranslated yet transcribed sequences can be present between the promoter sequence and the nucleic acid sequence and the promoter sequence can still be considered "operably linked" to the coding sequence.

A number of expression systems have been described in the art, each of which typically consists of a vector containing a gene or nucleotide sequence of interest operably linked to expression control sequences. These control sequences include transcriptional promoter sequences and transcriptional start and termination sequences. The vectors of the invention may be for example, plasmid, virus or phage vectors provided with an origin of replication, optionally a promoter for the expression of the said polynucleotide and optionally a regulator of the promoter. A "plasmid" is a vector in the form of an extrachromosomal genetic element. The vectors may contain one or more selectable marker genes, for example an ampicillin resistance gene in the case of a bacterial plasmid or a resistance gene for a fungal vector. Vectors may be used in vitro, for example for the production of DNA or RNA or used to transfect or transform a host cell, for example, a mammalian host cell. The vectors may also be adapted to be used in vivo, for example to allow in vivo expression of the polypeptide.

A "promoter" is a nucleotide sequence which initiates and regulates transcription of a polypeptide-encoding polynucleotide. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is repressed by an analyte, cofactor, regulatory protein, etc.), and constitutive promoters. It is intended that the term "promoter" or "control element" includes full-length promoter regions and functional (e.g., controls transcription or translation) segments of these regions.

A polynucleotide, expression cassette or vector according to the present invention may additionally comprise a signal peptide sequence. The signal peptide sequence is generally inserted in operable linkage with the promoter such that the signal peptide is expressed and facilitates secretion of a polypeptide encoded by coding sequence also in operable linkage with the promoter.

Typically a signal peptide sequence encodes a peptide of 10 to 30 amino acids for example 15 to 20 amino acids. Often the amino acids are predominantly hydrophobic. In a typical situation, a signal peptide targets a growing polypeptide chain bearing the signal peptide to the endoplasmic reticulum of the expressing cell. The signal peptide is cleaved off in the endoplasmic reticulum, allowing for secretion of the polypeptide via the Golgi apparatus. Thus, a peptide of the invention may be provided to an individual by expression from cells within the individual, and secretion from those cells.

Alternatively, polynucleotides of the invention may be expressed in a suitable manner to allow presentation of a peptide of the invention by an MHC class II molecule at the surface of an antigen presenting cell. For example, a polynucleotide, expression cassette or vector of the invention may be targeted to antigen presenting cells, or the expression of encoded peptide may be preferentially stimulated or induced in such cells.

Polynucleotides of interest may be used in vitro, ex vivo or in vivo in the production of a peptide of the invention. Such polynucleotides may be administered or used in the prevention or treatment of allergy to cats by tolerisation.

Methods for gene delivery are known in the art. See, e.g., U.S. Pat. Nos. 5,399,346, 5,580,859 and 5,589,466. The nucleic acid molecule can be introduced directly into the recipient subject, such as by standard intramuscular or intradermal injection; transdermal particle delivery; inhalation; topically, or by oral, intranasal or mucosal modes of administration. The molecule alternatively can be introduced ex vivo into cells that have been removed from a subject. For example, a polynucleotide, expression cassette or vector of the invention may be introduced into APCs of an individual ex vivo. Cells containing the nucleic acid molecule of interest are re-introduced into the subject such that an immune response can be mounted against the peptide encoded by the nucleic acid molecule. The nucleic acid molecules used in such immunization are generally referred to herein as "nucleic acid vaccines."

The polypeptides, polynucleotides, vectors or cells of the invention may be present in a substantially isolated form. They may be mixed with carriers or diluents which will not interfere with their intended use and still be regarded as substantially isolated. They may also be in a substantially purified form, in which case they will generally comprise at least 90%, e.g. at least 95%, 98% or 99%, of the proteins, polynucleotides, cells or dry mass of the preparation.

Antigen Presenting Cells (APCs)

The invention encompasses the use in vitro of a method of producing a population of APCs that present the peptides of the invention on their surface, that may be subsequently used in therapy. Such a method may be carried out ex vivo on a sample of cells that have been obtained from a patient. The APCs produced in this way therefore form a pharmaceutical agent that can be used in the treatment or prevention of cat allergy by tolerisation. The cells should be accepted by the immune system of the individual because they derive from that individual. Delivery of cells that have been produced in this way to the individual from whom they were originally obtained, thus forms a therapeutic embodiment of the invention.

Formulations and Compositions

The peptides, polynucleotides, vectors and cells of the invention may be provided to an individual either singly or in combination. Each molecule or cell of the invention may be provided to an individual in an isolated, substantially isolated, purified or substantially purified form. For example, a peptide of the invention may be provided to an individual substantially free from the other peptides.

Whilst it may be possible for the peptides, polynucleotides or compositions according to the invention to be presented in raw form, it is preferable to present them as a pharmaceutical formulation. Thus, according to a further aspect of the invention, the present invention provides a pharmaceutical formulation for use in preventing or treating allergy to cats by tolerisation comprising a composition, vector or product according to the invention together with one or more pharmaceutically acceptable carriers or diluents and optionally one or more other therapeutic ingredients. The carrier (s) must be 'acceptable' in the sense of being compatible with the other ingredients of the formulation and not deleterious to the recipient thereof. Typically, carriers for injection, and the final formulation, are sterile and pyrogen free. Formulation of a composition comprising the peptide, polynucleotides or cells of the invention can be carried out using standard pharmaceutical formulation chemistries and methodologies all of which are readily available to the reasonably skilled artisan.

For example, compositions containing one or more molecules or cells of the invention can be combined with one or more pharmaceutically acceptable excipients or vehicles. Auxiliary substances, such as wetting or emulsifying agents, pH buffering substances and the like, may be present in the excipient or vehicle. These excipients, vehicles and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid, glycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in Remington's Pharmaceutical Sciences (Mack Pub. Co., N.J. 1991).

Such compositions may be prepared, packaged, or sold in a form suitable for bolus administration or for continuous administration. Injectable compositions may be prepared, packaged, or sold in unit dosage form, such as in ampoules or in multi-dose containers containing a preservative. Compositions include, but are not limited to, suspensions, solutions, emulsions in oily or aqueous vehicles, pastes, and implantable sustained-release or biodegradable formulations. Such compositions may further comprise one or more additional ingredients including, but not limited to, suspending, stabilizing, or dispersing agents. In one embodiment of a composition for parenteral administration, the active ingredient is provided in dry (for e.g., a powder or granules) form for reconstitution with a suitable vehicle (e.g., sterile pyrogen-free water) prior to parenteral administration of the reconstituted composition. The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable compositions which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Alternatively, the peptides or polynucleotides of the present invention may be encapsulated, adsorbed to, or associated with, particulate carriers. Suitable particulate carriers include those derived from polymethyl methacrylate polymers, as well as PLG microparticles derived from poly(lactides) and poly(lactide-co-glycolides). See, e.g., Jeffery et al. (1993) Pharm. Res. 10:362-368. Other particulate systems and polymers can also be used, for example, polymers such as polylysine, polyarginine, polyornithine, spermine, spermidine, as well as conjugates of these molecules.

The formulation of any of the peptides, polynucleotides or cells mentioned herein will depend upon factors such as the nature of the substance and the method of delivery. Any such substance may be administered in a variety of dosage forms. It may be administered orally (e.g. as tablets, troches, lozenges, aqueous or oily suspensions, dispersible powders or granules), parenterally, subcutaneously, by inhalation, intradermally, intravenously, intramuscularly, intrasternally, transdermally or by infusion techniques. The substance may also be administered as suppositories. A physician will be able to determine the required route of administration for each particular individual.

The compositions of formulations of the invention will comprise a suitable concentration of each peptide/polynucleotide/cell to be effective without causing adverse reaction. Typically, the concentration of each peptide in the composition will be in the range of 0.03 to 200 nmol/ml. More preferably in the range of 0.3 to 200 nmol/ml, 3 to 180 nmol/ml, 5 to 75 nmol/ml or 10 to 50 nmol/ml. The composition or formulations should have a purity of greater than 95% or 98% or a purity of at least 99%.

Therapeutic Methods and Individual to be Treated

The present invention relates to peptides, polynucleotides, vectors and cells that are capable of desensitising or tolerising human individuals to Fel d1 allergen and are therefore useful in the prevention or treatment of cat allergy. The invention provides compositions, products, vectors and formulations for use in preventing or treating allergy to cats by tolerisation. The invention also provides a method of tolerising or desensitizing a cat allergic individual comprising administering, either singly or in combination the polypeptides/polynucleotides/cells of the invention as described above.

The individual to be treated or provided with the composition or formulation of the invention is preferably human. It will be appreciated that the individual to be treated may be known to be sensitised to Fel d1 allergy, at risk of being sensitised or suspected of being sensitised. The individual can be tested for sensitisation using techniques well known in the art and as described herein. Alternatively, the individual may have a family history of allergy to cats. It may not be necessary to test an individual for sensitisation to Fel d1 because the individual may display symptoms of allergy when brought into proximity to a cat. By proximity is meant 10 metres or less, 5 metres or less, 2 metres or less, 1 metre or less, or 0 metres from the cat. Symptoms of allergy can include itchy eyes, runny nose, breathing difficulties, red itchy skin or rash.

The individual to be treated may be of any age. However, preferably, the individual may be in the age group of 1 to 90, 5 to 60, 10 to 40, or more preferably 18 to 35. Groups of individuals that are likely to benefit from the treatment are for example cat owners, veterinarians and other cat handlers.

Preferably, the individual to be treated is from a population that has MHC allele frequencies within the range of frequencies that are representative of the Caucasian population. Reference population allele frequencies for 11 common DRB1 allele families are shown in Table 3 of Example 2 (Data from HLA Facts Book, Parham and Barber). Reference frequencies were obtained by analysis of multiple studies reporting frequencies and the figures shown are mean values. Preferably therefore, the individual to be treated is from a population that has equivalent MEC allele frequencies as the reference population for the alleles referred to Table 3 (such as for at least 1, 2, 3, 4, 5 or all of the alleles), for example within the ranges of those figures plus or minus 1, 2, 3, 5, 10, 15 or 20%.

Preferably the individual is from a population where the allele frequencies of the following DRB1 alleles is:
4—at least 9%
7—at least 10%
11—at least 8%.

The individual may have had allergy to cat for at least 2 weeks, 1 month, 6 months, 1 year or 5 years. The individual may suffer from a rash, nasal congestion, nasal discharge and/or coughing caused by the allergy. The individual may or may not have been administered with other compositions/compounds which treat cat allergy. The individual may live in a population comprising at least 0.1 cats per human habitant.

Diagnostic Method

The invention also provides a method of detecting whether an individual has or is at risk of developing a disorder, wherein the disorder comprises allergic symptoms in response to cat allergen.

The individual is typically a mammal, preferably a human. The individual to be tested in the method is preferably between the ages of 1 year and 80 years, more preferably between the ages of 1 year and 60, 50, 40, 30 or 20 years, and most preferably between the ages of 1 year and 16 years.

The individual may have been diagnosed or may be suspected of suffering from a disorder which is classified as intrinsic or non-allergic, for example, intrinsic or non-allergic asthma. The individual may lack a detectable antibody response to a cat allergen, in particular an IgE response to cat allergen. Suitable assays to detect IgE include the Pharmacia™ CAP system. Using this system, the individual typically scores 0 or 0/1.

The individual may be a patient suffering from or diagnosed as suffering from symptoms which are typically associated with allergy such as itchy eyes, runny nose, breathing difficulties, red itchy skin or rash, in the absence of an identifiable trigger. The first occurrence or diagnosis of these symptoms may occur when the individual is older than 15 years of age. For example, the individual may be at least 15, 16, 17, 18, 20, 22, 24, 26, 28 or 30 years of age at the first occurrence or diagnosis of symptoms of allergy which are typically associated with allergy.

The method of the invention concerns determining whether an individual has a T cell response to a cat allergen, in particular the major cat allergen, Fel d 1. Such a T cell response will be present in cat allergic individuals. Without being bound by any hypothesis, the inventors consider that intrinsic or non-allergic disorders are also in fact caused by a T cell-driven, IgE independent, immune response. Accordingly these disorders also have an allergen trigger, but it does not give rise to allergen-specific IgE. Rather, it gives rise to a T cell response which can be characterised by T cell proliferation or the release of cytokines. For example, the cytokines released may include IL-5, which is involved in the recruitment of eosinophils. Accordingly, the T cell response can drive the induction of eosinophilic reactions in an individual.

Whether an individual has a T cell response to Fel d 1 is determined by measuring whether or not the individual has a T cell response to a peptide or combination of peptides according to the invention. Whether or not the individual has such a response may be determined by any suitable method, typically a method which can be used to detect proliferation of allergen-experienced T cells or the presence of cytokine released by allergen-experienced T cells. A positive response by the patient's T cells to the peptide or combination of the invention indicates that the patient has or is more likely to develop allergy-like symptoms in response to the allergen. A negative response indicates that the patient has allergy-like symptoms which are not caused by the cat allergen, or is less likely to develop allergy-like symptoms in response to the cat allergen.

The T cells which respond to the peptide or combination in the method are generally T cells which have been pre-sensitised in vivo to allergen. These allergen-experienced T cells are generally present in the peripheral blood of a individual, i.e. within the population of peripheral blood mononuclear cells (PBMCs) in the individual. The T cells may be CD4 and/or CD8 T cells.

In the method the T cells can be contacted with the peptide or combination of the invention in vitro or in vivo, preferably in vitro in a sample from the individual.

Generally the T cells which are contacted in the method are taken from the individual in a blood sample, although other types of samples which contain T cells can be used. The sample may be added directly to the assay or may be processed first. Typically the processing may comprise standard techniques such as gradient centrifugation to separate the T cells, with resuspension in any suitable volume. Alternatively, the processing may comprise diluting of the sample, for example with water, buffer or media. The sample may be diluted from 1.5 to 100 fold, for example 2 to 50 or 5 to 10 fold.

The processing may comprise separation of components of the sample. Typically mononuclear cells (MCs) are separated from the samples. The MCs will comprise the T cells and antigen presenting cells (APCs). Thus in the method the APCs present in the separated MCs can present the peptide to the T cells. In another embodiment only T cells, such as only CD4 T cells, can be purified from the sample. PBMCs, MCs and T cells can be separated from the sample using techniques known in the art.

Preferably the T cells used in the assay are in the form of unprocessed or diluted samples, are freshly isolated T cells (such as in the form of freshly isolated MCs or PBMCs) which are used directly ex vivo, i.e. they are not cultured before being used in the method or are thawed cells (which were previously frozen). However the T cells can be cultured before use, for example in the presence of the allergen, and generally also exogenous growth promoting cytokines. During culturing the allergen is typically present on the surface of APCs, such as the APC used in the method. Pre-culturing of the T cells may lead to an increase in the sensitivity of the method. Thus the T cells can be converted into cell lines, such as short term cell lines.

The APC which is typically present in the method may come from the same individual as the T cell or from a different individual. The APC may be a naturally occurring APC or an artificial APC. The APC is a cell which is capable of presenting the antigen to a T cell. It is typically a B-cell, dendritic cell or macrophage. It is typically separated from the same sample as the T cell and is typically co-purified with the T cell. Thus the APC may be present in MCs or PBMCs. The APC is typically a freshly isolated ex vivo cell or a cultured cell. It may be in the form of a cell line, such as a short term or immortalised cell line. The APC may express empty MHC class II molecules on its surface.

In one embodiment the peptide or combination of the invention is added directly to an assay comprising T cells and APCs. As discussed above the T cells and APCs in such an assay could be in the form of MCs.

In one embodiment the peptide or combination of peptides is provided to the APC in the absence of the T cell. The APC is then provided to the T cell, typically after being allowed to present the allergen on its surface. The peptide or combination of peptides may have been taken up inside the APC and presented, or simply be taken up onto the surface without entering inside the APC.

Typically $10^5$ to $10^7$, preferably $2.5 \times 10^5$ to $10^6$ PBMCs are added to each assay. In the case where the peptide or combination or peptides is added directly to the assay it is typically added as a peptide with a concentration from $10^{-1}$ to $10^3$ µg/ml, preferably 0.5 to 50 µg/ml or 1 to 10 µg/ml.

Typically the length of time for which the T cells are incubated with the peptide or combination is from 4 to 24 hours (preferably 5 to 18 hours) for effector T cells or for more than 24 hours for central memory cells. When using ex vivo PBMCs it has been found that $5.0 \times 10^6$ PBMCs can be incubated in 10 µg/ml of peptide for 5 hours at 37° C.

Proliferation of the incubated T cells may be measured by any suitable method. For example by flow cytometric measurement of incorporation of the fluorescent compound CFSE following incubation with peptide, or by measuring incorporation of the radiolabelled compound $^3$H-thymidine following incubation with peptide. A typical example of the latter method is as follows:

100 µl of the appropriate peptide concentration is distributed into the appropriate wells of 96 well plates. The plates are then placed into a humidified 5% $CO_2$ incubator set at 37° C. for a maximum of 4 hours. PBMC's isolated as standard in the art are prepared to a concentration of $2 \times 10^6$ cells/ml in complete medium at room temperature. 100 µl of cell solution is then distributed into each of the wells of the 96 well plates containing antigen/peptide. The plates are then incubated for 6 to 8 days. The cultures are pulsed with tritiated thymidine solution by adding 10 µl of tritiated thymidine stock solution (1.85 MBq/ml in serum-free RPMI medium) to each well. The plates are then returned to the incubator for between 8 and 16 hours. Cultures are then harvested on to filter mats and dried filter mats are counted using an appropriate beta scintillation counter. Counts from wells containing peptide are compared statistically to wells containing media alone (12 wells per group). A statistically significant difference between media only wells and peptide-stimulated wells is considered a positive stimulation of PBMC's by the peptide or combination of peptides.

Cytokine release may be measured by any suitable method such as ELISA assay as described above. Such methods are well known in the art.

Combination Immunotherapy

Since many individuals are allergic, or may require desensitizing to several polypeptide antigens, the current invention also provides means of desensitizing individuals that are allergic to multiple antigens. "Tolerance" induced in an individual to a first polypeptide antigen or allergen can create in the individual a "tolergeneic environment" wherein inappropriate immune responses to other antigens can be downregulated in order to provide tolerance to other antigens.

This finding means that individuals allergic to multiple allergens can be treated in a greatly reduced time period, and that individuals seriously allergic to some allergens (e.g., peanuts) but more mildly allergic to other allergens (e.g., cat dander) can benefit from a therapy wherein tolerance to the milder allergen is established and then this tolergeneic environment is used to provide tolerance to the other, more extreme allergen. In addition, individuals suffering from an autoimmune disorder who are additionally sensitised (or otherwise immune) to an unrelated antigen or allergen can benefit from a treatment regime wherein tolerance to the unrelated antigen or allergen is first established and then this tolergeneic environment is used to provide tolerance to the autoantigen associated with the autoimmune disorder.

A method is therefore provided for desensitising a cat allergic individual to Feld1 antigen and one or more further different polypeptide antigens. The method entails, in a first step, administering to the individual a composition/product/formulation (primary composition) according to the invention as described herein and wherein the administration is carried out in a manner sufficient to generate a hyporesponsive state against the Feld1 antigen. Once a hyporesponsive state has been established toward Feld1 antigen, or at least a shift toward desensitisation has occurred, the method entails administration of a secondary composition comprising a second, different polypeptide antigen to which the individual is to be sensitised. Administration of the secondary composition is carried out in such a way as to take advantage of the tolergeneic environment established by use of the primary composition, where it is now possible to establish tolerance to the second, different polypeptide antigen. The secondary composition is coadministered with either the first primary composition or a larger fragment of Feld1. By "coadministered" it is meant either the simultaneous or concurrent administration, e.g., when the two are present in the same composition or administered in separate compositions at nearly the same time but at different sites, as well as the delivery of polypeptide antigens in separate compositions at different times. For example, the secondary composition may be delivered prior to or subsequent to delivery of the first composition (or a larger fragment of Feld1) at the same or a different site. The timing between deliveries can range from about several seconds apart to about several minutes apart, several hours apart, or even several days apart. Furthermore, different delivery methods can be employed.

The second polypeptide antigen is preferably an allergen different to Feld1 allergen. Suitable allergens for use in the methods of the invention can of course be obtained and/or produced using known methods. Classes of suitable allergens include, but are not limited to, pollens, animal dander other than cat dander, grasses, molds, dusts, antibiotics, stinging insect venoms, and a variety of environmental (including chemicals and metals), drug and food allergens. Common tree allergens include pollens from cottonwood, popular, ash, birch, maple, oak, elm, hickory, and pecan trees; common plant allergens include those from mugwort, ragweed, English plantain, sorrel-dock and pigweed; plant contact allergens include those from poison oak, poison ivy and nettles; common grass allergens include rye grass, Timothy, Johnson, Bermuda, fescue and bluegrass allergens; common allergens can also be obtained from molds or fungi such as *Alternaria, Fusarium, Hormodendrum, Aspergillus, Micropolyspora, Mucor* and thermophilic actinomycetes; epidermal allergens can be obtained from house or organic dusts (typically fungal in origin), from arthropods such as house mites (*Dermatophagoides pteronyssinus*), or from animal sources such as feathers, and dog dander; common food allergens include milk and cheese (diary), egg, wheat, nut (e.g., peanut), seafood (e.g., shellfish), pea, bean and gluten allergens; common environmental allergens include metals (nickel and gold), chemicals (formaldehyde, trinitrophenol and turpentine), Latex, rubber, fiber (cotton or wool), burlap, hair dye, cosmetic, detergent and perfume allergens; common drug allergens include local anesthetic and salicylate allergens; antibiotic allergens include penicillin, tetracycline and sulfonamide allergens; and common insect allergens include bee, wasp and ant venom, and cockroach calyx allergens. Particularly well characterized allergens include, but are not limited to, the major and cryptic epitopes of the Der p I allergen (Hoyne et al. (1994) *Immunology* 83190-195), bee venom phospholipase A2 (PLA) (Akdis et al. (1996) *J. Clin. Invest.* 98:1676-1683), birch pollen allergen Bet v 1 (Bauer et al. (1997) *Clin. Exp. Immunol.* 107:536-541), and the multi-epitopic recombinant grass allergen rKBG8.3 (Cao et al. (1997) *Immunology* 90:46-51). These and other suitable allergens are commercially available and/or can be readily prepared as extracts following known techniques.

Preferably, the second polypeptide allergen is selected from the list of allergen sequences and database accession numbers (NCBI Entrez accession numbers) below. NCBI is the National Center for Biotechnology information and is a division of the US National Institutes of Health. The NCBI web site, from which access to the database may be sought, is www.ncbi.nlm.nih.gov/. Allergen sequences and database accession numbers (NCBI Entrez accession numbers):

House Dust Mite

*Dermatophagoides pteronyssinus*

Der p 1
(SEQ ID NO: 23)
MKIVLAIASLLALSAVYARPSSIKTFEEYKKAFNKSYATFEDEEAARKNFLES

VKYVQSNGGAINHLSDLSLDEFKNRFLMSAEAFEHLKTQFDLNAETNACSIN

GNAPAEIDLRQMRTVTPIRMQGGCGSCWAFSGVAATESAYLAYRNQSLDLA

EQELVDCASQHGCHGDTIPRGIEYIQHNGVVQESYYRYVAREQSCRRPNAQR

FGISNYCQIYPPNVNKIREALAQTHSAIAVIIGIKDLDAFRHYDGRTIIQRDNGY

QPNYHAVNIVGYSNAQGVDYWIVRNSWDTNWGDNGYGYFAANIDLMMIEE

YPYVVIL

Der p 2
(SEQ ID NO: 24)
MMYKILCLSLLVAAVARDQVDVKDCANHEIKKVLVPGCHGSEPCIIHRGKPF

QLEAVFEANQNTKTAKIEIKASIDGLEVDVPGIDPNACHYMKCPLVKGQQYD

IKYTWNVPKIAPKSENVVVTVKVMGDDGVLACAIATHAKIRD

Der p 3
(SEQ ID NO: 25)
MIIYNILIVLLLAINTLANPILPASPNATIVGGEKALAGECPYQISLQSSSHFCGG

TILDEYWILTAAHCVAGQTASKLSIRYNSLKHSLGGEKISVAKIFAHEKYDSY

QIDNDIALIKLKSPMKLNQKNAKAVGLPAKGSDVKVGDQVRVSGWGYLEEG

SYSLPSELRRVDIAVVSRKECNELYSKANAEVTDNMICGGDVANGGKDSCQ

GDSGGPVVDVKNNQVVGIVSWGYGCARKGYPGVYTRVGNFIDWIESKRSQ

Der p 4
(SEQ ID NO: 26)
KYXNPHFIGXRSVITXLME

Der p 5
(SEQ ID NO: 27)
MKFIIAFFVATLAVMTVSGEDKKHDYQNEFDFLLMERIHEQIKKGELALFYLQ

EQINHFEEKPTKEMKDKIVAEMDTIIAMIDGVRGVLDRLMQRKDLDIFEQYN

LEMAKKSGDILERDLKKEEARVKKIEV

Der p 6
(SEQ ID NO: 28)
AIGXQPAAEAEAPFQISLMK

Der p 7
(SEQ ID NO: 29)
MMKLLLIAAAAFVAVSADPIHYDKITEEINKAVDEAVAAIEKSETFDPMKVP

DHSDKFERHIGIIDLKGELDMRNIQVRGLKQMKRVGDANVKSEDGVVKAHL

LVGVHDDVVSMEYDLAYKLGDLHPNTHVISDIQDFVVELSLEVSEEGNMTLT

SFEVRQFANVVNHIGGLSILDPIFAVLSDVLTAIFQDTVRAEMTKVLAPAFKK

ELERNNQ

Der p9
(SEQ ID NO: 30)
IVGGSNASPGDAVYQIAL

*Dermatophagoides farinae*

Der f 1
(SEQ ID NO: 31)
MKFVLAIASLLVLTVYARPASIKTFEFKKAFNKNYATVEEEEVARKNFLE

SLKYVEANKGAINHLSDLSLDEFKNRYLMSAEAFEQLKTQFDLNAETSAC

RINSVNVPSELDLRSLRTVTPIRMQGGCGSCWAFSGVAATESAYLAYRNT

SLDLSEQELVDCASQHGCHGDTIPRGIEYIQQNGVVEERSYPYVAREQRC

RRPNSQHYGISNYCQIYPPDVKQIREALTQTHTAIAVIIGIKDLRAFQHY

DGRTIIQHDNGYQPNYHAVNIVGYGSTQGDDYWIVRNSWDTTWGDSGYGY

FQAGNNLMMIEQYPYVVIM

Der f 2
(SEQ ID NO: 32)
MISKILCLSLLVAAVVADQVDVKDCANNEIKKVMVDGCHGSDPCIIHRGK

PFTLEALFDANQNTKTAKIEIKASLDGLEIDVPGIDTNACHFMKCPLVKG

QQYDIKYTWNVPKIAPKSENVVVTVKLIGDNGVLACAIATHGKIRD

Der f 3
(SEQ ID NO: 33)
MMILTIVVLLAANILATPILPSSPNATIVGGVKAQAGDCPYQISLQSSSH

FCGGSILDEYWILTAAHCVNGQSAKKLSIRYNTLKHASGGEKIQVAEIYQ

HENYDSMTIDNDVALIKLKTPMTLDQTNAKPVPLPAQGSDVKVGDKIRVS

GWGYLQEGSYSLPSELQRVDIDVVSREQCDQLYSKAGADVSENMICGGDV

ANGGVDSCQGDSGGPVVDVATKQIVGIVSWGYGCARKGYPGVYTRVGNF

VDWIESKRSQ

Der f 4
(SEQ ID NO: 34)
AVGGQDADLAEAPFQISLLK

Der f 7
(SEQ ID NO: 35)
MMKFLLIAAVAFVAVSADPIHYDKITEEINKAIDDAIAAIEQSETIDPMK

VPDHADKFERHVGIVDFKGELAMRNIEARGLKQMKRQGDANVKGEEGIV

KAHLLIGVHDDIVSMEYDLAYKLGDLHPTTHVISDIQDFVVALSLEISDE

GNITMTSFEVRQFANVVNHIGGLSILDPIFGVLSDVLTAIFQDTVRKEMT

KVLAPAFKRELEKN

Additional mite allergen sequences (NCBI entrez accession):
1170095; 1359436; 2440053; 666007; 487661; 1545803;
84702; 84699; 625532; 404370; 1091577; 1460058; 7413;
9072; 387592.

Cat
*Felis* sequences (NCBI entrez accession):
539716; 539715; 423193; 423192; 423191; 423190;
1364213; 1364212; 395407; 163827; 163823; 163825;
1169665; 232086; 1169666.
Latex
*Hevea* sequences:

Hev b 1
(SEQ ID NO: 36)
MAEDEDNQQGQGEGLKYLGFVQDAATYAVTTFSNVYLFAKDKSGPLQPGV

DIIEGPVKNVAVPLYNRFSYIPNGALKFVDSTVVASVTIIDRSLPPIVKD

ASIQVVSAIRAAPEAARSLASSLPGQTKILAKVFYGEN

Hev b 3
(SEQ ID NO: 37)
MAEEVEEERLKYLDFVRAAGVYAVDSFSTLYLYAKDISGPLKPGVDTIEN

VVKTVVTPVYYIPLEAVKFVDKTVDVSVTSLDGVVPPVIKQVSAQTYSV

AQDAPRIVLDVASSVFNTGVQEGAKALYANLEPKAEQYAVITWRALNKL

PLVPQVANVVVPTAVYFSEKYNDVVRGTTEQGYRVSSYLPLLPTEKITKV

FGDEAS

Additional *Hevea* sequences (NCBI entrez accession):
3319923; 3319921; 3087805; 1493836; 1480457; 1223884;
3452147; 3451147; 1916805; 232267; 123335; 2501578;
3319662; 3288200; 1942537; 2392631; 2392630; 1421554;
1311006; 494093; 3183706; 3172534; 283243; 1170248;
1708278; 1706547; 464775; 266892; 231586; 123337;
116359; 123062; 2213877; 542013; 2144920; 1070656;
2129914; 2129913; 2129912; 100135; 82026; 1076559;
82028; 82027; 282933; 280399; 100138; 1086972; 108697;
1086976; 1086978; 1086978; 1086976; 1086974; 1086972;
913758; 913757; 913756; 234388; 1092500; 228691;
1177405; 18839; 18837; 18835; 18833; 18831; 1209317;
1184668; 168217; 168215; 168213; 168211; 168209;
348137.
Rye Grass
*Lolium* sequences:

126385 Lol p 1
(SEQ ID NO: 38)
MASSSSVLLVVALFAVFLGSAHGIAKVPPGPNITAEYGDKWLDAKSTWY

GKPTGAGPKDNGGACGYKNVDKAPFNGMTGCGNTPIFKDGRGCGSCFEI

KCTKPESCSGEAVTVTITDDNEEPIAPYHFDLSGHAFGSMAKKGEEQNVR

SAGELELQFRRVKCKYPDDTKPTFHVEKASNPNYLAILVKYVDGDGDVV

-continued

126386 Lol p 2a
(SEQ ID NO: 39)
AVDIKEKGSKDKWIELKESWGAVWRIDTPDKLTGPFTVRYTTEGGTKSEFE
DVIPEGWKADTSYSAK

126386 Lol p 2a
(SEQ ID NO: 39)
AAPVEFTVEKGSDEKNLALSIKYNKEGDSMAEVELKEHGSNEWLALKKN
GDGVWEIKSDKPLKGPFNFRFVSEKGMRNVFDDVVPADFKVGTTYKPE

126387 Lol p 3
(SEQ ID NO: 40)
TKVDLTVEKGSDAKTLVLNIKYTRPGDTLAEVELRQHGSEEWEPMTKKG
NLWEVKSAKPLTGPMNFRFLSKGGMKNVFDEVIPTAFTVGKTYTPEYN

2498581 Lol p 5a
(SEQ ID NO: 41)
MAVQKYTVALFLRRGPRGGPGRSYAADAGYTPAAAATPATPAATPAGGWR
EGDDRRAEAAGGRQRLASRQPWPPLPTPLRRTSSRSSRPPSPSPPRASSP
TSAAKAPGLIPKLDTAYDVAYKAAEAHPRGQVRRLRHCPHRSLRVIAGA
LEVHAVKPATEEVLAAKIPTGELQIVDKIDAAFKIAATAANAAPTNDKF
TVFESAFNKALNECTGGAMRPTSSSPPSRPRSSRPTPPPSPAAPEVKYA
VFEAALTKAITAMTQAQKAGKPAAAAATAAATVATAAATAAAVLPPPLL
VVQSLISLLIYY

2498582 Lol p 5b
(SEQ ID NO: 42)
MAVQKHTVALFLAVALVAGPAASYAADAGYAPATPATPAAPATAATPATP
ATPATPAAVPSGKATTEEQKLIEKINAGFKAAVAAAAVVPPADKYKTFV
ETFGTATNKAFVEGLASGYADQSKNQLTSKLDAALKLAYEAAQGATPEA
KYDAYVATLTEALRVIAGTLEVHAVKPAAEEVKVGAIPAAEVQLIDKVD
AAYRTAATAANAAPANDKFTVFENTFNNAIKVSLGAAYDSYKFIPTLVA
AVKQAYAAKQATAPEVKYTVSETALKKAVTAMSEAEKEATPAAAATATP
TPAAATATATPAAAYATATPAAATATATPAAATATPAAAGGYKV

455288 Lol p isoform 9
(SEQ ID NO: 43)
MAVQKHTVALFLAVALVAGPAASYAADAGYAPATPATPAAPATAATPATP
ATPATPAAVPSGKATTEEQKLIEKINAGFKAAVAAAAVVPPADKYKTFV
ETFGTATNKAFVEGLASGYADQSKNQLTSKLDAALKLAYEAAQGATPEA
KYDAYVATLTEALRVIAGTLEVHAVKPAAEEVKVGAIPAAEVQLIDKVD
AAYRTAATAANAAPANDKFTVFENTFNNAIKVSLGAAYDSYKFIPTLVA
AVKQAYAAKQATAPEVKYTVSETALKKAVTAMSEAEKEATPAAAATATP
TPAAATATATPAAAYATATPAAATATATPAAATATPAAAGGYKV 1582249 Lol p 11
(SEQ ID NO: 44)
DKGPGFVVTGRVYCDPCRAGFETNVSHNVEGATVAVDCRPFDGGESKLK
AEATTDKDGWYKIEIDQDHQEEICEVVLAKSPDKSCSEIEEFRDRARVP
LTSNXGIKQQGIRYANPIAFFRKEPLKECGGILQAY Additional *Lolium* sequences (NCBI entrez accession):
135480; 417103; 687261; 687259; 1771355; 2388662;
631955; 542131; 542130; 542129; 100636; 626029; 542132;
320616; 320615; 320614; 100638; 100634; 82450; 626028;
100639; 283345; 542133; 1771353; 1763163; 1040877;
1040875; 250525; 551047; 515377; 510911; 939932;
439950; 2718; 168316; 168314; 485371; 2388664; 2832717;
2828273; 548867.

Olive Tree
Olive sequences

416610 Ole e 1
(SEQ ID NO: 45)
EDIPQPPVSQFHIQGQVYCDTCRAGFITELSEFIPGASLRLQCKDKENGD
VTFTEVGYTRAEGLYSMLVERDHKNEFCEITLISSGRKDCNEIPTEGWAK
PSLKFKLNTVNGTTRTVNPLGFFKKEALPKCAQVYNKLGMYPPNM

Parietaria
*Parietaria* sequences:

2497750 Par j P2
(SEQ ID NO: 46)
MRTVSMAALVVIAAALAWTSSAEPAPAPAPGEEACGKVVQDIMPCLHFV
KGEEKEPSKECCSGTKKLSEEVKTTEQKREACKCIVRATKGISGIKNEL
VAEVPKKCDIKTTLPPITADFDCSKIQSTIFRGYY

1352506 Par j P5
(SEQ ID NO: 47)
MVRALMPCLPFVQGKEKEPSKGCCSGAKRLDGETKTGPQRVHACECIQT
AMKTYSDIDGKLVSEVPKHCGIVDSKLPPIDVNMDCKTVGVVPRQPQLP
VSLRHGPVTGPSDPAHKARLERPQIRVPPPAPEKA

1532056 Par j P8
(SEQ ID NO: 48)
MRTVSMAALVVIAAALAWTSSAELASAPAPGEGPCGKVVHHIMPCLKFV
KGEEKEPSKSCCSGTKKLSEEVKTTEQKREACKCIVAATKGISGIKNEL
VAEVPKKCGITTTLPPITADFDCSKIESTIFRGYY

1532058 Par j P9
(SEQ ID NO: 49)
MRTVSAPSAVALVVIVAAGLAWTSLASVAPPAPAPGSEETCGTVVRALM
PCLPFVQGKEKEPSKGCCSGAKRLDGETKTGLQRVHACECIQTAMKTYS
DIDGKLVSEVPKHCGIVDSKLPPIDVNMDCKTLGVVPRQPQLPVSLRHG
PVTGPSDPAHKARLERPQIRVPPPAPEKA

2497749 Par j P9
(SEQ ID NO: 50)
MRTVSARSSVALVVIVAAVLVWTSSASVAPAPAPGSEETCGTVVGALMP
CLPFVQGKEKEPSKGCCSGAKRLDGETKTGPQRVHACECIQTAMKTYSD
IDGKLVSEVPKHCGIVDSKLPPIDVNMDCKTLGVLHYKGN

1086003 Par j 1
(SEQ ID NO: 51)
MVRALMPCLPFVQGKEKEPSKGCCSGAKRLDGETKTGPQRVHACECIQT
AMKTYSDIDGKLVSEVPKHCGIVDSKLPPIDVNMDCKTVGVVPRQPQLP
VSLRHGPVTGPSRSRPPTKHGWRDPRLEFRPPHRKKPNPAFSTLG

Additional *Parietaria* sequences (NCBI entrez accession):
543659; 1836011; 1836010; 1311513; 1311512; 1311511;
1311510; 1311509; 240971.

Timothy Grass
*Phleum* sequences:

Phl p 1
(SEQ ID NO: 52)
MASSSSVLLVVVLFAVFLGSAYGIPKVPPGPNITATYGDKWLDAKSTWYGKP

TGAGPKDNGGACYKDVDKPPFSGMTGCGNTPIFKSGRGCGSCFEIKCTKPE

ACSGEPVVVHITDDNEEPIAPYHFDLSGHAFGAMAKKGDEQKLRSAGELELQ

FRRVKCKYPEGTKVTFHVEKGSNPNYLALLVKYVNGDGDVVAVDIKEKGK

DKWIELKESWGAIWRIDTPDKLTGPFTVRYTTEGGTKTEAEDVIPEGWKADT

SYESK

Phl p 1
(SEQ ID NO: 53)
MASSSSVLLVVALFAVFLGSAHGIPKVPPGPNITATYGDKWLDAKSTWYGKP

TAAGPKDNGGACYKDVDKPPFSGMTGCGNTPIFKSGRGCGSCFEIKCTKPE

ACSGEPVVVHITDDNEEPIAAYHFDLSGIAFGSMAKKGDEQKLRSAGEVEIQF

RRVKCKYPEGTKVTFHVEKGSNPNYLALLVKFSGDGDVVAVDIKEKGKDK

WIALKESWGAIWRIDTPEVLKGPFTVRYTTEGGTKARAKDVIPEGWKADTA

YESK

Phlp 2
(SEQ ID NO: 54)
MSMASSSSSLLAMAVLAALFAGAWCVPKVTFTVEKGSNEKHLAVLVKYE

GDTMAEVELREHGSDEWVAMTKGEGGVWTFDSEEPLQGPFNFRFLTEKGM

KNVFDDVVPEKYTIGATYAPEE

Phl p 5
(SEQ ID NO: 55)
ADLGYGGPATPAAPAEAAPAGKATTEEQKLIEKINDGFKAALAAAAGVPPA

DKYKTFVATFGAASNKAFAEGLSAEPKGAAESSSKAALTSKLDAAYKLAYK

TAEGATPEAKYDAYVATLSEALRIIAGTLEVHAVKPAAEEVKVIPAGELQVIE

KVDSAFKVAATAANAAPANDKFTVFEAAFNNAIKASTGGAYESYKFIPALEA

AVKQAYAATVATAPEVKYTVFETALKKAFTAMSEAQKAAKPATEATATAT

AAVGAATGAATAATGGYKV

Phl p 5
(SEQ ID NO: 56)
ADLGYGGPATPAAPAEAAPAGKATTEEQKLIEKINDGFKAALAAAAGVPPA

DKYKTFVATFGAASNKAFAEGLSAEPKGAAESSSKAALTSKLDAAYKLAYK

TAEGATPEAKYDAYVATLSEALRIIAGTLEVHAVKPAAEEVKVIPAGELQVIE

KVDSAFKVAATAANAAPANDKFTVFEAAFNNAIKASTGGAYESYKFIPALEA

AVKQAYAATVATAPEVKYTVFETALKKAITAMSEAQKAAKPATEATATAT

AAVGAATGAATAATGGYKV

Phl p 5b
(SEQ ID NO: 57)
AAAAVPRRGPRGGPGRSYTADAGYAPATPAAAGAAAGKATTEEQKLIEDIN

VGFKAAVAAAASVPAADKFKTFEAAFTSSSKAAAAKAPGLVPKLDAAYSVA

YKAAVGATPEAKFDSFVASLTEALRVIAGALEVHAVKPVTEEPGMAKIPAGE

LQIIDKIDAAFKVAATAAATAPADDKFTVFEAAFNKAIKESTGGAYDTYKCIP

SLEAAVKQAYAATVAAAPQVKYAVFEAALTKAITAMSEVQKVSQPATGAA

TVAAGAATTAAGAASGAATVAAGGYKV

-continued

Phl p 5a
(SEQ ID NO: 58)
ADLGYGPATPAAPAAGYTPATPAAPAGADAAGKATTEEQKLIEKINAGFKA

ALAGAGVQPADKYRTFVATFGPASNKAFAEGLSGEPKGAAESSSKAALTSK

LDAAYKLAYKTAEGATPEAKYDAYVATLSEALRIIAGTLEVHAVKPAAEEV

KVIPAGELQVIEKVDAAFKVAATAANAAPANDKFTVFEAAFNDEIKASTGGA

YESYKFIPALEAAVKQAYAATVATAPEVKYTVFETALKKAITAMSEAQKAA

KPAAAATATATAAVGAATGAATAATGGYKV

Phl p 5
(SEQ ID NO: 59)
MAVQKYTVALFLAVALVAGPAASYAADAGYAPATPAAAGAEAGKATTEEQ

KLIEDINVGFKAAVAAAASVPAADKFKTFEAAFTSSSKAATAKAPGLVPKLD

AAYSVSYKAAVGATPEAKFDSFVASLTEALRVIAGALEVHAVKPVTEEPGM

AKIPAGELQIIDKIDAAFKVAATAAATAPADTVFEAAFNKAIKESTGGAYDTY

KCIPSLEAAVKQAYAATVAAAPQVKYAVFEAALTKAITAMSEVQKVSQPAT

GAATVAAGAATTAAGAASGAATVAAGGYKV

Phl p 5
(SEQ ID NO: 60)
MAVQKYTVALFLAVALVAGPAASYAADAGYAPATPAAAGAEAGKATTEEQ

KLIEDINVGFKAAVAAAASVPAADKFKTFEAAFTSSSKAATAKAPGLVPKLD

AAYSVAYKAAVGATPEAKFDSFVASLTEALRVIAGALEVHAVKPVTEDPAW

PKIPAGELQIIDKIDAAFKVAATAAATAPADDKFTVFEAAFNKAIKESTGGAY

DTYKCIPSLEAAVKQAYAATVAAAPQVKYAVFEAALTKAITAMSEVQKVSQ

PATGAATVAAGAATTATGAASGAATVAAGGYKV

Phl p 5
(SEQ ID NO: 61)
ADAGYAPATPAAAGAEAGKATTEEQKLIEDINVGFKAAVAAAASVPAADKF

KTFEAAFTSSSKAATAKAPGLVPKLDAAYSVAYKAAVGATPEAKFDSFVAS

LTEALRVIAGALEVHAVKPVTEEPGMAKIPAGELQIIDKIDAAFKVAATAAAT

APADDKFTVFEAAFNKAIKESTGGAYDTYKCIPSLEAAVKQAYAATVAAAP

QVKYAVFEAALTKAITAMSEVQKVSQPATGAATVAAGAATTAAGAASGAA

TVAAGGYKV

Phl p 5
(SEQ ID NO: 62)
SVKRSNGSAEVHRGAVPRRGPRGGPGRSYAADAGYAPATPAAAGAEAGKA

TTEEQKLIEDINVGFKAAVAAAASVPAADKFKTFEAAFTSSSKAATAKAPGL

VPKLDAAYSVAYKAAVGATPEAKFDSFVASLTEALRVIAGALEVHAVKPVT

EEPGMAKIPAGELQIIDKIDAAFKVAATAAATAPADDKFTVFEAAFNKAIKES

TGGAYDTYKCIPSLEAAVKQAYAATVAAAPQVKYAVFEAALTKAITAMSEV

QKVSQPATGAATVAAGAATTAAGAASGAATVAAGGYKV

Phl p 5
(SEQ ID NO: 63)
MAVHQYTVALFLAVALVAGPAGSYAADLGYGPATPAAPAAGYTPATPAAP

AGAEPAGKATTEEQKLIEKINAGFKAALAAAAGVPPADKYRTFVATFGAAS

NKAFAEGLSGEPKGAAESSSKAALTSKLDAAYKLAYKTAEGATPEAKYDAY

VATVSEALRIIAGTLEVHAVKPAAEEVKVIPAGELQVIEKVDAAFKVAATAA

NAAPANDKFTVFEAAFNDAIKASTGGAYESYKFIPALEAAVKQAYAATVAT

-continued

APEVKYTVFETALKKAITAMSEAQKAAKPAAAATATATAAVGAATGAATA

ATGGYKV

Phl p 5
(SEQ ID NO: 64)
ADLGYGGPATPAAPAEAAPAGKATTEEQKLIEKINDGFKAALAAAAGVPPA

DKYKTFVATFGAASNKAFAEGLSAEPKGAAESSSKAALTSKLDAAYKLAYK

TAEGATPEAKYDAYVATLSEALRIIAGTLEVHAVKPAAEEVKVIPAGELQVIE

KVDSAFKVAATAANAAPANDKFTVFEAAFNNAIKASTGGAYESYKFIPALEA

AVKQAYAATVATAPEVKYTVFETALKKAFTAMSEAQKAAKPATEATATAT

AAVGAATGAATAATGGYKV

Phl p5b
(SEQ ID NO: 65)
AAAAVPRRGPRGGPGRSYTADAGYAPATPAAAGAAAGKATTEEQKLIEDIN

VGFKAAVAAAASVPAADKFKTFEAAFTSSSKAAAAKAPGLVPKLDAAYSVA

YKAAVGATPEAKFDSFVASLTEALRVIAGALEVHAVKPVTEEPGMAKIPAGE

LQIIDKIDAAFKVAATAAATAPADDKFTVFEAAFNKAIKESTGGAYDTYKCIP

SLEAAVKQAYAATVAAAPQVKYAVFEAALTKAITAMSEVQKVSQPATGAA

TVAAGAATTAAGAASGAATVAAGGYKV

Phl p5a
(SEQ ID NO: 66)
ADLGYGPATPAAPAAGYTPATPAAPAGADAAGKATTEEQKLIEKINAGFKA

ALAGAGVQPADKYRTFVATFGPASNKAFAEGLSGEPKGAAESSSKAALTSK

LDAAYKLAYKTAEGATPEAKYDAYVATLSEALRIIAGTLEVHAVKPAAEEV

KVIPAGELQVIEKVDAAFKVAATAANAAPANDKFTVFEAAFNDEIKASTGGA

YESYKFIPALEAAVKQAYAATVATAPEVKYTVFETALKKAITAMSEAQKAA

KPAAAATATATAAVGAATGAATAATGGYKV

Phl p 5
(SEQ ID NO: 67)
AVPRRGPRGGPGRSYAADAGYAPATPAAAGAEAGKATTEEQKLIEDINVGF

KAAVAAAASVPAGDKFKTFEAAFTSSSKAATAKAPGLVPKLDAAYSVAYKA

AVGATPEAKFDSFVASLTEALRVIAGALEVHAVKPVTEEPGMAKIPAGELQII

DKIDAAFKVAATAAATAPADDKFTVFEAAFNKAIKESTGGAYDTYKCIPSLE

AAVKQAYAATVAAAPQVKYAVFEAALTKAITAMSEVQKVSQPATGAATVA

AGAATTATGAASGAATVAAGGYKV

Phl p 5b
(SEQ ID NO: 68)
MAVPRRGPRGGPGRSYTADAGYAPATPAAAGAAAGKATTEEQKLIEDINVG

FKAAVAARQRPAADKFKTFEAASPRHPRPLRQGAGLVPKLDAAYSVAYKAA

VGATPEAKFDSFVASLTEALRVIAGALEVHAVKPVTEEPGMAKIPAGELQIID

KIDAAFKVAATAAATAPADDKFTVFEAAFNKAIKESTGGAYDTYKCIPSLEA

AVKQAYAATVAAAAEVKYAVFEAALTKAITAMSEVQKVSQPATGAATVAA

GAATTAAGAASGAATVAAGGYKV

Phl p 5
(SEQ ID NO: 69)
MAVHQYTVALFLAVALVAGPAASYAADLGYGPATPAAPAAGYTPATPAAP

AEAAPAGKATTEEQKLIEKINAGFKAALAAAAGVQPADKYRTFVATFGAAS

```
NKAFAEGLSGEPKGAAESSSKAALTSKLDAAYKLAYKTAEGATPEAKYDAY

VATLSEALRIIAGTLEVHAVKPAAEEVKVIPAGELQVIEKVDAAFKVAATAA

NAAPANDKFTVFEAAFNDAIKASTGGAYESYKFIPALEAAVKQAYAATVAT

APEVKYTVFETALKKAITAMSEAQKAAKPAAAATATATAAVGAATGAATA

ATGGYKV

Phl p 5
                                                  (SEQ ID NO: 70)
EAPAGKATTEEQKLIEKINAGFKAALARRLQPADKYRTFVATFGPASNKAFA

EGLSGEPKGAAESSSKAALTSKLDAAYKLAYKTAEGATPEAKYDAYVATLS

EALRIIAGTLEVHAVKPAAEEVKVIPAAELQVIEKVDAAFKVAATAANAAPA

NDKFTVFEAAFNDEIKASTGGAYESYKFIPALEAAVKQAYAATVATAPEVKY

TVFETALKKAITAMSEAQKAAKPPPLPPPPQPPPLAATGAATAATGGYKV

Phl p 5
                                                  (SEQ ID NO: 71)
MAVHQYTVALFLAVALVAGPAASYAADLGYGPATPAAPAAGYTPATPAAP

AEAAPAGKATTEEQKLIEKINAGFKAALAAAAGVQPADKYRTFVATFGAAS

NKAFAEGLSGEPKGAAESSSKAALTSKLDAAYKLAYKTAEGATPEAKYDAY

VATLSEALRIIAGTLEVHAVKPAAEEVKVIPAGELQVIEKVDAAFKVAATAA

NAAPANDKFTVFEAAFNDAIKASTGGAYESYKFIPALEAAVKQAYAATVAT

APEVKYTVFETALKKAITAMSEAQKAAKPAAAATATATAAVGAATGAATA

ATGGYKV

Phl p 5b
                                                  (SEQ ID NO: 72)
MAVPRRGPRGGPGRSYTADAGYAPATPAAAGAAAGKATTEEQKLIEDINVG

FKAAVAARQRPAADKFKTFEAASPRHPRPLRQGAGLVPKLDAAYSVAYKAA

VGATPEAKFDSFVASLTEALRVIAGALEVHAVKPVTEEPGMAKIPAGELQIID

KIDAAFKVAATAAATAPADDKFTVFEAAFNKAIKESTGGAYDTYKCIPSLEA

AVKQAYAATVAAAAEVKYAVFEAALTKAITAMSEVQKVSQPATGAATVAA

GAATTAAGAASGAATVAAGGYKV

Phl p 5a
                                                  (SEQ ID NO: 73)
ADLGYGPATPAAPAAGYTPATPAAPAGADAAGKATTEEQKLIEKINAGFKA

ALAGAGVQPADKYRTFVATFGPASNKAFAEGLSGEPKGAAESSSKAALTSK

LDAAYKLAYKTAEGATPEAKYDAYVATLSEALRIIAGTLEVHAVKPAAEEV

KVIPAGELQVIEKVDAAFKVAATAANAAPANDKFTVFEAAFNDEIKASTGGA

YESYKFIPALEAAVKQAYAATVATAPEVKYTVFETALKKAITAMSEAQKAA

KPPPLPPPPQPPPLAATGAATAATGGYKV

Phl p 5
                                                  (SEQ ID NO: 74)
MAVHQYTVALFLAVALVAGPAASYAADLGYGPATPAAPAAGYTPATPAAP

AEAAPAGKATTEEQKLIEKINAGFKAALAAAAGVQPADKYRTFVATFGAAS

NKAFAEGLSGEPKGAAESSSKAALTSKLDAAYKLAYKTAEGATPEAKYDAY

VATLSEALRIIAGTLEVHAVKPAAEEVKVIPAGELQVIEKVDAAFKVAATAA

NAAPANDKFTVFEAAFNDAIKASTGGAYESYKFIPALEAAVKQAYAATVAT

APEVKYTVFETALKKAITAMSEAQKAAKPAAAATATATAAVGAATGAATA

ATGGYKV
```

```
Phl p 6
                                                    (SEQ ID NO: 75)
MAAHKFMVAMFLAVAVVLGLATSPTAEGGKATTEEQKLIEDVNASFRAAM

ATTANVPPADKYKTFEAAFTVSSKRNLADAVSKAPQLVPKLDEVYNAAYNA

ADHAAPEDKYEAFVLHFSEALRIIAGTPEVHAVKPGA

Phl p 6
                                                    (SEQ ID NO: 76)
SKAPQLVPKLDEVYNAAYNAADHAAPEDKYEAFVLHFSEALHIIAGTPEVHA

VKPGA

Phl p 6
                                                    (SEQ ID NO: 77)
ADKYKTFEAAFTVSSKRNLADAVSKAPQLVPKLDEVYNAAYNAADHAAPE

DKYEAFVLHFSEALHIIAGTPEVHAVKPGA

Phl p 6
                                                    (SEQ ID NO: 78)
TEEQKLIEDVNASFRAAMATTANVPPADKYKTLEAAFTVSSKRNLADAVSK

APQLVPKLDEVYNAAYNAADHAAPEDKYEAFVLHFSEALRIIAGTPEVHAVK

PGA

Phl p 6
                                                    (SEQ ID NO: 79)
MAAHKFMVAMFLAVAVVLGLATSPTAEGGKATTEEQKLIEDINASFRAAMA

TTANVPPADKYKTFEAAFTVSSKRNLADAVSKAPQLVPKLDEVYNAAYNAA

DHAAPEDKYEAFVLHFSEALHIIAGTPEVHAVKPGA

Phl p 6
                                                    (SEQ ID NO: 80)
MVAMFLAVAVVLGLATSPTAEGGKATTEEQKLIEDVNASFRAAMATTANVP

PADKYKTFEAAFTVSSKRNLADAVSKAPQLVPKLDEVYNAAYNAADHAAP

EDKYEAFVLHFSEALRIIAGTPEVHAVKPGA

Phl p 7
                                                    (SEQ ID NO: 81)
MADDMERIFKRFDTNGDGKISLSELTDALRTLGSTSADEVQRMMAEIDTDGD

GFIDFNEFISFCNANPGLMKDVAKVF

Phl p 11
                                                    (SEQ ID NO: 82)
MSWQTYVDEHLMCEIEGHHLASAAILGHDGTVWAQSADFPQFKPEEITGIM

KDFDEPGHLAPTGMFVAGAKYMVIQGEPGRVIRGKKGAGGITIKKTGQALV

VGIYDEPMTPGQCNMVVERLGDYLVEQGM
```

Additional *Phleum* sequences (NCBI entrez accession): 458878; 548863; 2529314; 2529308; 2415702; 2415700; 2415698; 542168; 542167; 626037; 542169; 541814; 542171; 253337; 253336; 453976; 439960.

Wasp (and Related)

*Vespula* sequences:

```
465054 ALLERGEN VES V 5
                                                    (SEQ ID NO: 83)
MEISGLVYLIIIVTIIDLPYGKANNYCKIKCLKGGVHTACKYGSLKPNCGNKV

VVSYGLTKQEKQDILKEHNDFRQKIARGLETRGNPGPQPPAKNMKNLVWND

ELAYVAQVWANQCQYGHDTCRDVAKYQVGQNVALTGSTAAKYDDPVKLV

KMWEDEVKDYNPKKKFSGNDFLKTGHYTQMVWANTKEVGCGSIKYIQEK
```

-continued

WHKHYLVCNYGPSGNFMNEELYQTK

1709545 ALLERGEN VES M 1
(SEQ ID NO: 84)
GPKCPFNSDTVSIIIETRENRNRDLYTLQTLQNHPEFKKKTITRPVVFITHGFTS

SASEKNFINLAKALVDKDNYMVISIDWQTAACTNEYPGLKYAYYPTAASNT

RLVGQYIATITQKLVKDYKISMANIRLIGHSLGAHVSGFAGKRVQELKLGKYS

EIIGLDPARPSFDSNHCSERLCETDAEYVQIIHTSNYLGTEKILGTVDFYMNNG

KNNPGCGRFFSEVCSHTRAVIYMAECIKHECCLIGIPRSKSSQPISRCTKQECVCGLNA

KKYPSRGSFYVPVESTAPFCNNKGKII

1352699 ALLERGEN VES V 1
(SEQ ID NO: 85)
MEENMNLKYLLLFVYFVQVLNCCYGHGDPLSYELDRGPKCPFNSDTVSIIIET

RENRNRDLYTLQTLQNHPEFKKKTITRPVVFITHGFTSSASETNFINLAKALVD

KDNYMVISIDWQTAACTNEAAGLKYLYYPTAARNTRLVGQYIATITQKLVK

HYKISMANIRLIGHSLGAHASGFAGKKVQELKLGKYSEIIGLDPARPSFDSNH

CSERLCETDAEYVQIIHTSNYLGTEKTLGTVDFYMNNGKNQPGCGRFFSEVC

SHSRAVIYMAECIKHECCLIGIPKSKSSQPISSCTKQECVCGLNAKKYPSRGS

FYVPVESTAPFCNNKGKII

1346323 ALLERGEN VES V 2
(SEQ ID NO: 86)
SERPKRVFNIYWNVPTFMCHQYDLYFDEVTNFNIKRNSKDDFQGDKIAIFYD

PGEFPALLSLKDGKYKKRNGGVPQEGNITIHLQKFIENLDKIYPNRNFSGIGVI

DFERWRPIFRQNWGNMKIHKNFSIDLVRNEHPTWNKKMIELEASKRFEKYA

RFFMEETLKLAKKTRKQADWGYYGYPYCFNMSPNNLVPECDVTAMHENDK

MSWLFNNQNVLLPSVYVRQELTPDQRIGLVQGRVKEAVRISNNLKHSPKVLS

YWWYVYQDETNTFLTETDVKKTFQEIVINGGDGIIIWGSSSDVNSLSKCKRL

QDYLLTVLGPIAINVTEAVN

549194 ALLERGEN VES VI
(SEQ ID NO: 87)
5KVNYCKIKCLKGGVHTACKYGTSTKPNCGKMVVKAYGLTEAEKQEILKVH

NDFRQKVAKGLETRGNPGPQPPAKNMNNLVWNDELANIAQVWASQCNYG

HDTCKDTEKYPVGQNIAKRSTTAALFDSPGKLVKMWENEVKDFNPNIEWSK

NNLKKTGHYTQMVWAKTKEIGCGSVKYVKDEWYTHYLVCNYGPSGNFRN

EKLYEKK

Additional *vespula* sequences (NCBI entrez accession):
549193; 549192; 549191; 549190; 549189; 117414; 126761; 69576; 625255; 627189; 627188; 627187; 482382; 112561; 627186; 627185; 1923233; 897645; 897647; 745570; 225764; 162551.
Tree Allergen Sequences (Mainly Birch) Sequences:

114922 Bet v 1
(SEQ ID NO: 88)
MGVFNYETETTSVIPAARLFKAFILDGDNLFPKVAPQAISSVENIEGNGGPGTI

KKISFPEGFPFKYVKDRVDEVDHTNFKYNYSVIEGGPIGDTLEKISNEIKIVAT

PDGGSILKISNKYHTKGDHEVKAEQVKASKEMGETLLRAVESYLLAHSDAYN

130975 Bet v 2

(SEQ ID NO: 89)

MSWQTYVDEHLMCDIDGQASNSLASAIVGHDGSVWAQSSSFPQFKPQEITGI

MKDFEEPGHLAPTGLHLGGIKYMVIQGEAGAVIRGKKGSGGITIKKTGQALV

FGIYEEPVTPGQCNMVVERLGDYLIDQGL

1168696 Bet v 3

(SEQ ID NO: 90)

MPCSTEAMEKAGHGHASTPRKRSLSNSSFRLRSESLNTLRLRRIFDLFDKNSD

GIITVDELSRALNLLGLETDLSELESTVKSFTREGNIGLQFEDFISLHQSLNDSY

FAYGGEDEDDNEEDMRKSILSQEEADSFGGFKVFDEDGDGYISARELQMVL

GKLGFSEGSEIDRVEKMIVSVDSNRDGRVDFFEFKDMMRSVLVRSS

809536 Bet v 4

(SEQ ID NO: 91)

MADDHPQDKAERERIFKRFDANGDGKISAAELGEALKTLGSITPDEVKHMM

AEIDTDGDGFISFQEFTDFGRANRGLLKDVAKIF

543675 Que a I - Quercus alba = oak trees (fragment)

(SEQ ID NO: 92)

GVFTXESQETSVIAPAXLFKALFL

543509 Car b I - Carpinus betulus = hornbeam trees (fragment)

(SEQ ID NO: 93)

GVFNYEAETPSVIPAARLFKSYVLDGDKLIPKVAPQAIXK

543491 Aln g I - Alnus glutinosa = alder trees (fragment)

(SEQ ID NO: 94)

GVFNYEAETPSVIPAARLFKAFILDGDKLLPKVAPEAVSSVENI

1204056 Rubisco (SEQ ID NO: 95)

VQCMQVWPPLGLKKFETLSYLPPLSSEQLAKEVDYLLRKNLIPCLEFELEHGF

VYREHNRSPGYYDGRYWTMWKLPMFGCNDSSQVLKELEECKKAYPSAFIRI

IGFDDK

Additional tree allergen sequences (NCBI entrez accession number):
131919; 128193; 585564; 1942360; 2554672; 2392209; 2414158; 1321728; 1321726; 1321724; 1321722; 1321720; 1321718; 1321716; 1321714; 1321712; 3015520; 2935416; 464576; 1705843; 1168701; 1168710; 1168709; 1168708; 1168707; 1168706; 1168705; 1168704; 1168703; 1168702; 1842188; 2564228; 2564226; 2564224; 2564222; 2564220; 2051993; 1813891; 1536889; 534910; 534900; 534898; 1340000; 1339998; 2149808; 66207; 2129477; 1076249; 1076247; 629480; 481805; 81443; 1361968; 1361967; 1361966; 1361965; 1361964; 1361963; 1361962; 1361961; 1361960; 1361959; 320546; 629483; 629482; 629481; 541804; 320545; 81444; 541814; 629484; 474911; 452742; 1834387; 298737; 298736; 1584322; 1584321; 584320; 1542873; 1542871; 1542869; 1542867; 1542865; 1542863; 1542861; 1542859; 1542857; 1483232; 1483230; 1483228; 558561; 551640; 488605; 452746; 452744; 452740; 452738; 452736; 452734; 452732; 452730; 452728; 450885; 17938; 17927; 17925; 17921; 297538; 510951; 289331; 289329; 166953.

Peanut

Peanut sequences

1168391 Ara h 1

(SEQ ID NO: 96)

MRGRVSPLMLLLGILVLASVSATHAKSSPYQKKTENPCAQRCLQSCQQEP

DDLKQKACESRCTKLEYDPRCVYDPRGHTGTTNQRSPPGERTRGRQPG

DYDDDRRQPRREEGGRWGPAGPREREREEDWRQPREDWRRPSHQQPR

KIRPEGREGEQEWGTPGSHVREETSRNNPFYFPSRRFSTRYGNQNGRI

RVLQRFDQRSRQFQNLQNHRIVQIEAKPNTLVLPKHADADNILVIQQGQ

ATVTVANGNNRKSFNLDEGHALRIPSGFISYILNRHDNQNLRVAKISMPV

NTPGQFEDFFPASSRDQSSYLQGFSRNTLEAAFNAEFNEIRRVLLEEN

AGGEQEERGQRRWSTRSSENNEGVIVKVSKEHVEELTKHAKSVSKK

GSEEEGDITNPINLREGEPDLSNNFGKLFEVKPDKKNPQLQDLDMMLT

CVEIKEGALMLPHFNSKAMVIVVVNKGTGNLELVAVRKEQQQRGRRE

EEEDEDEEEEGSNREVRRYTARLKEGDVFIMPAAHPVAINASSELHLL

GFGINAENNHRIFLAGDKDNVIDQIEKQAKDLAFPGSGEQVEKLIKNQK

ESHFVSARPQSQSQSPSSPEKESPEKEDQEEENQGGKGPLLSILKAFN

Ragweed
*Ambrosia* sequences

113478 Amb a 1
(SEQ ID NO: 97)
MGIKHCCYILYFTLALVTLLQPVRSAEDLQQILPSANETRSLTTCGTYNIIDGC

WRGKADWAENRKALADCAQGFAKGTIGGKDGDIYTVTSELDDDVANPKEG

TLRFGAAQNRPLWIIFARDMVIRLDRELAINNDKTIDGRGAKVEIINAGFAIYN

VKNIIIHNIIMHDIVVNPGGLIKSHDGPPVPRKGSDGDAIGISGGSQIWIDHCSLS

KAVDGLIDAKHGSTHFTVSNCLFTQHQYLLLFWDFDERGMLCTVAFNKFTD

NVDQRMPNLRHGFVQVVNNNYERWGSYALGGSAGPTILSQGNRFLASDIKK

EVVGRYGESAMSESINWNWRSYMDVFENGAIFVPSGVDPVLTPEQNAGMIP

AEPGEAVLRLTSSAGVLSCQPGAPC

113479 Amb a 2
(SEQ ID NO: 98)
MGIKHCCYILYFTLALVTLVQAGRLGEEVDILPSPNDTRRSLQGCEAHNIIDK

CWRCKPDWAENRQALGNCAQGFGKATHGGKWGDIYMVTSDQDDDVVNP

KEGTLRFGATQDRPLWIIFQRDMIIYLQQEMVVTSDKTIDGRGAKVELVYGGI

TLMNVKNVIIHNIDIHDVRVLPGGRIKSNGGPAIPRHQSDGDAIHVTGSSDIWI

DHCTLSKSFDGLVDVNWGSTGVTISNCKFTHHEKAVLLGASDTHFQDLKMH

VTLAYNIFTNTVHERMPRCRFGFFQIVNNFYDRWDKYAIGGSSNPTILSQGNK

FVAPDFIYKKNVCLRTGAQEPEWMTWNWRTQNDVLENGAIFVASGSDPVLT

AEQNAGMMQAEPGDMVPQLTMNAGVLTCSPGAPC

113477 Amb a 1.3
(SEQ ID NO: 99)
MGIKQCCYILYFTLALVALLQPVRSAEGVGEILPSVNETRSLQACEALNIIDKC

WRGKADWENNRQALADCAQGFAKGTYGGKWGDVYTVTSNLDDDVANPK

EGTLRFAAAQNRPLWIIFKNDMVINLNQELVVNSDKTIDGRGVKVEIINGGLT

LMNVKNIIIHNINIHDVKVLPGGMIKSNDGPPILRQASDGDTINVAGSSQIWID

HCSLSKSFDGLVDVTLGSTHVTISNCKFTQQSKAILLGADDTHVQDKGMLAT

VAFNMFTDNVDQRMPRCRFGFFQVVNNNYDRWGTYAIGGSSAPTILCQGNR

FLAPDDQIKKNVLARTGTGAAESMAWNWRSDKDLLENGAIFVTSGSDPVLT

PVQSAGMIPAEPGEAAIKLTSSAGVFSCHPGAPC

113476 Amb a 1.2
(SEQ ID NO: 100)
MGIKHCCYILYFTLALVTLLQPVRSAEDVEEFLPSANETRRSLKACEAHNIIDK

CWRCKADWANNRQALADCAQGFAKGTYGGKHGDVYTVTSDKDDDVANP

KEGTLRFAAAQNRPLWIIFKRNMVIHLNQELVVNSDKTIDGRGVKVNIVNAG

LTLMNVKNIIIHNINIHDIKVCPGGMIKSNDGPPILRQQSDGDAINVAGSSQIWI

DHCSLSKASDGLLDITLGSSHVTVSNCKFTQHQFVLLLGADDTHYQDKGML

ATVAFNMFTDHVDQRMPRCRFGFFQVVNNNYDRWGTYAIGGSSAPTILSQG

NRFFAPDDIIKKNVLARTGTGNAESMSWNWRTDRDLLENGAIFLPSGSDPVLTPEQKAGM

IPAEPGEAVLRLTSSAGVLSCHQGAPC

113475 Amb a 1.1
(SEQ ID NO: 101)
MGIKHCCYILYFTLALVTLLQPVRSAEDLQEILPVNETRRLTTSGAYNIIDGCW

RGKADWAENRKALADCAQGFGKGTVGGKDGDIYTVTSELDDDVANPKEGT

LRFGAAQNRPLWIIFERDMVIRLDKEMVVNSDKTIDGRGAKVEIINAGFTLNG

-continued

VKNVIIHNINMHDVKVNPGGLIKSNDGPAAPRAGSDGDAISISGSSQIWIDHCS

LSKSVDGLVDAKLGTTRLTVSNSLFTQHQFVLLFGAGDENIEDRGMLATVAF

NTFTDNVDQRMPRCRHGFFQVVNNNYDKWGSYAIGGSASPTILSQGNRFCA

PDERSKKNVLGRHGEAAAESMKWNWRTNKDVLENGAIFVASGVDPVLTPEQSAGMIP

AEPGESALSLTSSAGVLSCQPGAPC

Cedar Sequences

493634 Cry j IB precursor
(SEQ ID NO: 102)
MDSPCLVALLVFSFVIGSCFSDNPIDSCWRGDSNWAQNRMKLADCAVGFGS

STMGGKGGDLYTVTNSDDDPVNPPGTLRYGATRDRPLWIIFSGNMNIKLKM

PMYIAGYKTFDGRGAQVYIGNGGPCVFIKRVSNVIIHGLYLYGCSTSVLGNVL

INESFGVEPVHPQDGDALTLRTATNIWIDHNSFSNSSDGLVDVTLTSTGVTISN

NLFFNHHKVMSLGHDDAYSDDKSMKVTVAFNQFGPNCGQRMPRARYGLV

HVANNNYDPWTIYAIGGSSNPTILSEGNSFTAPNESYKKQVTIRIGCKTSSSCS

NWVWQSTQDVFYNGAYFVSSGKYEGGNIYTKKEAFNVENGNATPHLTQNA

GVLTCSLSKRC

493632 Cry j IA precursor
(SEQ ID NO: 103)
MDSPCLVALLVLSFVIGSCFSDNPIDSCWRGDSNWAQNRMKLADCAVGFGS

STMGGKGGDLYTVTNSDDDPVNPAPGTLRYGATRDRPLWIIFSGNMNIKLK

MPMYIAGYKTFDGRGAQVYIGNGGPCVFIKRVSNVIIHGLHLYGCSTSVLGN

VLINESFGVEPVHPQDGDALTLRTATNIWIDHNSFSNSSDGLVDVTLSSTGVTI

SNNLFFNHHKVMLLGHDDAYSDDKSMKVTVAFNQFGPNCGQRMPRARYGL

VHVANNNYDPWTIYAIGGSSNPTILSEGNSFTAPNESYKKQVTIRIGCKTSSSC

SNWVWQSTQDVFYNGAYFVSSGKYEGGNIYTKKEAFNVENGNATPQLTKN

AGVLTCSLSKRC

1076242 Cry j II precursor - Japanese cedar
(SEQ ID NO: 104)
MAMKLIAPMAFLAMQLIIMAAAEDQSAQIMLDSVVEKYLRSNRSLRKVEHS

RHDAINIFNVEKYGAVGDGKHDCTEAFSTAWQAACKNPSAMLLVPGSKKFV

VNNLFFNGPCQPHFTFKVDGIIAAYQNPASWKNNRIWLQFAKLTGFTLMGKG

VIDGQGKQWWAGQCKWVNGREICNDRDRPTAIKFDFSTGLIIQGLKLMNSPE

FHLVFGNCEGVKIIGISITAPRDSPNTDGIDIFASKNFHLQKNTIGTGDDCVAIG

TGSSNIVIEDLICGPGHGISIGSLGRENSRAEVSYVHVNGAKFIDTQNGLRIKT

WQGGSGMASHIIYENVEMINSENPILINQFYCTSASACQNQRSAVQIQDVTYK

NIRGTSATAAAIQLKCSDSMPCKDIKLSDISLKLTSGKIASCLNDNANGYFSGH

VIPACKNLSPSAKRKESKSHKHPKTVMVENMRAYDKGNRTRILLGSRPPNCT

NKCHGCSPCKAKLVIVHRIMPQEYYPQRWICSCHGKIYHP

1076241 Cry j II protein - Japanese cedar
(SEQ ID NO: 105)
MAMKFIAPMAFVAMQLIIMAAAEDQSAQIMLDSDIEQYLRSNRSLRKVEHSR

HDAINIFNVEKYGAVGDGKHDCTEAFSTAWQAACKKPSAMLLVPGNKKFV

VNNLFFNGPCQPHFTFKVDGIIAAYQNPASWKNNRIWLQFAKLTGFTLMGKG

-continued

```
VIDGQGKQWWAGQCKWVNGREICNDRDRPTAIKFDFSTGLIIQGLKLMNSPE

FHLVFGNCEGVKIIGISITAPRDSPNTDGIDIFASKNFHLQKNTIGTDDCVAIG

TGSSNIVIEDLICGPGHGISIGSLGRENSRAEVSYVHVNGAKFIDTQNGLRIKT

WQGGSGMASHIIYENVEMINSENPILINQFYCTSASACQNQRSAVQIQDVTYK

NIRGTSATAAAIQLKCSDSMPCKDIKLSDISLKLTSGKIASCLNDNANGYFSGH

VIPACKNLSPSAKRKESKSHKHPKTVMVKNMGAYDKGNRTRILLGSRPPNCT

NKCHGCSPCKAKLVIVHRIMPQEYYPQRWMCSRHGKIYHP
```

541803 Cry j I precursor - Japanese cedar
(SEQ ID NO: 106)
```
MDSPCLVALLVLSFVIGSCFSDNPIDSCWRGDSNWAQNRMKLADCAVGFGS

STMGGKGGDLYTVTNSDDDPVNPPGTLRYGATRDRPLWIIFSGNMNIKLKM

PMYIAGYKTFDGRGAQVYIGNGGPCVFIKRVSNVIIHGLHLYGCSTSVLGNVL

INESFGVEPVHPQDGDALTLRTATNIWIDHNSFSNSSDGLVDVTLSSTGVTISN

NLFFNHHKVMLLGHDDAYSDDKSMKVTVAFNQFGPNCGQRMPRARYGLV

HVANNNYDPWTIYAIGGSSNPTILSEGNSFTAPNESYKKQVTIRIGCKTSSSCS

NWVWQSTQDVFYNGAYFVSSGKYEGGNIYTKKEAFNVENGNATPQLTKNAGVLTCSL

SKRC
```

541802 Cry j I precursor- Japanese cedar
(SEQ ID NO: 107)
```
MDSPCLVALLVFSFVIGSCFSDNPIDSCWRGDSNWAQNRMKLADCAVGFGS

STMGGKGGDLYTVTNSDDDPVNPAPGTLRYGATRDRPLWIIFSGNMNIKLK

MPMYIAGYKTFDGRGAQVYIGNGGPCVFIKRVSNVIIHGLYLYGCSTSVLGN

VLINESFGVEPVHPQDGDALTLRTATNIWIDHNSFSNSSDGLVDVTLTSTGVTI

SNNLFFNHHKVMSLGHDDAYSDDKSMKVTVAFNQFGPNCGQRMPRARYGL

VHVANNNYDPWTIYAIGGSSNPTILSEGNSFTAPNESYKKQVTIRIGCKTSSSCSNWVWQ

STQDVFYNGAYFVSSGKYEGGNIYTKKEAFNVENGNATPHLTQNAGVLTCSLSKRC
```

Dog
*Canis* sequences:

Can f 1
(SEQ ID NO: 108)
```
MKTLLLLTIGFSLIAILQAQDTPALGKDTVAVSGKWYLKAMTADQEVPEKP

DSVTPMILKAQKGGNLEAKITMLTNGQCQNITVVLHKTSEPGKYTAYEGQ

RVVFIQPSPVRDHYILYCEGELHGRQIRMAKLLGRDPEQSQEALEDFRE

FSRAKGLNQEILELAQSETCSPGGQ
```

Serum albumin fragment (SEQ ID NO: 109)
```
         EAYKSEIAHRYNDLGEEHFRGLVL
```

Serum albumin fragment (SEQ ID NO: 110)
```
LSSAKERFKCASLQKFGDRAFKAWSVARLSQRFPKADFAEISKVVTDLT

KVHKECCHGDLLECADDRADLAKYMCENQDSISTKLKECCDKPVLEKS

QCLAEVERDELPGDLPSLAADFVEDKEVCKNYQEAKDVFLGTFLYEYS

RRHPEYSVSLLLRLAKEYEATLEKCCATDDPPTCYAKVLDEFKPLVDEP

QNLVKTNCELFEKLGEYGFQNALLVRYTKKAPQVSTPTLVVEVSRKLG

KVGTKCCKKPESERMSCADDFLS
```

Can f 2
(SEQ ID NO: 111)
```
MQLLLLTVGLALICGLQAQEGNHEEPQGGLEELSGRWHSVALASNKSDLI

KPWGHFRVFIHSMSAKDGNLHGDILIPQDGQCEKVSLTAFKTATSNKFD

LEYWGHNDLYLAEVDPKSYLILYMINQYNDDTSLVAHLMVRDLSRQQDF

LPAFESVCEDIGLHKDQIVVLSDDDRCQGSRD
```

Additional dog allergen protein (NCBI entrez accession):
1731859

Horse
*Equus* sequences:

1575778 Equ c1
(SEQ ID NO: 112)
```
MKLLLLCLGLILVCAQQEENSDVAIRNFDISKISGEWYSIFLASDVKEKI

EENGSMRVFVDVIRALDNSSLYAEYQTKVNGECTEFPMVFDKTEED

GVYSLNYDGYNVFRISEFENDEHIILYLVNFDKDRPFQLFEFYAREPD
```

-continued

VSPEIKEEFVKIVQKRGIVKENIIDLTKIDRCFQLRGNGVAQA

3121755 Equ c 2
(SEQ ID NO: 113)
SQXPQSETDYSQLSGEWNTIYGAASNIXK

*Euroglyphus* (mite)

*Euroglyphus* sequences:

Eur m 1 (variant)
(SEQ ID NO: 114)
TYACSINSVSLPSELDLRSLRTVTPIRMQGGCGSCWAFSGVASTESAYLAYRN

MSLDLAEQELVDCASQNGCHGDTIPRGIEYIQQNGVVQEHYYPYVAREQSC

HRPNAQRYGLKNYCQISPPDSNKIRQALTQTHTAVAVIIGIKDLNAFRHYDGRTIMQH

DNGYQPNYHAVNIVGYGNTQGVDYWIVRNSWDTTWGDNGYGYFAANINL

Eur m 1 (variant)
(SEQ ID NO: 115)
TYACSINSVSLPSELDLRSLRTVTPIRMQGGCGSCWAFSGVASTESAYLAYRN

MSLDLAEQELVDCASQNGCHGDTIPRGIEYIQQNGVVQEHYYPYVAREQSC

HRPNAQRYGLKNYCQISPPDSNKIRQALTQTHTAVAVIIGIKDLNAFRHYDGRTIMQH

DNGYQPNYHAVNIVGYGNTQGVDYWIVRNSWDTTWGDNGYGYFAANINL

Eur m 1 (variant)
(SEQ ID NO: 116)
ETNACSINGNAPAEIDLRQMRTVTPIRMQGGCGSCWAFSGVAATESAYLAY

RNQSLDLAEQELVDCASQHGCHGDTIPRGIEYIQHNGVVQESYYRYVAREQS

CRRPNAQRFGISNYCQIYPPNANKIREALAQTHSAIAVIIGIKDLDAFRHYDGRTIIQRD

NGYQPNYHAVNIVGYSNAQGVDYWIVRNSWDTNWGDNGYGYFAANIDL

Eur m 1 (variant)
(SEQ ID NO: 117)
ETSACRINSVNVPSELDLRSLRTVTPIRMQGGCGSCWAFSGVAATESAYLAY

RNTSLDLSEQELVDCASQHGCHGDTIPRGIEYIQQNGVVEERSYPYVAREQQ

CRRPNSQHYGISNYCQIYPPDVKQIREALTQTHTAIAVIIGIKDLRAFQHYDGRTIIQHD

NGYQPNYHAVNIVGYGSTQGVDYWIVRNSWDTTWGDSGYGYFQAGNNL

Poa (Grass) Sequences

113562 POLLEN ALLERGEN POA P 9
(SEQ ID NO: 118)
MAVQKYTVALFLVALVVGPAASYAADLSYGAPATPAAPAAGYTPAAPAGA

APKATTDEQKMIEKINVGFKAAVAAAGGVPAANKYKTFVATFGAASNKAFA

EALSTEPKGAAVDSSKAALTSKLDAAYKLAYKSAEGATPEAKYDDYVATLS

EALRIIAGTLEVHGVKPAAEEVKATPAGELQVIDKVDAAFKVAATAANAAPA

NDKFTVFEAAFNDAIKASTGGAYQSYKFIPALEAAVKQSYAATVATAPAVK

YTVFETALKKAITAMSQAQKAAKPAAAATGTATAAVGAATGAATAAAGGYKV

113561 POA P 9
(SEQ ID NO: 119)
MAVHQYTVALFLAVALVAGPAASYAADVGYGAPATLATPATPAAPAAGYT

PAAPAGAAPKATTDEQKLIEKINAGFKAAVAAAAGVPAVDKYKTFVATFGT

ASNKAFAEALSTEPKGAAAASSNAVLTSKLDAAYKLAYKSAEGATPEAKYD

AYVATLSEALRIIAGTLEVHAVKPAGEEVKAIPAGELQVIDKVDAAFKVAAT

-continued

AANAAPANDKFTVFEAAFNDAIKASTGGAYQSYKFIPALEAAVKQSYAATV

ATAPAVKYTVFETALKKAITAMSQAQKAAKPAAAVTATATGAVGAATGAVGAATGAAT

AAAGGYKTGAATPTAGGYKV

113560 POA P 9

(SEQ ID NO: 120)
MDKANGAYKTALKAASAVAPAEKFPVFQATFDKNLKEGLSGPDAVGFAKK

LDAFIQTSYLSTKAAEPKEKFDLFVLSLTEVLRFMAGAVKAPPASKFPAKPAP

KVAAYTPAAPAGAAPKATTDEQKLIEKINVGFKAAVAAAAGVPAASKYKTF

VATFGAASNKAFAEALSTEPKGAAVASSKAVLTSKLDAAYKLAYKSAEGAT

PEAKYDAYVATLSEALRIIAGTLEVHGVKPAAEEVKAIPAGELQVIDKVDAA

FKVAATAANAAPANDKFTVFEAAFNDAIKASTGGAYQSYKFIPALEAAVKQ

SYAATVATAPAVKYTVFETALKKAITAMSQAQKAAKPAAAVTGTATSAVGAATGAATAA

AGGYKV

Cockroach sequences

2833325 Cr p1

(SEQ ID NO: 121)
MKTALVFAAVVAFVAARFPDHKDYKQLADKQFLAKQRDVLRLFHRVHQHN

ILNDQVEVGIPMTSKQTSATTVPPSGEAVHGVLQEGHARPRGEPFSVNYEKH

REQAIMLYDLLYFANDYDTFYKTACWARDRVNEGMFMYSFSIAVFHRDDM

QGVMLPPPYEVYPYLFVDHDVIHMAQKYWMKNAGSGEHHSHVIPVNFTLR

TQDHLLAYFTSDVNLNAFNTYYRYYYPSWYNTTLYGHNIDRRGEQFYYTYK

QIYARYFLERLSNDLPDVYPFYYSKPVKSAYNPNLRYHNGEEMPVRPSNMY

VTNFDLYYIADIKNYEKRVEDAIDFGYAFDEHMKPHSLYHDVHGMEYLADM

IEGNMDSPNFYFYGSIYHMYHSMIGHIVDPYHKMGLAPSLEHPETVLRDPVF

YQLWKRVDHLFQKYKNRLPRYTHDELAFEGVKVENVDVGKLYTYFEQYD

MSLDMAVYVNNVDQISNVDVQLAVRLNHKPFTYNIEVSSDKAQDVYVAVF

LGPKYDYLGREYDLNDRRHYFVEMDRFPYHVGAGKTVIERNSHDSNIIAPER

DSYRTFYKKVQEAYEGKSQYYVDKGHNYCGYPENLLIPKGKKGGQAYTFY

VIVTPYVKQDEHDFEPYNYKAFSYCGVGSERKYPDNKPLGYPFDRKIYSNDF

YTPNMYFKDVIIFHKKYDEVGVQGH

2231297 Cr p2

(SEQ ID NO: 122)
INEIHSIIGLPPFVPPSRRHARRGVGINGLIDDVIAILPVDELKALFQEKLETSPDFKAL

YDAIRSPEFQSIISTLNAMQRSEHHQNLRDKGVDVDHFIQLIRALFGLSR

AARNLQDDLNDFLHSLEPISPRHRHGLPRQRRRSARVSAYLHADDFHKIITTIE

ALPEFANFYNFLKEHGLDVVDYINEIHSIIGLPPFVPPSRRHARRGVGINGLIDD

VIAILPVDELKALFQEKLETSPDFKALYDAIRSPEFQSIISTLNAMPEYQELLQN

LRDKGVDVDHFIRVDQGTLRTLSSGQRNLQDDLNDFLALIPTDQILAIAMDYL

ANDAEVQELVAYLQSDDFHKIITTIEALPEFANFYNFLKEHGLDVVDYINEIHS

IIGLPPFVPPSQRHARRGVGINGLIDDVIAILPVDELKALFQEKLETSPDFKALY

DAIDLRSSRA

-continued

1703445 Bla g 2
(SEQ ID NO: 123)
MIGLKLVTVLFAVATITHAAELQRVPLYKLVHVFINTQYAGITKIGNQNFLTV

FDSTSCNVVVASQECVGGACVCPNLQKYEKLKPKYISDGNVQVKFFDTGSA

VGRGIEDSLTISNLTTSQQDIVLADELSQEVCILSADVVVGIAAPGCPNALKGK

TVLENFVEENLIAPVFSIHHARFQDGEHFGEIIFGGSDWKYVDGEFTYVPLVG

DDSWKFRLDGVKIGDTTVAPAGTQAIIDTSKAIIVGPKAYVNPINEAIGCVVE

KTTTRRICKLDCSKIPSLPDVTFVINGRNFNISSQYYIQQNGNLCYSGFQPCGH

SDHFFIGDFFVDHYYSEFNWENKTMGFGRSVE

SV

1705483 Bla g 4
(SEQ ID NO: 124)
AVLALCATDTLANEDCFRHESLVPNLDYERFRGSWIIAAGTSEALTQYKCWI

DRFSYDDALVSKYTDSQGKNRTTIRGRTKFEGNKFTIDYNDKGKAFSAPYSV

LATDYENYAIVEGCPAAANGHVIYVQIRFSVRRFHPKLGDKEMIQHYTLDQV

NQHKKAIEEDLKHFNLKYEDLHSTCH

2326190 Bla g 5
(SEQ ID NO: 125)
YKLTYCPVKALGEPIRFLLSYGEKDFEDYRFQEGDWPNLKPSMPFGKTPVLEI

DGKQTHQSVAISRYLGKQFGLSGKDDWENLEIDMIVDTISDFRAAIANYHYD

ADENSKQKKWDPLKKETIPYYTKKFDEVVKANGGYLAAGKLTWADFYFVA

ILDYLNHMAKEDLVANQPNLKALREKVLGLPAIKAWVAKRPPTDL

Additional Cockroach Sequences (NCBI Entrez Accession Numbers):
2580504; 1580797; 1580794; 1362590; 544619; 544618; 1531589; 1580792; 1166573; 1176397; 2897849.

Allergen (General) Sequences:
NCBI Accession Numbers
2739154; 3719257; 3703107; 3687326; 3643813; 3087805; 1864024; 1493836; 1480457; 2598976; 2598974; 1575778; 763532; 746485; 163827; 163823; 3080761; 163825; 3608493; 3581965; 2253610; 2231297; 2897849; 3409499; 3409498; 3409497; 3409496; 3409495; 3409494; 3409493; 3409492; 3409491; 3409490; 3409489; 3409488; 3409487; 3409486; 3409485; 3409484; 3409483; 3409482; 3409481; 3409480; 3409479; 3409478; 3409477; 3409476; 3409475; 3409474; 3409473; 3409472; 3409471; 3409470; 3409469; 3409468; 3409467; 3409466; 3409465; 3409464; 3409463; 3409462; 3409461; 3409460; 3409459; 3409458; 3409457; 3409456; 3318885; 3396070; 3367732; 1916805; 3337403; 2851457; 2851456; 1351295; 549187; 136467; 1173367; 2499810; 2498582; 2498581; 1346478; 1171009; 126608; 114091; 2506771; 1706660; 1169665; 1169531; 232086; 416898; 114922; 2497701; 1703232; 1703233; 1703233; 1703232; 3287877; 3122132; 3182907; 3121758; 3121756; 3121755; 3121746; 3121745; 3319925; 3319923; 3319921; 3319651; 3318789; 3318779; 3309647; 3309047; 3309045; 3309043; 3309041; 3309039; 3288200; 3288068; 2924494; 3256212; 3256210; 3243234; 3210053; 3210052; 3210051; 3210050; 3210049; 3210048; 3210047; 3210046; 3210045; 3210044; 3210043; 3210042; 3210041; 3210040; 3210039; 3210038; 3210037; 3210036; 3210035; 3210034; 3210033; 3210032; 3210031; 3210030; 3210029; 3210028; 3210027; 3210026; 3210025; 3210024; 3210023; 3210022; 3210021; 3210020; 3210019; 3210018; 3210017; 3210016; 3210015; 3210014; 3210013; 3210012; 3210011; 3210010; 3210009; 3210008; 3210007; 3210006; 3210005; 3210004; 3210003; 3210002; 3210001; 3210000; 3209999; 3201547; 2781152; 2392605; 2392604; 2781014; 1942360; 2554672; 2392209; 3114481; 3114480; 2981657; 3183706; 3152922; 3135503; 3135501; 3135499; 3135497; 2414158; 1321733; 1321731; 1321728; 1321726; 1321724; 1321722; 1321720; 1321718; 1321716; 1321714; 1321712; 3095075; 3062795; 3062793; 3062791; 2266625; 2266623; 2182106; 3044216; 2154736; 3021324; 3004467; 3005841; 3005839; 3004485; 3004473; 3004471; 3004469; 3004465; 2440053; 1805730; 2970629; 2959898; 2935527; 2935416; 809536; 730091; 585279; 584968; 2498195; 2833325; 2498604; 2498317; 2498299; 2493414; 2498586; 2498585; 2498576; 2497749; 2493446; 2493445; 1513216; 729944; 2498099; 548449; 465054; 465053; 465052; 548671; 548670; 548660; 548658; 548657; 2832430; 232084; 2500822; 2498118; 2498119; 2498119; 2498118; 1708296; 1708793; 416607; 416608; 416608; 416607; 2499791; 2498580; 2498579; 2498578; 2498577; 2497750; 1705483; 1703445; 1709542; 1709545; 1710589; 1352699; 1346568; 1346323; 1346322; 2507248; 11352240; 1352239; 1352237; 1352229; 1351935; 1350779; 1346806; 1346804; 1346803; 1170095; 1168701; 1352506; 1171011; 1171008; 1171005; 1171004; 1171002; 1171001; 1168710; 1168709; 1168708; 1168707; 1168706; 1168705; 1168704; 1168703; 1168702; 1168696; 1168391; 1168390; 1168348; 1173075; 1173074; 1173071; 1169290; 1168970; 1168402; 729764; 729320; 729979; 729970; 729315; 730050; 730049; 730048; 549194; 549193; 549192; 549191; 549190; 549189; 549188; 549185; 549184; 549183; 549182; 549181; 549180; 549179; 464471; 585290; 416731; 1169666; 113478; 113479; 113477; 113476; 113475; 130975; 119656; 113562; 113561; 113560; 416610; 126387; 126386; 126385; 132270; 416611; 416612; 416612; 416611; 730035; 127205; 1352238; 125887; 549186; 137395; 730036; 133174;

114090; 131112; 126949; 129293; 124757; 129501; 416636; 2801531; 2796177; 2796175; 2677826; 2735118; 2735116; 2735114; 2735112; 2735110; 2735108; 2735106; 2735104; 2735102; 2735100; 2735098; 2735096; 2707295; 2154730; 2154728; 1684720; 2580504; 2465137; 2465135; 2465133; 2465131; 2465129; 2465127; 2564228; 2564226; 2564224; 2564222; 2564220; 2051993; 1313972; 1313970; 1313968; 1313966; 2443824; 2488684; 2488683; 2488682; 2488681; 2488680; 2488679; 2488678; 2326190; 2464905; 2415702; 2415700; 2415698; 2398759; 2398757; 2353266; 2338288; 1167836; 414703; 2276458; 1684718; 2293571; 1580797; 1580794; 2245508; 2245060; 1261972; 2190552; 1881574; 511953; 1532058; 1532056; 1532054; 1359436; 666007; 487661; 217308; 1731859; 217306; 217304; 1545803; 1514943; 577696; 516728; 506858; 493634; 493632; 2154734; 2154732; 543659; 1086046; 1086045; 2147643; 2147642; 1086003; 1086002; 1086001; 543675; 543623; 543509; 543491; 1364099; 2147108; 2147107; 1364001; 1085628; 631913; 631912; 631911; 2147092; 477301; 543482; 345521; 542131; 542130; 542129; 100636; 2146809; 480443; 2114497; 2144915; 72355; 71728; 319828; 1082946; 1082945; 1082944; 539716; 539715; 423193; 423192; 423191; 423190; 1079187; 627190; 627189; 627188; 627187; 482382; 1362656; 627186; 627185; 627182; 482381; 85299; 85298; 2133756; 2133755; 1079186; 627181; 321044; 321043; 112559; 112558; 1362590; 2133564; 1085122; 1078971; 627144; 627143; 627142; 627141; 280576; 102835; 102834; 102833; 102832; 84703; 84702; 84700; 84699; 84698; 84696; 477888; 477505; 102575; 102572; 478272; 2130094; 629813; 629812; 542172; 542168; 542167; 481432; 320620; 280414; 626029; 542132; 320615; 320614; 100638; 100637; 100635; 82449; 320611; 320610; 280409; 320607; 320606; 539051; 539050; 539049; 539048; 322803; 280407; 100501; 100498; 100497; 100496; 1362137; 1362136; 1362135; 1362134; 1362133; 1362132; 1362131; 1362130; 1362129; 1362128; 100478; 2129891; 1076531; 1362049; 1076486; 2129817; 2129816; 2129815; 2129814; 2129813; 2129812; 2129805; 2129804; 2129802; 2129801; 2129800; 2129799; 479902; 479901; 2129477; 1076247; 629480; 1076242; 1076241; 541803; 541802; 280372; 280371; 1361968; 1361967; 1361966; 1361965; 1361964; 1361963; 1361962; 1361961; 1361960; 1361959; 320546; 2119763; 543622; 541804; 478825; 478824; 478823; 421788; 320545; 81444; 626037; 626028; 539056; 483123; 481398; 481397; 100733; 100732; 100639; 625532; 1083651; 322674; 322673; 81719; 81718; 2118430; 2118429; 2118428; 2118427; 419801; 419800; 419799; 419798; 282991; 100691; 322995; 322994; 101824; 626077; 414553; 398830; 1311457; 1916292; 1911819; 1911818; 1911659; 1911582; 467629; 467627; 467619; 467617; 915347; 1871507; 1322185; 1322183; 897645; 897647; 1850544; 1850542; 1850540; 288917; 452742; 1842045; 1839305; 1836011; 1836010; 1829900; 1829899; 1829898; 1829897; 1829896; 1829895; 1829894; 1825459; 1808987; 159653; 1773369; 1769849; 1769847; 608690; 1040877; 1040875; 1438761; 1311513; 1311512; 1311511; 1311510; 1311509; 1311689; 1246120; 1246119; 1246118; 1246117; 1246116; 1478293; 1478292; 1311642; 1174278; 1174276; 1086972; 1086974; 1086976; 1086978; 1086978; 1086976; 1086974; 1086972; 999009; 999356; 999355; 994866; 994865; 913758; 913757; 913756; 913285; 913283; 926885; 807138; 632782; 601807; 546852; 633938; 544619; 544618; 453094; 451275; 451274; 407610; 407609; 404371; 409328; 299551; 299550; 264742; 261407; 255657; 250902; 250525; 1613674; 1613673; 1613672; 1613671; 1613670; 1613304; 1613303; 1613302; 1613240; 1613239; 1613238; 1612181; 1612180; 1612179; 1612178; 1612177; 1612176; 1612175; 1612174; 1612173; 1612172; 1612171; 1612170; 1612169; 1612168; 1612167; 1612166; 1612165; 1612164; 1612163; 1612162; 1612161; 1612160; 1612159; 1612158; 1612157; 1612156; 1612155; 1612154; 1612153; 1612152; 1612151; 1612150; 1612149; 1612148; 1612147; 1612146; 1612145; 1612144; 1612143; 1612142; 1612141; 1612140; 1612139; 1093120; 447712; 447711; 447710; 1587177; 158542; 1582223; 1582222; 1531589; 1580792; 886215; 1545897; 1545895; 1545893; 1545891; 1545889; 1545887; 1545885; 1545883; 1545881; 1545879; 1545877; 1545875; 166486; 1498496; 1460058; 972513; 1009442; 1009440; 1009438; 1009436; 1009434; 7413; 1421808; 551228; 452606; 32905; 1377859; 1364213; 1364212; 395407; 22690; 22688; 22686; 22684; 488605; 17680; 1052817; 1008445; 1008443; 992612; 706811; 886683; 747852; 939932; 19003; 1247377; 1247375; 1247373; 862307; 312284; 999462; 999460; 999458; 587450; 763064; 886209; 1176397; 1173557; 902012; 997915; 997914; 997913; 997912; 997911; 997910; 99790; 997908; 997907; 997906; 997905; 997904; 997903; 997902; 997901; 997900; 997899; 997898; 997897; 997896; 997895; 997894; 997893; 997892; 910984; 910983; 910982; 910981; 511604; 169631; 169629; 169627; 168316; 168314; 607633; 555616; 293902; 485371; 455288; 166447; 166445; 166443; 166435; 162551; 160780; 552080; 156719; 156715; 515957; 515956; 515955; 515954; 515953; 459163; 166953; 386678; 169865.

Delivery Methods

Once formulated the compositions of the invention can be delivered to a subject in vivo using a variety of known routes and techniques. For example, a composition can be provided as an injectable solution, suspension or emulsion and administered via parenteral, subcutaneous, epidermal, intradermal, intramuscular, intraarterial, intraperitoneal, intravenous injection using a conventional needle and syringe, or using a liquid jet injection system. Compositions can also be administered topically to skin or mucosal tissue, such as nasally, intratracheally, intestinal, rectally or vaginally, or provided as a finely divided spray suitable for respiratory or pulmonary administration. Other modes of administration include oral administration, suppositories, sublingual administration, and active or passive transdermal delivery techniques.

Where a peptide of the invention is to be administered, it is preferred to administer the peptide to a site in the body where it will have the ability to contact suitable antigen presenting cells, and where it, or they, will have the opportunity to contact T cells of the individual. Where an APC is to be administered, it is preferred to administer the APC to a site in the body where it will have the ability to contact, and activate, suitable T cells of the individual.

Delivery Regimes

Administration of the peptides/polynucleotides/cells (such as the composition containing a plurality of peptides) may be by any suitable method as described above. Suitable amounts of the peptide may be determined empirically, but typically are in the range given below. A single administration of each peptide may be sufficient to have a beneficial effect for the patient, but it will be appreciated that it may be beneficial if the peptide is administered more than once, in which case typical administration regimes may be, for example, once or twice a week for 2-4 weeks every 6 months, or once a day for a week every four to six months. As will be appreciated, each peptide or polynucleotide, or combination of peptides and/or polynucleotides may be administered to a patient singly or in combination.

Dosages for administration will depend upon a number of factors including the nature of the composition, the route of administration and the schedule and timing of the administration regime. Suitable doses of a molecule or a combination of molecules of the invention may be in the order of up to 10 µg, up to 15 µg, up to 20 µg, up to 25 µg, up to 30 µg, up to 35 µg, up to 50 µg, up to 100 µg, up to 500 µg or more per administration. Suitable doses may be less than 15 µg, but at least 1 ng, or at least 2 ng, or at least 5 ng, or at least 50 ng, or least 100 ng, or at least 500 ng, or at least 1 µg, or at least 10 µg. For some molecules or combinations of the invention, the dose used may be higher, for example, up to 1 mg, up to 2 mg, up to 3 mg, up to 4 mg, up to 5 mg or higher. Such doses may be provided in a liquid formulation, at a concentration suitable to allow an appropriate volume for administration by the selected route. It will be understood that the above doses refer to total dose in the case of a combination of molecules. For example, "up to 35 µg" refers to a total peptide concentration of up to 35 µg in a composition comprising a combination of more than one peptide.

Kits

The invention also relates to a combination of components described herein suitable for use in a treatment of the invention which are packaged in the form of a kit in a container. Such kits may comprise a series of components to allow for a treatment of the invention. For example, a kit may comprise four or more different peptides, polynucleotides and/or cells of the invention, or four or more peptides, polynucleotides or cells of the invention and one or more additional therapeutic agents suitable for simultaneous administration, or for sequential or separate administration. The kit may optionally contain other suitable reagent(s) or instructions and the like.

The invention is illustrated by the following Examples.

Example 1

Screening of Peptide Mixtures for MHC Binding Characteristics

Binding Assays

Peptides

The following peptides that encompass the sequences of Fel d1 were investigated for their capacity to bind the nine HLA-DR molecules: DR1, DR3, DR4, DR7, DR11, DR13, DR15, B4 and B5.

| | | | | SEQ ID NO: |
|---|---|---|---|---|
| MLA1 | H$_2$N EICPAVKRDVDLFLTGT COOH | Derived from Fel d1 chain 1 | | 1 |
| MLA2 | H$_2$N LFLTGTPDEYVEQVAQY COOH | Derived from Fel d1 chain 1 | | 8 |
| MLA3 | H$_2$N EQVAQYKALPVVLENA COOH | Derived from Fel d1 chain 1 | | 2 |
| MLA4 | H$_2$N KALPVVLENARILKNCV COOH | Derived from Fel d1 chain 1 | | 3 |
| MLA5 | H$_2$N RILKNCVDAKMTEEDKE COOH | Derived from Fel d1 chain 1 | | 4 |
| MLA6 | H$_2$N KMTEEDKENALSLLDK COOH | Derived from Fel d1 chain 1 | | 9 |
| MLA7 | H$_2$N KENALSVLDKIYTSPL COOH | Derived from Fel d1 chain 1 | | 5 |
| MLA8* | H$_2$N *VKMAETCPIFYDVFFA* COOH | Derived from Fel d1 chain 2 | | 13 |
| MLA9* | H$_2$N *CPIFYDVFFAVANGNEL* COOH | Derived from Fel d1 chain 2 | | 14 |
| MLA10* | H$_2$N *GNELLLKLSLTKVNAT* COOH | Derived from Fel d1 chain 2 | | 15 |
| MLA11 | H$_2$N LTKVNATEPERTAMKK COOH | Derived from Fel d1 chain 2 | | 10 |
| MLA12 | H$_2$N TAMKKIQDCYVENGLI COOH | Derived from Fel d1 chain 2 | | 6 |
| MLA13* | H$_2$N *CYVENGLISRVLDGLV* COOH | Derived from Fel d1 chain 2 | | 16 |
| MLA14 | H$_2$N SRVLDGLVMTTISSSK COOH | Derived from Fel d1 chain 2 | | 7 |
| MLA15 | H$_2$N ISSSKDCMGEAVQNTV COOH | Derived from Fel d1 chain 2 | | 11 |
| MLA16 | H$_2$N AVQNTVEDLKLNTLGR COOH | Derived from Fel d1 chain 2 | | 12 |

*Peptides shown in italics were assessed for binding but not considered further in these experiments due to relatively poor solubility.

Binding Conditions for MHC Binding Assays

EBV homozygous cell lines were used as sources of human HLA class II molecules (Tab. 4). HLA-DR molecules were purified by affinity chromatography using the monomorphic Mab L243 (ATCC, Rockville, USA) coupled to protein A sepharose CL 4B gel (Pharmacia, France). Briefly, cells were lysed on ice at 5×10$^8$ cells/ml in 150 mM NaCl, 10 mM Tris HCl pH=8.3 buffer containing 1% Nonidet P40 (NP40), 10 mg/l aprotinin, 5 mM EDTA and 10 mM PMSF. After centrifugation at 100 000 g for 1 h, the supernatant was applied to a sepharose 4B and protein A-sepharose 4B columns and then to the specific affinity column. HLA-DR molecules were eluted with 1.1 mM n-dodecyl b-D-maltoside (DM), 500 mM NaCl and 500 mM Na2CO3 is pH=11.5. Fractions were immediately neutralized to pH=7 with 2 M Tris HCl pH=6.8 buffer and extensively dialysed against 1 mM DM, 150 mM NaCl, 10 mM phosphate pH=7 buffer. For HLA-DR molecules beyond lot number 40 the 1 mM DM in dialysis buffer was replaced by 1 mM NOGP.

HLA-DR molecules were diluted in 10 mM phosphate, 150 mM NaCl, 1 mM DM, 10 mM citrate, 0.003% thimerosal buffer with an appropriate biotinylated peptide and serial dilutions of competitor peptides. Binding conditions of each molecule are detailed in Tab 4. Samples (100 µl per well) were incubated in 96-wells polypropylene plates (Nunc, Denmark) at 37° C. for 24 h to 72 h. After neutralization with 50 µl of 450 mM Tris HCl pH=7.5, 0.003% thimerosal, 0.3% BSA, 1 mM DM buffer, samples were applied to 96-well maxisorp ELISA plates (Nunc, Denmark) previously coated with 10 mg/ml L243 Mab and saturated with 100 mM Tris HCl pH=7.5, 0.3% BSA, 0.003% thimerosal buffer. They were allowed to bind to the antibody-coated plates for 2 h at room temperature. Bound biotinylated peptide was detected by incubating streptavidine-alkaline phosphatase conjugate (Amersham, U.K.), and after washings, by adding 4-methylumbelliferyl phosphate substrate (Sigma, France). Emitted fluorescence was measured at 450 nm upon excitation at 365 nm on a Wallac Victor2 1420 multilabel counter fluorimeter (Perkin Elmer). Maximal binding was determined by incubating the biotinylated peptide with the MHC II molecule in the absence of competitor. Binding specificity was assessed by adding an excess of non biotinylated peptide. Background did not significantly differ from that obtained by incubating the biotinylated peptide without MHC II molecules. Data were expressed as the peptide concentration that prevented binding of 50% of the labeled peptide (IC50). Binding ability was then evaluated relative to known strong binding control (reference) peptide. Suitable reference peptides for the HLA alleles tested in these experiments are: DR1 (DRB1*0101 allele): HA 306-318 (PKYVKQNTLKLAT) (SEQ ID NO:17); DR3 (DRB1*0301 allele): MT216 (AKTIAYDEE-ARRGLE) (SEQ ID NO:18); DR4 (DRB1*0401 allele): HA 306-318 (PKYVKQNTLKLAT) (SEQ ID NO:17); DR7 (DRB1*0701 allele):YKL (AAYAAAKAAALAA) (SEQ ID NO:19); DRB1*1101: HA 306-318 (PKYVKQNTLKLAT) (SEQ ID NO:17); DR13 (DRB1*1301 allele): B1 21-36 (TERVRLVTRHIYNREE) (SEQ ID NO:20); DR15 (DRB1*1501 allele): A3 152-166 (EAEQLRRAYLDGT-GVE) (SEQ ID NO:21); DRB4 (DRB4*0101 allele): E2/E7 (AGDLLAIETDKATI) (SEQ ID NO:22); and DRB5 (DRB5*0101 allele): HA 306-318 (PKYVKQNTLKLAT) (SEQ ID NO:17).

Results

Binding and non-binding peptides were first discriminated on the basis of an upper 1000 nM threshold as it is generally described in the literature (Southwood et al (1998). J Immunol 160:3363; Geluk et al (1998) Proc Natl Acad Sci USA 95:10797), but are additionally assessed by comparison to reference peptides. The reference peptides are selected from among the best binding peptides of each given HLA molecule. Relative to the reference peptides, a peptide is a weak binder for a given HLA molecule if it has an IC50 more than 100 fold lower than the reference peptide for the given HLA molecule. A peptide is a moderate binder is it has an IC50 more than 20 fold lower but less than a 100 fold lower than the reference peptide for the given HLA molecule. A peptide is a strong binder if it has an 1050 less than 20 fold lower than the reference peptide for the given HLA molecule.

Analysis of Preferred Peptide Mixtures

The nine HLA alleles used for these experiments encompass a high proportion of the Caucasian population. (Reference frequencies of HLA alleles in the population are provided in Table 3 of Example 2). Accordingly, combinations of peptides were evaluated to determine which would give the broadest coverage of different HLA molecules. The target criteria for a mixture was therefore defined as follows: For a given HLA molecule, a mixture must comprise either 2 strong binding peptides and 1 moderate binding peptide, or 1 strong binding peptide and 3 moderate binding peptides. Preferred mixtures achieve these criteria for all nine tested HLA types. Only the peptides with sequences corresponding to SEQ ID NOS: 1 to 12 were considered in this analysis as peptides with sequences corresponding to SEQ ID NOS: 13 to 16 were found to be poorly soluble. From SEQ ID NOS: 1 to 12 there are over 3000 possible combinations of peptides which could potentially fulfill the target criteria set out above.

To enable visualization of these combinations, a binary scoring system was applied such that for each HLA type, where a combination of peptides achieves one of the above criteria a score of "1" was entered and where the criteria were not met a score of "0" is entered. The scores across all HLA types are then added up, such that a mixture which fulfills the criteria for none of the HLA types will score 0, whereas a mixture which fulfills the criteria for all nine HLA types scores 9. The scores for each peptide combination are plotted in FIG. 1 A to Q. The highest score of nine was achieved by the 10 mixtures shown below:

FIG. 1 A point 16 MLA 01, 02, 03, 04, 05, 12, 14
FIG. 1 B point 272 MLA 01, 03, 04, 05, 07, 12, 14
FIG. 1 C point 472 MLA 02, 03, 04, 05, 06, 12, 14
FIG. 1 C point 482 MLA 02, 03, 04, 05, 07, 12, 14
FIG. 1 C point 488 MLA 02, 03, 04, 05, 11, 12, 14
FIG. 1 C point 494 MLA 02, 03, 04, 05, 12, 14, 15
FIG. 1 C point 495 MLA 02, 03, 04, 05, 12, 14, 16
FIG. 1 D point 699 MLA 03, 04, 05, 07, 12, 14, 15
FIG. 1 D point 700 MLA 03, 04, 05, 07, 12, 14, 16
FIG. 1 G point 1271 MLA 02, 03, 04, 05, 12, 14

Thus theses mixtures are preferred combinations of peptides for use in vaccination.

Example 2

Cross-Sectional Screening of Cat Allergic Subjects for T Cell Responses and Basophil Histamine Release by Fel d 1-Derived, MHC Characterised T Cell Peptide Epitopes

1. INTRODUCTION 1.1 Histamine Release Assay

The purpose of this assay was to identify individual peptides that are capable of activating blood basophils (as a surrogate for tissue mast cells) resulting in histamine release that may result in allergic reactions during therapy. Peptides or combinations of peptides that induce histamine release frequently may be considered unsuitable for inclusion in the peptide vaccine.

Histamine release requires the crosslinking of adjacent specific IgE molecules on the surface of the basophil. The peptides being evaluated were small (13 to 17 amino acids in length) and should not, therefore, possess significant tertiary structure that would enable them to retain the conformation of an IgE-binding epitope of the whole molecule. Furthermore, peptide monomers in solution, even if they are bound by IgE, should not be able to crosslink adjacent IgE molecules. It should be noted however, that some of the peptides contain cysteine residues that may result in disulphide bond formation between single peptides and also between different peptides in a mixture. Thus, dimers of peptides may be generated that may have IgE crosslinking potential In the present analysis, no excipients were used in peptide formulation to prevent or reduce dimer formation through disulphide linkage.

Histamine release from fresh peripheral whole blood from cat allergic subjects was evaluated. Peripheral blood basophils were used as a surrogate for tissue mast cells which were not practical to assay. Blood was incubated in vitro with 9 individual peptides from the sequence of the major cat allergen Fel d 1 (MLA01, 03, 04, 05, 07, 12, 14, 15 and 16). These peptides were selected as potential T cell epitopes following peptide-MHC binding assays as explained in Example 1. Additionally, responses to a preferred mixtures of a mixture of 7 peptides identified in Example 1 were analysed. The tested preferred mixture of 7 peptides consisted of peptides MLA01, 03, 04, 05, 07, 12, 14 (SEQ ID NOS: 1 to 7). Histamine release in response to whole cat dander allergen extract acted as a positive control.

1.2 Proliferation Assay

The purpose of the proliferation assay was to determine the percentage of the population that responded to each individual peptide/back-up peptide and the preferred mixture of 7 peptides.

1.3 Cytokine Assays

The purpose of the cytokine assays was two-fold; (1) to determine the percentage of the population that responded to each individual peptide and the preferred mixture of 7 peptides, and (2) to identify individual peptides possessing intrinsic Th2 (IL-13)-inducing characteristics which would be undesirable in a peptide vaccine for allergic disease, and also to identify individual peptides possessing intrinsic IL-10-inducing characteristics which may be beneficial for a peptide vaccine for allergic disease.

2. MATERIALS AND METHODS

2.1 Isolation of Peripheral Blood Mononuclear Cells

Peripheral blood mononuclear cells (PBMC) were isolated from the heparinised blood sample obtained from the subject. PBMC's were isolated by Ficoll-Hypaque density gradient separation. Once isolated, the cells were used in the cell proliferation assay, histamine release and ELISA assay and the cytokine release assay.

2.2 Histamine Release Assay and Histamine ELISA

Assays were performed on PBMC (which contain basophils). Each peptide and combinations of peptides was compared with whole allergen molecules in a histamine release assay. Histamine concentrations were measured by ELISA.

The assay required $3 \times 10^6$ PBMC's per subject. The assay was performed using the Immunotech Histamine Release Immunoassay kit according to the manufacturer's instructions. Following the histamine release assay, acylated samples were tested by histamine ELISA. The histamine ELISA used 50 µl of the 100 µl acylated sample generated by the histamine release assay. The remaining 50 µl of sample was retained, by freezing at −20° C. until the data analysis section of the ELISA has been completed. Once the results had been analysed and the ELISA performed in a satisfactory manner, the samples were discarded.

Peptides were assayed for their ability to induce histamine release over a 5 $\log_{10}$ range (10 µg/ml to 1 ng/ml). The concentration range assayed was selected based on theoretical in vivo doses of peptide that may be achieved during therapy. For example, a 10 µg dose of peptide entering a blood volume of 5 litres, would result in a blood concentration of 2 ng/ml ($2 \times 10^{-6}$ mg/ml), at the lower end of the histamine release assay dose range. Whole cat dander extract (C.B.F. LETI) was used as a positive control for release over a slightly higher concentration range (100 µg to 10 ng/ml). Single measurements (i.e. not duplicate or triplicate) were performed for each dilution. One duplicate blood sample was assayed for spontaneous histamine release and the mean value of these samples was subtracted from all peptide/allergen results.

After completion of the histamine ELISA, individual histamine levels were determined by interpolation for the standard curve generated in the ELISA assay. Results from samples were adjusted to allow for any dilution of the samples. Where two or more dilutions of a peptide/allergen preparation elicited 10% or more histamine release above background, or where a single value of 10% or more above background was achieved at the highest concentration tested, this was considered a "positive histamine release".

2.3 Cell Proliferation Assay

The cell proliferation assay was performed on PBMC's ($140 \times 10^6$ cells required for all parameters to be tested). Proliferation was measured by the incorporation of the radiolabelled compound $^3$H-thymidine.

In more detail, 100 µl of the appropriate antigen or peptide concentration was distributed into the appropriate wells of 96 well plates. The plates were then placed into a humidified 5% $CO_2$ incubator set at 37° C. for a maximum of 4 hours. PBMC's isolated as described above were prepared to a concentration of $2 \times 10^6$ cells/ml in complete medium at room temperature. 100 µl of cell solution was then distributed into each of the wells of the 96 well plates containing antigen/peptide. The plates were then incubated for 6 to 8 days. The cultures were pulsed with tritiated thymidine solution by adding 10 µl of tritiated thymidine stock solution (1.85 MBq/ml in serum-free RPMI medium) to each well. The plates were then returned to the incubator for between 8 and 16 hours. Cultures were then harvested using a Canberra Packard FilterMate 196 cell harvester. Dried filter mats were counted using an appropriate beta scintillation counter.

Counts from wells containing peptide were compared statistically to wells containing media alone (12 wells per group). The non-parametric Mann-Whitney test was used. The same statistical test was used for all subjects. A statistically significant difference between media only wells and peptide-stimulated wells was considered a positive stimulation of PBMC's by the peptide.

2.4 Cytokine Release Assay

Cytokine secretion profiles from PBMC's was analysed in response to the peptide stimulation. Supernatants from the cytokine release assay were tested for the presence of 3 cytokines, IFN-γ, IL-10 and IL-13, using ELISA assays.

The cytokine release assay required $40 \times 10^6$ PBMC's per subject. In more detail, 250 µl of a 200 µg/ml solution of the appropriate antigen or peptide concentration was distributed into the appropriate wells of 48 well plates. Plates were the incubated in a humidified 5% $CO_2$ incubator at 37° C. for a maximum of 4 hours. 250 µl of a $5 \times 10^6$ cell/ml PBMC suspension was then added to each well and the plates returned to the incubator for 5 days.

Following stimulation, samples of culture supernatant were harvested into 3 aliquots and frozen until the ELISA assays could be performed. One aliquot was tested for the presence of one cytokine (therefore all 3 aliquots were required to test for the 3 cytokines). The cytokine levels in the samples were determined by interpolation from standard curves also generated in the assay.

3. RESULTS

Results Overview

3.1 Histamine Release

TABLE 1

Histamine Release Overview

| Subject | Positive control (release 10% above baseline) | | Individual peptide (release 10% above baseline) | | Peptide mixture (release 10% above baseline) | |
| --- | --- | --- | --- | --- | --- | --- |
|  | 2 or more dilutions | Highest conc only | 2 or more dilutions | Highest conc only | 2 or more dilutions | Highest conc only |
| % age of subjects showing release | 70.4 | 7.4 | 17.3 | 18.5 | 2.5 | 2.5 |
| Total percentage showing histamine release per group | 77.8 | | 30.9* | | 5 | |

*in some subjects some peptides caused release at 2 or more concentrations and others at the highest dose only. Thus the two numbers cannot simply be added as they are for cat dander extract and the peptide mixture. Similarly, values for individual peptide release cannot be added to values for the mixture of peptides since 2 of the subjects with histamine release to the mixture also had release to individual peptides.

Histamine release from peripheral blood basophils was observed in response to both positive control and peptides. Table 1 shows the percentage of individuals in which histamine release (as defined by the acceptance criteria) occurred. Histamine release to one or more individual peptide occurred frequently but this rarely translated into histamine release from the mixture of 7 preferred peptides. However, a total of 5% of individuals displayed histamine release in response to the peptide mixture. The details of dose and number of consecutive doses of peptide mixture that elicit release of histamine are relevant to the interpretation of these results and are discussed in more detail below.

Table 2 shows the number of individuals in whom histamine release was detected in response to each individual peptide. MLA15 and MLA16 most commonly released histamine.

3.2 Proliferation Assay Overview

Figure 3:
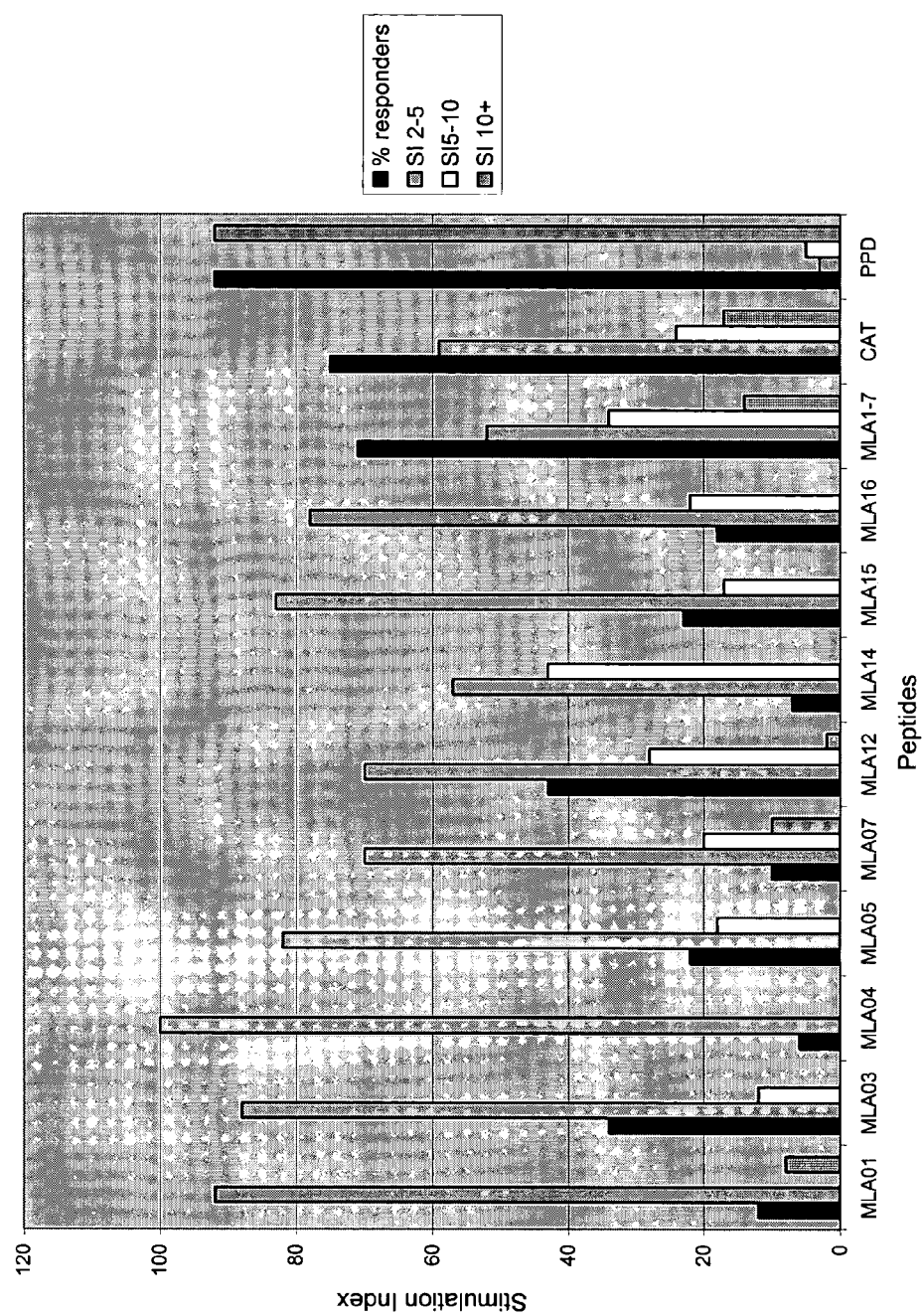
FIG. 3—Proliferation: percentage responders and quality of response.

FIG. 3 summarises proliferative responses to peptides and antigens. The percentage of individuals mounting a detectable proliferative response is shown in the black bars. Grey (weak), white (moderate) and hashed (strong) bars provide a breakdown of the quality of these responses. Quality is arbitrarily defined by Stimulation Index (SI: ratio of counts in the presence of antigen/peptide divided by counts in medium alone). Thus for peptide 1 (MLA01), 12% of subjects made a proliferative response and of these 92% were weak, none were moderate and 8% were high. Proliferative responses to individual peptides/antigens were variable (black bar). 92% of subjects had positive proliferative responses to the positive control antigen PPD. The majority of these were strong responses (hashed bar). 75% of subjects responded to cat dander extract, with 59% of the responses (i.e. 59% of the 75%) being weak. The response to the mixture of 7 preferred peptides (SEQ ID NOS: 1 TO 7) was almost identical to cat dander extract (CAT). Peptides MLA15 and MLA16 induced more frequent responses that four of the preferred peptides. However, MLA15 and MLA16 induced the most frequent basophil histamine release responses (see section 3.1). Few individual peptides induced strong proliferative responses as expected (low precursor frequency of peptide-specific precursor T cells).

3.3 Cytokine Assay Overview

Figure 4:
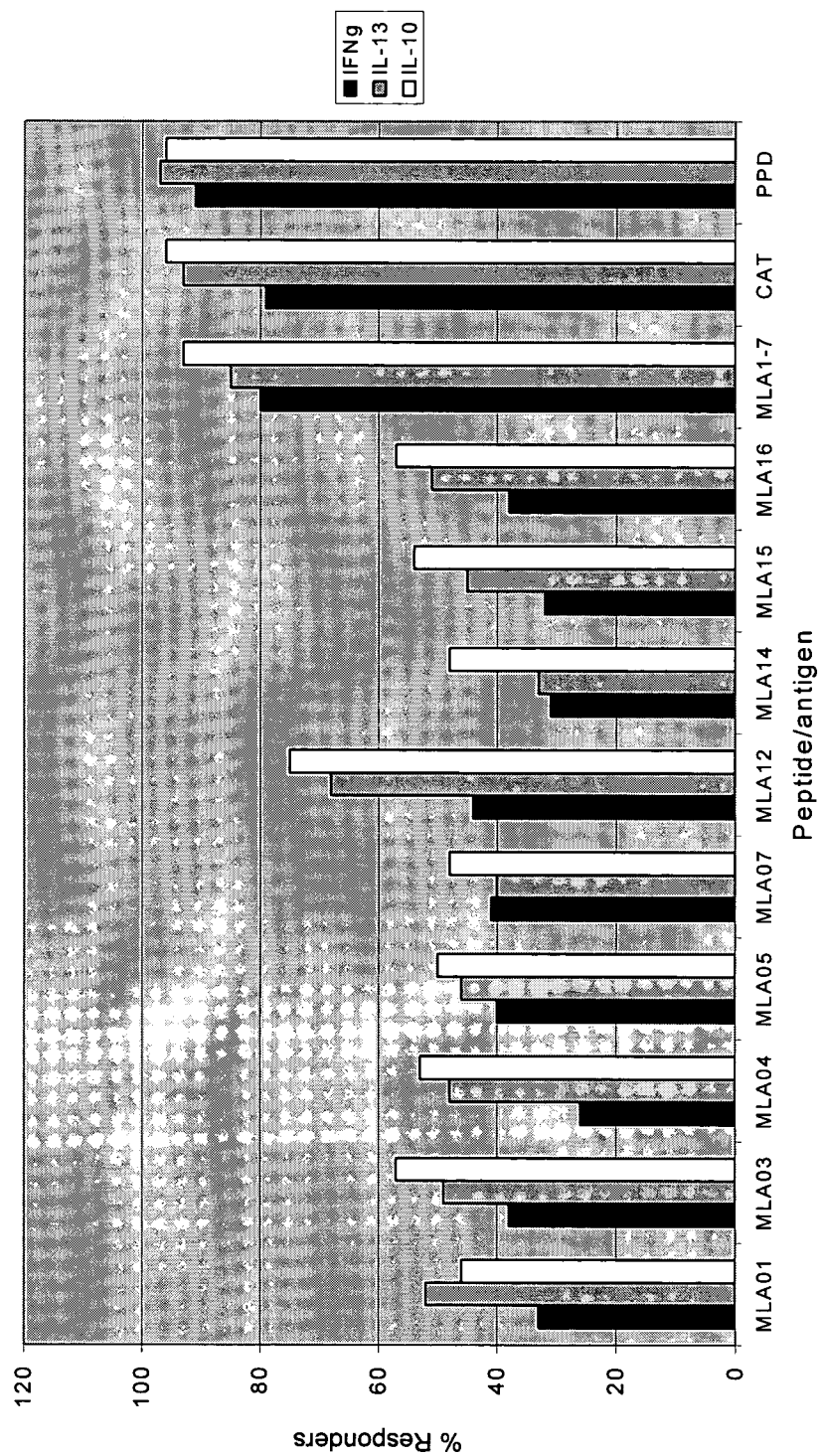
FIG. 4—Percentage of responders by cytokine.

FIG. 4 summarises the percentage of individuals who mounted a detectable response to each of the peptides/antigens by production of the three cytokines measured. The black bars represent production of IFN-γ, the grey bars IL-13 and the white bars IL-10. The positive control antigen PPD elicited a cytokine production in almost all individuals (IFN-γ: 91%, IL-13: 97% and IL-10: 96%). Whole cat allergen and the mixture of 7 peptides elicited a cytokine response in approximately 80% or more of subjects. Individual peptides elicited responses of differing frequency. In general cytokine production appeared to be a more sensitive method of detecting responses with larger percentages of individuals giving positive cytokine responses than proliferative responses. In most cases, IL-10 secretion was detected in the largest number of subjects and IFN-γ detected least frequently.

TABLE 2

Individual Peptide Histamine Release Overview

| MLA01 (Related to SEQ ID NO: 1) | MLA03 (SEQ ID NO: 2) | MLA04 (SEQ ID NO: 3) | MLA05 (SEQ ID NO: 4) | MLA07 (SEQ ID NO: 5) | MLA12 (SEQ ID NO: 6) | MLA14 (SEQ ID NO: 7) | MLA15 | MLA16 |
| --- | --- | --- | --- | --- | --- | --- | --- | --- |
| 4 | 6 | 6 | 1 | 6 | 6 | 2 | 7 | 11 |

3.4 Tissue Typing

TABLE 3

| | DRB1 | | | | | | | | | | |
|---|---|---|---|---|---|---|---|---|---|---|---|
| | 1 | 3 | 4 | 7 | 8 | 11 | 12 | 13 | 14 | 15 | 16 |
| % | 6.4 | 14.7 | 15.7 | 8.8 | 3.4 | 8.3 | 3.9 | 14.7 | 2.9 | 17.6 | 2.5 |
| Reference population % | 9.4 | 11.1 | 12.8 | 13.2 | 3.7 | 13.4 | 2.3 | 10.2 | 3.2 | 10.7 | 3.6 |

Tissue typing was performed in order to ensure that the study population (predominantly Caucasian) was representative of the general Caucasian population in which the vaccine will be used. Eleven common DRB1 allele families are shown. Allele frequencies in 102 typed study subjects are shown, not the percentage of individuals expressing an allele, since each individual has two DRB1 alleles and some individuals are homozygous for particular alleles. Reference population allele frequencies are also shown for comparison (Data from HLA Facts Book, Parham & Barber). Reference frequencies were obtained by analysis of multiple studies reporting frequencies and the figures shown are mean values. All of the frequencies detected in the current analysis were within the ranges reported in the reference data. Therefore the population examined in the current study is representative of a Caucasian population.

4. FIGURES

4. Histamine Release Assay

TABLE 4

Individual Subject Profiles

| Subject | Spontaneous Release (between 10%-20%) | Positive control (release 10% above baseline) | | Individual peptide (release 10% above baseline) | | Peptide mixture (release 10% above baseline) | | Comments: |
|---|---|---|---|---|---|---|---|---|
| | | 2 or more dilutions | Highest conc only | 2 or more dilutions | Highest conc only | 2 or more dilutions | Highest conc only | |
| 002 | | Y | N | N | N | N | N | No release |
| 007 | | Y | N | Y | N | N | N | MLA16 |
| 008 | | Y | N | N | N | N | N | No release |
| 009 | | Y | N | N | N | N | N | No release |
| 010 | | Y | N | N | N | N | N | No release |
| 011 REJECT | 30% | | | | | | | HIGH SPONTANEOUS RELEASE |
| 012 | | Y | N | N | N | N | N | No release |
| 013 | | Y | N | N | N | N | N | No release |
| 014 | | Y | N | N | N | N | N | No release |
| 015 | 13% | N | Y | Y | N | N | N | MLA01, MLA04, MLA07, MLA15 |
| 016 | 12% | Y | N | N | N | N | N | No release |
| 017 | | Y | N | N | N | N | N | No release |
| 018 | | Y | N | N | N | N | N | No release |
| 019 REJECT | 47% | | | | | | | HIGH SPONTANEOUS RELEASE |

TABLE 4-continued

Individual Subject Profiles

| | | | | | | | | |
|---|---|---|---|---|---|---|---|---|
| 020 REJECT | 77% | | | | | | | HIGH SPONTANEOUS RELEASE |
| 022 | | Y | N | Y | N | N | N | MLA01 |
| 023 | | Y | N | N | N | N | N | No release |
| 024 | | N | N | N | N | N | N | No release (no positive) |
| 026 | | Y | N | N | N | N | N | No release |
| 027 | | Y | N | N | N | N | N | No release |
| 028 | | Y | N | N | N | N | N | No release |
| 029 | | N | N | N | N | N | N | No release (no positive) |
| 030 | | Y | N | N | N | N | N | No release |
| 031 | | Y | N | N | Y | N | N | MLA03, MLA12 |
| 032 REJECT | 32% | | | | | | | HIGH SPONTANEOUS RELEASE |
| 033 | | Y | N | N | N | N | N | No release |
| 034 | | N | N | N | N | N | N | No release (no positive) |
| 035 | | N | Y | N | N | N | N | No release |
| 040 | | N | Y | N | N | N | N | No release |
| 041 | | N | N | N | N | N | N | No release (no positive) |
| 042 | | Y | N | N | N | N | N | No release |
| 043 | | N | N | Y | N | N | N | MLA04 (no positive) |
| 044 | | Y | N | N | N | N | Y | MIX 28% |
| 046 | | N | N | Y | N | N | N | MLA16 (no positive) |
| 047 | | Y | N | N | N | N | N | No release |
| 049 | | N | N | N | Y | N | N | MLA03 MLA16 (no positive) |
| 050 | | Y | N | N | N | N | N | No release |
| 051 | | Y | N | Y$_{MLA12}$ | Y$_{MLA16}$ | N | N | MLA12, MLA16 |
| 052 | | N | Y | N | Y | N | N | MLA16 |
| 053 | | N | Y | N | N | N | N | |
| 054 REJECT | 54% | | | | | | | UNITERPRETABLE RESULT, HIGH BACKGROUND OF 40-50% RELEASE |
| 055 | | Y | N | N | N | Y | N | MIX RELEASE AT 2 CONSECUTIVE MIDDLE CONCENTRATIONS |
| 056 | | Y | N | Y$_{MLA16}$ | Y$_{MLA03}$ | Y | N | MIX RELEASE AT 4 CONSEC CONCS |
| 057 | | N | N | Y | N | N | N | MLA15 JUST ABOVE THE 10% CUTOFF (no positive) |
| 058 | | N | N | Y | N | N | N | MLA04 (no positive) |
| 059 | | Y | N | Y | N | N | N | MLA12 AND MLA16 |
| 060 | | N | N | N | N | N | N | NO RELEASE (NO POSITIVE) |
| 061 | | Y | N | N | N | N | N | NO RELEASE |
| 062 | | Y | N | Y$_{MLA03}$ | Y$_{MLA01,MLA15}$ | N | N | MLA03, MLA01 |
| 063 | | Y | N | N | N | N | N | NO RELEASE |
| 064 REJECT | 33% | | | | | | | HIGH SPONTANEOUS RELEASE |
| 065 | | Y | N | N | N | N | N | NO RELEASE |
| 066 | | Y | N | N | N | N | N | NO RELEASE |
| 067 | | Y | N | N | N | N | N | NO RELEASE |
| 068 | | N | N | N | N | N | N | NO RELEASE (NO POSITIVE) |
| 069 | | Y | N | N | Y | N | N | MLA03, MLA05, MLA07, MLA12 |
| 070 | | Y | N | Y$_{MLA04,14,15}$ | Y$_{MLA07,12,1}$ | N | N | MLA04, MLA07, MLA12, MLA14 MLA12, MLA15, MLA16 |
| 071 | | Y | N | N | N | N | N | NO RELEASE |
| 072 | | Y | N | N | N | N | N | NO RELEASE |

TABLE 4-continued

Individual Subject Profiles

| Subject | Spont. Release | C1 | C2 | C3 | C4 | C5 | C6 | Comments |
|---|---|---|---|---|---|---|---|---|
| 073 | | Y | N | N | Y | N | N | MLA03 |
| 076 | | N | N | N | N | N | N | NO RELEASE (NO POSITIVE) |
| 080 | | Y | N | N | N | N | N | NO RELEASE |
| 081 | | N | N | N | N | N | N | NO RELEASE (NO POSITIVE) |
| 082 | | Y | N | N | $Y_{MLA16}$ | N | N | MLA16 |
| 083 REJECT | 39% | | | | | | | UNINTERPRETABLE ASSAY |
| 084 REJECT | 37% | | | | | | | UNINTERPRETABLE ASSAY (VERY HIGH BACKGROUND) |
| 085 | | Y | N | N | N | N | N | NO RELEASE |
| 086 | | N | N | N | N | N | N | NO RELEASE (NO POSITIVE) |
| 087 | | N | N | N | N | N | N | NO RELEASE (NO POSITIVE) |
| 088 | | Y | N | N | N | N | N | NO RELEASE |
| 089 | | Y | N | N | N | N | N | NO RELEASE |
| 090 | | Y | N | $Y_{MLA03}$ | $Y_{MLA07}$ | N | N | MLA03, MLA07 |
| 091 | | Y | N | N | N | N | N | NO RELEASE |
| 092 | 10.6% | Y | N | N | N | N | N | NO RELEASE |
| 093 REJECT | 29% | | | | | | | HIGH SPONTANEOUS RELEASE |
| 094 | | Y | N | N | N | N | N | NO RELEASE |
| 095 | | Y | N | N | N | N | N | NO RELEASE |
| 096 | | Y | N | N | N | N | N | NO RELEASE |
| 097 REJECT | | | | | | | | UNINTERPRETABLE ASSAY (APPEARS TO BE A FALSELY LOW TOTAL RELEASE COUNT) |
| 099 | | Y | N | N | N | N | N | NO RELEASE |
| 100 | 11.5% | Y | N | Y | N | N | N | MLA15 |
| 101 | | N | N | N | Y | N | N | MLA07, MLA14, MLA15, MLA16 NO POSITIVE |
| 103 | | Y | N | N | Y | N | Y | MLA01, MLA04, MLA15, MIX |
| 104 | | Y | N | N | Y | N | N | MLA012 |
| 105 REJECT | 28% | | | | | | | HIGH SPONTANEOUS RELEASE |
| 106 REJECT | 41% | | | | | | | HIGH SPONTANEOUS RELEASE |
| 107 REJECT | 35% | | | | | | | HIGH SPONTANEOUS RELEASE |
| 108 | | Y | N | N | N | N | N | NO RELEASE |
| 109 | | Y | N | N | N | N | N | NO RELEASE |
| 111 | | Y | N | N | Y | N | N | MLA07 |
| 112 | | Y | N | N | Y | N | N | MLA04, MLA16 |
| 113 | | N | N | N | N | N | N | NO RELEASE (NO POSITIVE) |
| 117 | | N | N | N | N | N | N | NO RELEASE (NO POSITIVE) |
| 118 | | Y | N | N | N | N | N | NO RELEASE |
| % age of subjects showing release | | 70.4 | 7.4 | 17.3 | 18.5 | 2.5 | 2.5 | |

Mix: mixture of 7 peptides (i.e MLA 01, 03, 04, 05, 07, 12, 14; SEQ ID NOS: 1 to 7)

Grey: histamine release to one or more individual peptide from the preferred mixture, or to the preferred mixture itself.

Comments: this column lists the individual peptides giving rise to histamine release/other relevant comments for each subject.

A total of 94 histamine release assays were completed during the study. Of these 13 assays were rejected, mainly due to unacceptably high levels of spontaneous release. Assays with spontaneous histamine release of 20% or more of the total histamine release were rejected. Those assays with a spontaneous release of between 10% and 20% are indicated in Table 4. All other assays had spontaneous release values of less than 10%.

Approximately 78% of the subjects assayed demonstrated positive histamine release to the sensitising allergen. Existing literature reports 10-20% of allergic individuals being resistant to allergen-induced basophil histamine release.

Histamine release was considered positive if (a) the highest concentration of peptide alone induced release of 10% or more of the total release value or (b) if two consecutive values were 10% or more of the total release. Approximately 31%

(25/81) of subjects showed histamine release to one or more individual peptide. Of these, 6/81 (7.4%) had not positive control release to whole cat allergen extract.

In two individuals the mixture of 7 peptides also induced histamine release in addition to certain individual peptides. In two further individuals, only the mixture of 7 peptides induced release. Thus, 4/81 individuals (~5%) displayed histamine release with the mixture of peptides.

Subject 044 showed release (28% of total release) at the highest concentration (10 ug/ml) of peptide only. Subject 055 showed release at 0.1 ug/ml (72% of total) and 1 ug/ml (47% of total) only. Subject 056 showed release at 0.01 ug/ml (11%), 0.1 ug/ml (12%), 1.0 ug/ml (17%) and 10 ug/ml (10 ug/ml). Subject 103 showed histamine release (33%) at the highest concentration (10 ug/ml) of peptide only.

4.2 Proliferation Assay

For the proliferation assay, individual proliferation data for all subjects and all peptide concentrations was analysed. Stimulation indices to each peptide/antigen were summarised for the entire population of 100 subjects.

Complex antigens such as cat dander extract and PPD induce significant proliferative responses in the population as a whole. The peptides that induce significant responses are those that elicit proliferative responses in a larger percentage of the population.

Stimulation indices of less than 1 arise when counts in wells containing peptides are lower than those containing culture medium alone. Such an effect may be attributable to slight changes in pH upon the addition of peptides which are prepared in acid solution. The absence of a proliferative response to the peptide would then result in counts slightly lower than those in the medium alone wells.

4.3 Cytokine Release Assay

Figure 5:
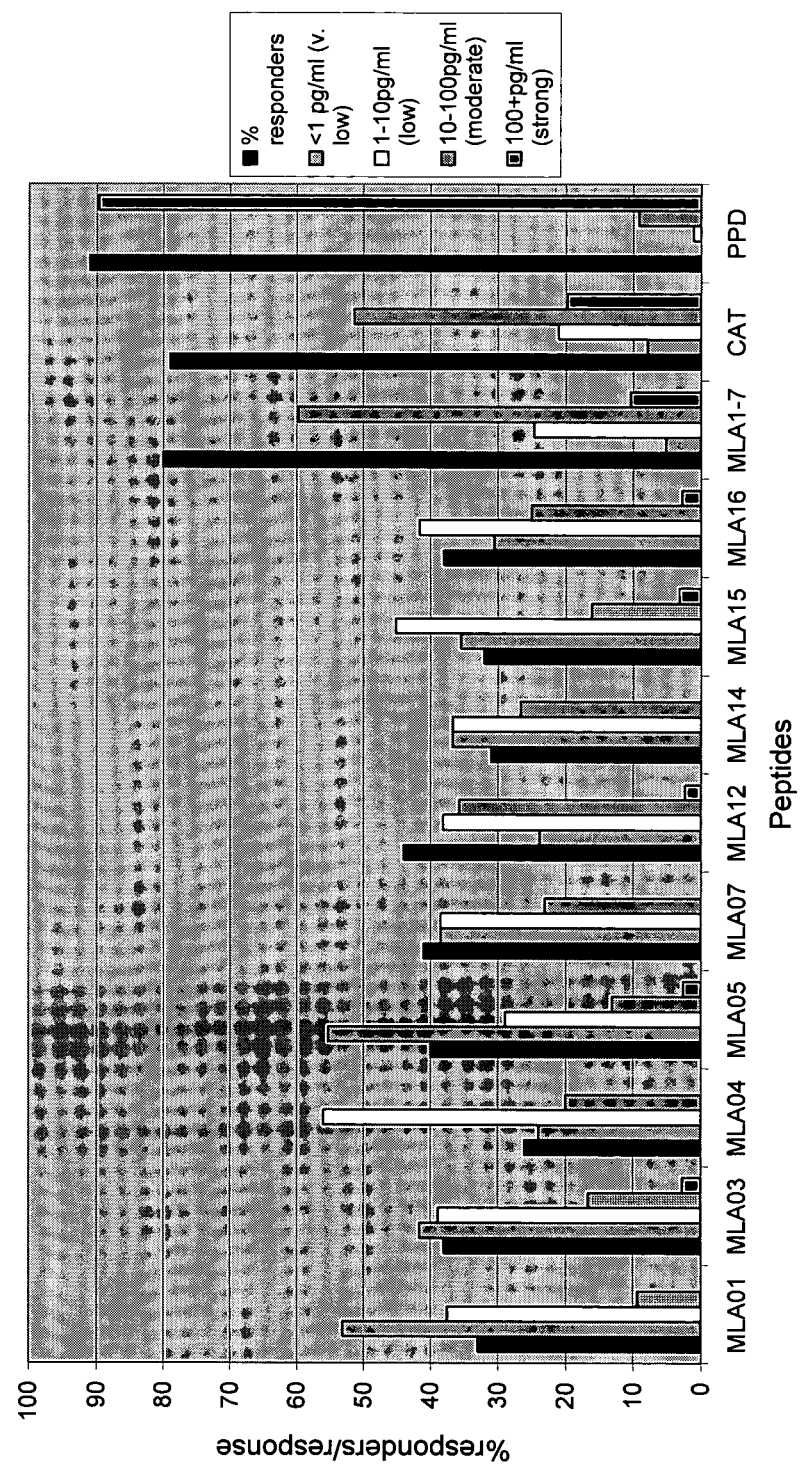
FIG. 5—Percentage of individuals producing IFN-γ and strength of response following cell culture with peptide/antigen. IFN-γ responses were detected in 26-44% of subjects in response to individual peptides. These responses were predominantly very low to low to moderate. Complex antigens induced more frequent responses (peptide mixture 80%, cat dander 79%, PPD 91%). These responses were low to moderate to high. PPD responses were particularly high (89 of PPD responses were above 100 pg/ml).
Figure 6:
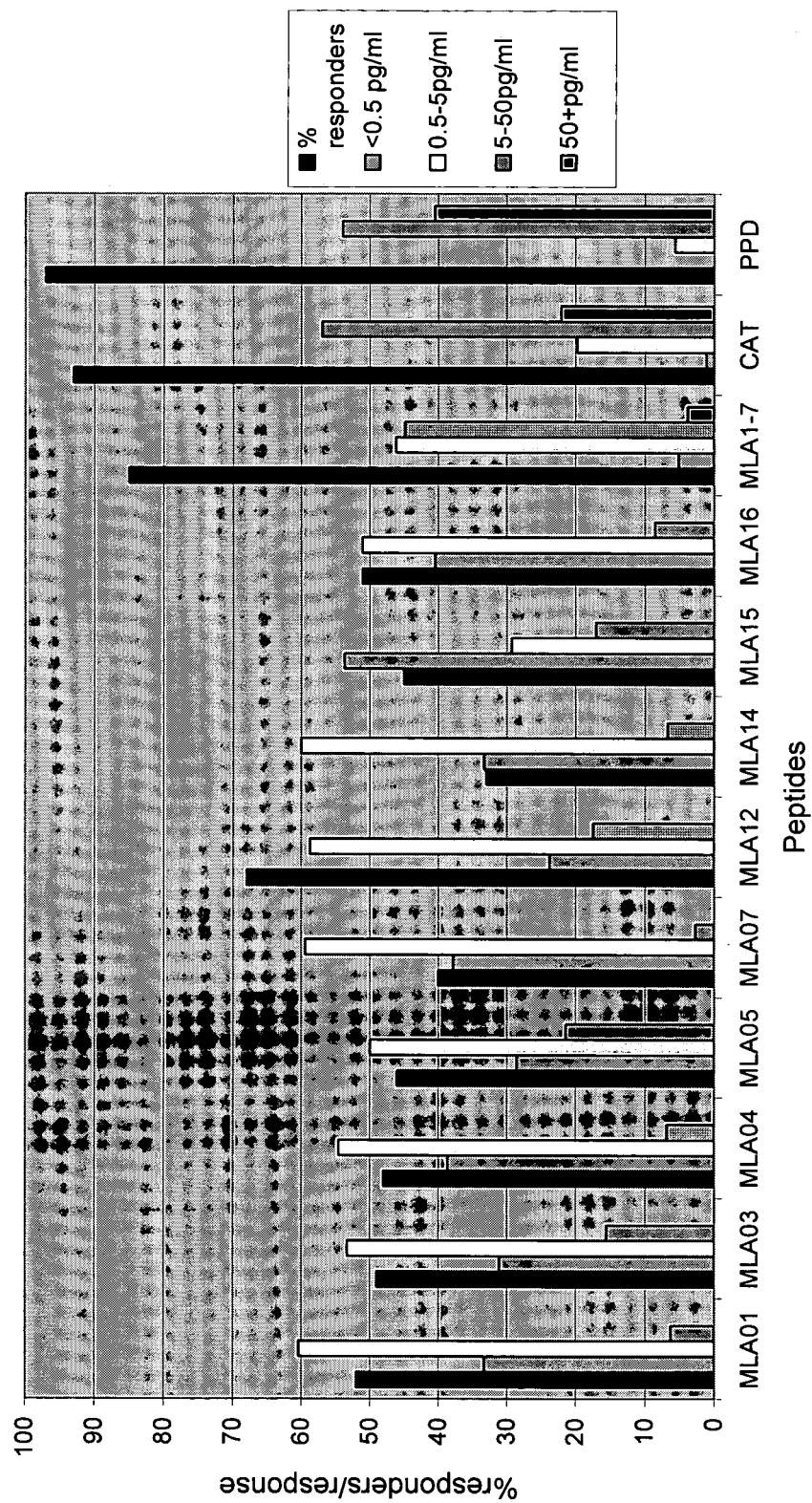
FIG. 6—Percentage of individuals producing IL-13 and strength of response following cell culture with peptide/antigen. IL-13 responses were detected in between 33-68% of subjects in response to individual peptides. These responses were predominantly very low to low, although a significant number of moderate responses were detected. This may reflect the Th2 nature of allergic sensitisation in these subjects. Complex antigens induced more frequent responses (peptide mixture 85%, cat dander 93%, PPD 97%). These responses were low to moderate to high.
Figure 7:
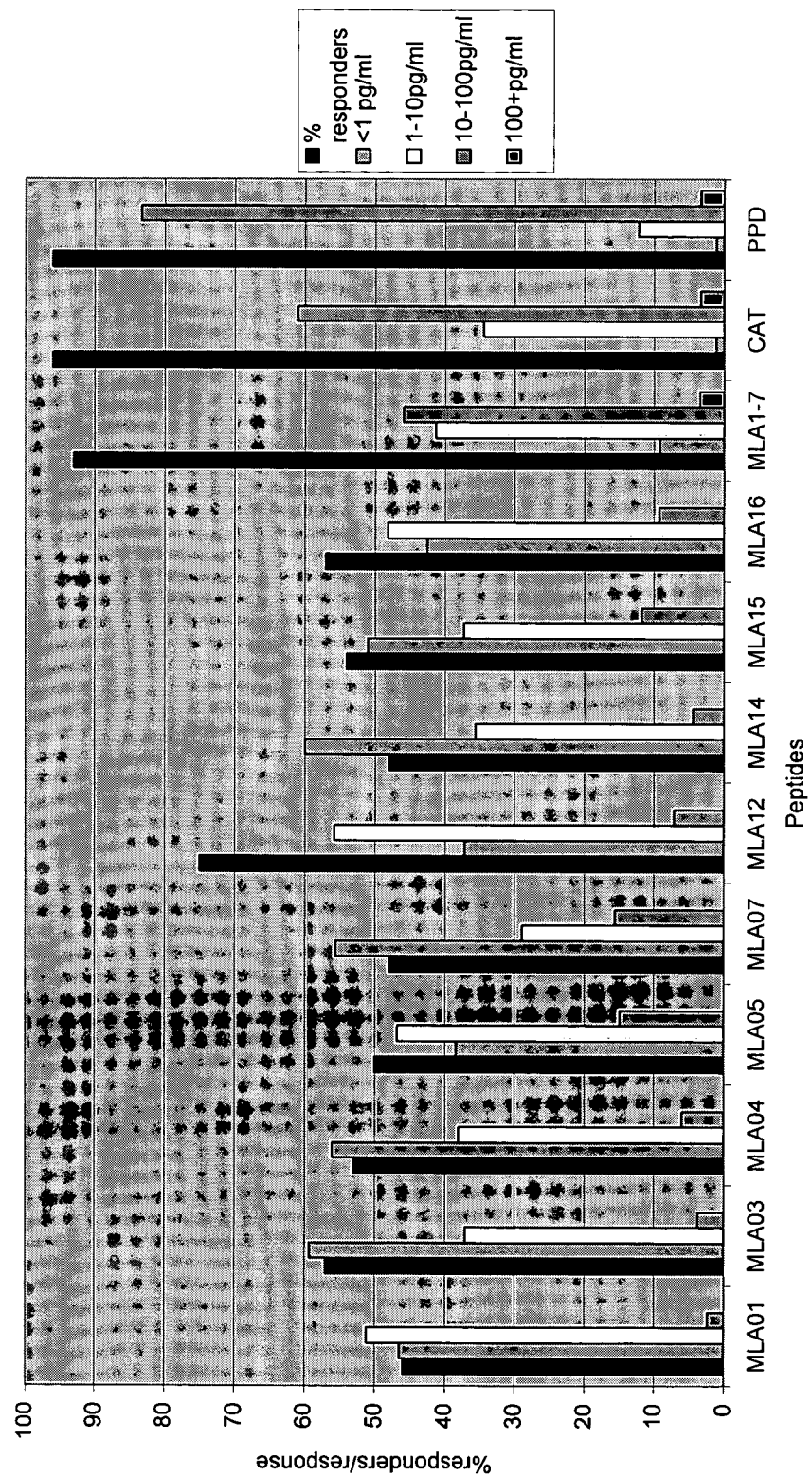
FIG. 7—Percentage of individuals producing IL-10 and strength of response following cell culture with peptide/antigen. IL-10 responses were detected in between 46-75% of subjects in response to individual peptides. These responses were predominantly very low to low. Complex antigens induced more frequent responses (peptide mixture 93%, cat dander 96%, PPD 96%). These responses were low to moderate. Very few "high" M-10 responses were observed.

FIGS. 4 to 6 show, for each peptide/antigen, the percentage of individuals who made a response of any detectable magnitude (i.e. production of detectable IFN-γ, IL-13 or IL-10). The strength of those responses is then split into four levels of cytokine production. For example, 35% of the study population may have made an IFN-γ response. Of that 35% of individuals, half (50%) made a very weak response, 20% a weak response, 15% a moderate response and 15% a strong response (giving a total of 100% of the responders). The boundaries of each cytokine level were arbitrarily assigned based on the detection range of the ELISA assay. The boundaries are different between IFN-γ/IL-10 and IL-13 since for IFN-γ and IL-10 the detection range was approximately 1-100 pg/ml whereas the range for the IL-13 assay was approximately 0.5-50 pg/ml.

4.3.1 Interferon-γ Production

FIG. 4 shows the percentage of individuals producing IFN-γ and the strength of the response following cell culture with peptide/antigen. IFN-γ responses were detected between 26-44% of subjects in response to individual peptides. These responses were predominantly very low to low to moderate. Complex antigens induced more frequent responses (peptide mixture 80%, cat dander 79%, PPD 91%). These responses were low to moderate to high. PPD responses were particularly high (89 of PPD responses were above 100 pg/ml).

4.3.2 IL-13 Production

FIG. 5 demonstrates the percentage of individuals producing IL-13 and strength of the response following cell culture with peptide/antigen. IL-13 responses were detected in between 33-68% of subjects in response to individual peptides. These responses were predominantly very low to low, although a significant number of moderate responses were detected. This may reflect the Th2 nature of allergic sensitisation in these subjects. Complex antigens induced more frequent responses (peptide mixture 85%, cat dander 93%, PPD 97%). These responses were low to moderate to high.

4.3.3 IL-10 Production

FIG. 6 demonstrates the percentage of individuals producing IL-10 and strength of the response following cell culture with peptide/antigen. IL-10 responses were detected in between 46-75% of subjects in response to individual peptides. These responses were predominantly very low to low. Complex antigens induced more frequent responses (peptide mixture 93%, cat dander 96%, PPD 96%). These responses were low to moderate. Very few "high" IL-10 responses were observed.

5. DISCUSSION

5.1 Histamine Release Assay

In interpreting the histamine release results it is important to consider several points relating to the assay design:
1) The estimated blood dose of peptides that will be achieved during treatment lies towards the bottom of the dose response curve employed in the assay. For example, a 10 ug dose of peptide entering a blood volume of 5 litres, would result in a blood concentration of 2 ng/ml ($2 \times 10^{-6}$ mg/ml; this assumes that no peptide is degraded which is unlikely). This concentration is just above the lower dose limit of the assay (1 ng/ml). The 2 lowest concentrations of peptide used in the assay correspond approximately to injected doses of 5 μg (1 ng/ml) and 50 μg (10 ng/ml). Thus, the assay is designed to detect histamine release at or above doses of peptide used for therapy. In only 3 instances was histamine release associated with the lowest two (consecutive values above 10%) concentrations of peptide. In two of these cases values were less than 11%. The 7 peptide mixture did not show any release at the lowest 2 concentrations of peptide. Thus, although histamine release in response to individual peptides or the mixture was relatively common, it was generally not seen at the concentrations of peptide that will be achieved during therapy.
2) For reasons of cost and complexity, only single wells were assayed for each concentration of peptide. This increases the risk that any one value may be spurious. This is particularly relevant to the second condition defined for a positive result; that the highest concentration alone of peptide/antigen shows release of 10% or more of the total release. Several cases of histamine release to individual peptides were only associated with the single highest concentration of peptide and this was also true for 2/4 individuals with histamine release triggered by the mixture of 7 peptides.
3) In some cases, histamine release from peptides was not associated with histamine release from cat dander extract (absence of positive control).
4) Peptides with cysteine residues (MLA01, MLA04, MLA05, MLA12 and MLA15) were previously shown to be capable of varying degrees of homo-dimerisation. Although not formally quantified, these peptides when mixed are likely to also form hetero-dimers (i.e. within the SEQ ID NOS: 1 TO 7 mixture). Dimers may be sufficient to crosslink IgE molecules on the surface of mast cells and basophils giving rise to histamine release. No excipients to reduce disulphide bond formation between homologous or heterologous peptides were used in this study. Clinical preparations of the vaccine will contain thioglycerol to block disulphide bond formation.

Approximately 78% of the subjects assayed demonstrated positive histamine release to the sensitising allergen. This is slightly lower than reports in the literature which suggest that 10-20% of allergic individuals are resistant to allergen-induced basophil histamine release.

30.9% of subjects showed histamine release to one or more individual peptide. Histamine release was also detected in 5% of subjects (4/81) to the mixture of 7 peptides (SEQ ID NOS: 1 TO 7; likely vaccine candidates). Two of these 4 individuals displayed release to individual peptides and 2 did not. In several subjects showing histamine release to individual peptides (6/81; 7.4%), release only occurred with peptide MLA15 or MLA16, which are not included in the SEQ ID NOS: 1 TO 7 mixture. MLA16 was the peptide most frequently associated with histamine release. Adjusting values for individual peptide release to include only those peptides in the preferred 7 vaccine candidates, 23.5% of subjects displayed histamine release to individual components of the vaccine.

5.2 Proliferation Assay

Proliferation of PBMC was assayed in response to culture with 3 concentrations of individual peptides, a mixture of 7 peptides (selected by MHC binding assays) and whole cat dander allergen extract. Responses to PPD at a single concentration were also measured as a marker of a positive recall response.

PPD responses: 92% of subjects mounted a detectable proliferative response to PPD. The response is largely dependent upon prior vaccination with BCG. Non-responders may have originated from countries in which BCG is not mandatory (e.g. USA), or may not have received the immunisation for other reasons. The majority of responses (92%) resulted in an SI of greater than 10. These were arbitrarily assigned as "strong" responses.

Cat dander allergen extract responses: 75% of subjects mounted a detectable proliferative response to cat dander allergen extract. More frequent responses were detected through measurement of cytokines highlighting the importance of assaying multiple parameters of activation to determine reactivity. The majority of responses were weak (SI 2-5; 59%) although significant numbers of moderate (SI 5-10; 24%) and strong (SI 10+; 17%) were observed.

Peptide mixture (P1-7): 71% of subjects mounted a response to the peptide mixture, similar to cat dander allergen extract. A similar percentage of weak (52%), moderate (34%) and strong (14%) responses were observed. Proliferative responses to cat dander allergen extract and peptide mixture correlated closely indicating that the majority of T cell reactivity to cat dander can be accounted for by the epitopes contained within the peptide mixture.

Individual peptide responses: Proliferative responses to individual peptides were generally weak to moderate. Most peptides generated 70-80% of their responses in the weak category with 20-30% in the moderate category. Few peptide elicited strong responses. Weaker responses to individual peptides than to complex antigens or mixtures of peptides is an expected finding resulting from lower precursor frequencies of T cells specific for individual epitopes.

The strongest proliferative responses to an individual peptide were to P12 from Fel d 1 chain 2 (43%) and the weakest to P4 from chain 1 (6%). However, cytokine responses to all peptides were detected more frequently than proliferative responses.

5.3 Cytokine Assays

Cytokine measurement proved to be the most sensitive method of measuring responses to the peptides. Generally a higher percentage of subjects displayed measurable cytokine responses compared to measurable proliferative responses. Production of each of the three cytokines varied with IL-10 generally being produced by a greater proportion of subjects than IL-13 and IFN-γ. The lowest frequency of response was detected with IFN-γ. The atopic allergic status of these subjects is likely to mean that the memory T cell response to Fel d 1 and its epitopes will be dominated by Th2 responses which may account for the less frequent Th1 (IFN-γ) response. The high frequency of IL-10 responses was a surprise. IL-10 is considered to be a Th2 cytokine in the murine system but this is not well established in the human system. IL-10 is generally regarded as a regulatory/immunosuppressive cytokine. Previous reports have suggested that some peptide sequences may have intrinsic IL-10 inducing properties. Such peptides were not observed in this study. The detection of such responses in other systems may simply reflect the nature of T cell priming to whole allergen which is recalled by culture of memory T cells with peptide. Thus, production of IL-10 may be a recall response rather than the result of intrinsic IL-10-inducing characteristics of the peptide.

No single peptide induced the preferential production of a particular cytokine. Thus, none of the peptides screened induced a particularly unfavourable Th2 (IL-13) response which would have been considered undesirable for inclusion in the peptide vaccine.

5.4 Tissue Typing

Tissue typing results show that a representative population was assayed in this study.

6. CONCLUSION

6.1 Histamine Release Assay

Individual peptides induced histamine release in some individuals. The mixture of preferred peptides SEQ ID NOS: 1 TO 7 induced histamine release in 4 individuals although in 2 of these the release was detected at a single point (highest concentration). MLA16 caused most frequent release but is absent from SEQ ID NOS: 1 TO 7. Some positive release was observed with peptides in the absence of "positive control release" from whole cat dander. The assay was designed to detect histamine release at concentrations of peptide approximating to treatment doses and above. Histamine release at concentrations of peptide corresponding to treatment doses was extremely rare (only one clear example) and only occurred with individual peptides, not with SEQ ID NOS: 1 TO 7.

The results of the in vitro histamine release assay are likely to over-represent the histamine releasing potential of the vaccine since no steps were taken to minimise disulphide bond formation between peptides.

Histamine was released by basophils from the majority of individuals in the presence of whole cat dander extract. Histamine release occurred in a dose-dependent fashion in many subjects in contrast to release with peptides which frequently occurred at concentrations in the middle of the dose range. In individuals where histamine was released by peptides, sensitivity to cat dander extract was usually apparent at lower doses of extract.

6.2 Proliferation Assay

Proliferative responses to peptides were weaker than to peptide mixtures or complex protein antigens as expected. Most individual peptide elicited proliferative responses in less than 20% of individuals. Considerable variation was seen between peptides but no single peptide failed to elicit proliferative responses in at least some subjects, although one of the preferred 7 peptides MLA04 was poor at inducing proliferation. Peptides MLA15 and MLA16 were more potent in induction of proliferation than several of the preferred 7 peptides but gave the highest histamine release.

6.3 Cytokine Assays

Cytokine production was a more sensitive method than proliferation for detecting responses to peptides in this study. No evidence was obtained to support the idea that certain peptides may have an intrinsic ability to induce a particular pattern of cytokine production. No single peptide preferentially elicited a Th1, Th2 or Treg (IL-10) response. IFN-γ response tended to be less common than IL-13 and IL-10. The cytokine assay data does not indicate that any of the preferred peptide mixture be substituted nor that any single peptide or the mixture will preferentially induce a Th2 response in vivo.

Example 3

Clinical Trial of Preferred Combination

A preferred mixture of 7 peptides consisting of peptides MLA01, 03, 04, 05, 07, 12, 14 (SEQ ID NOS: 1 to 7) has been tested in a randomised, placebo-controlled, blind clinical trial. The efficacy of this mixture in reducing allergic symptoms was evaluated. The study design of the clinical trial was in accordance with good clinical practice guidelines.

Baseline skin responses to cat allergen for all subjects were established using a Baseline Challenge which took place between 6 and 8 days prior to study medication administration. Two intradermal injections of 0.010 HEP (histamine equivalent prick) units of commercially available standard cat allergen (supplied by Laboratorios Leti, Spain) were administered, separated by a 30 minute time interval, into the volar surface of the left and right forearms respectively. Subjects were assessed to ensure that they experience a Late-Phase Skin Response (LPSR) to whole cat allergen, and the magnitude of the baseline reaction was recorded as follows:

Eight hours after each injection the outline of any late-phase response was drawn onto the skin with a ballpoint pen. The longest and orthogonal diameters were measured and recorded for each response, and the area of the response in each arm was calculated. The average area of response in both arms of each subject was then calculated to provide the baseline reaction. Subjects who produced a suitable baseline reaction were assigned to dosing groups, randomised and entered into the Treatment Phase.

The Treatment Phase consisted of a period of 21 days for each subject. During this period one group of subjects received a single intradermal injection of either the preferred mixture (0.03, 0.3, 3, 12 nmol of each peptide per dose) or diluent placebo at Treatment Phase Visit 1 on day one. A cohort of 8 subjects received treatment at each dose level (6 received the preferred mixture and 2 placebo). The first cohort of the intradermal group received 0.03 nmol of each peptide in the mixture and each subsequent cohort in the group received the next higher dose level.

Intradermal injections were made into the flexor surface of the left forearm. The total volume of the injection was 60 µL for all injections. After treatment, subjects had their skin response to whole allergen retested at Treatment Phase Visit 2 on day 21 (±3 days). Skin responses to cat allergen were assessed by measurement of the late-phase responses 8 hours following intradermal administration of 0.010 HEP (histamine equivalent prick) units of commercially available standard cat allergen (supplied by Laboratorios Leti, Spain) as described above. The average area of response for both arms of each subject was then calculated as described above.

This average LPSR area after treatment was then compared to the baseline LPSR area for each subject. The overall change in LPSR area for all eight patients in each cohort was then evaluated. The results of this analysis are shown in the table below. This analysis was performed without unblinding the data.

| DOSE (nmol) | REDUCTION IN LPSR AREA FOLLOWING TREATMENT |
|---|---|
| 0.03 | + |
| 0.3 | ++ |
| 3.0 | ++ |
| 12.0 | ++ |

Figure 8:
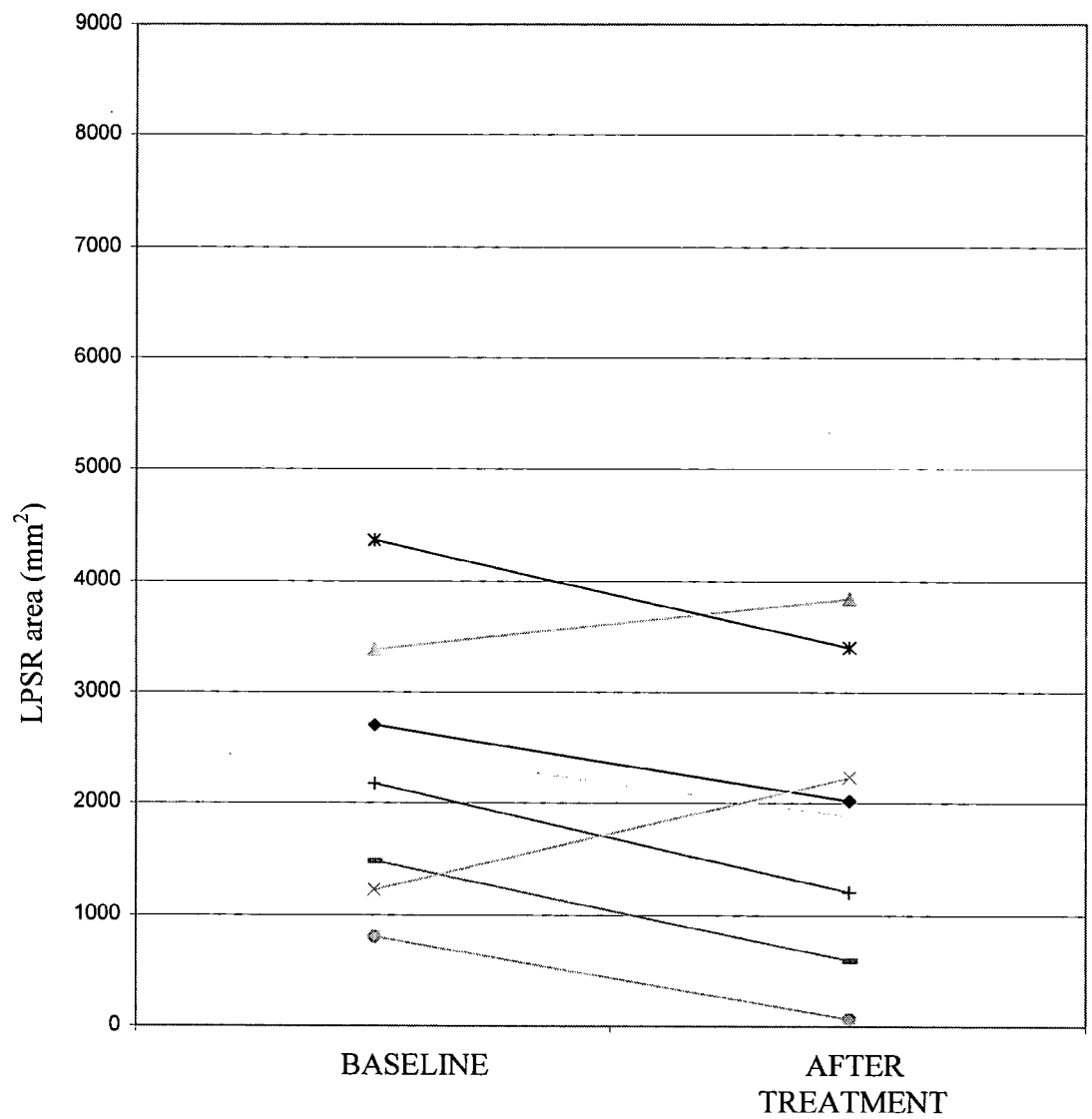
FIG. 8—A representative plot showing the average LPSR area before and after treatment for all eight patients in the 12.0 nmol cohort of the clinical trial of a preferred mixture of peptides of the invention.

FIG. 8 is a representative plot showing the average LPSR area before and after treatment for all eight patients in the 12.0 nmol cohort. Taken together, these data indicate that the preferred mixture of peptides is effective at reducing the LPSR to whole allergen in cat allergic individuals.

The invention claimed is:

1. A method of treating allergy to cats, the method comprising administering to a subject in need of such treatment a therapeutically effective amount of a composition comprising:
   (a) as the only therapeutic ingredients, the polypeptides which consist of the following sequences:

| | |
   |---|---|
   | CPAVKRDVDLFLT; | (SEQ ID NO: 1) |
   | EQVAQYKALPVVLENA; | (SEQ ID NO: 2) |
   | KALPVVLENARILKNCV; | (SEQ ID NO: 3) |
   | RILKNCVDAKMTEEDKE; | (SEQ ID NO: 4) |
   | KENALSLLDKIYTSPL; | (SEQ ID NO: 5) |
   | TAMKKIQDCYVENGLI; and | (SEQ ID NO: 6) |
   | SRVLDGLVMTTISSSK; | (SEQ ID NO: 7) | and
   (b) a pharmaceutically acceptable carrier or diluent.

2. The method of claim 1, wherein said subject is a human.

3. The method of claim 2, wherein said subject is cat allergic.

4. The method of claim 2, wherein said subject experiences a Late-Phase Skin Response (LPSR) to whole cat allergen.

5. The method of claim 2, wherein said subject:
   is sensitised to Fel d 1;
   has a family history of allergy to cats; or
   displays symptoms of allergy when brought into proximity to a cat.

6. The method of claim 1, wherein said composition is provided as an injectable solution, suspension or emulsion.

7. The method of claim 1, wherein said composition is formulated for administration parenterally, subcutaneously, intradermally or transdermally.

* * * * *